(12) United States Patent
Caravella et al.

(10) Patent No.: US 9,902,775 B2
(45) Date of Patent: Feb. 27, 2018

(54) ANTI-BLOOD DENDRITIC CELL ANTIGEN 2 ANTIBODIES AND USES THEREOF

(71) Applicant: Biogen MA Inc., Cambridge, MA (US)

(72) Inventors: Justin A. Caravella, Cambridge, MA (US); Ellen A. Garber Stark, Cambridge, MA (US); Dania Mounir Rabah, Cambridge, MA (US); Frederick R. Taylor, Milton, MA (US)

(73) Assignee: Biogen MA Inc., Cambridge, MA (US)

( * ) Notice: Subject to any disclaimer, the term of this patent is extended or adjusted under 35 U.S.C. 154(b) by 134 days.

(21) Appl. No.: 14/649,297

(22) PCT Filed: Dec. 10, 2013

(86) PCT No.: PCT/US2013/074208
§ 371 (c)(1),
(2) Date: Jun. 3, 2015

(87) PCT Pub. No.: WO2014/093396
PCT Pub. Date: Jun. 19, 2014

(65) Prior Publication Data
US 2015/0299325 A1 Oct. 22, 2015

Related U.S. Application Data

(60) Provisional application No. 61/735,362, filed on Dec. 10, 2012, provisional application No. 61/763,270, filed on Feb. 11, 2013.

(51) Int. Cl.
*A61K 39/00* (2006.01)
*C07K 16/28* (2006.01)

(52) U.S. Cl.
CPC .... *C07K 16/2851* (2013.01); *A61K 2039/505* (2013.01); *C07K 2317/24* (2013.01); *C07K 2317/33* (2013.01); *C07K 2317/51* (2013.01); *C07K 2317/515* (2013.01); *C07K 2317/54* (2013.01); *C07K 2317/55* (2013.01); *C07K 2317/565* (2013.01); *C07K 2317/567* (2013.01); *C07K 2317/622* (2013.01); *C07K 2317/626* (2013.01); *C07K 2317/73* (2013.01); *C07K 2317/732* (2013.01); *C07K 2317/734* (2013.01); *C07K 2317/76* (2013.01); *C07K 2317/92* (2013.01)

(58) Field of Classification Search
CPC ............................................... A61K 2039/505
See application file for complete search history.

(56) References Cited

U.S. PATENT DOCUMENTS

| 6,210,671 | B1 | 4/2001 | Co |
| 7,030,228 | B1 * | 4/2006 | Schmitz ............. C07K 14/7056 435/810 |
| 8,282,964 | B2 * | 10/2012 | Gallagher ............... A61K 38/21 424/534 |

FOREIGN PATENT DOCUMENTS

| WO | WO2001/36487 | 5/2001 |
| WO | 2010/117980 | 10/2010 |
| WO | 2011/023389 | 3/2011 |

OTHER PUBLICATIONS

Dzionek et al. (J. Exp. Med. Dec. 17, 2001; 194 (12): 1823-34).*
Weber et al. (Exp. Mol. Med. Mar. 24, 2017; 49 (3): e305; pp. 1-12).*
Wu et al. (Clin. Immunol. Oct. 2008; 129 (1): 40-8).*
Jaye et al. (Mod. Pathol. Dec. 2006; 19 (12): 1555-62).*
Pellerin et al. (Embo Mol. Med. Apr. 2015; 7 (4): 464-476).*
George et al. (Circulation. 1998; 97: 900-906).*
Holm et al. (Mol. Immunol. Feb. 2007; 44 (6): 1075-1084).*
MacCallum et al. (J. Mol. Biol. Oct. 11, 1996; 262 (5): 732-745).*
Casset et al. (Biochem. Biophys. Res. Commun. Jul. 18, 2003; 307 (1): 198-205).*
Wu et al. (J. Mol. Biol. Nov. 19, 1999; 294 (1): 151-162).*
De Pascalis et al. (J. Immunol. 2002; 169 (6): 3076-3084).*
Vajdos et al. (J. Mol. Biol. Jul. 5, 2002; 320 (2): 415-428).*
Caldas et al. (Mol. Immunol. May 2003; 39 (15): 941-952).*
Chien et al. (Proc. Natl. Acad. Sci. USA. Jul. 1989; 86 (14): 5532-5536).*
Giusti et al. (Proc. Natl. Acad. Sci. USA. May 1987; 84 (9): 2926-2930).*
Winkler et al. (J. Immunol. Oct. 15, 2000; 165 (8): 4505-4514).*
Gussow et al. (Methods in Enzymology. 1991; 203: 99-121).*
Mariuzza et al. (Annu. Rev. Biophys. Biophys. Chem. 1987; 16: 139-159).*
Rudikoff et al. (Proc. Natl. Acad. Sci. USA. 1982; 79: 1979-1983).*
Stancoviski et al. (Proceedings of the National Academy of Science USA. 1991; 88: 8691-8695).*
Yamaguchi et al. (Biochem. Biophys. Res. Commun. Nov. 1, 2014; 454 (4): 600-603).*
Riemer et al. (Mol. Immunol. 2005; 42: 1121-1124).*
Jiang et al. (J. Biol. Chem. Feb. 11, 2005; 280 (6): 4656-4662).*
Blomberg, et al: "Expression of the markers BDCA-2 and BDCA-4 and production of interferon-alpha by plasmacytoid dendritic cells in systemic lupus erythematosus", Arthritis & Rheumatism, 48(9):2524-2532 (2003).
Cao, et al: "BDCA2/FcδR1γ Complex Signals through a Novel BCR-Like Pathway in Human Plasmacytoid Dendritic Cells", PLOS Biology, 100(10):183 (2007).
Dzionek, et al: "BDCA-2, BDCA-3, and BDCA-4: Three Markers for Distinct Subsets of Dendritic Cells in Human Peripheral Blood", Immunology, 165(11):6037-6046 (2000).

(Continued)

Primary Examiner — Stephen Rawlings
(74) Attorney, Agent, or Firm — Fish & Richardson P.C.

(57) ABSTRACT

Antibodies and antibody fragments that bind to BDCA2 are disclosed. Also disclosed are methods of using the antibodies and antibody fragments to induce death of a plasmacytoid dendritic cell, inhibit production or secretion of inflammatory cytokines and chemokines, and treat or prevent immunological disorders such as inflammatory and autoimmune conditions.

53 Claims, 63 Drawing Sheets

(56) References Cited

OTHER PUBLICATIONS

Dzionek, et al: "BDCA-2, a novel plasmacytoid dendritic cell-specific type II C-type lectin, mediates antigen capture and is a potent inhibitor of interferon alpha/beta induction", The Journal of Experimental Medicine, 194(12):1823-1834 (2001).
International Search Report for PCT/US2013/074208, dated Mar. 31, 2014.
Jähn, et al: "BDCA-2 signaling inhibits TLR-9-agonist-induced plasmacytoid dendritic cell activation and antigen presentation", Cellular Immunology, 265(1):15-22 (2010).
Nestle, et al: "Plasmocytoid predendritic cells initiate psoriasis through interferon-alpha production", The Journal of Experimental Medicine, 202(1):135-143 (2005).
Riboldi, et al: "Engagement of BDCA-2 blocks Trail-mediated cytotoxic activity of plasmacytoid dendritic cells", Immunobiology, 214(9-10):868-876 (2009).
Wu, et al: "TLR9/TLR7-triggered downregulation of BDCA2 expression on human plasmacytoid dendritic cells from healthy individuals and lupus patients", Clinical Immunology, 129(1):40-48 (2008).
International Preliminary Report on Patentability for International Application No. PCT/US2013/074208, dated Jun. 16, 2015, 7 pages.
IEDB Analysis Resource, "Cross-blocking analysis," available at URL http://tools.immuneepitope.org/crossblock/crossblock_tool.html, accessed Sep. 25, 2015, 1 page.
Pellerin et al., "Anti-BDCA2 monoclonal antibody inhibits plasmacytoid dendritic cell activation through Fc-dependent and Fc-independent mechanisms," EMBO Molecular Medicine, 2015, 7(4):464-476.
Rock et al., "CD303 (BDCA-2) signals in plasmacytoid dendritic cells via a BCR-like signalosome involving Syk, Lsp65 and PLCγ2," European Journal of Immunology, 2007, 37:3564-3575.
Supplementary Figure S1, Pellerin et al., 2015, pp. 464-476 (1 page).
Supplementary Materials and Methods, Supplementary Figure and Table Legends, Pellerin et al., 2015, pp. 464-4761, (9 total pages).
Supplementary Table S1, "Supplementary References", Pellerin et al., 2015, pp. 464-476 (1 page).
Third Party Observations filed in the name of Laboratoire Français du Fractionnement et des Biotechnologies against EP Application No. 13814340.9, dated Oct. 30, 2015, 70 pages (includes English translation).
Chennamsetty et al., "Design of therapeutic proteins with enhanced stability," PNAS, 106(29):11937-42 (Jul. 2009).
Li et al., "Antibody Aggregation: Insights from Sequence and Structure," Antibodies, 23 pages. (Sep. 2016).
Nichols et al., "Rational design of viscosity reducing mutants of a monoclonal antibody: Hydrophobic versus electrostatic inter-molecular interactions," mAbs, 7(1):212-230 (2015).

\* cited by examiner

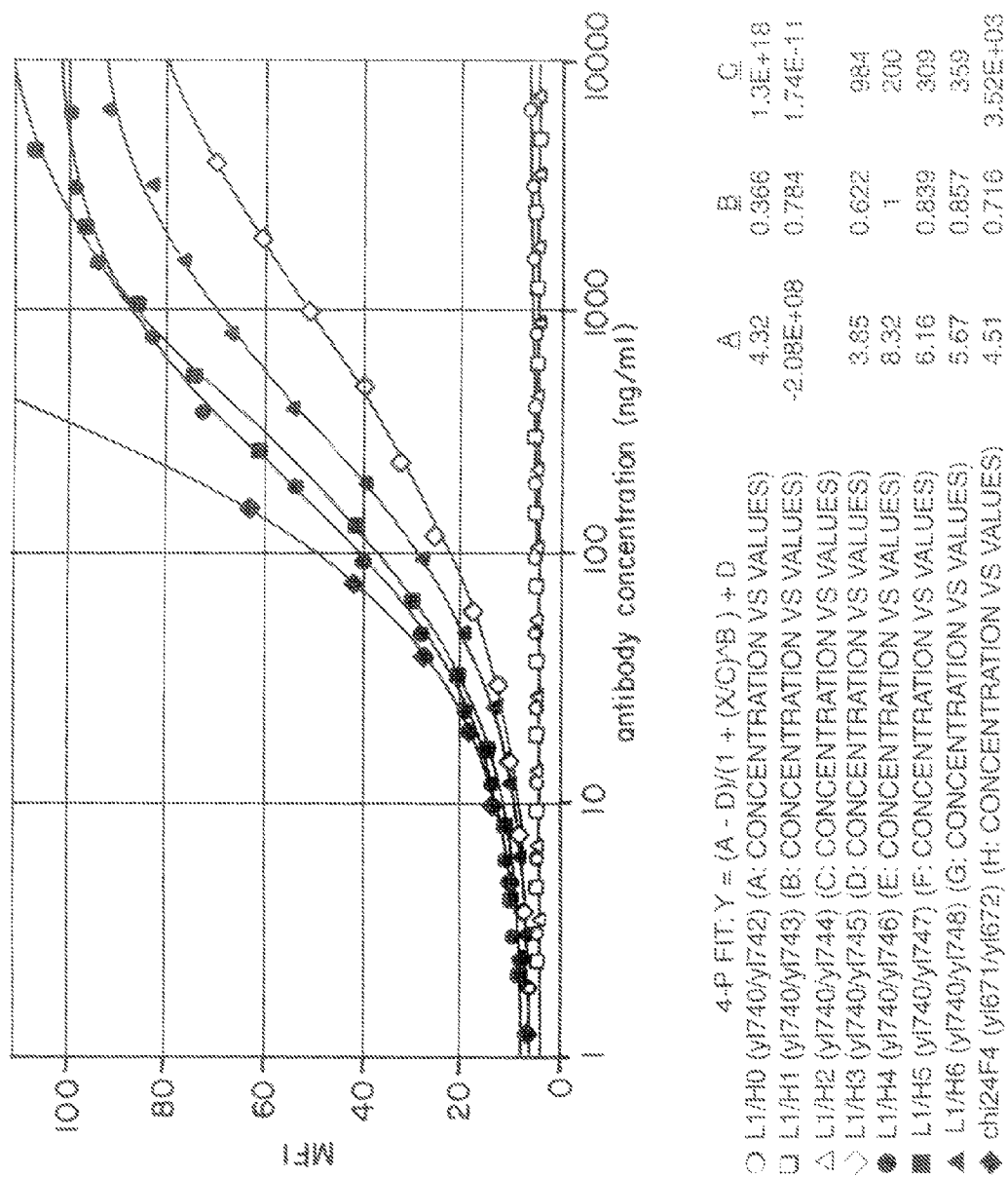

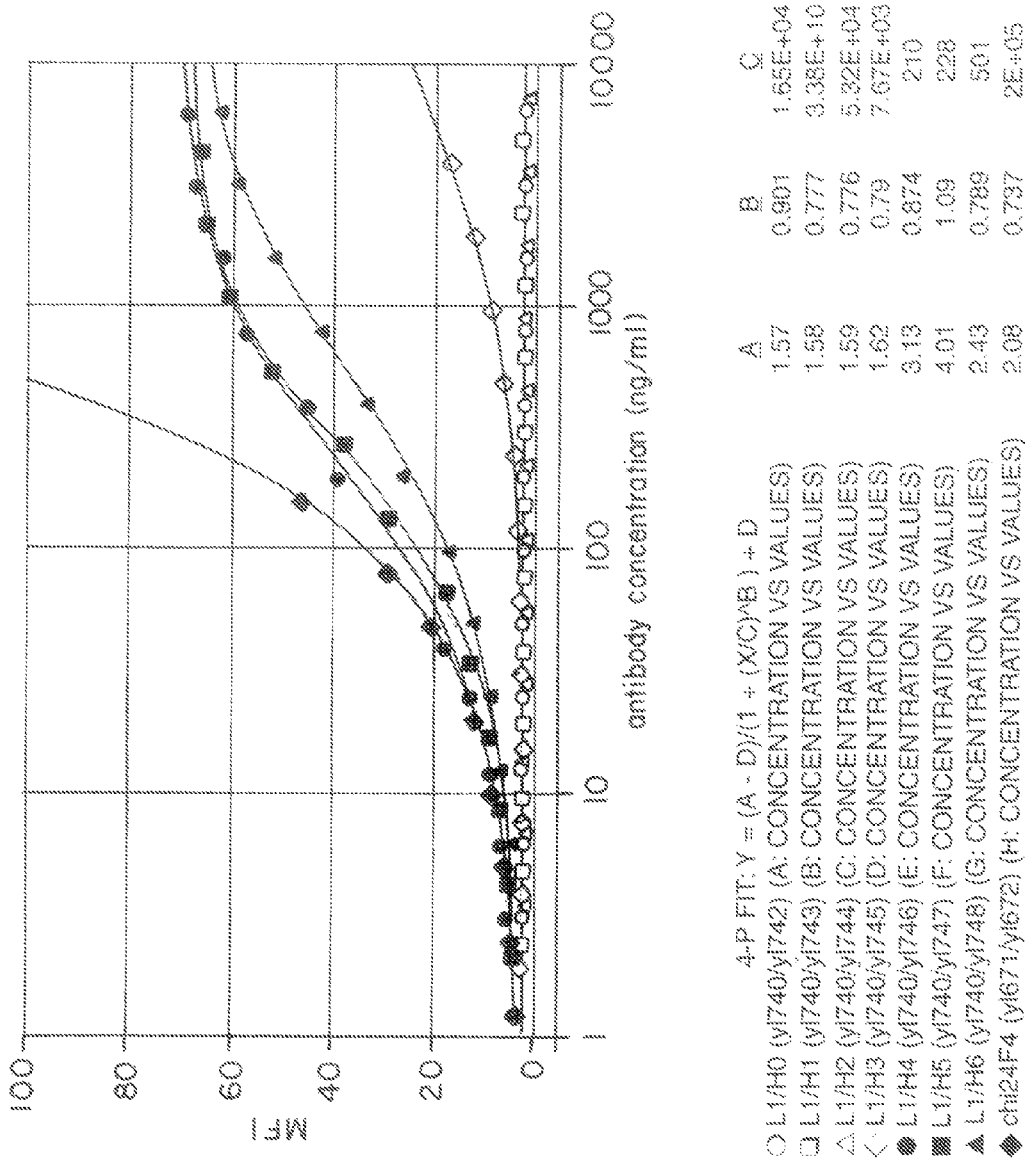

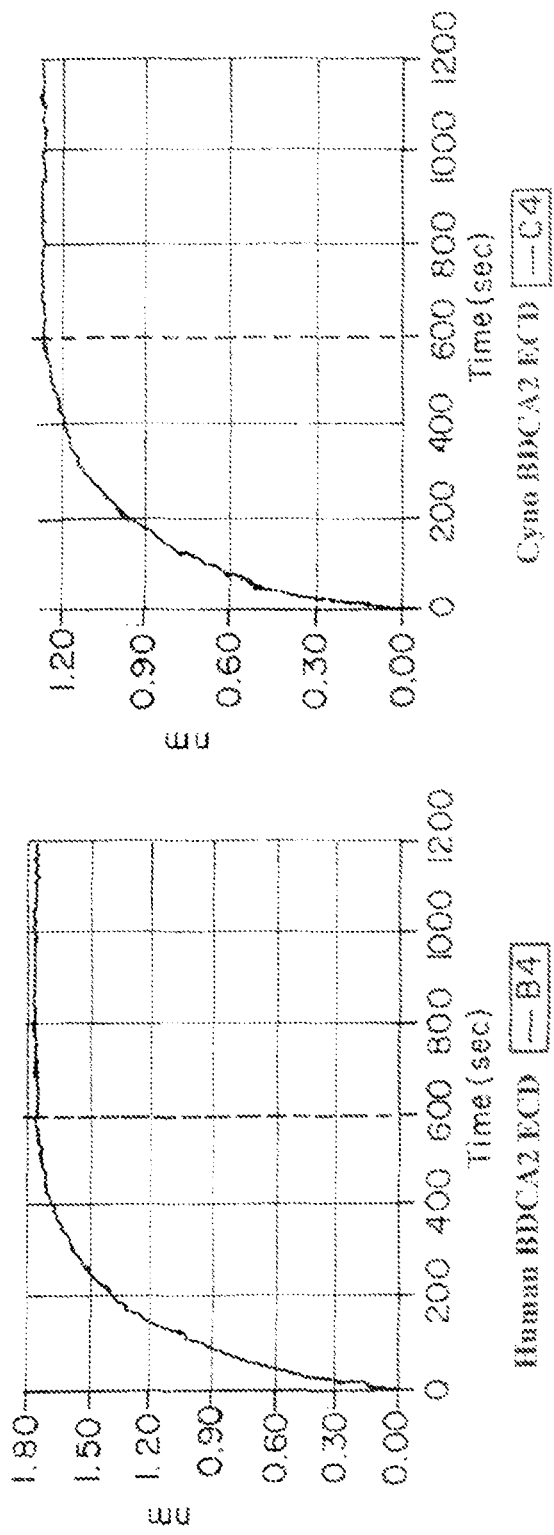

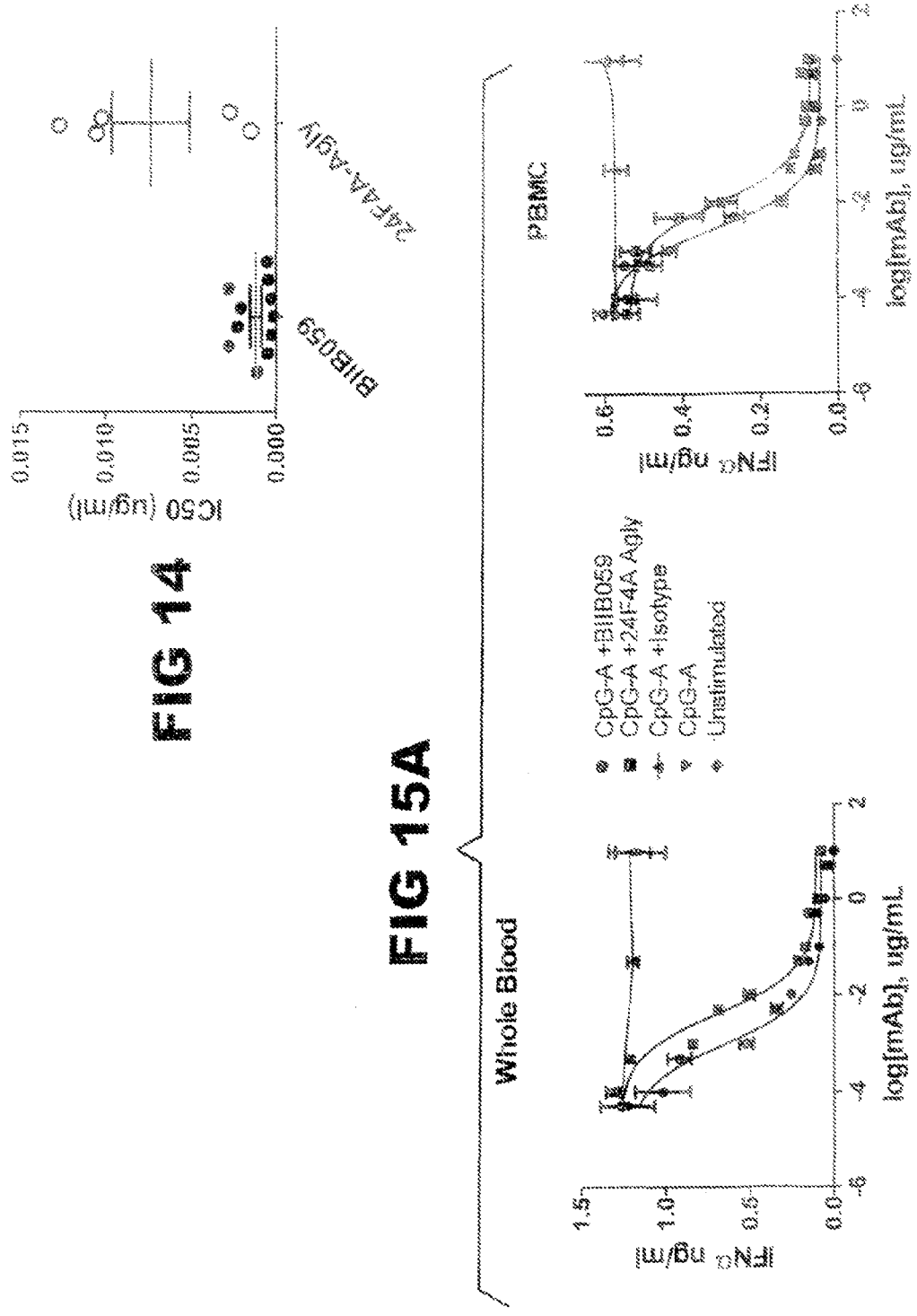

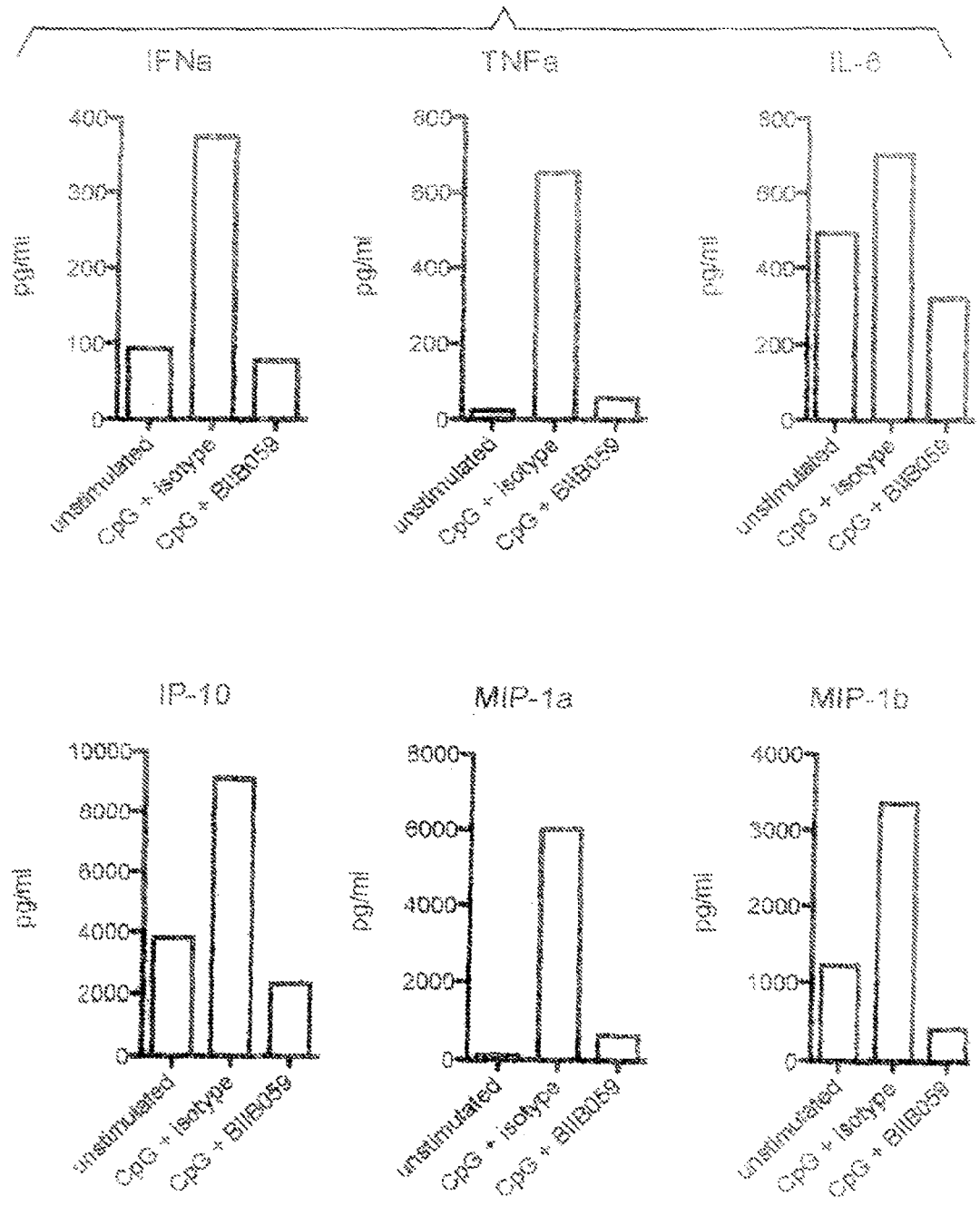

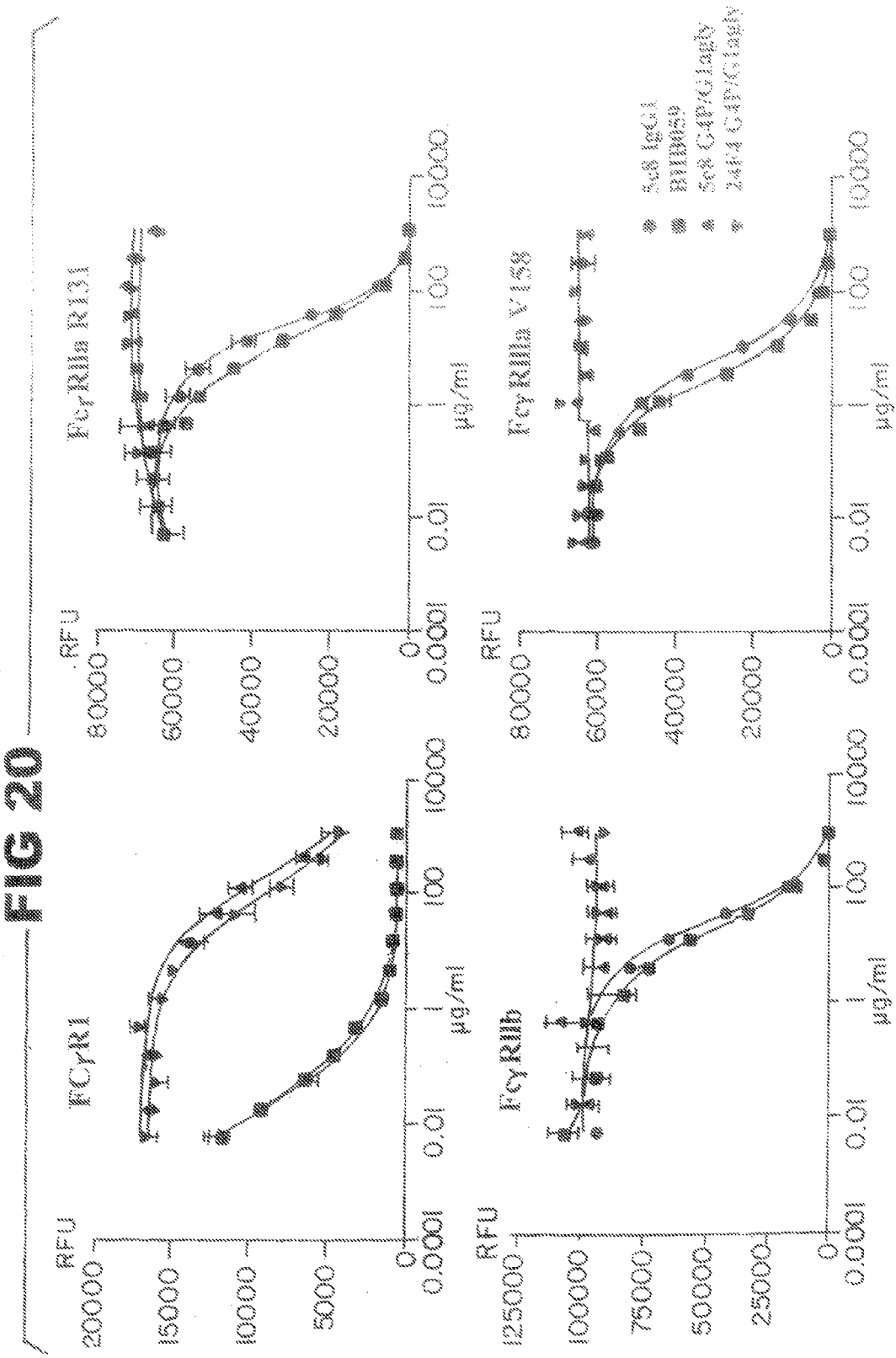

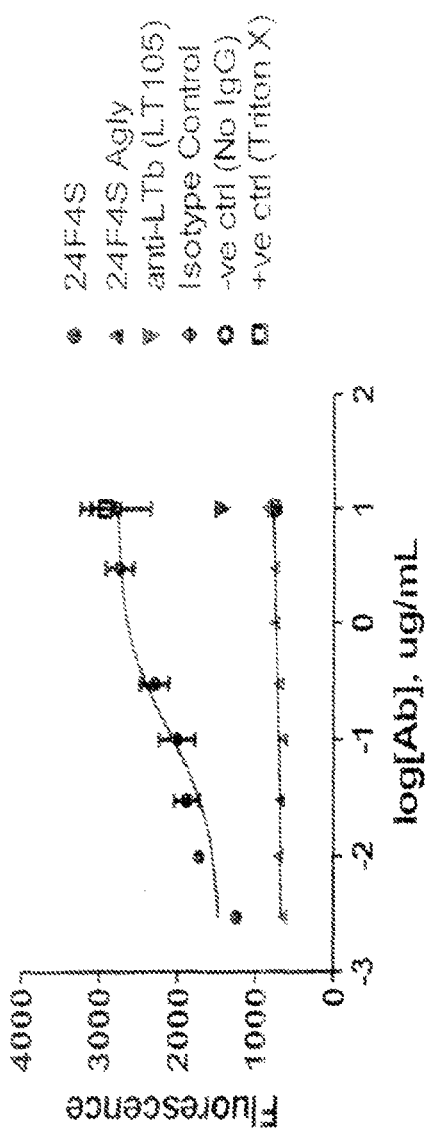
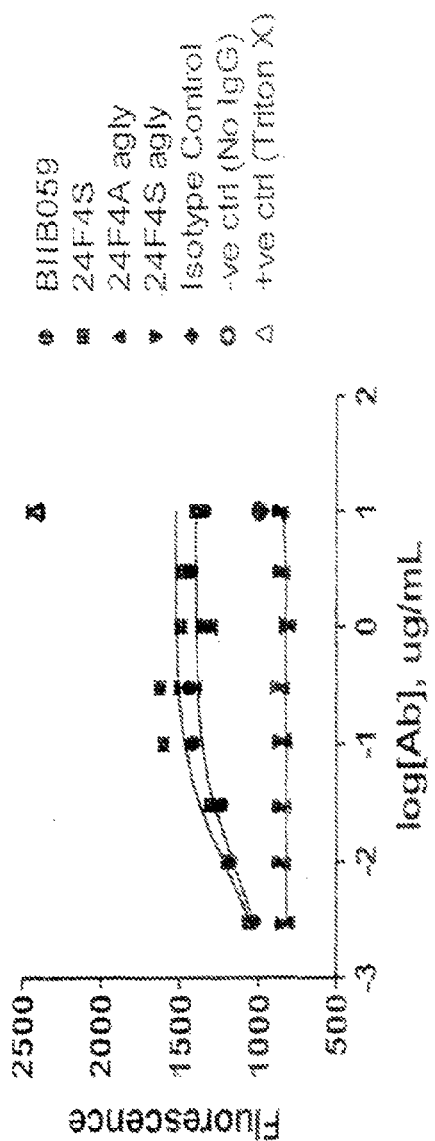
FIG 22A
FIG 22B

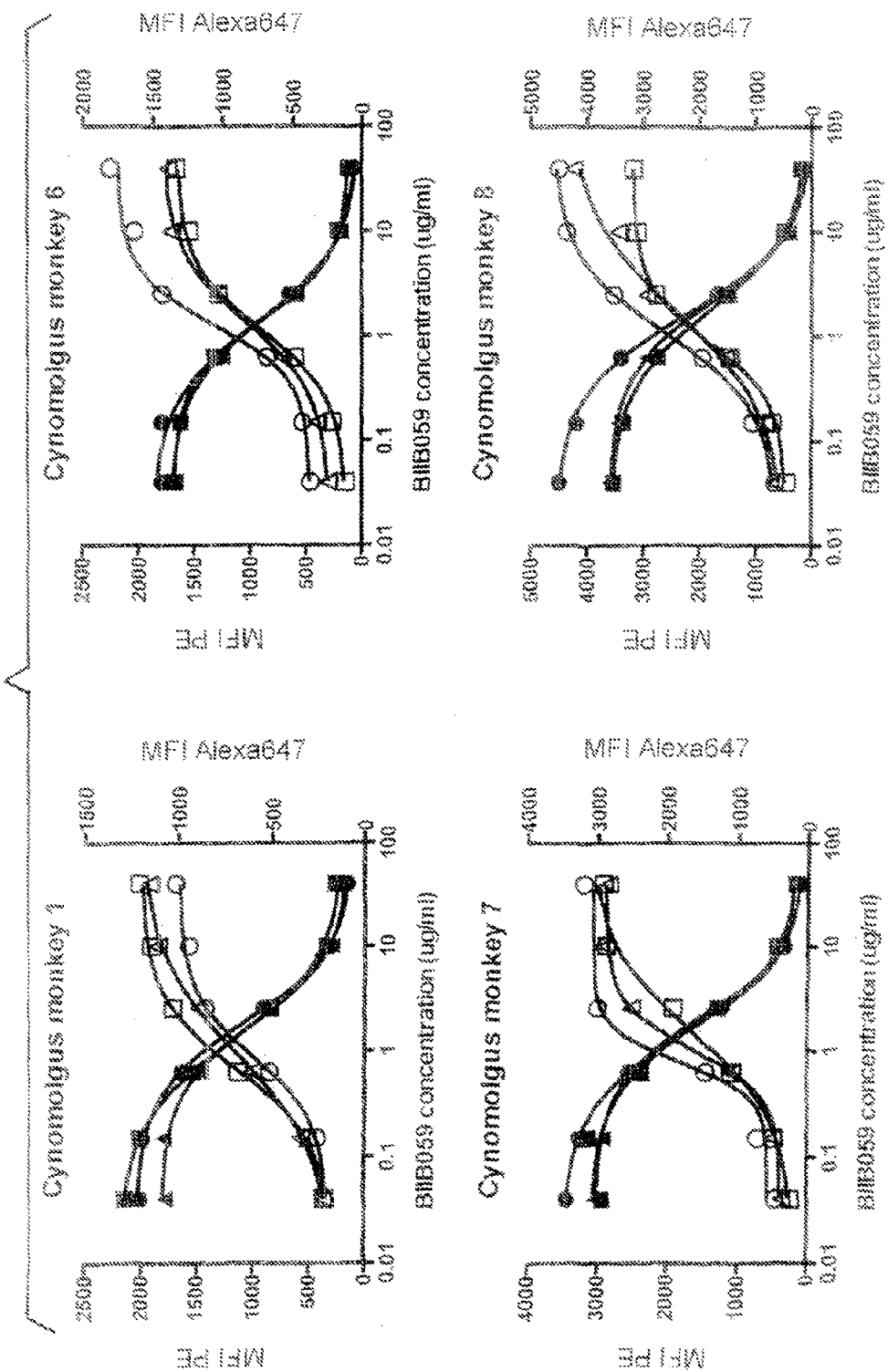

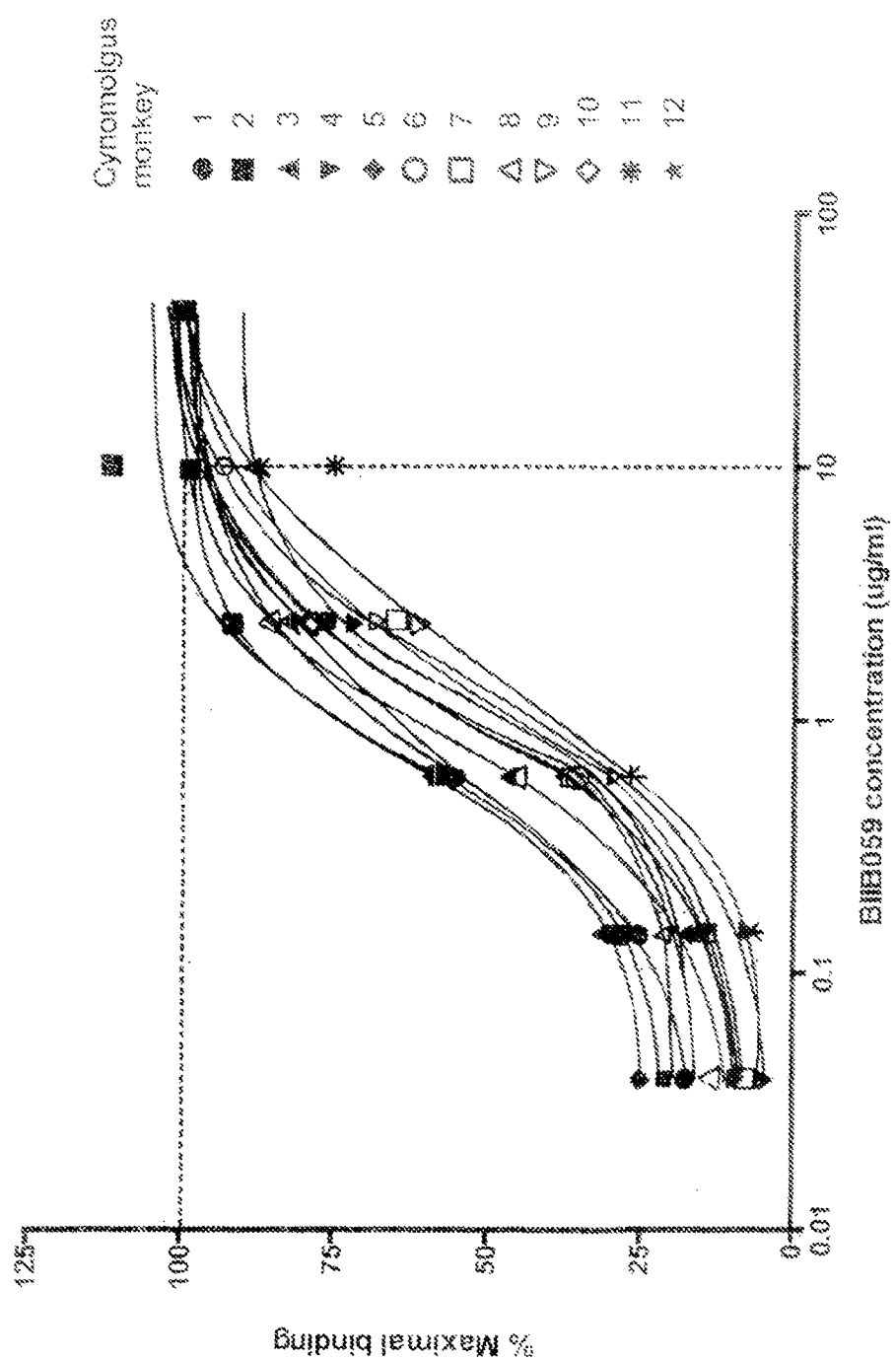

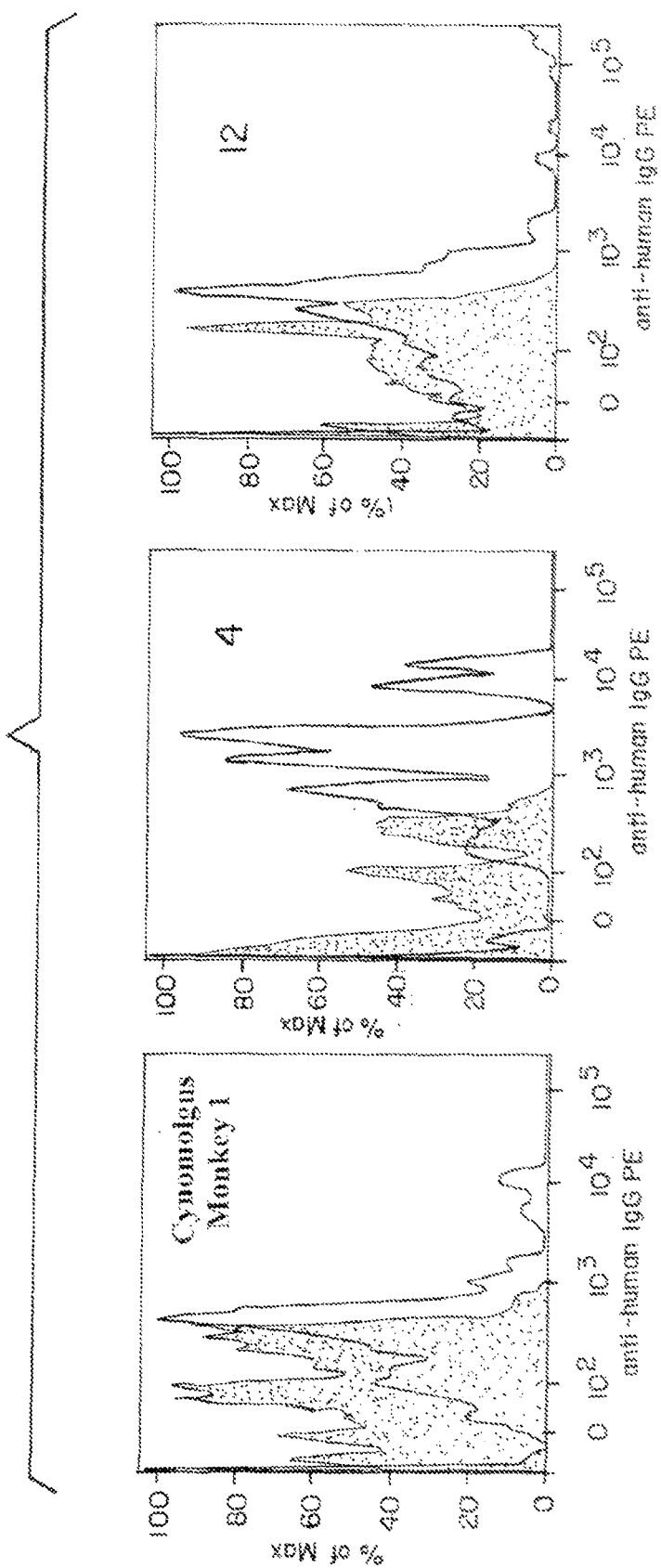

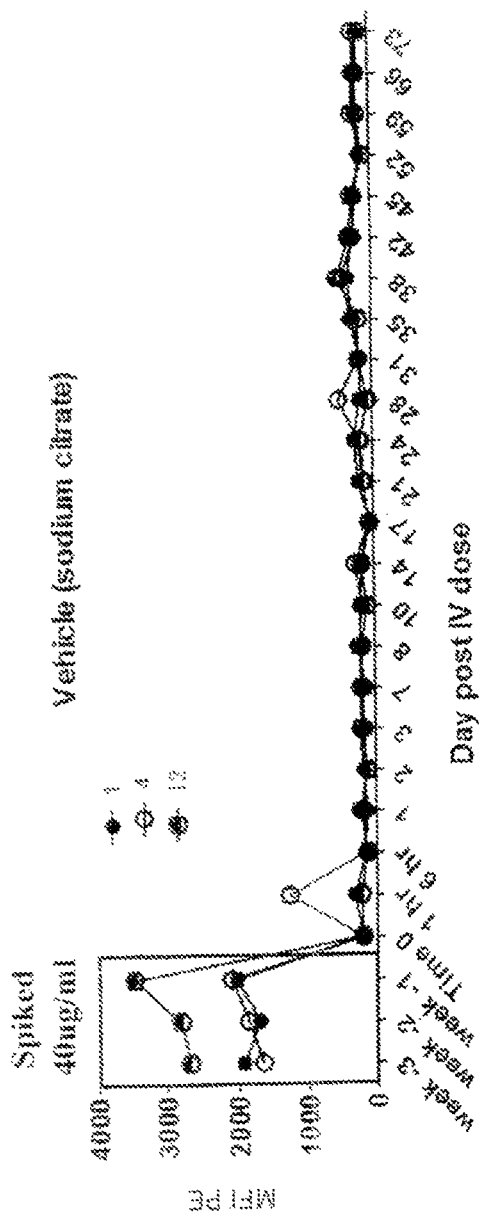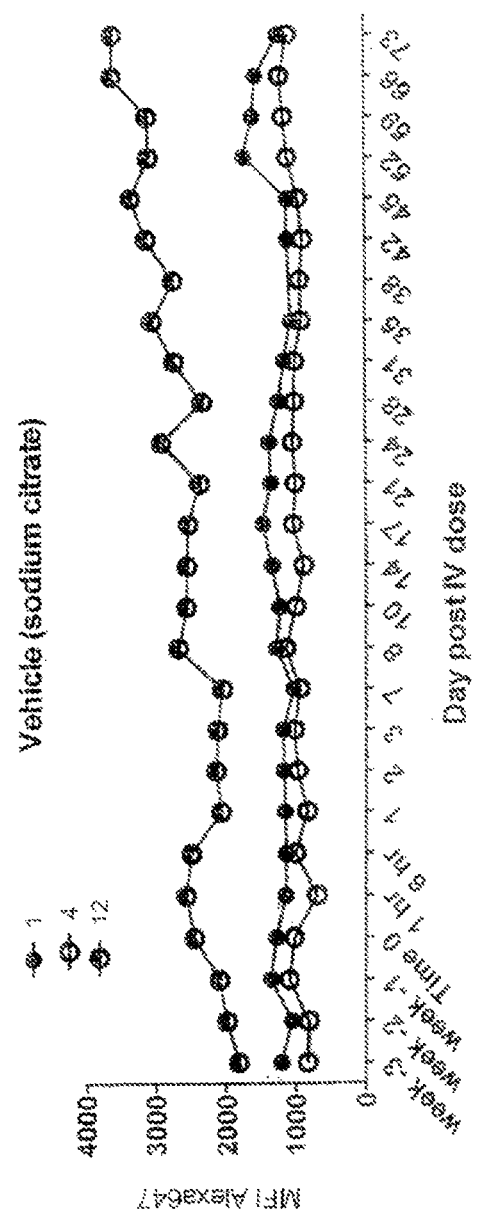

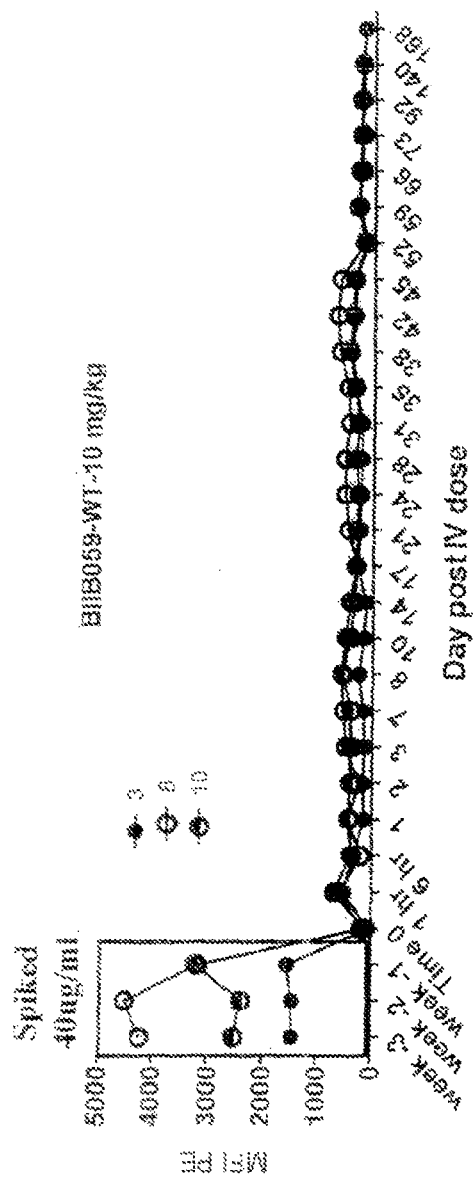
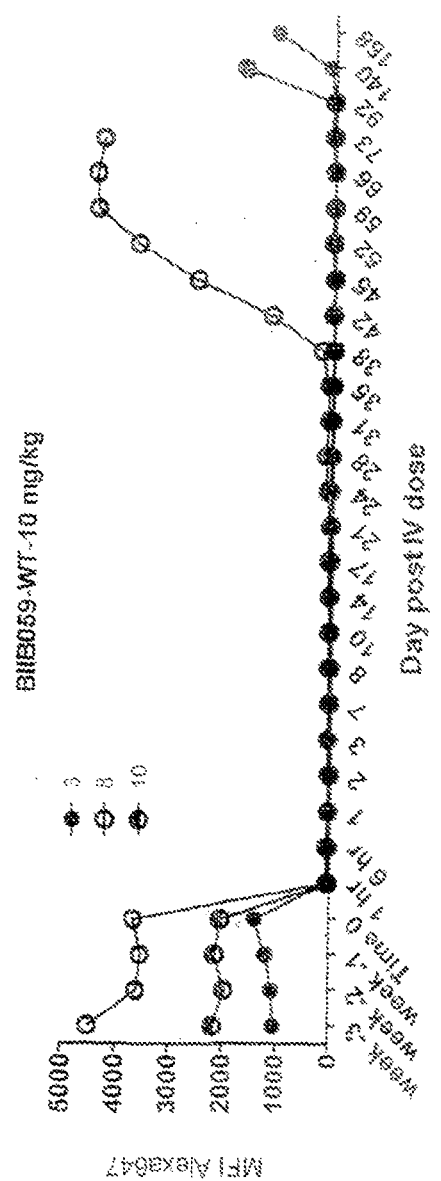
FIG 27B
FIG 27C

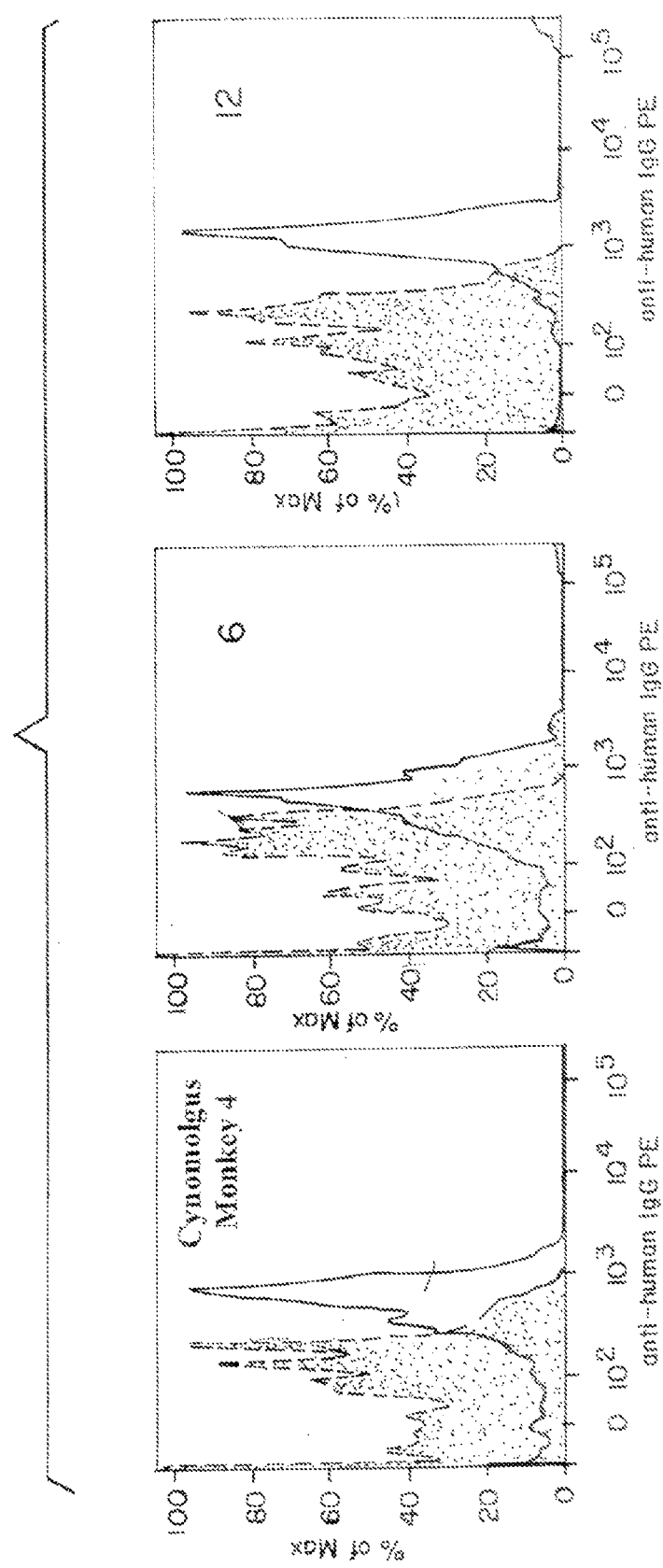

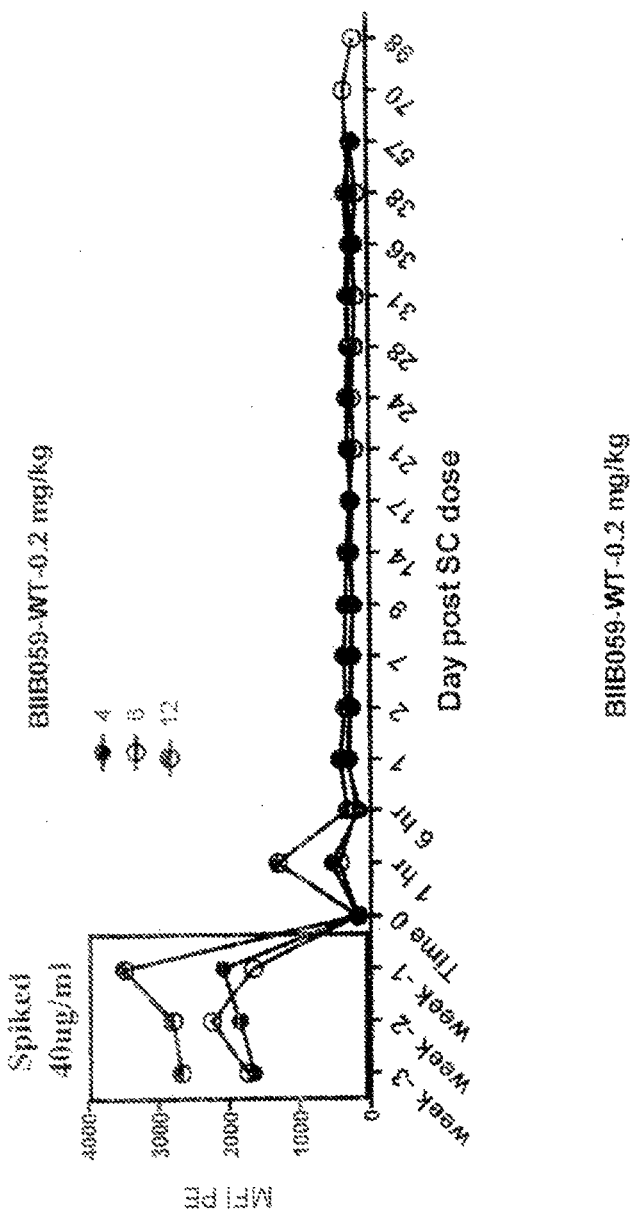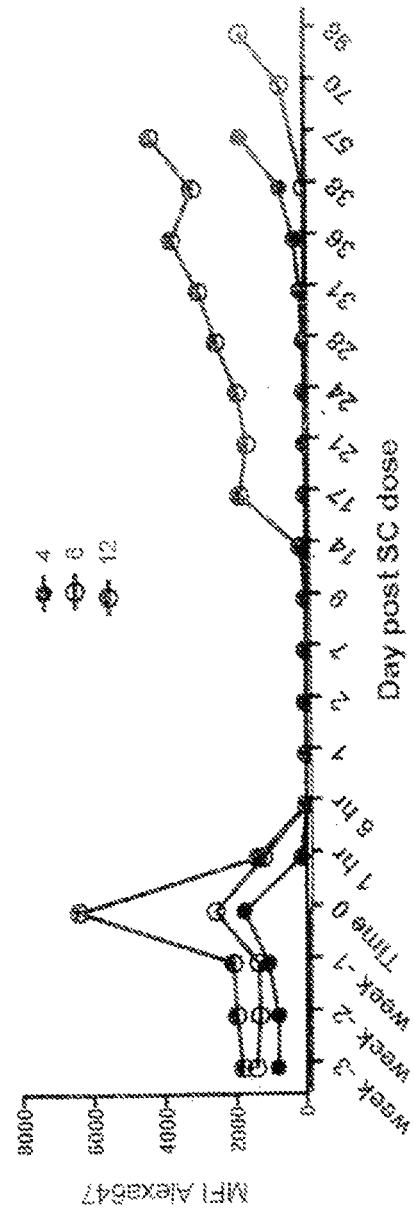

FIG 30A
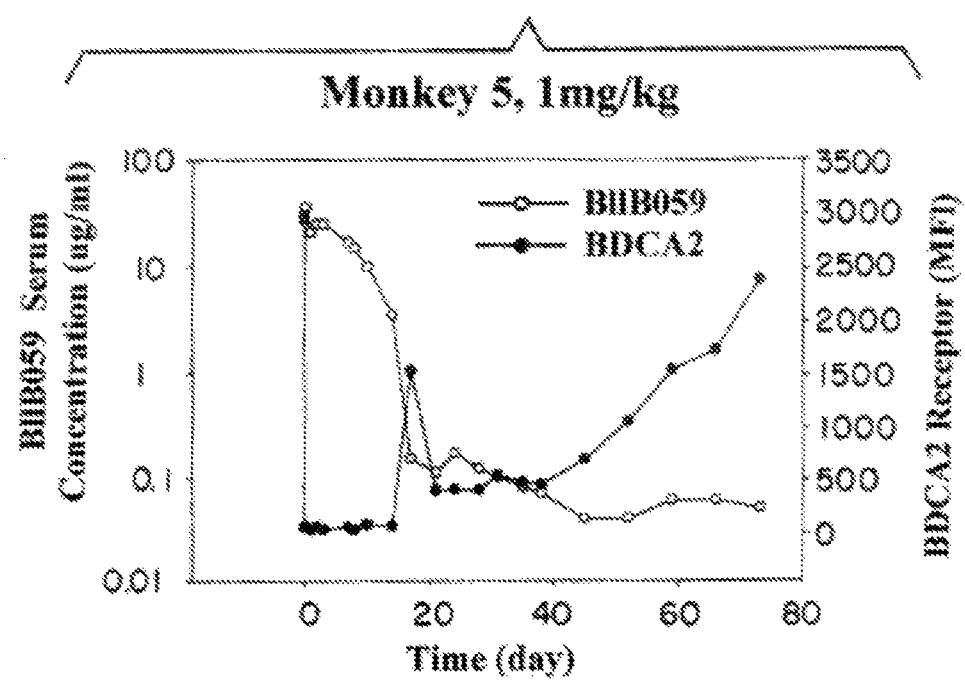
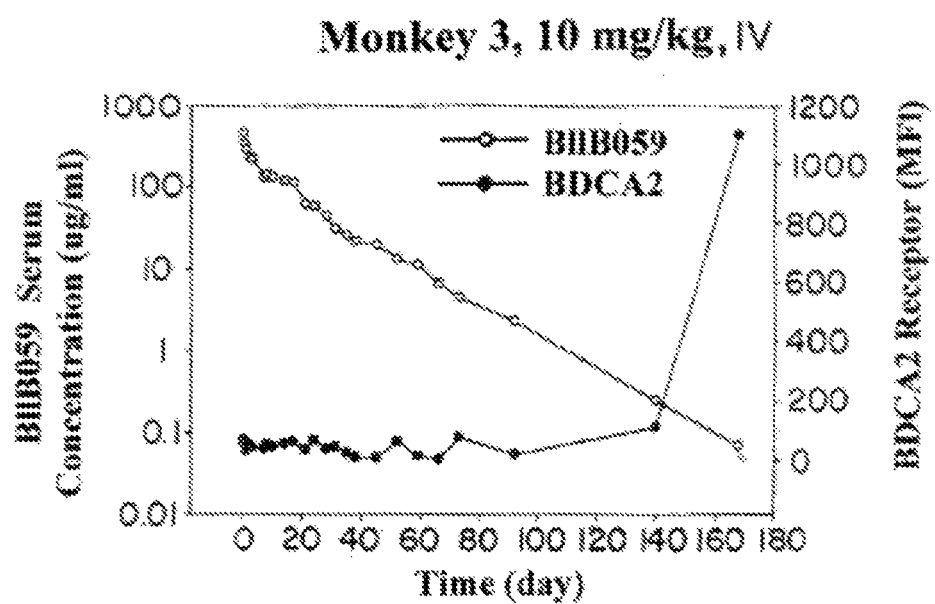

FIG 30B
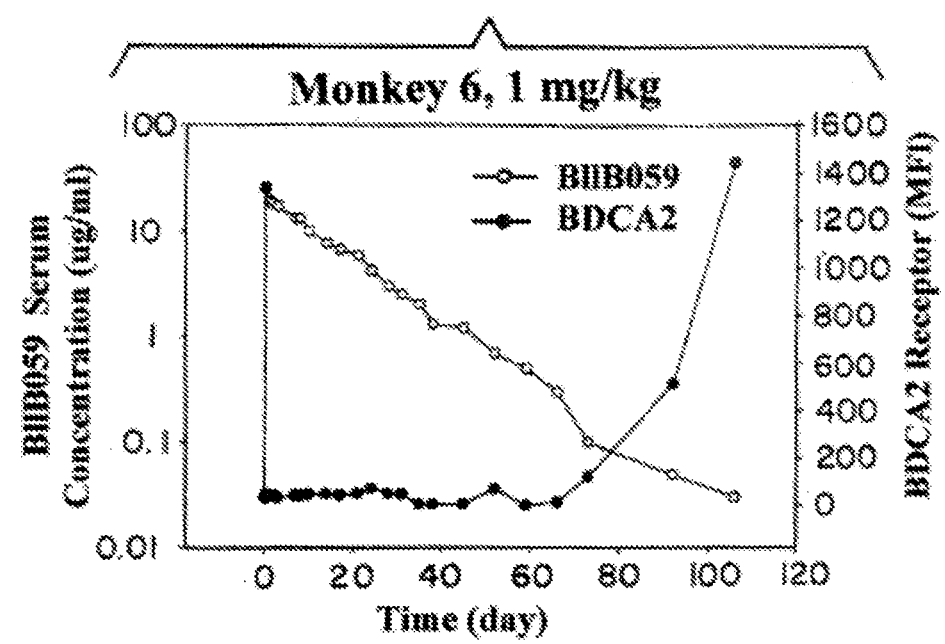
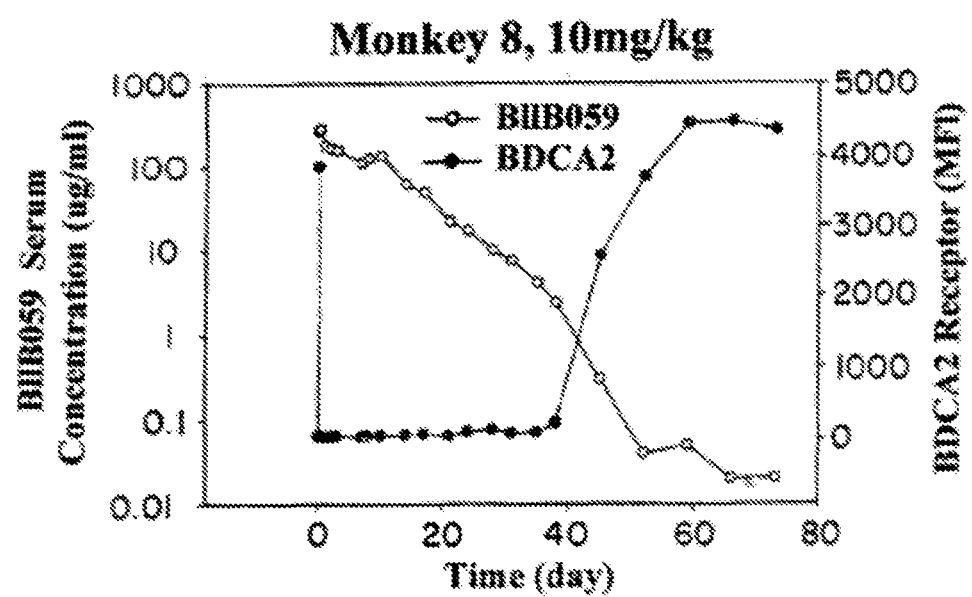

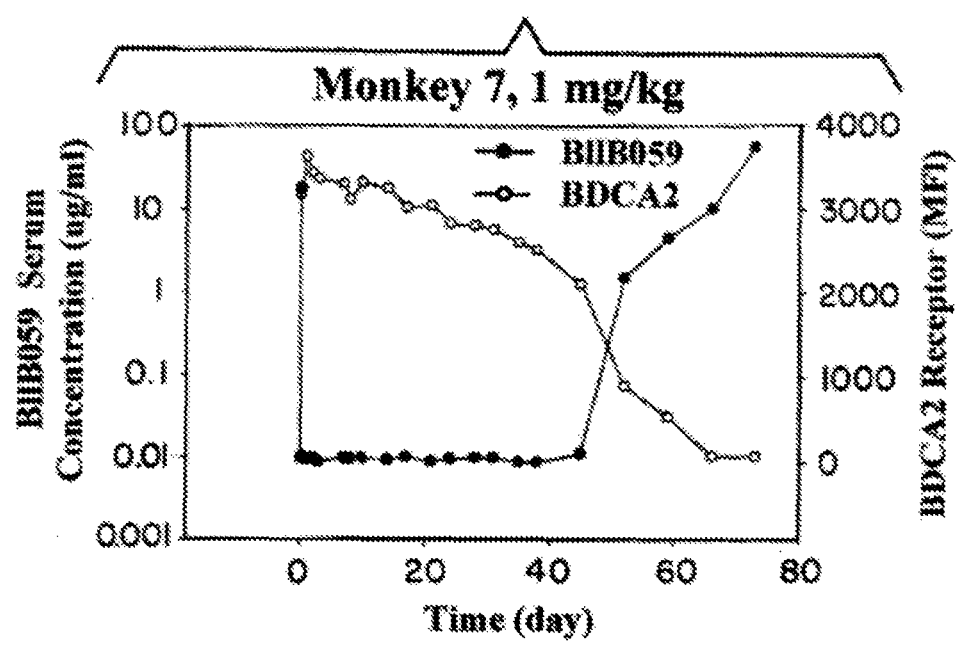
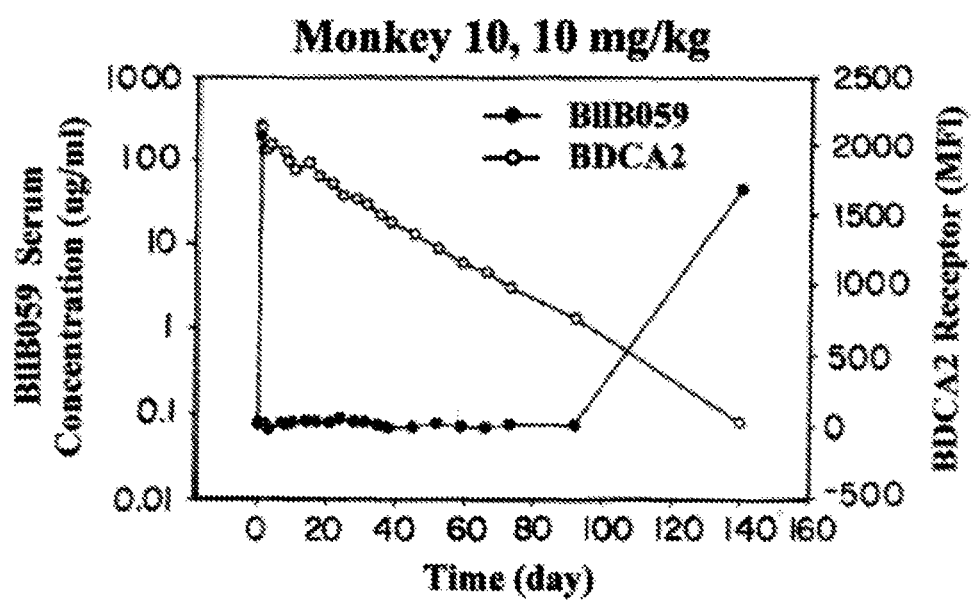

FIG 31A
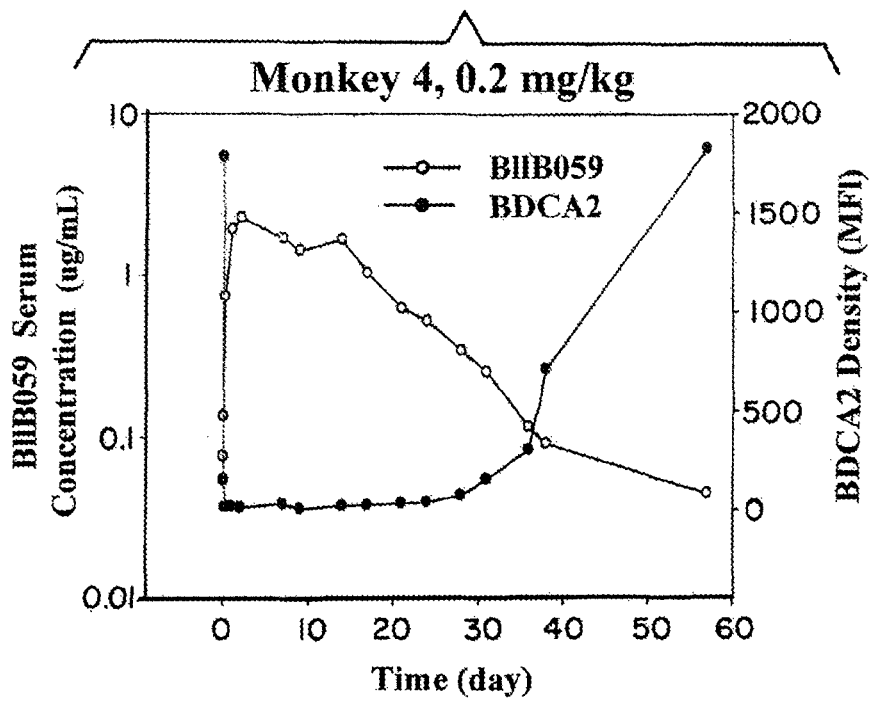
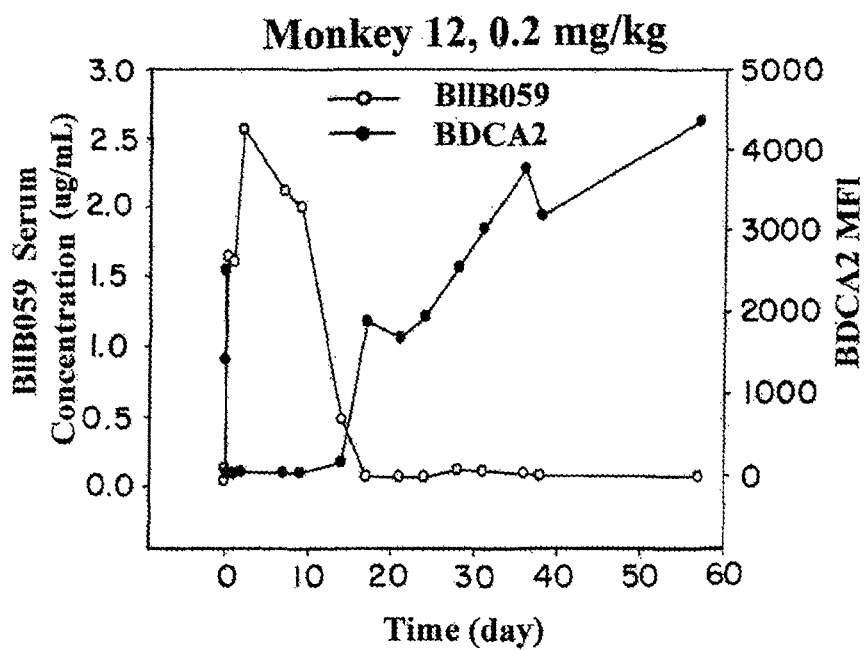

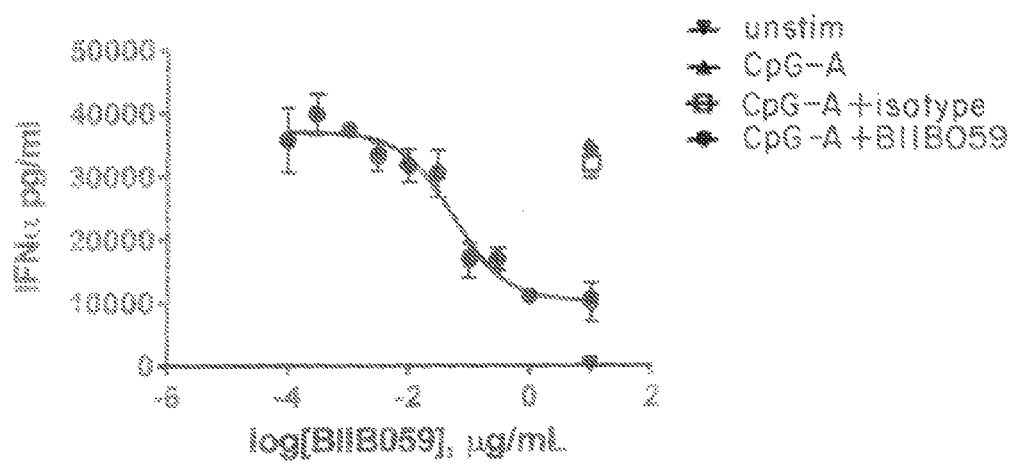
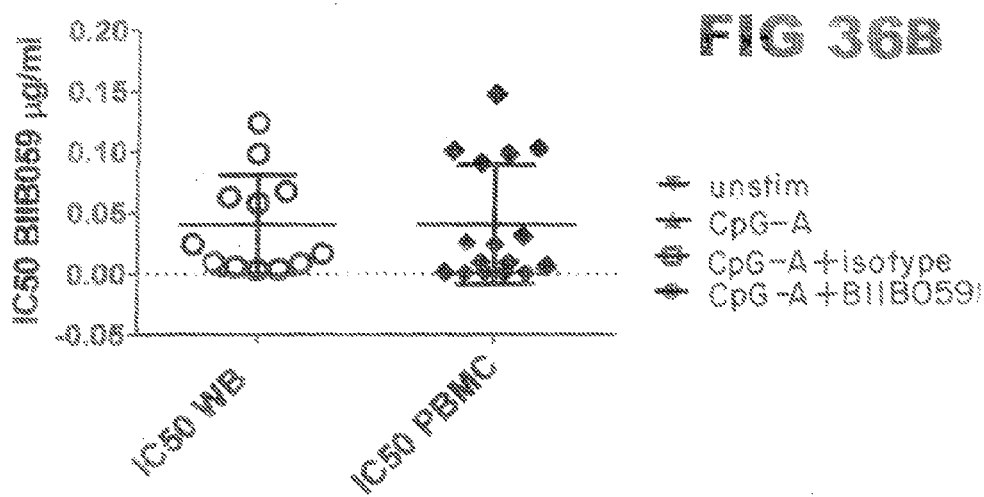
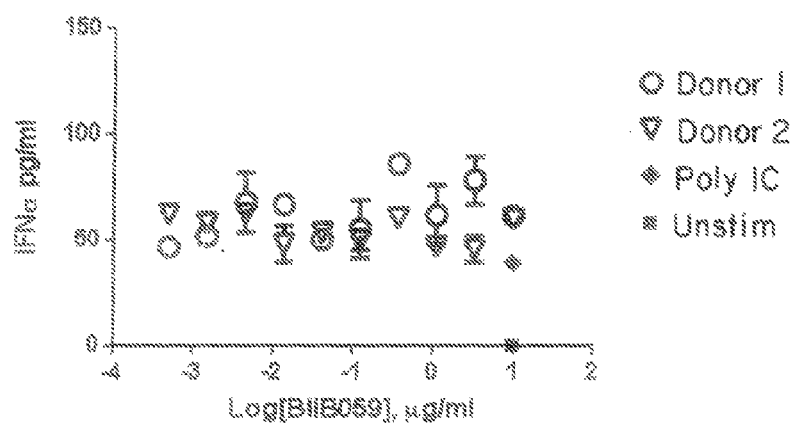

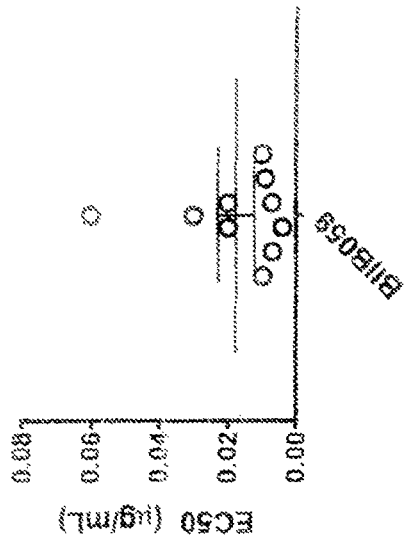
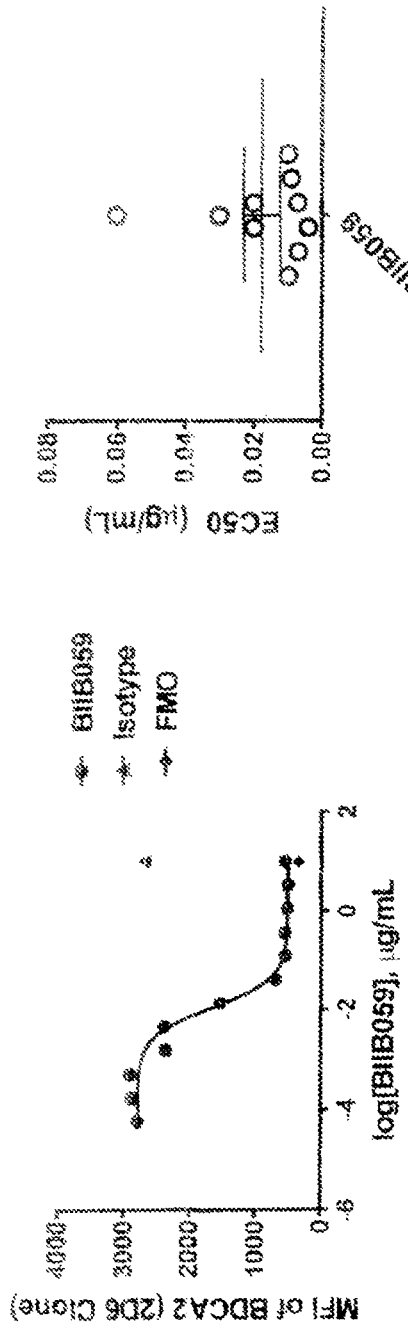
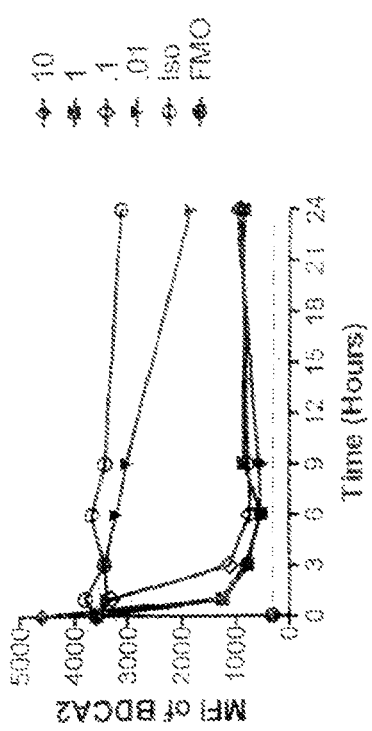

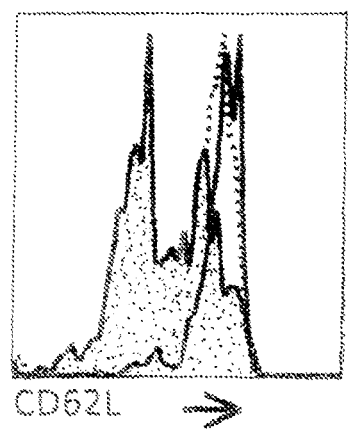
FIG 44A
FIG 44B
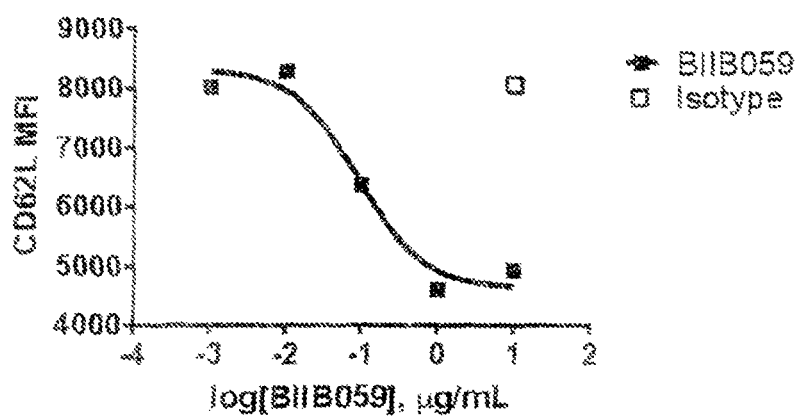
FIG 45
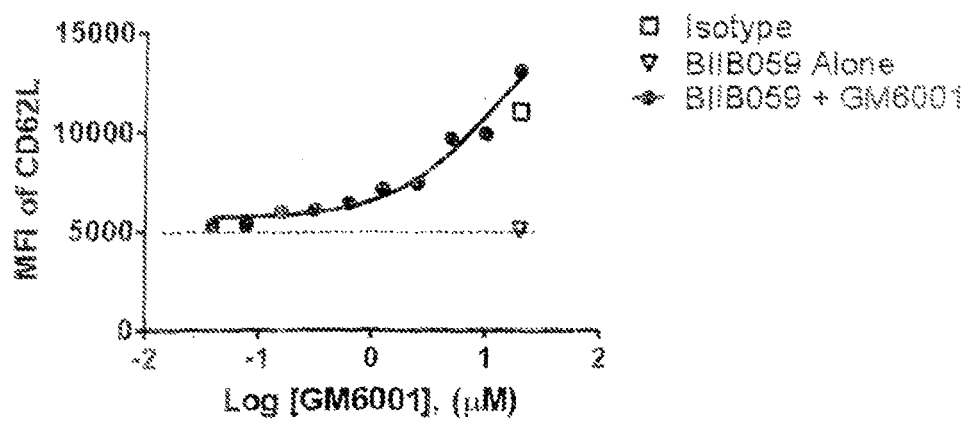

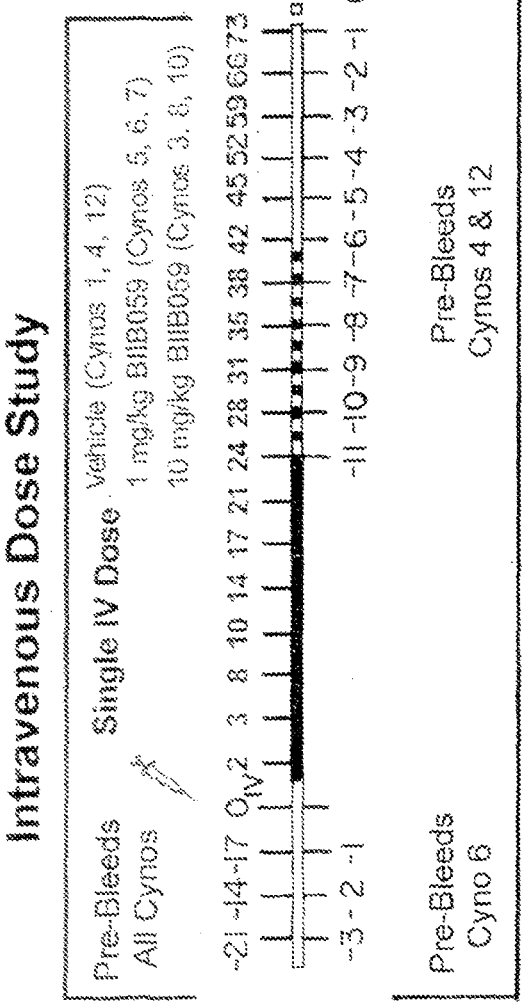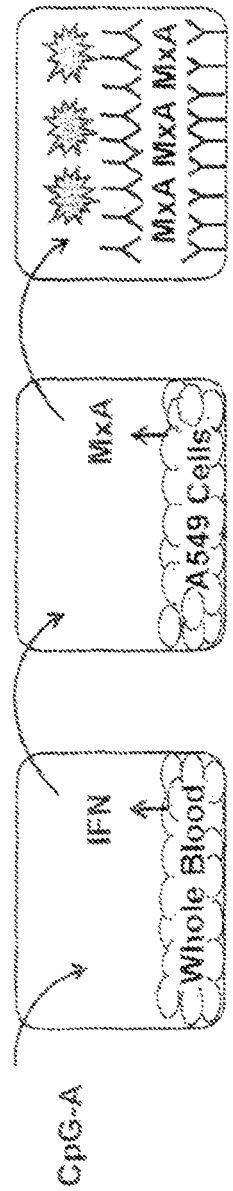
FIG 58

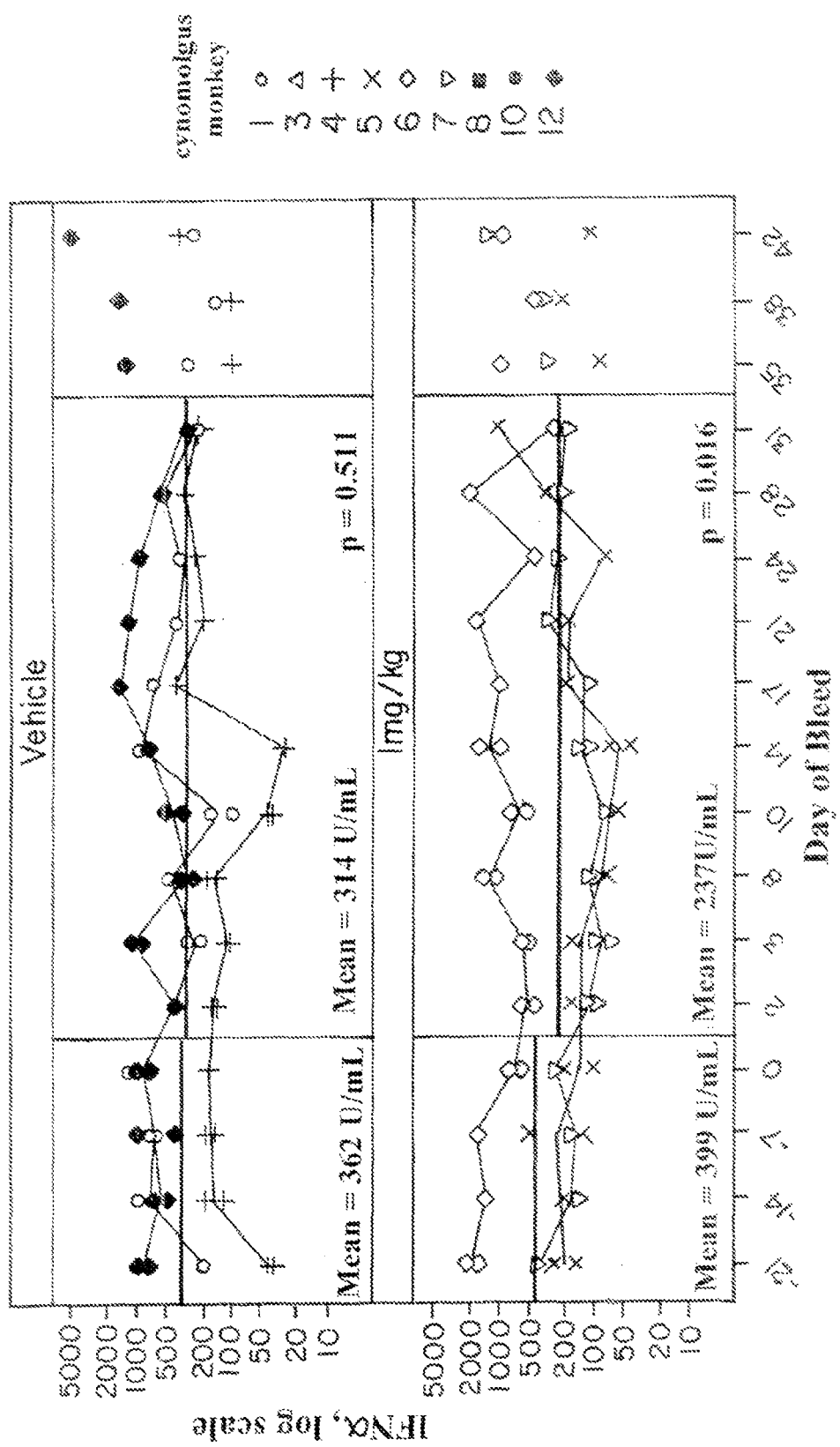

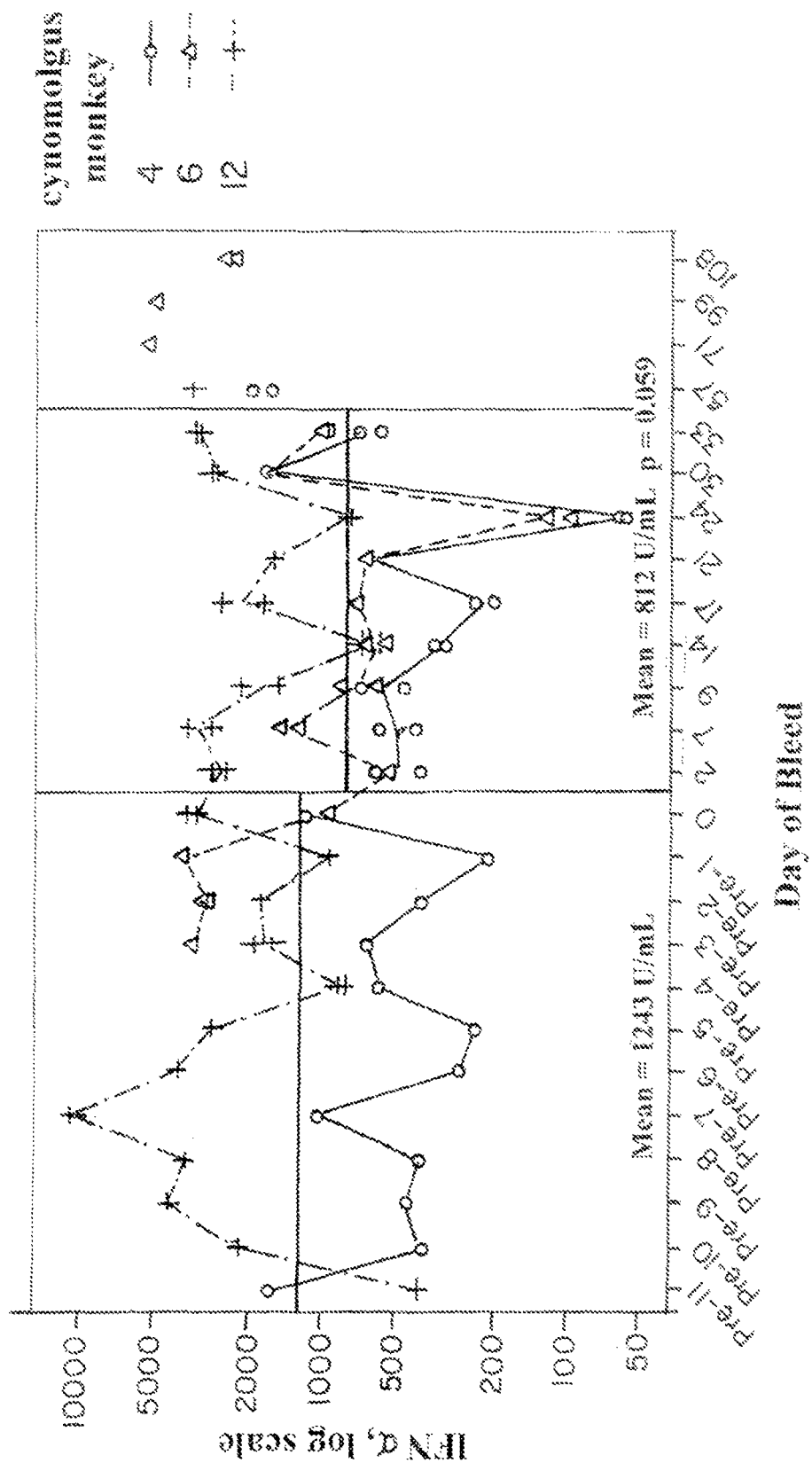

SEQUENCE LISTING

```
<160> NUMBER OF SEQ ID NOS: 99

<210> SEQ ID NO 1
<211> LENGTH: 213
<212> TYPE: PRT
<213> ORGANISM: Homo sapiens

<400> SEQUENCE: 1

Met Val Pro Glu Glu Pro Gln Asp Arg Glu Lys Gly Leu Trp Trp
1               5                   10                  15

Phe Gln Leu Lys Val Trp Ser Met Ala Val Val Ser Ile Leu Leu Leu
```

20                  25                  30
Ser Val Cys Phe Thr Val Ser Ser Val Val Pro His Asn Phe Met Tyr
            35                  40                  45
Ser Lys Thr Val Lys Arg Leu Ser Lys Leu Arg Glu Tyr Gln Gln Tyr
        50                  55                  60
His Pro Ser Leu Thr Cys Val Met Glu Gly Lys Asp Ile Glu Asp Trp
65                  70                  75                  80
Ser Cys Cys Pro Thr Pro Trp Thr Ser Phe Gln Ser Ser Cys Tyr Phe
                85                  90                  95
Ile Ser Thr Gly Met Gln Ser Trp Thr Lys Ser Gln Lys Asn Cys Ser
            100                 105                 110
Val Met Gly Ala Asp Leu Val Val Ile Asn Thr Arg Glu Glu Gln Asp
        115                 120                 125
Phe Ile Ile Gln Asn Leu Lys Arg Asn Ser Ser Tyr Phe Leu Gly Leu
    130                 135                 140
Ser Asp Pro Gly Gly Arg Arg His Trp Gln Trp Val Asp Gln Thr Pro
145                 150                 155                 160
Tyr Asn Glu Asn Val Thr Phe Trp His Ser Gly Glu Pro Asn Asn Leu
                165                 170                 175
Asp Glu Arg Cys Ala Ile Ile Asn Phe Arg Ser Ser Glu Glu Trp Gly
            180                 185                 190
Trp Asn Asp Ile His Cys His Val Pro Gln Lys Ser Ile Cys Lys Met
        195                 200                 205
Lys Lys Ile Tyr Ile
    210

<210> SEQ ID NO 2
<211> LENGTH: 86
<212> TYPE: PRT
<213> ORGANISM: Homo sapiens

<400> SEQUENCE: 2

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 3
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Asp Ile Gln Leu Thr Gln Ser Pro Ser Ser Leu Ser Ala Ser Val Gly
1               5                   10                  15

```
Asp Arg Val Thr Ile Thr Cys Lys Ala Ser Gln Ser Val Asp Tyr Asp
             20                  25                  30

Gly Asp Ser Tyr Met Asn Trp Tyr Gln Gln Lys Pro Gly Lys Ala Pro
         35                  40                  45

Lys Leu Leu Ile Tyr Ala Ala Ser Thr Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ala Asn
                 85                  90                  95

Glu Asp Pro Arg Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 4
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Asp Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
             20                  25                  30

Thr Met Ser Trp Val Arg Gln Ala Pro Gly Lys Gly Leu Glu Trp Val
         35                  40                  45

Ala Thr Ile Ser Pro Gly Asp Ser Phe Gly Tyr Tyr Tyr Pro Asp Ser
     50                  55                  60

Val Gln Gly Arg Phe Thr Ile Ser Arg Asp Asn Ala Lys Asn Ser Leu
 65                  70                  75                  80

Tyr Leu Gln Met Asn Ser Leu Arg Ala Glu Asp Thr Ala Val Tyr Tyr
                 85                  90                  95

Cys Thr Arg Asp Ile Tyr Tyr Asn Tyr Gly Ala Trp Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
```

```
               145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
                275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Arg Asp Glu Leu Thr Lys Asn Gln Val
                355                 360                 365
Ser Leu Thr Cys Leu Val Lys Gly Phe Tyr Pro Ser Asp Ile Ala Val
                370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
                435                 440                 445
Ser Pro Gly
    450

<210> SEQ ID NO 5
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Lys Ala Ser Gln Ser Val Asp Tyr Asp Gly Asp Ser Tyr Met Asn
1               5                   10                  15

<210> SEQ ID NO 6
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 6

Ala Ala Ser Thr Leu Glu Ser
1               5

<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gln Gln Ala Asn Glu Asp Pro Arg Thr
1               5

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Thr Tyr Thr Met Ser
1               5

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Phe Thr Phe Ser Thr Tyr Thr Met Ser
1               5                   10

<210> SEQ ID NO 10
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Thr Ile Ser Pro Gly Asp Ser Phe Gly Tyr Tyr Pro Asp Ser Val
1               5                   10                  15

Gln Gly

<210> SEQ ID NO 11
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 11

Asp Ile Tyr Tyr Asn Tyr Gly Ala Trp Phe Ala Tyr
1               5                   10

<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Phe Thr Phe Ser
1               5

<210> SEQ ID NO 13
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Gly Gly Ser
1

<210> SEQ ID NO 14
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Gly Gly Gly
1

<210> SEQ ID NO 15
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Gly Gly Gly Ser
1               5

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16
```

```
Ser Gly Gly Gly Gly
1               5

<210> SEQ ID NO 17
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Gly Gly Gly Gly Ser
1               5

<210> SEQ ID NO 18
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ser Gly Gly Gly Gly Gly
1               5

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Gly Gly Gly Gly Gly Ser
1               5

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Gly Gly Gly Gly Gly Gly
1               5

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gly Gly Gly Gly Ser
1               5
```

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

Ser Gly Gly Gly Gly
1               5

<210> SEQ ID NO 23
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

Asp Ile Gln Leu Thr Gln Ser Pro Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Thr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ala Asn
                85                  90                  95

Glu Asp Pro Arg Thr Phe Gly Gln Gly Thr Lys Val Glu Ile Lys
            100                 105                 110

<210> SEQ ID NO 24
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

Asp Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
                20                  25                  30

Thr Met Ser Trp Val Arg Gln Ala Pro Gly Lys Gly Leu Glu Trp Val
            35                  40                  45

Ala Thr Ile Ser Pro Gly Asp Ser Phe Gly Tyr Tyr Pro Asp Ser
50                  55                  60

Val Gln Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Thr Arg Asp Ile Tyr Tyr Asn Tyr Gly Ala Trp Phe Ala Tyr Trp 100                 105                 110
Gly Gln Gly Thr Leu Val Thr Val Ser Ser
        115                 120

<210> SEQ ID NO 25
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
actagtcgac atgractttg ggytcagctt grttt                             35

<210> SEQ ID NO 26
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
aggtctagaa yctccacaca caggrrccag tggatagac                         39

<210> SEQ ID NO 27
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
actagtcgac atggagwcag acacactcct gytatgggt                         39

<210> SEQ ID NO 28
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
gcgtctagaa ctggatggtg ggagatgga                                    29

<210> SEQ ID NO 29
<211> LENGTH: 122
<212> TYPE: PRT
<213> ORGANISM: Mus sp.

<400> SEQUENCE: 29

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Thr Ile Ser Pro Gly Asp Ser Phe Gly Tyr Tyr Tyr Pro Asp Ser

```
                        50                  55                  60
Val Gln Gly Arg Phe Thr Ile Ser Arg Asp Asn Ala Lys Asn Thr Leu
 65                  70                  75                  80

Phe Leu Gln Met Ser Ser Leu Lys Ser Glu Asp Thr Ala Met Tyr Tyr
                 85                  90                  95

Cys Thr Arg Asp Ile Tyr Tyr Asn Tyr Gly Ala Trp Phe Ala Tyr Trp
                100                 105                 110

Gly Gln Gly Thr Leu Val Thr Val Ser Ala
            115                 120

<210> SEQ ID NO 30
<211> LENGTH: 111
<212> TYPE: PRT
<213> ORGANISM: Mus sp.

<400> SEQUENCE: 30

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
             35                  40                  45

Lys Leu Leu Ile Tyr Ala Ala Ser Thr Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Cys Asn
                 85                  90                  95

Glu Asp Pro Arg Thr Phe Gly Gly Gly Thr Lys Leu Glu Ile Lys
                100                 105                 110

<210> SEQ ID NO 31
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
gatccgcggc cgcaccatgg actttgggtt cagcttg                            37

<210> SEQ ID NO 32
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gatgggccct tggtggaagc tgcagagaca gtgaccagag                         40

<210> SEQ ID NO 33
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 33

```
Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Thr Ile Ser Pro Gly Asp Ser Phe Gly Tyr Tyr Tyr Pro Asp Ser
    50                  55                  60

Val Gln Gly Arg Phe Thr Ile Ser Arg Asp Asn Ala Lys Asn Thr Leu
65                  70                  75                  80

Phe Leu Gln Met Ser Ser Leu Lys Ser Glu Asp Thr Ala Met Tyr Tyr
                85                  90                  95

Cys Thr Arg Asp Ile Tyr Tyr Asn Tyr Gly Ala Trp Phe Ala Tyr Trp
            100                 105                 110

Gly Gln Gly Thr Leu Val Thr Val Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 34
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Val Arg Gln Thr Pro Glu Lys Arg Leu Glu Trp Val
        35                  40                  45

Ala Thr Ile Ser Pro Gly Asp Ser Phe Gly Tyr Tyr Tyr Pro Asp Ser
    50                  55                  60

Val Gln Gly Arg Phe Thr Ile Ser Arg Asp Asn Ala Lys Asn Thr Leu
65                  70                  75                  80

Phe Leu Gln Met Ser Ser Leu Lys Ser Glu Asp Thr Ala Met Tyr Tyr
                85                  90                  95

Cys Thr Arg Asp Ile Tyr Tyr Asn Tyr Gly Ala Trp Phe Ala Tyr Trp
            100                 105                 110

Gly Gln Gly Thr Leu Val Thr Val Ser Ala Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Gln Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 35
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
gatccgcggc cgccaccatg gagacagaca cactcctg                            38

<210> SEQ ID NO 36
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
ccaccgtacg tttgatttcc agcttggtgc                                     30

<210> SEQ ID NO 37
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Thr Leu Glu Ser Gly Val Pro Ala
```

```
                50                  55                  60
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Cys Asn
                 85                  90                  95

Glu Asp Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 38
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 38
gcaacctatt actgtcaaca aagtaatgag gatcctcgga c     41

<210> SEQ ID NO 39
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 39
caacctatta ctgtcagcaa actaatgaag atcctcggac gttcg     45

<210> SEQ ID NO 40
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Tyr
             20                  25                  30

Thr Met Ser Trp Val Arg Gln Ala Pro Gly Lys Gly Leu Glu Trp Val
```

```
                35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Tyr Tyr Asn Tyr Gly Ala Trp Phe Ala Tyr Trp Gly
                100                 105                 110

Gln Gly Thr Leu Val Thr Val Ser Ser
        115                 120

<210> SEQ ID NO 41
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
gaagtgcagc tggtggagtc tgggggaggc ttagtgaagc ctggagggtc cctgagactc       60
tcctgtgcag cctctggatt cactttcagt acctatacca tgtcttgggt tcgccaagca      120
ccgggcaagg gactggagtg ggtctctgct attagtggta gcggaggtag tacatactat      180
gcagacagtg tgaagggccg attcaccatc tccagagaca atgccaagaa cagtctgtac      240
ctgcaaatga acagtctgag gcagaggac acagccgtgt attactgtgc tcgagatatc      300
tactataatt acggagcctg gtttgcttac tggggccaag gactctggt cactgtctct      360 agc                                                                   363

<210> SEQ ID NO 42
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
                20                  25                  30

Thr Met Ser Trp Val Arg Gln Ala Pro Gly Lys Gly Leu Glu Trp Val
            35                  40                  45

Ser Thr Ile Ser Pro Gly Asp Ser Phe Gly Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Tyr Tyr Asn Tyr Gly Ala Trp Phe Ala Tyr Trp Gly
                100                 105                 110

Gln Gly Thr Leu Val Thr Val Ser Ser
        115                 120
```

<210> SEQ ID NO 43
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43

```
gaagtgcagc tggtggagtc tgggggaggc ttagtgaagc ctggagggtc cctgagactc      60
tcctgtgcag cctctggatt cactttcagt acctatacca tgtcttgggt tcgccaagca     120
ccgggcaagg gactggagtg ggtctctacc attagtccag agacagtttt cggatactat     180
ccagacagtg tgaagggccg attcaccatc tccagagaca atgccaagaa cagtctgtac     240
ctgcaaatga acagtctgag ggcagaggac acagccgtgt attactgtgc tcgagatatt     300
tactataatt acggagcctg gtttgcttac tggggccaag gactctggt cactgtctct     360
agc                                                                   363
```

<210> SEQ ID NO 44
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Ala Pro Gly Lys Gly Leu Glu Trp Val
        35                  40                  45

Ser Thr Ile Ser Pro Gly Asp Ser Ser Thr Ile Tyr Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Tyr Tyr Asn Tyr Gly Ala Trp Phe Ala Tyr Trp
            100                 105                 110

Gly Gln Gly Thr Leu Val Thr Val Ser Ser
        115                 120

<210> SEQ ID NO 45
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
gaagtgcagc tggtggagtc tgggggaggc ttagtgaagc ctggagggtc cctgagactc      60
tcctgtgcag cctctggatt cactttcagt acctatacca tgtcttgggt tcgccaagca     120
ccgggcaagg gactggagtg ggtctctacc attagtccag agacagtag cactatctac     180
```

```
tatgcagaca gtgtgaaggg ccgattcacc atctccagag acaatgccaa gaacagtctg    240
tacctgcaaa tgaacagtct gagggcagag gacacagccg tgtattactg tgcccgagat    300
atttactata attacggagc ctggtttgct tactggggcc aagggactct ggtcactgtc    360
tctagc                                                               366
```

<210> SEQ ID NO 46
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Ala Pro Gly Lys Gly Leu Glu Trp Val
        35                  40                  45

Ser Thr Ile Ser Pro Gly Asp Ser Phe Gly Tyr Tyr Pro Asp Ser
    50                  55                  60

Val Gln Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Tyr Tyr Asn Tyr Gly Ala Trp Phe Ala Tyr Trp
            100                 105                 110

Gly Gln Gly Thr Leu Val Thr Val Ser Ser
        115                 120
```

<210> SEQ ID NO 47
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47

```
gaagtgcagc tggtggagtc tgggggaggc ttagtgaagc ctggagggtc cctgagactc    60
tcctgcgcag cctctggatt cactttcagt acctatacca tgtcttgggt tcgccaagca    120
ccgggcaagg gactggagtg gtctctacc attagtccag agacagtttt cggctactac    180
tatccagaca gtgtgcaggg ccgattcacc atctccagag acaatgccaa gaacagtctg    240
tacctgcaaa tgaacagtct gagggcagag gacacagccg tgtattactg tgcccgagat    300
atttactata attacggagc ctggtttgct tactggggcc aagggactct ggtcactgtc    360
tctagc                                                               366
```

<210> SEQ ID NO 48
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 48

```
gacgtccagc tggtggagtc tgggggaggc ttagtgaagc ctggagggtc cctgagactc 60
tcctgcgcag cctctggatt cactttcagt acctatacca tgtcttgggt tcgccaagca 120
ccgggcaagg gactggagtg ggtcgcaacc attagtccag gagacagttt cggctactac 180
```

```
tatccagaca gtgtccaggg ccgattcacc atctccagag acaatgccaa gaacagtctg 240
tacctgcaaa tgaacagtct gagggcagag gacacagccg tgtattactg tacccgagat 300
atttactata attacggagc ctggtttgct tactggggcc aagggactct ggtcactgtc 360
tctagc 366
```

<210> SEQ ID NO 49
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 49

```
Asp Val Gln Leu Val Gln Ser Gly Gly Gly Leu Val Lys Pro Gly Gly
1 5 10 15

Ser Leu Arg Leu Ser Cys Ala Ala Ser Gly Phe Thr Phe Ser Thr Tyr
20 25 30

Thr Met Ser Trp Val Arg Gln Ala Pro Gly Lys Gly Leu Glu Trp Val
35 40 45

Ala Thr Ile Ser Pro Gly Asp Ser Phe Gly Tyr Tyr Tyr Pro Asp Ser
50 55 60

Val Gln Gly Arg Phe Thr Ile Ser Arg Asp Asn Ala Lys Asn Ser Leu
65 70 75 80

Tyr Leu Gln Met Asn Arg Leu Arg Ala Glu Asp Thr Ala Val Tyr Tyr
85 90 95

Cys Thr Arg Asp Ile Tyr Tyr Asn Tyr Gly Ala Trp Phe Ala Tyr Trp
100 105 110

Gly Arg Gly Thr Leu Val Thr Val Ser Ser
115 120
```

<210> SEQ ID NO 50
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 50

```
gacgtccagc tggtgcagtc tgggggaggc ttagtgaagc ctggagggtc cctgagactc 60
tcctgcgcag cctctggatt cactttcagt acctatacca tgtcttgggt tcgccaagca 120
ccgggcaagg gactggagtg ggtcgcaacc attagtccag gagacagttt cggctactac 180
tatccagaca gtgtccaggg ccgattcacc atctccagag acaatgccaa gaacagtctg 240
tacctgcaaa tgaacaggct gagggcagag gacacagccg tgtattactg tacccgagat 300
atttactata attacggagc ctggtttgct tactggggca gagggactct ggtcactgtc 360
tctagc 366
```

<210> SEQ ID NO 51

<400> SEQUENCE: 51

000

<210> SEQ ID NO 52
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Asp Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Val Arg Gln Ala Pro Gly Lys Gly Leu Glu Trp Val
        35                  40                  45

Ala Thr Ile Ser Gly Gly Asn Asn Tyr Gly Tyr Ser Tyr Pro Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Thr Arg Asp Ile Tyr Tyr Asn Tyr Gly Ala Trp Phe Ala Tyr Trp
            100                 105                 110

Gly Gln Gly Thr Leu Val Thr Val Ser Ser
        115                 120

<210> SEQ ID NO 53
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
gacgtccagc tggtggagtc tgggggaggc ttagtgaagc ctggagggtc cctgagactc      60
tcctgcgcag cctctggatt cactttcagt acctatacca tgtcttgggt tcgccaagca     120
ccgggcaagg gactggagtg gtcgcaacc attagtggcg aaataacta cggctactcc       180 tatccagaca gtgtcaaggg ccgattcacc atctctagag acaatgccaa gaacagtctg     240
tacctgcaaa tgaactccct gagggcagag gacacagccg tgtattactg tacccgagat     300
atttactata attacggagc ctggtttgct tactggggcc aggggactct ggtcactgtc     360
tctagc                                                                366

<210> SEQ ID NO 54
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Thr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Arg Thr Phe Gly Gln Gly Thr Lys Val Glu Ile Lys
            100                 105                 110

<210> SEQ ID NO 55
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
gctattcagc tgacccaatc tccatcctct ttgtccgcct ctgtggggga cagggtcacc      60
atcacctgca aggccagcca aagtgttgat tatgatggtg atagttatat gaactggtat     120
caacagaaac cagggaaggc tcccaaactc ctcatctacg ctgcatccac tctcgagtct     180
ggggtcccat ccaggtttag tggcagtggg tctgggacag acttcaccct cacaatcagc     240
tcactccagc cagaggattt cgcaacctat tactgtcagc aaagcaacga ggatcctcgg     300
acgttcggtc agggcaccaa gtggaaatc aag                                    333

<210> SEQ ID NO 56
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Thr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Arg Thr Phe Gly Gln Gly Thr Lys Val Glu Ile Lys

<210> SEQ ID NO 57
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

```
gacattcagc tgacccaatc tccatcctct ttgtccgcct ctgtggggga cagggtcacc      60
atcacctgca aggccagcca agtgttgat tatgatggtg atagttatat gaactggtat     120
caacagaaac cagggaaggc tcccaaactc ctcatctacg ctgcatccac tctcgagtct    180
ggggtcccat ccaggtttag tggcagtggg tctgggacag acttcaccct cacaatcagc    240
tcactccagc cagaggattt cgcaacctat tactgtcagc aaagcaacga ggatcctcgg    300
acgttcggtc agggcaccaa agtggaaatc aag                                 333
```

<210> SEQ ID NO 58
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

```
Asp Ile Gln Leu Thr Gln Ser Pro Ser Ser Leu Ser Val Ser Val Gly
1               5                   10                  15
Asp Arg Ala Thr Ile Ser Cys Lys Ala Ser Gln Ser Val Asp Tyr Asp
            20                  25                  30
Gly Asp Ser Tyr Met Asn Trp Tyr Gln Gln Lys Pro Gly Lys Ala Pro
        35                  40                  45
Lys Leu Leu Ile Tyr Ala Ala Ser Thr Leu Glu Ser Gly Val Pro Ser
    50                  55                  60
Arg Phe Ser Gly Ser Gly Ser Gly Thr Asp Phe Thr Leu Thr Ile Ser
65                  70                  75                  80
Ser Val Gln Pro Glu Asp Phe Ala Thr Tyr Tyr Cys Gln Gln Ser Asn
                85                  90                  95
Glu Asp Pro Arg Thr Phe Gly Gln Gly Thr Lys Val Glu Ile Lys
            100                 105                 110
```

<210> SEQ ID NO 59
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59

```
gacattcagc tgacccaatc tccatcctct ttgtccgtct ctgtggggga cagggcaacc      60
atctcctgca aggccagcca agtgttgat tatgatggtg atagttatat gaactggtat     120
caacagaaac cagggaaggc tcccaaactc ctcatctacg ctgcatccac tcttgagtct    180
ggggtcccat ccaggtttag tggcagtggg tctgggacag acttcaccct cacaatcagc    240
```

```
tcagtgcagc cagaggattt cgcaacctat tactgtcagc aaagcaacga ggatcctcgg    300
acgttcggtc agggcaccaa agtggaaatc aag                                 333
```

<210> SEQ ID NO 60
<211> LENGTH: 723
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(720)

<400> SEQUENCE: 60

```
atg gac atg agg gtc ccc gct cag ctc ctg ggg ctc ctt ctg ctc tgg     48
Met Asp Met Arg Val Pro Ala Gln Leu Leu Gly Leu Leu Leu Leu Trp
1               5                  10                  15 ctc cct gga gca cga tgt gac att cag ctg acc caa tct cca tcc tct     96
Leu Pro Gly Ala Arg Cys Asp Ile Gln Leu Thr Gln Ser Pro Ser Ser
            20                  25                  30 ttg tcc gcc tct gtg ggg gac agg gtc acc atc acc tgc aag gcc agc    144
Leu Ser Ala Ser Val Gly Asp Arg Val Thr Ile Thr Cys Lys Ala Ser
        35                  40                  45 caa agt gtt gat tat gat ggt gat agt tat atg aac tgg tat caa cag    192
Gln Ser Val Asp Tyr Asp Gly Asp Ser Tyr Met Asn Trp Tyr Gln Gln
    50                  55                  60 aaa cca ggg aag gct ccc aaa ctc ctc atc tac gct gca tcc act ctc    240
Lys Pro Gly Lys Ala Pro Lys Leu Leu Ile Tyr Ala Ala Ser Thr Leu
65                  70                  75                  80 gag tct ggg gtc cca tcc agg ttt agt ggc agt ggg tct ggg aca gac    288
Glu Ser Gly Val Pro Ser Arg Phe Ser Gly Ser Gly Ser Gly Thr Asp
                85                  90                  95 ttc acc ctc aca atc agc tca ctc cag cca gag gat ttc gca acc tat    336
Phe Thr Leu Thr Ile Ser Ser Leu Gln Pro Glu Asp Phe Ala Thr Tyr
            100                 105                 110 tac tgt caa caa gcc aac gaa gat cct cgg acc ttc ggt cag ggc acc    384
Tyr Cys Gln Gln Ala Asn Glu Asp Pro Arg Thr Phe Gly Gln Gly Thr
        115                 120                 125 aaa gtg gaa atc aag cgg acc gtg gct gca cca tct gtc ttc atc ttc    432
Lys Val Glu Ile Lys Arg Thr Val Ala Ala Pro Ser Val Phe Ile Phe
    130                 135                 140 cct cca tct gat gag cag ttg aaa tct gga act gcc tct gtt gtg tgc    480
Pro Pro Ser Asp Glu Gln Leu Lys Ser Gly Thr Ala Ser Val Val Cys
145                 150                 155                 160 ctg ctg aat aac ttc tat ccc aga gag gcc aaa gtg cag tgg aag gtg    528
Leu Leu Asn Asn Phe Tyr Pro Arg Glu Ala Lys Val Gln Trp Lys Val
                165                 170                 175 gat aac gcc ctc caa tct ggc aac tcc cag gag agt gtc aca gag cag    576
Asp Asn Ala Leu Gln Ser Gly Asn Ser Gln Glu Ser Val Thr Glu Gln
            180                 185                 190 gac agc aag gac agc acc tac agc ctc agc agc acc ctg acc ctg agc    624
Asp Ser Lys Asp Ser Thr Tyr Ser Leu Ser Ser Thr Leu Thr Leu Ser
        195                 200                 205 aaa gca gac tac gag aaa cac aaa gtc tac gcc tgc gaa gtc acc cat    672
Lys Ala Asp Tyr Glu Lys His Lys Val Tyr Ala Cys Glu Val Thr His
    210                 215                 220 cag ggc ctg agc tct ccc gtc aca aag agc ttc aac agg gga gag tgt    720
Gln Gly Leu Ser Ser Pro Val Thr Lys Ser Phe Asn Arg Gly Glu Cys
225                 230                 235                 240
```

-continued

```
tga                                                                        723
```

<210> SEQ ID NO 61
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

```
Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Ser
            20                  25                  30

Leu Ser Ala Ser Val Gly Asp Arg Val Thr Ile Thr Cys Lys Ala Ser
        35                  40                  45

Gln Ser Val Asp Tyr Asp Gly Asp Ser Tyr Met Asn Trp Tyr Gln Gln
    50                  55                  60

Lys Pro Gly Lys Ala Pro Lys Leu Leu Ile Tyr Ala Ala Ser Thr Leu
65                  70                  75                  80

Glu Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ala Asn Glu Asp Pro Arg Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 62
<211> LENGTH: 1413
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(1410)

<400> SEQUENCE: 62

```
atg ggt tgg agc ctc atc ttg ctc ttc ctt gtc gct gtt gct acc cgg    48
Met Gly Trp Ser Leu Ile Leu Leu Phe Leu Val Ala Val Ala Thr Arg
1               5                   10                  15 gtc ctg tcc gac gtc cag ctg gtg gag tct ggg gga ggc ctg gtg aag    96
```

```
                Val Leu Ser Asp Val Gln Leu Val Glu Ser Gly Gly Gly Leu Val Lys
                             20                  25                  30 cct gga ggg tcc ctg aga ctc tcc tgc gca gcc tct gga ttc act ttc        144
Pro Gly Gly Ser Leu Arg Leu Ser Cys Ala Ala Ser Gly Phe Thr Phe
             35                  40                  45 agt acc tat acc atg tct tgg gtt cgc caa gca cct ggc aag gga ctg        192
Ser Thr Tyr Thr Met Ser Trp Val Arg Gln Ala Pro Gly Lys Gly Leu
 50                  55                  60 gag tgg gtc gca acc att agt cca gga gac agt ttc ggc tac tac tat        240
Glu Trp Val Ala Thr Ile Ser Pro Gly Asp Ser Phe Gly Tyr Tyr Tyr
 65                  70                  75                  80 cca gac agt gtc cag ggc cga ttc acc atc tcc aga gac aat gcc aag        288
Pro Asp Ser Val Gln Gly Arg Phe Thr Ile Ser Arg Asp Asn Ala Lys
                 85                  90                  95 aac agt ctg tac ctg caa atg aac agt ctg agg gca gag gac aca gcc        336
Asn Ser Leu Tyr Leu Gln Met Asn Ser Leu Arg Ala Glu Asp Thr Ala
            100                 105                 110 gtg tat tac tgt acc cga gat att tac tat aat tac gga gcc tgg ttt        384
Val Tyr Tyr Cys Thr Arg Asp Ile Tyr Tyr Asn Tyr Gly Ala Trp Phe
            115                 120                 125 gct tac tgg ggc caa ggg act ctg gtc act gtc tct agc gct tcc acc        432
Ala Tyr Trp Gly Gln Gly Thr Leu Val Thr Val Ser Ser Ala Ser Thr
130                 135                 140 aag ggc cca tcc gtc ttc ccc ctg gca ccc tcc tcc aag agc acc tct        480
Lys Gly Pro Ser Val Phe Pro Leu Ala Pro Ser Ser Lys Ser Thr Ser
145                 150                 155                 160 ggg ggc aca gct gcc ctg ggc tgc ctg gtc aag gac tac ttc ccc gaa        528
Gly Gly Thr Ala Ala Leu Gly Cys Leu Val Lys Asp Tyr Phe Pro Glu
                165                 170                 175 ccc gtg acc gtg tcc tgg aac tca ggc gcc ctg acc agc ggc gtg cac        576
Pro Val Thr Val Ser Trp Asn Ser Gly Ala Leu Thr Ser Gly Val His
            180                 185                 190 acc ttc ccc gct gtc ctg caa tcc tca gga ctc tac tcc ctc tcc agc        624
Thr Phe Pro Ala Val Leu Gln Ser Ser Gly Leu Tyr Ser Leu Ser Ser
            195                 200                 205 gtg gtg acc gtg ccc tcc agc agc ttg ggc acc cag acc tac atc tgc        672
Val Val Thr Val Pro Ser Ser Ser Leu Gly Thr Gln Thr Tyr Ile Cys
        210                 215                 220 aac gtg aat cac aag ccc agc aac acc aag gtg gac aag aaa gtt gag        720
Asn Val Asn His Lys Pro Ser Asn Thr Lys Val Asp Lys Lys Val Glu
225                 230                 235                 240 ccc aaa tct tgt gac aag act cac aca tgc cca cct tgc cca gca cct        768
Pro Lys Ser Cys Asp Lys Thr His Thr Cys Pro Pro Cys Pro Ala Pro
                245                 250                 255 gaa ctc ctg ggg gga cct tca gtc ttc ctc ttc ccc cca aaa ccc aag        816
Glu Leu Leu Gly Gly Pro Ser Val Phe Leu Phe Pro Pro Lys Pro Lys
            260                 265                 270 gac acc ctc atg atc tcc cgg acc cct gag gtc aca tgc gtg gtg gtg        864
Asp Thr Leu Met Ile Ser Arg Thr Pro Glu Val Thr Cys Val Val Val
            275                 280                 285 gac gtg agc cac gaa gac cct gag gtc aag ttc aac tgg tat gtt gac        912
Asp Val Ser His Glu Asp Pro Glu Val Lys Phe Asn Trp Tyr Val Asp
        290                 295                 300 ggc gtg gag gtg cat aat gcc aag aca aag cct cgg gag gag cag tac        960
Gly Val Glu Val His Asn Ala Lys Thr Lys Pro Arg Glu Glu Gln Tyr
305                 310                 315                 320 aac agc acc tac cgg gtg gtc agc gtc ctc acc gtc ctg cac caa gac       1008
Asn Ser Thr Tyr Arg Val Val Ser Val Leu Thr Val Leu His Gln Asp
                325                 330                 335
```

```
tgg ctg aat ggc aag gag tac aag tgc aag gtc tcc aac aaa gcc ctc    1056
Trp Leu Asn Gly Lys Glu Tyr Lys Cys Lys Val Ser Asn Lys Ala Leu
            340             345             350 cca gcc ccc atc gag aaa acc atc tcc aaa gcc aaa ggg cag ccc cga    1104
Pro Ala Pro Ile Glu Lys Thr Ile Ser Lys Ala Lys Gly Gln Pro Arg
            355             360             365 gaa cca cag gtg tac acc ctg ccc cca tcc cgg gat gag ctg acc aag    1152
Glu Pro Gln Val Tyr Thr Leu Pro Pro Ser Arg Asp Glu Leu Thr Lys
            370             375             380 aac caa gtc agc ctg acc tgc ctg gtc aaa ggc ttc tat ccc agc gac    1200
Asn Gln Val Ser Leu Thr Cys Leu Val Lys Gly Phe Tyr Pro Ser Asp
385             390             395             400 atc gcc gtg gag tgg gag agc aat ggg cag cct gag aac aac tac aag    1248
Ile Ala Val Glu Trp Glu Ser Asn Gly Gln Pro Glu Asn Asn Tyr Lys
            405             410             415 acc aca cct ccc gtg ttg gac tcc gac ggc tcc ttc ttc ctc tac tcc    1296
Thr Thr Pro Pro Val Leu Asp Ser Asp Gly Ser Phe Phe Leu Tyr Ser
            420             425             430 aag ctc acc gtg gac aag agc agg tgg cag cag ggg aac gtc ttc tca    1344
Lys Leu Thr Val Asp Lys Ser Arg Trp Gln Gln Gly Asn Val Phe Ser
            435             440             445 tgc tcc gtg atg cat gag gct ctg cac aac cac tac acc cag aag agc    1392
Cys Ser Val Met His Glu Ala Leu His Asn His Tyr Thr Gln Lys Ser
450             455             460 ctc tcc ctg tct ccc ggt tga                                        1413
Leu Ser Leu Ser Pro Gly
465             470

<210> SEQ ID NO 63
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Met Gly Trp Ser Leu Ile Leu Leu Phe Leu Val Ala Val Ala Thr Arg
1               5                   10                  15

Val Leu Ser Asp Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Thr Tyr Thr Met Ser Trp Val Arg Gln Ala Pro Gly Lys Gly Leu
    50                  55                  60

Glu Trp Val Ala Thr Ile Ser Pro Gly Asp Ser Phe Gly Tyr Tyr Tyr
65                  70                  75                  80

Pro Asp Ser Val Gln Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Thr Arg Asp Ile Tyr Tyr Asn Tyr Gly Ala Trp Phe
        115                 120                 125

Ala Tyr Trp Gly Gln Gly Thr Leu Val Thr Val Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
```

```
                 165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val Asp
                290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
                355                 360                 365

Glu Pro Gln Val Tyr Thr Leu Pro Pro Ser Arg Asp Glu Leu Thr Lys
                370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly
465                 470

<210> SEQ ID NO 64
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Ser
                20                  25                  30

Leu Ser Ala Ser Val Gly Asp Arg Val Thr Ile Thr Cys Lys Ala Ser
                35                  40                  45
```

Gln Ser Val Asp Tyr Asp Gly Asp Ser Tyr Met Asn Trp Tyr Gln Gln
            50                  55                  60

Lys Pro Gly Lys Ala Pro Lys Leu Leu Ile Tyr Ala Ala Ser Thr Leu
65                  70                  75                  80

Glu Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ala Asn Glu Asp Pro Arg Thr Phe Gly Gln Gly Thr
            115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240

<210> SEQ ID NO 65
<211> LENGTH: 267
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
            100                 105                 110

Ala Glu Lys Val Ser Ile Met Ala Asp Ala Met Arg Arg Leu His Thr
            115                 120                 125

Leu Asp Pro Ala Thr Cys Pro Phe Asp His Gln Ala Lys His Arg Ile
        130                 135                 140

Glu Arg Ala Arg Thr Arg Met Glu Ala Gly Leu Val Asp Gln Asp Asp
145                 150                 155                 160

```
Leu Asp Glu Glu His Gln Gly Leu Ala Pro Ala Glu Leu Phe Ala Arg
                165                 170                 175

Leu Lys Ala Arg Met Pro Asp Gly Asp Leu Val Val Thr His Gly
            180                 185                 190

Asp Ala Cys Leu Pro Asn Ile Met Val Glu Asn Gly Arg Phe Ser Gly
            195                 200                 205

Phe Ile Asp Cys Gly Arg Leu Gly Val Ala Asp Arg Tyr Gln Asp Ile
        210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                245                 250                 255

Ile Ala Phe Tyr Arg Leu Leu Asp Glu Phe Phe
                260                 265

<210> SEQ ID NO 66
<211> LENGTH: 286
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
```

245                  250                      255
Val Val Ile Tyr Thr Thr Gly Ser Gln Ala Thr Met Asp Glu Arg Asn
            260                  265                      270

Arg Gln Ile Ala Glu Ile Gly Ala Ser Leu Ile Lys His Trp
        275                  280                  285

<210> SEQ ID NO 67
<211> LENGTH: 6927
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1263)..(1982)
<220> FEATURE:
<221> NAME/KEY: CDS
<222> LOCATION: (3142)..(3942)
<220> FEATURE:
<221> NAME/KEY: CDS
<222> LOCATION: (4890)..(5747)

<400> SEQUENCE: 67

| | |
|---|---:|
| ttgacattga ttattgacta gttattaata gtaatcaatt acggggtcat tagttcatag | 60 |
| cccatatatg gagttccgcg ttacataact tacggtaaat ggcccgcctg gctgaccgcc | 120 |
| caacgacccc cgcccattga cgtcaataat gacgtatgtt cccatagtaa cgccaatagg | 180 |
| gactttccat tgacgtcaat gggtggagta tttacggtaa actgcccact tggcagtaca | 240 |
| tcaagtgtat catatgccaa gtacgccccc tattgacgtc aatgacggta aatggcccgc | 300 |
| ctggcattat gcccagtaca tgaccttatg ggactttcct acttggcagt acatctacgt | 360 |
| attagtcatc gctattacca tggtgatgcg gttttggcag tacatcaatg ggcgtggata | 420 |
| gcggtttgac tcacggggat ttccaagtct ccaccccatt gacgtcaatg ggagtttgtt | 480 |
| ttggcaccaa aatcaacggg actttccaaa atgtcgtaac aactccgccc cattgacgca | 540 |
| aatgggcggt aggcgtgtac ggtgggaggt ctatataagc agagctcgtt tagtgaaccg | 600 |
| tcagatcgcc tggagacgcc atccacgctg ttttgacctc catagaagac accgggaccg | 660 |
| atccagcctc cgcggccggg aacggtgcat tggaacgcgg attccccgtg ccaagagtga | 720 |
| cgtaagtacc gcctatagag tctataggcc caccccttg gcttcttatg catgctatac | 780 |
| tgtttttggc ttggggtcta tacacccccg cttcctcatg ttataggtga tggtatagct | 840 |
| tagcctatag gtgtgggtta ttgaccatta ttgaccactc ccctattggt gacgatactt | 900 |
| tccattacta atccataaca tggctctttg ccacaactct ctttattggc tatatgccaa | 960 |
| tacactgtcc ttcagagact gacacggact ctgtatttt acaggatggg gtctcattta | 1020 |
| ttatttacaa attcacatat acaacaccac cgtccccagt gcccgcagtt tttattaaac | 1080 |
| ataacgtggg atctccacgc gaatctcggg tacgtgttcc ggaacggtgg agggcagtgt | 1140 |
| agtctgagca gtactcgttg ctgccgcgcg cgccaccaga cataatagct gacagactaa | 1200 |
| cagactgttc ctttccatgg gtcttttctg cagtcaccgt ccttgacacg ggatccgcca | 1260 |

| | | | | | | | | | | | | | | | | |
|---|---|---|---|---|---|---|---|---|---|---|---|---|---|---|---|---:|
| cc | atg | gac | atg | agg | gtc | ccc | gct | cag | ctc | ctg | ggg | ctc | ctt | ctg | ctc | 1307 |
|   | Met | Asp | Met | Arg | Val | Pro | Ala | Gln | Leu | Leu | Gly | Leu | Leu | Leu | Leu |   |
|   | 1   |     |     |     | 5   |     |     |     |     | 10  |     |     |     |     | 15  |   |

| | | | | | | | | | | | | | | | |
|---|---|---|---|---|---|---|---|---|---|---|---|---|---|---|---:|
| tgg | ctc | cct | gga | gca | cga | tgt | gac | att | cag | ctg | acc | caa | tct | cca | tcc | 1355 |
| Trp | Leu | Pro | Gly | Ala | Arg | Cys | Asp | Ile | Gln | Leu | Thr | Gln | Ser | Pro | Ser |   |
|     |     | 20  |     |     |     |     | 25  |     |     |     |     | 30  |     |     |     |   |

|  |  |
|---|---|
| tct ttg tcc gcc tct gtg ggg gac agg gtc acc atc acc tgc aag gcc<br>Ser Leu Ser Ala Ser Val Gly Asp Arg Val Thr Ile Thr Cys Lys Ala<br>              35                    40                    45 | 1403 |
| agc caa agt gtt gat tat gat ggt gat agt tat atg aac tgg tat caa<br>Ser Gln Ser Val Asp Tyr Asp Gly Asp Ser Tyr Met Asn Trp Tyr Gln<br>      50                    55                    60 | 1451 |
| cag aaa cca ggg aag gct ccc aaa ctc ctc atc tac gct gca tcc act<br>Gln Lys Pro Gly Lys Ala Pro Lys Leu Leu Ile Tyr Ala Ala Ser Thr<br>65                    70                    75 | 1499 |
| ctc gag tct ggg gtc cca tcc agg ttt agt ggc agt ggg tct ggg aca<br>Leu Glu Ser Gly Val Pro Ser Arg Phe Ser Gly Ser Gly Ser Gly Thr<br>80                85                    90                    95 | 1547 |
| gac ttc acc ctc aca atc agc tca ctc cag cca gag gat ttc gca acc<br>Asp Phe Thr Leu Thr Ile Ser Ser Leu Gln Pro Glu Asp Phe Ala Thr<br>                  100                  105              110 | 1595 |
| tat tac tgt caa caa gcc aac gaa gat cct cgg acc ttc ggt cag ggc<br>Tyr Tyr Cys Gln Gln Ala Asn Glu Asp Pro Arg Thr Phe Gly Gln Gly<br>            115                  120                  125 | 1643 |
| acc aaa gtg gaa atc aag cgg acc gtg gct gca cca tct gtc ttc atc<br>Thr Lys Val Glu Ile Lys Arg Thr Val Ala Ala Pro Ser Val Phe Ile<br>          130                  135                  140 | 1691 |
| ttc cct cca tct gat gag cag ttg aaa tct gga act gcc tct gtt gtg<br>Phe Pro Pro Ser Asp Glu Gln Leu Lys Ser Gly Thr Ala Ser Val Val<br>145                    150                  155 | 1739 |
| tgc ctg ctg aat aac ttc tat ccc aga gag gcc aaa gtg cag tgg aag<br>Cys Leu Leu Asn Asn Phe Tyr Pro Arg Glu Ala Lys Val Gln Trp Lys<br>160                    165                  170                  175 | 1787 |
| gtg gat aac gcc ctc caa tct ggc aac tcc cag gag agt gtc aca gag<br>Val Asp Asn Ala Leu Gln Ser Gly Asn Ser Gln Glu Ser Val Thr Glu<br>                  180                  185              190 | 1835 |
| cag gac agc aag gac agc acc tac agc ctc agc agc acc ctg acc ctg<br>Gln Asp Ser Lys Asp Ser Thr Tyr Ser Leu Ser Ser Thr Leu Thr Leu<br>            195                  200                  205 | 1883 |
| agc aaa gca gac tac gag aaa cac aaa gtc tac gcc tgc gaa gtc acc<br>Ser Lys Ala Asp Tyr Glu Lys His Lys Val Tyr Ala Cys Glu Val Thr<br>          210                  215                  220 | 1931 |
| cat cag ggc ctg agc tct ccc gtc aca aag agc ttc aac agg gga gag<br>His Gln Gly Leu Ser Ser Pro Val Thr Lys Ser Phe Asn Arg Gly Glu<br>          225                  230                  235 | 1979 |
| tgt tgaggatccc tgcccgggtg catccctgt gacccctccc cagtgcctct<br>Cys<br>240 | 2032 |
| cctggtcgtg gaaggtgcta ctccagtgcc caccagcctt gtcctaataa aattaagttg | 2092 |
| catcattttg tttgactagg tgtccttgta taatattatg gggtggaggc gggtggtatg | 2152 |
| gagcaagggg caggttggga agacaacctg tagggccttc agggtctatt gggaaccagg | 2212 |
| ctggagtgca gtggcacgat cttggctcgc tgcaatctcc gcctcctggg ttcaagcgat | 2272 |
| tctcctgcct cagtctcccg aatagttggg attccaggca tgcacgacca ggctcagcta | 2332 |
| atttttgtat ttttggtaga dacggggttt caccatattg gccagtctgg tctccatctc | 2392 |
| ctgacctcag gtaatccgcc cgcctcggcc tcccaaattg ctgggattac aggtatgagc | 2452 |
| cactgggccc ttccctgtcc tgtgatttta aaataattat accagcagaa ggacgtccag | 2512 |
| acacagcatg gctacctgg ccatgcccag ccagttggac atttgagttg tttgcttggc | 2572 |
| actgtcctct catgaattcc tgcaggattc gagggcccct gcaggtcaat tctaccgggt | 2632 |
| aggggaggcg cttttcccaa ggcagtctgg agcatgcgct ttagcagccc cgctgggcac | 2692 |
| ttggcgctac acaagtggcc tctggcctcg cacacattcc acatccaccg gtaggcgcca | 2752 |

```
accggctccg ttctttggtg gccccttcgc gccaccttct actcctcccc tagtcaggaa    2812 gttcccccc gccccgcagc tcgcgtcgtg caggacgtga caaatggaag tagcacgtct     2872
cactagtctc gtgcagatgg acagcaccgc tgagcaatgg aagcgggtag gcctttgggg    2932
cagcggccaa tagcagcttt gctccttcgc tttctgggct cagaggctgg aaggggtgg     2992 gtccggggc gggctcaggg gcgggctcag gggcggggcg ggcgcccgaa ggtcctccgg     3052
aggcccggca ttctgcacgc ttcaaaagcg cacgtctgcc gcgctgttct cctcttcctc    3112
atctccgggc ctttcgacct gcagccaat atg gga tcg gcc att gaa caa gat      3165
                                  Met Gly Ser Ala Ile Glu Gln Asp
                                                245 gga ttg cac gca ggt tct ccg gcc gct tgg gtg gag agg cta ttc ggc      3213
Gly Leu His Ala Gly Ser Pro Ala Ala Trp Val Glu Arg Leu Phe Gly
    250             255                 260 tat gac tgg gca caa cag aca atc ggc tgc tct gat gcc gcc gtg ttc      3261
Tyr Asp Trp Ala Gln Gln Thr Ile Gly Cys Ser Asp Ala Ala Val Phe
265             270                 275                 280 cgg ctg tca gcg cag ggg cgc ccg gtt ctt ttt gtc aag acc gac ctg      3309
Arg Leu Ser Ala Gln Gly Arg Pro Val Leu Phe Val Lys Thr Asp Leu
                285                 290                 295 tcc ggt gcc ctg aat gaa ctg cag gac gag gca gcg cgg cta tcg tgg      3357
Ser Gly Ala Leu Asn Glu Leu Gln Asp Glu Ala Ala Arg Leu Ser Trp
        300                 305                 310 ctg gcc acg acg ggc gtt cct tgc gca gct gtg ctc gac gtt gtc act      3405
Leu Ala Thr Thr Gly Val Pro Cys Ala Ala Val Leu Asp Val Val Thr
            315                 320                 325 gaa gcg gga agg gac tgg ctg cta ttg ggc gaa gtg ccg ggg cag gat      3453
Glu Ala Gly Arg Asp Trp Leu Leu Leu Gly Glu Val Pro Gly Gln Asp
                330                 335                 340 ctc ctg tca tct cac ctt gct cct gcc gag aaa gta tcc atc atg gct      3501
Leu Leu Ser Ser His Leu Ala Pro Ala Glu Lys Val Ser Ile Met Ala
345                 350                 355                 360 gat gca atg cgg cgg ctg cat acg ctt gat ccg gct acc tgc cca ttc      3549
Asp Ala Met Arg Arg Leu His Thr Leu Asp Pro Ala Thr Cys Pro Phe
                365                 370                 375 gac cac caa gcg aaa cat cgc atc gag cga gca cgt act cgg atg gaa      3597
Asp His Gln Ala Lys His Arg Ile Glu Arg Ala Arg Thr Arg Met Glu
            380                 385                 390 gcc ggt ctt gtc gat cag gat gat ctg gac gaa gag cat cag ggg ctc      3645
Ala Gly Leu Val Asp Gln Asp Asp Leu Asp Glu Glu His Gln Gly Leu
                395                 400                 405 gcg cca gcc gaa ctg ttc gcc agg ctc aag gcg cgc atg ccc gac ggc      3693
Ala Pro Ala Glu Leu Phe Ala Arg Leu Lys Ala Arg Met Pro Asp Gly
    410                 415                 420 gat gat ctc gtc gtg acc cat ggc gat gcc tgc ttg ccg aat atc atg      3741
Asp Asp Leu Val Val Thr His Gly Asp Ala Cys Leu Pro Asn Ile Met
425                 430                 435                 440 gtg gaa aat ggc cgc ttt tct gga ttc atc gac tgt ggc cgg ctg ggt      3789
Val Glu Asn Gly Arg Phe Ser Gly Phe Ile Asp Cys Gly Arg Leu Gly
                445                 450                 455 gtg gcg gac cgc tat cag gac ata gcg ttg gct acc cgt gat att gct      3837
Val Ala Asp Arg Tyr Gln Asp Ile Ala Leu Ala Thr Arg Asp Ile Ala
                460                 465                 470 gaa gag ctt ggc ggc gaa tgg gct gac cgc ttc ctc gtg ctt tac ggt      3885
Glu Glu Leu Gly Gly Glu Trp Ala Asp Arg Phe Leu Val Leu Tyr Gly
                475                 480                 485 atc gcc gct ccc gat tcg cag cgc atc gcc ttc tat cgc ctt ctt gac      3933
Ile Ala Ala Pro Asp Ser Gln Arg Ile Ala Phe Tyr Arg Leu Leu Asp
```

```
                 490              495              500
gag ttc ttc tgaggggatc gatccgctgt aagtctgcag aaattgatga       3982
Glu Phe Phe
505 tctattaaac aataaagatg tccactaaaa tggaagtttt tcctgtcata ctttgttaag   4042 aagggtgaga acagagtacc tacatttga atggaaggat tggagctacg ggggtggggg   4102 tggggtggga ttagataaat gcctgctctt tactgaaggc tctttactat tgctttatga   4162 taatgtttca tagttggata tcataattta aacaagcaaa accaaattaa gggccagctc   4222 attcctccca ctcatgatct atagatctat agatctctcg tgggatcatt gttttctct   4282 tgattcccac tttgtggttc taagtactgt ggtttccaaa tgtgtcagtt tcatagcctg   4342 aagaacgaga tcagcagcct ctgttccaca tacacttcat tctcagtatt gttttgccaa   4402 gttctaattc catcagaagc tgactctaga tctggatcga tgaattcggc gcctgatgcg   4462 gtatttctc cttacgcatc tgtgcggtat tcacaccgc atatggtgca ctctcagtac   4522 aatctgctct gatgccgcat agttaagcca gccccgacac ccgccaacac ccgctgacgc   4582 gccctgacgg gcttgtctgc tcccggcatc cgcttacaga caagctgtga ccgtctccgg   4642 gagctgcatg tgtcagaggt tttcaccgtc atcaccgaaa cgcgcgagac gaaagggcct   4702 cgtgatacgc ctattttat aggttaatgt catgataata atggtttctt agacgtcagg   4762 tggcactttt cggggaaatg tgcgcggaac ccctatttgt ttattttct aaatacattc   4822 aaatatgtat ccgctcatga gacaataacc ctgataaatg cttcaataat attgaaaaag   4882 gaagagt atg agt att caa cat ttc cgt gtc gcc ctt att ccc ttt ttt   4931
        Met Ser Ile Gln His Phe Arg Val Ala Leu Ile Pro Phe Phe
            510              515              520 gcg gca ttt tgc ctt cct gtt ttt gct cac cca gaa acg ctg gtg aaa   4979
Ala Ala Phe Cys Leu Pro Val Phe Ala His Pro Glu Thr Leu Val Lys
            525              530              535 gta aaa gat gct gaa gat cag ttg ggt gca cga gtg ggt tac atc gaa   5027
Val Lys Asp Ala Glu Asp Gln Leu Gly Ala Arg Val Gly Tyr Ile Glu
        540              545              550 ctg gat ctc aac agc ggt aag atc ctt gag agt ttt cgc ccc gaa gaa   5075
Leu Asp Leu Asn Ser Gly Lys Ile Leu Glu Ser Phe Arg Pro Glu Glu
    555              560              565 cgt ttt cca atg atg agc act ttt aaa gtt ctg cta tgt ggc gcg gta   5123
Arg Phe Pro Met Met Ser Thr Phe Lys Val Leu Leu Cys Gly Ala Val
570              575              580              585 tta tcc cgt att gac gcc ggg caa gag caa ctc ggt cgc cgc ata cac   5171
Leu Ser Arg Ile Asp Ala Gly Gln Glu Gln Leu Gly Arg Arg Ile His
            590              595              600 tat tct cag aat gac ttg gtt gag tac tca cca gtc aca gaa aag cat   5219
Tyr Ser Gln Asn Asp Leu Val Glu Tyr Ser Pro Val Thr Glu Lys His
            605              610              615 ctt acg gat ggc atg aca gta aga gaa tta tgc agt gct gcc ata acc   5267
Leu Thr Asp Gly Met Thr Val Arg Glu Leu Cys Ser Ala Ala Ile Thr
        620              625              630 atg agt gat aac act gcg gcc aac tta ctt ctg aca acg atc gga gga   5315
Met Ser Asp Asn Thr Ala Ala Asn Leu Leu Leu Thr Thr Ile Gly Gly
    635              640              645 ccg aag gag cta acc gct ttt ttg cac aac atg ggg gat cat gta act   5363
Pro Lys Glu Leu Thr Ala Phe Leu His Asn Met Gly Asp His Val Thr
650              655              660              665 cgc ctt gat cgt tgg gaa ccg gag ctg aat gaa gcc ata cca aac gac   5411
Arg Leu Asp Arg Trp Glu Pro Glu Leu Asn Glu Ala Ile Pro Asn Asp
            670              675              680
```

-continued

| | | |
|---|---|---|
| gag cgt gac acc acg atg cct gta gca atg gca aca acg ttg cgc aaa<br>Glu Arg Asp Thr Thr Met Pro Val Ala Met Ala Thr Thr Leu Arg Lys<br>685              690                695 | 5459 |
| cta tta act ggc gaa cta ctt act cta gct tcc cgg caa caa tta ata<br>Leu Leu Thr Gly Glu Leu Leu Thr Leu Ala Ser Arg Gln Gln Leu Ile<br>700              705                710 | 5507 |
| gac tgg atg gag gcg gat aaa gtt gca gga cca ctt ctg cgc tcg gcc<br>Asp Trp Met Glu Ala Asp Lys Val Ala Gly Pro Leu Leu Arg Ser Ala<br>715              720                725 | 5555 |
| ctt ccg gct ggc tgg ttt att gct gat aaa tct gga gcc ggt gag cgt<br>Leu Pro Ala Gly Trp Phe Ile Ala Asp Lys Ser Gly Ala Gly Glu Arg<br>730              735                740                745 | 5603 |
| ggg tct cgc ggt atc att gca gca ctg ggg cca gat ggt aag ccc tcc<br>Gly Ser Arg Gly Ile Ile Ala Ala Leu Gly Pro Asp Gly Lys Pro Ser<br>750              755                760 | 5651 |
| cgt atc gta gtt atc tac acg acg ggg agt cag gca act atg gat gaa<br>Arg Ile Val Val Ile Tyr Thr Thr Gly Ser Gln Ala Thr Met Asp Glu<br>765              770                775 | 5699 |
| cga aat aga cag atc gct gag ata ggt gcc tca ctg att aag cat tgg<br>Arg Asn Arg Gln Ile Ala Glu Ile Gly Ala Ser Leu Ile Lys His Trp<br>780              785                790 | 5747 |
| taactgtcag accaagttta ctcatatata ctttagattg atttaaaact tcattttttaa | 5807 |
| tttaaaagga tctaggtgaa gatcctttttt gataatctca tgaccaaaat cccttaacgt | 5867 |
| gagttttcgt tccactgagc gtcagacccc gtagaaaaga tcaaaggatc ttcttgagat | 5927 |
| ccttttttttc tgcgcgtaat ctgctgcttg caaacaaaaa aaccaccgct accagcggtg | 5987 |
| gtttgtttgc cggatcaaga gctaccaact ctttttccga aggtaactgg cttcagcaga | 6047 |
| gcgcagatac caaatactgt tcttctagtg tagccgtagt taggccacca cttcaagaac | 6107 |
| tctgtagcac cgcctacata cctcgctctg ctaatcctgt taccagtggc tgctgccagt | 6167 |
| ggcgataagt cgtgtcttac cgggttggac tcaagacgat agttaccgga taaggcgcag | 6227 |
| cggtcgggct gaacggggggg ttcgtgcaca cagcccagct tggagcgaac gacctacacc | 6287 |
| gaactgagat acctacagcg tgagctatga gaaagcgcca cgcttcccga agggagaaag | 6347 |
| gcggacaggt atccggtaag cggcagggtc ggaacaggag agcgcacgag ggagcttcca | 6407 |
| gggggaaacg cctggtatct ttatagtcct gtcgggtttc gccacctctg acttgagcgt | 6467 |
| cgatttttgt gatgctcgtc aggggggcgg agcctatgga aaaacgccag caacgcggcc | 6527 |
| ttttttacggt tcctggcctt ttgctggcct tttgctcaca tgttctttcc tgcgttatcc | 6587 |
| cctgattctg tggataaccg tattaccgcc tttgagtgag ctgataccgc tcgccgcagc | 6647 |
| cgaacgaccg agcgcagcga gtcagtgagc gaggaagcgg aagagcgccc aatacgcaaa | 6707 |
| ccgcctctcc ccgcgcgttg gccgattcat taatgcagct ggcacgacag gtttcccgac | 6767 |
| tggaaagcgg gcagtgagcg caacgcaatt aatgtgagtt agctcactca ttaggcaccc | 6827 |
| caggctttac actttatgct tccggctcgt atgttgtgtg gaattgtgag cggataacaa | 6887 |
| tttcacacag gaaacagcta tgaccatgat tacgccaagc | 6927 |

<210> SEQ ID NO 68
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 68

```
Met Gly Trp Ser Leu Ile Leu Leu Phe Leu Val Ala Val Ala Thr Arg
1               5                   10                  15

Val Leu Ser Asp Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Thr Tyr Thr Met Ser Trp Val Arg Gln Ala Pro Gly Lys Gly Leu
    50                  55                  60

Glu Trp Val Ala Thr Ile Ser Pro Gly Asp Ser Phe Gly Tyr Tyr Tyr
65                  70                  75                  80

Pro Asp Ser Val Gln Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Thr Arg Asp Ile Tyr Tyr Asn Tyr Gly Ala Trp Phe
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

```
Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
    450                 455                 460

Leu Ser Leu Ser Pro Gly
465             470

<210> SEQ ID NO 69
<211> LENGTH: 187
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

<210> SEQ ID NO 70
<211> LENGTH: 286
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30
```

```
Asp Ala Glu Asp Gln Leu Gly Ala Arg Val Gly Tyr Ile Glu Leu Asp
             35                  40                  45

Leu Asn Ser Gly Lys Ile Leu Glu Ser Phe Arg Pro Glu Glu Arg Phe
 50                  55                  60

Pro Met Met Ser Thr Phe Lys Val Leu Leu Cys Gly Ala Val Leu Ser
 65                  70                  75                  80

Arg Ile Asp Ala Gly Gln Glu Gln Leu Gly Arg Arg Ile His Tyr Ser
                 85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
            115                 120                 125

Asp Asn Thr Ala Ala Asn Leu Leu Leu Thr Thr Ile Gly Gly Pro Lys
130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
            195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
            275                 280                 285

<210> SEQ ID NO 71
<211> LENGTH: 7480
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1263)..(2672)
<220> FEATURE:
<221> NAME/KEY: CDS
<222> LOCATION: (3977)..(4537)
<220> FEATURE:
<221> NAME/KEY: CDS
<222> LOCATION: (5443)..(6300)

<400> SEQUENCE: 71
ttgacattga ttattgacta gttattaata gtaatcaatt acggggtcat tagttcatag      60
cccatatatg gagttccgcg ttacataact tacggtaaat ggcccgcctg gctgaccgcc     120
caacgacccc cgcccattga cgtcaataat gacgtatgtt cccatagtaa cgccaatagg     180
gactttccat tgacgtcaat gggtggagta tttacggtaa actgcccact tggcagtaca     240
tcaagtgtat catatgccaa gtacgccccc tattgacgtc aatgacggta aatggcccgc     300
```

```
ctggcattat gcccagtaca tgaccttatg ggactttcct acttggcagt acatctacgt    360
attagtcatc gctattacca tggtgatgcg gttttggcag tacatcaatg ggcgtggata    420
gcggtttgac tcacggggat tccaagtct ccaccccatt gacgtcaatg ggagtttgtt     480
ttggcaccaa aatcaacggg actttccaaa atgtcgtaac aactccgccc cattgacgca    540
aatgggcggt aggcgtgtac ggtgggaggt ctatataagc agagctcgtt tagtgaaccg    600
tcagatcgcc tggagacgcc atccacgctg ttttgacctc catagaagac accgggaccg    660
atccagcctc cgcggccggg aacggtgcat tggaacgcgg attccccgtg ccaagagtga    720
cgtaagtacc gcctatagag tctataggcc caccccttg gcttcttatg catgctatac     780 tgttttttggc ttggggtcta tacccccccg cttcctcatg ttataggtga tggtatagct    840
tagcctatag gtgtgggtta ttgaccatta ttgaccactc ccctattggt gacgatactt    900
tccattacta atccataaca tggctctttg ccacaactct ctttattggc tatatgccaa    960
tacactgtcc ttcagagact gacacggact ctgtattttt acaggatggg gtctcattta   1020
ttatttacaa attcacatat acaacaccac cgtccccagt gcccgcagtt tttattaaac   1080
ataacgtggg atctccacgc gaatctcggg tacgtgttcc ggaacggtgg agggcagtgt   1140
agtctgagca gtactcgttg ctgccgcgcg cgccaccaga cataaatagct gacagactaa   1200 cagactgttc ctttccatgg gtcttttctg cagtcaccgt ccttgacacg ggatccgcca   1260
```

```
cc atg ggt tgg agc ctc atc ttg ctc ttc ctt gtc gct gtt gct acc        1307
   Met Gly Trp Ser Leu Ile Leu Leu Phe Leu Val Ala Val Ala Thr
   1               5                  10                  15 cgg gtc ctg tcc gac gtc cag ctg gtg gag tct ggg gga ggc ctg gtg      1355
Arg Val Leu Ser Asp Val Gln Leu Val Glu Ser Gly Gly Gly Leu Val
                20                  25                  30 aag cct gga ggg tcc ctg aga ctc tcc tgc gca gcc tct gga ttc act      1403
Lys Pro Gly Gly Ser Leu Arg Leu Ser Cys Ala Ala Ser Gly Phe Thr
            35                  40                  45 ttc agt acc tat acc atg tct tgg gtt cgc caa gca cct ggc aag gga      1451
Phe Ser Thr Tyr Thr Met Ser Trp Val Arg Gln Ala Pro Gly Lys Gly
        50                  55                  60 ctg gag tgg gtc gca acc att agt cca gga gac agt ttc ggc tac tac      1499
Leu Glu Trp Val Ala Thr Ile Ser Pro Gly Asp Ser Phe Gly Tyr Tyr
    65                  70                  75 tat cca gac agt gtc cag ggc cga ttc acc atc tcc aga gac aat gcc      1547
Tyr Pro Asp Ser Val Gln Gly Arg Phe Thr Ile Ser Arg Asp Asn Ala
80                  85                  90                  95 aag aac agt ctg tac ctg caa atg aac agt ctg agg gca gag gac aca      1595
Lys Asn Ser Leu Tyr Leu Gln Met Asn Ser Leu Arg Ala Glu Asp Thr
                100                 105                 110 gcc gtg tat tac tgt acc cga gat att tac tat aat tac gga gcc tgg      1643
Ala Val Tyr Tyr Cys Thr Arg Asp Ile Tyr Tyr Asn Tyr Gly Ala Trp
            115                 120                 125 ttt gct tac tgg ggc caa ggg act ctg gtc act gtc tct agc gct tcc      1691
Phe Ala Tyr Trp Gly Gln Gly Thr Leu Val Thr Val Ser Ser Ala Ser
        130                 135                 140 acc aag ggc cca tcc gtc ttc ccc ctg gca ccc tcc tcc aag agc acc      1739
Thr Lys Gly Pro Ser Val Phe Pro Leu Ala Pro Ser Ser Lys Ser Thr
    145                 150                 155 tct ggg ggc aca gct gcc ctg ggc tgc ctg gtc aag gac tac ttc ccc      1787
Ser Gly Gly Thr Ala Ala Leu Gly Cys Leu Val Lys Asp Tyr Phe Pro
160                 165                 170                 175 gaa ccc gtg acc gtg tcc tgg aac tca ggc gcc ctg acc agc ggc gtg      1835
Glu Pro Val Thr Val Ser Trp Asn Ser Gly Ala Leu Thr Ser Gly Val
                180                 185                 190
```

```
cac acc ttc ccc gct gtc ctg caa tcc tca gga ctc tac tcc ctc tcc    1883
His Thr Phe Pro Ala Val Leu Gln Ser Ser Gly Leu Tyr Ser Leu Ser
            195                 200                 205 agc gtg gtg acc gtg ccc tcc agc agc ttg ggc acc cag acc tac atc    1931
Ser Val Val Thr Val Pro Ser Ser Ser Leu Gly Thr Gln Thr Tyr Ile
        210                 215                 220 tgc aac gtg aat cac aag ccc agc aac acc aag gtg gac aag aaa gtt    1979
Cys Asn Val Asn His Lys Pro Ser Asn Thr Lys Val Asp Lys Lys Val
    225                 230                 235 gag ccc aaa tct tgt gac aag act cac aca tgc cca cct tgc cca gca    2027
Glu Pro Lys Ser Cys Asp Lys Thr His Thr Cys Pro Pro Cys Pro Ala
240                 245                 250                 255 cct gaa ctc ctg ggg gga cct tca gtc ttc ctc ttc ccc cca aaa ccc    2075
Pro Glu Leu Leu Gly Gly Pro Ser Val Phe Leu Phe Pro Pro Lys Pro
                260                 265                 270 aag gac acc ctc atg atc tcc cgg acc cct gag gtc aca tgc gtg gtg    2123
Lys Asp Thr Leu Met Ile Ser Arg Thr Pro Glu Val Thr Cys Val Val
            275                 280                 285 gtg gac gtg agc cac gaa gac cct gag gtc aag ttc aac tgg tat gtt    2171
Val Asp Val Ser His Glu Asp Pro Glu Val Lys Phe Asn Trp Tyr Val
        290                 295                 300 gac ggc gtg gag gtc cat aat gcc aag aca aag cct cgg gag gag cag    2219
Asp Gly Val Glu Val His Asn Ala Lys Thr Lys Pro Arg Glu Glu Gln
    305                 310                 315 tac aac agc acc tac cgg gtg gtc agc gtc ctc acc gtc ctg cac caa    2267
Tyr Asn Ser Thr Tyr Arg Val Val Ser Val Leu Thr Val Leu His Gln
320                 325                 330                 335 gac tgg ctg aat ggc aag gag tac aag tgc aag gtc tcc aac aaa gcc    2315
Asp Trp Leu Asn Gly Lys Glu Tyr Lys Cys Lys Val Ser Asn Lys Ala
                340                 345                 350 ctc cca gcc ccc atc gag aaa acc atc tcc aaa gcc aaa ggg cag ccc    2363
Leu Pro Ala Pro Ile Glu Lys Thr Ile Ser Lys Ala Lys Gly Gln Pro
            355                 360                 365 cga gaa cca cag gtg tac acc ctg ccc cca tcc cgg gat gag ctg acc    2411
Arg Glu Pro Gln Val Tyr Thr Leu Pro Pro Ser Arg Asp Glu Leu Thr
        370                 375                 380 aag aac caa gtc agc ctg acc tgc ctg gtc aaa ggc ttc tat ccc agc    2459
Lys Asn Gln Val Ser Leu Thr Cys Leu Val Lys Gly Phe Tyr Pro Ser
    385                 390                 395 gac atc gcc gtg gag tgg gag agc aat ggg cag cct gag aac aac tac    2507
Asp Ile Ala Val Glu Trp Glu Ser Asn Gly Gln Pro Glu Asn Asn Tyr
400                 405                 410                 415 aag acc aca cct ccc gtg ttg gac tcc gac ggc tcc ttc ttc ctc tac    2555
Lys Thr Thr Pro Pro Val Leu Asp Ser Asp Gly Ser Phe Phe Leu Tyr
                420                 425                 430 tcc aag ctc acc gtg gac aag agc agg tgg cag cag ggg aac gtc ttc    2603
Ser Lys Leu Thr Val Asp Lys Ser Arg Trp Gln Gln Gly Asn Val Phe
            435                 440                 445 tca tgc tcc gtg atg cat gag gct ctg cac aac cac tac acc cag aag    2651
Ser Cys Ser Val Met His Glu Ala Leu His Asn His Tyr Thr Gln Lys
        450                 455                 460 agc ctc tcc ctg tct ccc ggt tgaggatccc tgcccgggtg gcatccctgt       2702
Ser Leu Ser Leu Ser Pro Gly
    465                 470 gacccctccc cagtgcctct cctggtcgtg gaaggtgcta ctccagtgcc caccagcctt  2762
gtcctaataa aattaagttg catcattttg tttgactagg tgtccttgta ataatattatg 2822 gggtggaggc gggtggtatg gagcaagggg caggttggga agacaacctg tagggccttc  2882
```

```
agggtctatt gggaaccagg ctggagtgca gtggcacgat cttggctcgc tgcaatctcc    2942
gcctcctggg ttcaagcgat tctcctgcct cagtctcccg aatagttggg attccaggca    3002
tgcacgacca ggctcagcta atttttgtat ttttggtaga gacggggttt caccatattg    3062
gccagtctgg tctccatctc ctgacctcag gtaatccgcc cgcctcggcc tcccaaattg    3122
ctgggattac aggtatgagc cactgggccc ttccctgtcc tgtgatttta aaataattat    3182
accagcagaa ggacgtccag acacagcatg ggctacctgg ccatgcccag ccagttggac    3242
atttgagttg tttgcttggc actgtcctct catgaattcg tcgacagatc tgcgcagcac    3302
catggcctga ataacctct gaaagaggaa cttggttagg taccttctga ggcggaaaga    3362
accagctgtg aatgtgtgt cagttagggt gtggaaagtc cccaggctcc ccagcaggca    3422
gaagtatgca aagcatgcat ctcaattagt cagcaaccag gtgtggaaag tccccaggct    3482
ccccagcagg cagaagtatg caaagcatgc atctcaatta gtcagcaacc atagtcccgc    3542
ccctaactcc gcccatcccg ccctaactc cgcccagttc cgcccattct ccgccccatg    3602
gctgactaat tttttttatt tatgcagagg ccgaggccgc ctcggcctct gagctattcc    3662
agaagtagtg aggaggcttt tttggaggcc taggcttttg caaaaagctt gattcttctg    3722
acacaacagt ctcgaactta agctgcagaa gttggtcgtg aggcactggg caggtaagta    3782
tcaaggttac aagacaggtt taaggagacc aatagaaact gggcttgtcg agacagagaa    3842
gactcttgcg tttctgatag gcacctattg gtcttactga catccacttt gcctttctct    3902
ccacaggtgt ccactcccag ttcaattaca gctcttaagg ctagagtact aatacgact    3962 cactataggc tagc atg gtt cga cca ttg aac tgc atc gtc gcc gtg tcc     4012
            Met Val Arg Pro Leu Asn Cys Ile Val Ala Val Ser
                                 475                 480 caa aat atg ggg att ggc aag aac gga gac cta ccc tgg cct ccg ctc     4060
Gln Asn Met Gly Ile Gly Lys Asn Gly Asp Leu Pro Trp Pro Pro Leu
            485                 490                 495 agg aac gag ttc aag tac ttc caa aga atg acc aca acc tct tca gtg    4108
Arg Asn Glu Phe Lys Tyr Phe Gln Arg Met Thr Thr Thr Ser Ser Val
500                 505                 510 gaa ggt aaa cag aat ctg gtg att atg ggt agg aaa acc tgg ttc tcc    4156
Glu Gly Lys Gln Asn Leu Val Ile Met Gly Arg Lys Thr Trp Phe Ser
515                 520                 525                 530 att cct gag aag aat cga cct tta aag gac aga att aat ata gtt ctc    4204
Ile Pro Glu Lys Asn Arg Pro Leu Lys Asp Arg Ile Asn Ile Val Leu
            535                 540                 545 agt aga gaa ctc aaa gaa cca cca cga gga gct cat ttt ctt gcc aaa    4252
Ser Arg Glu Leu Lys Glu Pro Pro Arg Gly Ala His Phe Leu Ala Lys
            550                 555                 560 agt ttg gat gat gcc tta aga ctt att gaa caa ccg gaa ttg gca agt    4300
Ser Leu Asp Asp Ala Leu Arg Leu Ile Glu Gln Pro Glu Leu Ala Ser
            565                 570                 575 aaa gta gac atg gtt tgg ata gtc gga ggc agt tct gtt tac cag gaa    4348
Lys Val Asp Met Val Trp Ile Val Gly Gly Ser Ser Val Tyr Gln Glu
            580                 585                 590 gcc atg aat caa cca ggc cac ctc aga ctc ttt gtg aca agg atc atg    4396
Ala Met Asn Gln Pro Gly His Leu Arg Leu Phe Val Thr Arg Ile Met
595                 600                 605                 610 cag gaa ttt gaa agt gac acg ttt ttc cca gaa att gat ttg ggg aaa    4444
Gln Glu Phe Glu Ser Asp Thr Phe Phe Pro Glu Ile Asp Leu Gly Lys
                615                 620                 625 tat aaa ctt ctc cca gaa tac cca ggc gtc ctc tct gag gtc cag gag    4492
Tyr Lys Leu Leu Pro Glu Tyr Pro Gly Val Leu Ser Glu Val Gln Glu
            630                 635                 640
```

```
gaa aaa ggc atc aag tat aag ttt gaa gtc tac gag aag aaa gac        4537
Glu Lys Gly Ile Lys Tyr Lys Phe Glu Val Tyr Glu Lys Lys Asp
        645                 650                 655 taactcgaga attcacgcgt ggtacctcta gagtcgaccc gggcggccgg ccgcttcgag   4597
cagacatgat aagatacatt gatgagtttg acaaaccac aactagaatg cagtgaaaaa    4657
aatgctttat ttgtgaaatt tgtgatgcta ttgctttatt tgtaaccatt ataagctgca   4717
ataaacaagt taacaacaac aattgcattc attttatgtt tcaggttcag gggaggtgt    4777 gggaggtttt ttaaagcaag taaaacctct acaaatgtgg taaaatcgat aaggatctgt   4837
cgacgaattc actggccgtc gttttacaac gtcgtgactg ggaaaaccct ggcgttaccc   4897
aacttaatcg ccttgcagca catccccctt tcgccagctg gcgtaatagc gaagaggccc   4957
gcaccgatcg cccttcccaa cagttgcgca gcctgaatgg cgaatggcgc ctgatgcggt   5017
attttctcct tacgcatctg tgcggtattt cacaccgcat atggtgcact ctcagtacaa   5077
tctgctctga tgccgcatag ttaagccagc cccgacaccc gccaacaccc gctgacgcgc   5137
cctgacgggc ttgtctgctc ccggcatccg cttacagaca agctgtgacc gtctccggga   5197
gctgcatgtg tcagaggttt tcaccgtcat caccgaaacg cgcgagacga agggcctcg    5257 tgatacgcct attttatag gttaatgtca tgataataat ggtttcttag acgtcaggtg    5317
gcacttttcg gggaaatgtg cgcggaaccc ctatttgttt attttctaa atacattcaa    5377 atatgtatcc gctcatgaga caataaccct gataaatgct tcaataatat tgaaaaagga   5437 agagt atg agt att caa cat ttc cgt gtc gcc ctt att ccc ttt ttt gcg  5487
      Met Ser Ile Gln His Phe Arg Val Ala Leu Ile Pro Phe Phe Ala
          660                 665                 670 gca ttt tgc ctt cct gtt ttt gct cac cca gaa acg ctg gtg aaa gta    5535
Ala Phe Cys Leu Pro Val Phe Ala His Pro Glu Thr Leu Val Lys Val
        675                 680                 685 aaa gat gct gaa gat cag ttg ggt gca cga gtg ggt tac atc gaa ctg    5583
Lys Asp Ala Glu Asp Gln Leu Gly Ala Arg Val Gly Tyr Ile Glu Leu
        690                 695                 700 gat ctc aac agc ggt aag atc ctt gag agt ttt cgc ccc gaa gaa cgt    5631
Asp Leu Asn Ser Gly Lys Ile Leu Glu Ser Phe Arg Pro Glu Glu Arg
705                 710                 715                 720 ttt cca atg atg agc act ttt aaa gtt ctg cta tgt ggc gcg gta tta    5679
Phe Pro Met Met Ser Thr Phe Lys Val Leu Leu Cys Gly Ala Val Leu
                725                 730                 735 tcc cgt att gac gcc ggg caa gag caa ctc ggt cgc cgc ata cac tat    5727
Ser Arg Ile Asp Ala Gly Gln Glu Gln Leu Gly Arg Arg Ile His Tyr
            740                 745                 750 tct cag aat gac ttg gtt gag tac tca cca gtc aca gaa aag cat ctt    5775
Ser Gln Asn Asp Leu Val Glu Tyr Ser Pro Val Thr Glu Lys His Leu
        755                 760                 765 acg gat ggc atg aca gta aga gaa tta tgc agt gct gcc ata acc atg    5823
Thr Asp Gly Met Thr Val Arg Glu Leu Cys Ser Ala Ala Ile Thr Met
        770                 775                 780 agt gat aac act gcg gcc aac tta ctt ctg aca acg atc gga gga ccg    5871
Ser Asp Asn Thr Ala Ala Asn Leu Leu Leu Thr Thr Ile Gly Gly Pro
785                 790                 795                 800 aag gag cta acc gct ttt ttg cac aac atg ggg gat cat gta act cgc    5919
Lys Glu Leu Thr Ala Phe Leu His Asn Met Gly Asp His Val Thr Arg
                805                 810                 815 ctt gat cgt tgg gaa ccg gag ctg aat gaa gcc ata cca aac gac gag    5967
Leu Asp Arg Trp Glu Pro Glu Leu Asn Glu Ala Ile Pro Asn Asp Glu
            820                 825                 830
```

| | | | | | | | | | | | | | | | | |
|---|---|---|---|---|---|---|---|---|---|---|---|---|---|---|---|---|
| cgt | gac | acc | acg | atg | cct | gta | gca | atg | gca | aca | acg | ttg | cgc | aaa | cta | 6015 |
| Arg | Asp | Thr | Thr | Met | Pro | Val | Ala | Met | Ala | Thr | Thr | Leu | Arg | Lys | Leu | |
| | | 835 | | | | 840 | | | | | 845 | | | | | |
| tta | act | ggc | gaa | cta | ctt | act | cta | gct | tcc | cgg | caa | caa | tta | ata | gac | 6063 |
| Leu | Thr | Gly | Glu | Leu | Leu | Thr | Leu | Ala | Ser | Arg | Gln | Gln | Leu | Ile | Asp | |
| | 850 | | | | | 855 | | | | | 860 | | | | | |
| tgg | atg | gag | gcg | gat | aaa | gtt | gca | gga | cca | ctt | ctg | cgc | tcg | gcc | ctt | 6111 |
| Trp | Met | Glu | Ala | Asp | Lys | Val | Ala | Gly | Pro | Leu | Leu | Arg | Ser | Ala | Leu | |
| 865 | | | | | 870 | | | | | 875 | | | | | 880 | |
| ccg | gct | ggc | tgg | ttt | att | gct | gat | aaa | tct | gga | gcc | ggt | gag | cgt | ggg | 6159 |
| Pro | Ala | Gly | Trp | Phe | Ile | Ala | Asp | Lys | Ser | Gly | Ala | Gly | Glu | Arg | Gly | |
| | | | | 885 | | | | | 890 | | | | | 895 | | |
| tct | cgc | ggt | atc | att | gca | gca | ctg | ggg | cca | gat | ggt | aag | ccc | tcc | cgt | 6207 |
| Ser | Arg | Gly | Ile | Ile | Ala | Ala | Leu | Gly | Pro | Asp | Gly | Lys | Pro | Ser | Arg | |
| | | 900 | | | | | 905 | | | | | 910 | | | | |
| atc | gta | gtt | atc | tac | acg | acg | ggg | agt | cag | gca | act | atg | gat | gaa | cga | 6255 |
| Ile | Val | Val | Ile | Tyr | Thr | Thr | Gly | Ser | Gln | Ala | Thr | Met | Asp | Glu | Arg | |
| | 915 | | | | | 920 | | | | | 925 | | | | | |
| aat | aga | cag | atc | gct | gag | ata | ggt | gcc | tca | ctg | att | aag | cat | tgg | | 6300 |
| Asn | Arg | Gln | Ile | Ala | Glu | Ile | Gly | Ala | Ser | Leu | Ile | Lys | His | Trp | | |
| 930 | | | | | 935 | | | | | 940 | | | | | | |

```
taactgtcag accaagttta ctcatatata ctttagattg atttaaaact tcattttaa    6360
tttaaaagga tctaggtgaa gatccttttt gataatctca tgaccaaaat cccttaacgt    6420
gagttttcgt tccactgagc gtcagacccc gtagaaaaga tcaaaggatc ttcttgagat    6480
cctttttttc tgcgcgtaat ctgctgcttg caaacaaaaa aaccaccgct accagcggtg    6540
gtttgtttgc cggatcaaga gctaccaact cttttccga aggtaactgg cttcagcaga    6600
gcgcagatac caaatactgt tcttctagtg tagccgtagt taggccacca cttcaagaac    6660
tctgtagcac cgcctacata cctcgctctg ctaatcctgt taccagtggc tgctgccagt    6720
ggcgataagt cgtgtcttac cgggttggac tcaagacgat agttaccgga taaggcgcag    6780
cggtcgggct gaacggggggg ttcgtgcaca gcccagct tggagcgaac gacctacacc    6840
gaactgagat acctacagcg tgagctatga aaagcgcca cgcttccga agggagaaag    6900
gcggacaggt atccggtaag cggcagggtc ggaacaggag agcgcacgag ggagcttcca    6960
gggggaaacg cctggtatct ttatagtcct gtcgggtttc gccacctctg acttgagcgt    7020
cgatttttgt gatgctcgtc agggggggcgg agcctatgga aaaacgccag caacgcggcc    7080
tttttacggt tcctggcctt ttgctggcct tttgctcaca tgttctttcc tgcgttatcc    7140
cctgattctg tggataaccg tattaccgcc tttgagtgag ctgataccgc tcgccgcagc    7200
cgaacgaccg agcgcagcga gtcagtgagc gaggaagcgg aagagcgccc aatacgcaaa    7260
ccgcctctcc ccgcgcgttg gccgattcat taatgcagct ggcacgacag gtttcccgac    7320
tggaaagcgg gcagtgagcg caacgcaatt aatgtgagtt agctcactca ttaggcaccc    7380
caggctttac actttatgct tccggctcgt atgttgtgtg gaattgtgag cggataacaa    7440
tttcacacag gaaacagcta tgaccatgat tacgccaagc                           7480
```

<210> SEQ ID NO 72
<211> LENGTH: 212
<212> TYPE: PRT
<213> ORGANISM: Macaca mulatta

<400> SEQUENCE: 72

```
Met Val Pro Glu Glu Glu Pro Gln Asp Arg Glu Lys Gly Val Trp Trp
1               5                   10                  15
```

Phe Gln Leu Lys Val Trp Ser Val Ala Val Ser Ile Leu Leu Leu
                20                  25                  30

Cys Val Cys Phe Thr Val Ser Ser Val Ala Ser His Asn Phe Met Tyr
                35                  40                  45

Ser Lys Thr Val Lys Arg Leu Ser Lys Leu Gln Glu Tyr Gln Gln Tyr
 50                  55                  60

Tyr Pro Ser Leu Thr Cys Val Met Glu Gly Lys Asp Met Glu Asp Trp
 65                  70                  75                  80

Ser Cys Cys Pro Thr Pro Trp Thr Ser Phe Gln Ser Ser Cys Tyr Phe
                85                  90                  95

Ile Ser Thr Val Met Gln Ser Trp Thr Lys Ser Gln Asn Asn Cys Ser
                100                 105                 110

Val Met Gly Ala Asp Leu Val Val Ile Asn Thr Lys Glu Glu Gln Asp
                115                 120                 125

Phe Ile Thr Gln Asn Leu Lys Ile Asn Ser Ala Tyr Phe Leu Gly Leu
                130                 135                 140

Ser Asp Pro Lys Gly Trp Arg His Trp Gln Trp Val Asp Gln Thr Pro
145                 150                 155                 160

Tyr Asn Lys Asn Val Thr Phe Trp His Ser Gly Glu Pro Asn Ser Pro
                165                 170                 175

Asp Glu Arg Cys Ala Ile Ile Asn Phe Arg Ser Glu Glu Trp Gly Trp
                180                 185                 190

Asn Asp Val His Cys His Val Pro Gln Lys Ser Ile Cys Lys Met Lys
                195                 200                 205

Lys Ile Tyr Ile
    210

<210> SEQ ID NO 73
<211> LENGTH: 86
<212> TYPE: PRT
<213> ORGANISM: Macaca fascicularis

<400> SEQUENCE: 73

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
                20                  25                  30

Phe Leu Tyr Gly Ile Val Leu Thr Leu Leu Tyr Cys Arg Leu Lys Ile
                35                  40                  45

Gln Val Arg Lys Ala Ala Ile Ala Ser Tyr Glu Lys Ser Asp Gly Val
 50                  55                  60

Tyr Thr Gly Leu Ser Thr Arg Asn Gln Glu Thr Tyr Glu Thr Leu Lys
 65                  70                  75                  80

His Glu Lys Pro Pro Gln
                85

<210> SEQ ID NO 74
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
cagtgtctgt tcactcccg ggggtggcgg tggtagcaat tttatgtata gc            52

<210> SEQ ID NO 75
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 75
ccagggagaa taggatcctt atatgtagat ctt        33

<210> SEQ ID NO 76
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

```
Met Lys Leu Pro Val Arg Leu Leu Val Leu Met Phe Trp Ile Pro Ala
1               5                   10                  15

Ser Ser Ser Glu Pro Lys Ser Ser Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Gly Gly Gly Ser Asn
                245                 250                 255

Phe Met Tyr Ser Lys Thr Val Lys Arg Leu Ser Lys Leu Arg Glu Tyr
            260                 265                 270

Gln Gln Tyr His Pro Ser Leu Thr Cys Val Met Glu Gly Lys Asp Ile
        275                 280                 285
```

Glu Asp Trp Ser Cys Cys Pro Thr Pro Trp Thr Ser Phe Gln Ser Ser
            290                 295                 300

Cys Tyr Phe Ile Ser Thr Gly Met Gln Ser Trp Thr Lys Ser Gln Lys
305                 310                 315                 320

Asn Cys Ser Val Met Gly Ala Asp Leu Val Val Ile Asn Thr Arg Glu
                325                 330                 335

Glu Gln Asp Phe Ile Ile Gln Asn Leu Lys Arg Asn Ser Ser Tyr Phe
                340                 345                 350

Leu Gly Leu Ser Asp Pro Gly Gly Arg Arg His Trp Gln Trp Val Asp
            355                 360                 365

Gln Thr Pro Tyr Asn Glu Asn Val Thr Phe Trp His Ser Gly Glu Pro
            370                 375                 380

Asn Asn Leu Asp Glu Arg Cys Ala Ile Ile Asn Phe Arg Ser Ser Glu
385                 390                 395                 400

Glu Trp Gly Trp Asn Asp Ile His Cys His Val Pro Gln Lys Ser Ile
                405                 410                 415

Cys Lys Met Lys Lys Ile Tyr Ile
            420

<210> SEQ ID NO 77
<211> LENGTH: 425
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Met Lys Leu Pro Val Arg Leu Leu Val Leu Met Phe Trp Ile Pro Ala
1               5                   10                  15

Ser Ser Ser Glu Pro Arg Gly Pro Thr Ile Lys Pro Ser Pro Pro Cys
                20                  25                  30

Lys Cys Pro Ala Pro Asn Leu Leu Gly Gly Pro Ser Val Phe Ile Phe
            35                  40                  45

Pro Pro Lys Ile Lys Asp Val Leu Met Ile Ser Leu Ser Pro Ile Val
        50                  55                  60

Thr Cys Val Val Asp Val Ser Glu Asp Asp Pro Asp Val Gln Ile
65                  70                  75                  80

Ser Trp Phe Val Asn Asn Val Glu Val His Thr Ala Gln Thr Gln Thr
                85                  90                  95

His Arg Glu Asp Tyr Asn Ser Thr Leu Arg Val Val Ser Ala Leu Pro
            100                 105                 110

Ile Gln His Gln Asp Trp Met Ser Gly Lys Glu Phe Lys Cys Lys Val
        115                 120                 125

Asn Asn Lys Asp Leu Pro Ala Pro Ile Glu Arg Thr Ile Ser Lys Pro
130                 135                 140

Lys Gly Ser Val Arg Ala Pro Gln Val Tyr Val Leu Pro Pro Pro Glu
145                 150                 155                 160

Glu Glu Met Thr Lys Lys Gln Val Thr Leu Thr Cys Met Val Thr Asp
                165                 170                 175

Phe Met Pro Glu Asp Ile Tyr Val Glu Trp Thr Asn Asn Gly Lys Thr
            180                 185                 190

Glu Leu Asn Tyr Lys Asn Thr Glu Pro Val Leu Asp Ser Asp Gly Ser
        195                 200                 205

-continued

```
Tyr Phe Met Tyr Ser Lys Leu Arg Val Glu Lys Lys Asn Trp Val Glu
            210                 215                 220

Arg Asn Ser Tyr Ser Cys Ser Val Val His Glu Gly Leu His Asn His
225                 230                 235                 240

His Thr Thr Lys Ser Phe Ser Arg Thr Pro Gly Gly Gly Gly Gly Ser
                245                 250                 255

Asn Phe Met Tyr Ser Lys Thr Val Lys Arg Leu Ser Lys Leu Arg Glu
            260                 265                 270

Tyr Gln Gln Tyr His Pro Ser Leu Thr Cys Val Met Glu Gly Lys Asp
                275                 280                 285

Ile Glu Asp Trp Ser Cys Cys Pro Thr Pro Trp Thr Ser Phe Gln Ser
290                 295                 300

Ser Cys Tyr Phe Ile Ser Thr Gly Met Gln Ser Trp Thr Lys Ser Gln
305                 310                 315                 320

Lys Asn Cys Ser Val Met Gly Ala Asp Leu Val Ile Asn Thr Arg
                325                 330                 335

Glu Glu Gln Asp Phe Ile Ile Gln Asn Leu Lys Arg Asn Ser Ser Tyr
                340                 345                 350

Phe Leu Gly Leu Ser Asp Pro Gly Gly Arg Arg His Trp Gln Trp Val
                355                 360                 365

Asp Gln Thr Pro Tyr Asn Glu Asn Val Thr Phe Trp His Ser Gly Glu
            370                 375                 380

Pro Asn Asn Leu Asp Glu Arg Cys Ala Ile Ile Asn Phe Arg Ser Ser
385                 390                 395                 400

Glu Glu Trp Gly Trp Asn Asp Ile His Cys His Val Pro Gln Lys Ser
                405                 410                 415

Ile Cys Lys Met Lys Lys Ile Tyr Ile
                420                 425
```

<210> SEQ ID NO 78
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 78
ctctgtgtct gtttcactcc cgggggtggc ggtggtagca attttatgta tagc         54

<210> SEQ ID NO 79
<211> LENGTH: 424
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 79

```
Met Lys Leu Pro Val Arg Leu Leu Val Leu Met Phe Trp Ile Pro Ala
1               5                   10                  15

Ser Ser Ser Glu Pro Arg Gly Pro Thr Ile Lys Pro Ser Pro Pro Cys
            20                  25                  30

Lys Cys Pro Ala Pro Asn Leu Leu Gly Gly Pro Ser Val Phe Ile Phe
        35                  40                  45

Pro Pro Lys Ile Lys Asp Val Leu Met Ile Ser Leu Ser Pro Ile Val
    50                  55                  60
```

Thr Cys Val Val Asp Val Ser Glu Asp Pro Asp Val Gln Ile
65                  70                  75                  80

Ser Trp Phe Val Asn Asn Val Glu Val His Thr Ala Gln Thr Gln Thr
                85                  90                  95

His Arg Glu Asp Tyr Asn Ser Thr Leu Arg Val Ser Ala Leu Pro
            100                 105                 110

Ile Gln His Gln Asp Trp Met Ser Gly Lys Glu Phe Lys Cys Lys Val
            115                 120                 125

Asn Asn Lys Asp Leu Pro Ala Pro Ile Glu Arg Thr Ile Ser Lys Pro
130                 135                 140

Lys Gly Ser Val Arg Ala Pro Gln Val Tyr Val Leu Pro Pro Pro Glu
145                 150                 155                 160

Glu Glu Met Thr Lys Lys Gln Val Thr Leu Thr Cys Met Val Thr Asp
                165                 170                 175

Phe Met Pro Glu Asp Ile Tyr Val Glu Trp Thr Asn Asn Gly Lys Thr
            180                 185                 190

Glu Leu Asn Tyr Lys Asn Thr Glu Pro Val Leu Asp Ser Asp Gly Ser
            195                 200                 205

Tyr Phe Met Tyr Ser Lys Leu Arg Val Glu Lys Asn Trp Val Glu
210                 215                 220

Arg Asn Ser Tyr Ser Cys Ser Val Val His Glu Gly Leu His Asn His
225                 230                 235                 240

His Thr Thr Lys Ser Phe Ser Arg Thr Pro Gly Gly Gly Gly Ser
                245                 250                 255

Asn Phe Met Tyr Ser Lys Thr Val Lys Arg Leu Ser Lys Leu Gln Glu
            260                 265                 270

Tyr Gln Gln Tyr Tyr Pro Ser Leu Thr Cys Val Met Glu Gly Lys Asp
            275                 280                 285

Met Glu Asp Trp Ser Cys Cys Pro Thr Pro Trp Thr Ser Phe Gln Ser
290                 295                 300

Ser Cys Tyr Phe Ile Ser Thr Val Met Gln Ser Trp Thr Lys Ser Gln
305                 310                 315                 320

Asn Asn Cys Ser Val Met Gly Ala Asp Leu Val Ile Asn Thr Lys
            325                 330                 335

Glu Glu Gln Asp Phe Ile Thr Gln Asn Leu Lys Ile Asn Ser Ala Tyr
            340                 345                 350

Phe Leu Gly Leu Ser Asp Pro Lys Gly Trp Arg His Trp Gln Trp Val
            355                 360                 365

Asp Gln Thr Pro Tyr Asn Lys Asn Val Thr Phe Trp His Ser Gly Glu
            370                 375                 380

Pro Asn Ser Pro Asp Glu Arg Cys Ala Ile Ile Asn Phe Arg Ser Glu
385                 390                 395                 400

Glu Trp Gly Trp Asn Asp Val His Cys His Val Pro Gln Lys Ser Ile
                405                 410                 415

Cys Lys Met Lys Lys Ile Tyr Ile
                420

<210> SEQ ID NO 80
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 80

Met Lys Leu Pro Val Arg Leu Leu Val Leu Met Phe Trp Ile Pro Ala
1               5                   10                  15

Ser Ser Ser Glu Pro Lys Ser Ser Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Glu Asn Leu Tyr Phe Gln
                245                 250                 255

Gly Asn Phe Met Tyr Ser Lys Thr Val Lys Arg Leu Ser Lys Leu Arg
            260                 265                 270

Glu Tyr Gln Gln Tyr His Pro Ser Leu Thr Cys Val Met Glu Gly Lys
        275                 280                 285

Asp Ile Glu Asp Trp Ser Cys Cys Pro Thr Pro Trp Thr Ser Phe Gln
290                 295                 300

Ser Ser Cys Tyr Phe Ile Ser Thr Gly Met Gln Ser Trp Thr Lys Ser
305                 310                 315                 320

Gln Lys Asn Cys Ser Val Met Gly Ala Asp Leu Val Val Ile Asn Thr
                325                 330                 335

Arg Glu Glu Gln Asp Phe Ile Ile Gln Asn Leu Lys Arg Asn Ser Ser
            340                 345                 350

Tyr Phe Leu Gly Leu Ser Asp Pro Gly Gly Arg Arg His Trp Gln Trp
        355                 360                 365

Val Asp Gln Thr Pro Tyr Asn Glu Asn Val Thr Phe Trp His Ser Gly
370                 375                 380

Glu Pro Asn Asn Leu Asp Glu Arg Cys Ala Ile Ile Asn Phe Arg Ser
385                 390                 395                 400

Ser Glu Glu Trp Gly Trp Asn Asp Ile His Cys His Val Pro Gln Lys

```
                    405                 410                 415

Ser Ile Cys Lys Met Lys Lys Ile Tyr Ile
                420                 425

<210> SEQ ID NO 81
<211> LENGTH: 425
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Met Lys Leu Pro Val Arg Leu Leu Val Leu Met Phe Trp Ile Pro Ala
1               5                   10                  15

Ser Ser Ser Glu Pro Lys Ser Ser Asp Lys Thr His Thr Cys Pro Pro
                20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
                180                 185                 190

Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Glu Asn Leu Tyr Phe Gln
                245                 250                 255

Gly Asn Phe Met Tyr Ser Lys Thr Val Lys Arg Leu Ser Lys Leu Gln
                260                 265                 270

Glu Tyr Gln Gln Tyr Tyr Pro Ser Leu Thr Cys Val Met Glu Gly Lys
            275                 280                 285

Asp Met Glu Asp Trp Ser Cys Cys Pro Thr Pro Trp Thr Ser Phe Gln
290                 295                 300

Ser Ser Cys Tyr Phe Ile Ser Thr Val Met Gln Ser Trp Thr Lys Ser
305                 310                 315                 320

Gln Asn Asn Cys Ser Val Met Gly Ala Asp Leu Val Val Ile Asn Thr
                325                 330                 335
```

```
Lys Glu Glu Gln Asp Phe Ile Thr Gln Asn Leu Lys Ile Asn Ser Ala
                340                 345                 350

Tyr Phe Leu Gly Leu Ser Asp Pro Lys Gly Trp Arg His Trp Gln Trp
                355                 360                 365

Val Asp Gln Thr Pro Tyr Asn Lys Asn Val Thr Phe Trp His Ser Gly
370                 375                 380

Glu Pro Asn Ser Pro Asp Glu Arg Cys Ala Ile Ile Asn Phe Arg Ser
385                 390                 395                 400

Glu Glu Trp Gly Trp Asn Asp Val His Cys His Val Pro Gln Lys Ser
                405                 410                 415

Ile Cys Lys Met Lys Lys Ile Tyr Ile
                420                 425

<210> SEQ ID NO 82
<211> LENGTH: 208
<212> TYPE: PRT
<213> ORGANISM: Rattus sp.

<400> SEQUENCE: 82

Met Met Gln Glu Lys Leu Pro Gln Gly Lys Gly Gly Cys Trp Thr Leu
1               5                   10                  15

Arg Leu Trp Ser Ala Ala Val Ile Ser Met Leu Leu Leu Ser Thr Cys
                20                  25                  30

Phe Ile Met Ser Cys Val Val Thr Tyr Gln Phe Met Met Glu Lys Pro
                35                  40                  45

Asn Arg Arg Leu Ser Glu Leu His Thr Tyr Asn Ser Asn Phe Thr Cys
50                  55                  60

Cys Ser Asp Gly Thr Met Val Ser Gly Lys Val Trp Ser Cys Cys Pro
65                  70                  75                  80

Lys Asp Trp Lys Pro Phe Gly Ser His Cys Tyr Phe Thr Thr Asp Phe
                85                  90                  95

Val Ala Asn Trp Asn Glu Ser Lys Glu Lys Cys Ser His Met Gly Ala
                100                 105                 110

His Leu Leu Val Ile His Ser Gln Glu Glu Gln Asp Phe Ile Asn Gly
                115                 120                 125

Ile Leu Asp Thr Arg Trp Gly Tyr Phe Thr Gly Leu Ser Asp Gln Gly
                130                 135                 140

Gln Asn Gln Trp Gln Trp Ile Asp Gln Thr Pro Tyr Asn Glu Ser Val
145                 150                 155                 160

Thr Phe Trp His Glu Asp Glu Pro Asn Asn Asp Tyr Glu Lys Cys Val
                165                 170                 175

Glu Ile Asn His His Lys Asp Ile Gly Trp Gly Trp Asn Asp Val Val
                180                 185                 190

Cys Ser Ser Glu His Lys Ser Ile Cys Gln Val Lys Lys Ile Tyr Leu
                195                 200                 205

<210> SEQ ID NO 83
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
gaccttctga atatatgcgg ccgccatgat gcaggaaaaa c                           41
```

<210> SEQ ID NO 84
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 84
cccacagcca tggaggacag gatcctcata agtatatttt c          41

<210> SEQ ID NO 85
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 85
caggatttca tcaacggaat cctagacact cgttggg          37

<210> SEQ ID NO 86
<211> LENGTH: 86
<212> TYPE: PRT
<213> ORGANISM: Rattus sp.

<400> SEQUENCE: 86

Met Ile Pro Ala Val Ile Leu Phe Leu Leu Leu Val Glu Glu Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Asp Ile Ala Ser Arg Glu Lys Ser Asp Ala Val
    50                  55                  60

Tyr Thr Gly Leu Asn Thr Arg Asn Gln Glu Thr Tyr Glu Thr Leu Lys
65                  70                  75                  80

His Glu Lys Pro Pro Gln
                85

<210> SEQ ID NO 87
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 87
cccagcgctg cagcccgcgg ccgccatgat cccagcggt          39

<210> SEQ ID NO 88
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

```
<400> SEQUENCE: 88
gaacacgtgt tgggatccta ttggggtggt ttctc                              35

<210> SEQ ID NO 89
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Phe Thr Phe Ser Thr Tyr
1               5

<210> SEQ ID NO 90
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Ser Thr Tyr Thr Met Ser
1               5

<210> SEQ ID NO 91
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ser Pro Gly Asp Ser Phe Gly
1               5

<210> SEQ ID NO 92
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Thr Ile Ser Pro Gly Asp Ser Phe Gly Tyr Tyr
1               5                   10

<210> SEQ ID NO 93
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Trp Val Ala Thr Ile Ser Pro Gly Asp Ser Phe Gly Tyr Tyr
1               5                   10
```

```
<210> SEQ ID NO 94
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Thr Arg Asp Ile Tyr Tyr Asn Tyr Gly Ala Trp Phe Ala
1               5                   10

<210> SEQ ID NO 95
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Asp Tyr Asp Gly Asp Ser Tyr Met Asn Trp Tyr
1               5                   10

<210> SEQ ID NO 96
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Leu Leu Ile Tyr Ala Ala Ser Thr Leu Glu
1               5                   10

<210> SEQ ID NO 97
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gln Gln Ala Asn Glu Asp Pro Arg
1               5

<210> SEQ ID NO 98
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Glu Asn Leu Tyr Phe Gln Cys
1               5

<210> SEQ ID NO 99
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Glu Asn Leu Tyr Phe Gln Gly
1               5
```

ANTI-BLOOD DENDRITIC CELL ANTIGEN 2 ANTIBODIES AND USES THEREOF

CROSS REFERENCE TO RELATED APPLICATIONS

This application claims the benefit of U.S. Provisional Application No. 61/735,362 filed Dec. 10, 2012 and U.S. Provisional Application No. 61/763,270 filed Feb. 11, 2013, the contents of both of which are incorporated herein by reference in their entireties.

BACKGROUND

Blood dendritic cell antigen 2 (BDCA2) is a C-type lectin expressed on human plasmacytoid dendritic cells (pDCs) (Dzionek et al., *J. Immunol.*, 165:6037-6046 (2000)), a specialized population of bone marrow-derived cells that secrete type I interferons (IFNs) in response to toll-like receptor (TLR) ligands. BDCA2 consists of a single extracellular carbohydrate recognition domain (CRD), which belongs to the type II C-type lectin group, at its C-terminus, a transmembrane region, and a short cytoplasmic tail at its N-terminus that does not harbor a signaling motif. BDCA2 transmits intracellular signals through an associated transmembrane adaptor, the FcεRIγ, and induces a B cell receptor (BCR)-like signaling cascade.

SUMMARY

This disclosure is based, at least in part, on the identification and characterization of antibodies that bind to BDCA2. Such antibodies can reduce or inhibit the secretion of inflammatory cytokines and chemokines. The anti-BDCA2 antibodies described herein are also capable of depleting pDCs by antibody dependent cellular cytotoxicity (ADCC) or complement-mediated cytotoxicity (CDC). In addition, anti-BDCA2 antibodies described herein can downregulate levels of CD32a and/or CD62L on the surface of pDCs. Furthermore, the anti-BDCA2 antibodies of this disclosure can mediate internalization of BDCA2 from the cell surface of pDCs. For at least these reasons, the anti-BDCA2 antibodies described herein are useful in treating or preventing autoimmune and inflammatory conditions. This disclosure also shows that anti-BDCA2 antibodies described herein can be combined with an antimalarial agent for improved effects.

In one aspect, the disclosure features an isolated antibody or antigen-binding fragment thereof that selectively binds to the ectodomain of human BDCA2 (SEQ ID NO:1) and competes with BIIB059 for binding to the extracellular domain of human BDCA2.

An anti-BDCA2 antibody or antigen-binding fragment thereof competes with BIIB059 for binding to BDCA2 when the anti-BDCA2 antibody or antigen-binding fragment thereof's prior binding to BDCA2 completely or partially inhibits later binding of BIIB059 to BDCA2. For example, an anti-BDCA2 antibody or antigen-binding fragment thereof competes with BIIB059 for binding to BDCA2 when the anti-BDCA2 antibody or antigen-binding fragment thereof's prior binding to BDCA2 completely inhibits later binding of BIIB059 to BDCA2. In certain embodiments, the anti-BDCA2 antibody or antigen-binding fragment thereof's prior binding to BDCA2 results in at least 30%, 50%, 70%, 80%, 90%, 95%, 98% or 99% inhibition of later binding of BIIB059 to BDCA2.

In another aspect, the disclosure features an isolated antibody or antigen-binding fragment thereof selectively binds to the ectodomain of human BDCA2 (SEQ ID NO:1) and: (i) inhibits secretion of type I interferons and/or type III interferons in addition to other cytokines and chemokines from plasmacytoid dendritic cells; or (ii) induces or enhances depletion of plasmacytoid dendritic cells in vitro. In certain embodiments, the anti-BDCA2 antibody downregulates CD32a and/or CD62L from the surface of pDCs. In some embodiments, the anti-BDCA2 antibody mediates internalization of BDCA2 from the cell surface of pDCs. In some embodiments, the antibody or antigen-binding fragment thereof binds to cynomolgus BDCA2 (SEQ ID NO:72) and rhesus BDCA2 (SEQ ID NO:72). In certain embodiments, the isolated antibody or antigen-binding fragment thereof inhibits secretion or production of type I interferon, interleukin-6 (IL-6), tumor necrosis factor-α (TNF-α), type III interferon, macrophage inflammatory protein-1 (MIP-1)-α/CCL3, MIP-1β/CCL4, chemokine (C—C motif) ligand 5 (CCL5/RANTES), or interferon γ-induced protein-10 (IP-10/CXCL10).

In some embodiments of the above two aspects, the isolated antibody or antigen-binding fragment thereof optionally further comprises or consists of one, two, three, four, five, or six, of the following features: an $EC_{50}$ (human BDCA2) of 0.5 to 3 µg/mL or 4 nM to 10 nM; an $EC_{50}$ (cynomolgus BDCA2) of 0.5 to 3 µg/mL or 5 nM to 10 nM; a pI of 7 to 7.5; does not bind rat Clec4b2, or binds rat Clec4b2 with a lower binding affinity than human, cynomolgus or rhesus BDCA2; inhibits production or secretion of chemokines such as MIP-1-α/CCL3, MIP-1β/CCL4, CCL5/RANTES, IP-10/CXCL10; a heavy chain CDR1, a heavy chain CDR2, and a heavy chain CDR3, wherein the heavy chain CDR1 has an amino acid sequence consisting of the amino acid sequence set forth in SEQ ID NO:9 or an amino acid sequence consisting of the amino acid sequence set forth in SEQ ID NO:8; the heavy chain CDR2 has an amino acid sequence consisting of the amino acid sequence set forth in SEQ ID NO:10; and the heavy chain CDR3 has an amino acid sequence consisting of the amino acid sequence set forth in SEQ ID NO:11; and a variable heavy chain comprising or consisting of the amino acid sequence set forth in SEQ ID NO:24. In certain embodiments, the antibody or antigen-binding fragment thereof has a heavy chain CDR1 consisting of the amino acid sequence set forth in SEQ ID NO:89; a heavy chain CDR2 consisting of the amino acid sequence set forth in SEQ ID NO:91; and a heavy chain CDR3 consisting of the amino acid sequence set forth in SEQ ID NO:11. In certain embodiments, the antibody or antigen-binding fragment thereof has a heavy chain CDR1 consisting of the amino acid sequence set forth in SEQ ID NO:9; a heavy chain CDR2 consisting of the amino acid sequence set forth in SEQ ID NO:92; and a heavy chain CDR3 consisting of the amino acid sequence set forth in SEQ ID NO:11. In certain embodiments, the antibody or antigen-binding fragment thereof has a heavy chain CDR1 consisting of the amino acid sequence set forth in SEQ ID NO:90; a heavy chain CDR2 consisting of the amino acid sequence set forth in SEQ ID NO:93; and a heavy chain CDR3 consisting of the amino acid sequence set forth in SEQ ID NO:94. In some embodiments, the isolated antibody or antigen-binding fragment has an EC50 (human BDCA2) of 4.5 nM, 4.6 nM, 4.7 nM, 4.8 nM, 4.9 nM, 5.0 nM, 5.1 nM, 5.2 nM, 5.3 nM, 5.4 nM, or 5.5 nM. In a specific embodiment, the isolated antibody or antigen-binding fragment has an EC50 (human BDCA2) of 4.9 nM. In some embodiments, the isolated antibody or antigen-binding fragment has an EC50 (cynomolgus BDCA2) of 4.0 nM, 4.1 nM, 4.2 nM, 4.3 nM, 4.4 nM, 4.5 nM, 4.6 nM, 4.7 nM, 4.8 nM, 4.9 nM, or 5.0 nM. In a specific embodiment, the isolated antibody or antigen-binding fragment has an EC50 (cynomolgus BDCA2) of 4.4 nM. In certain embodiments of this aspect, the antibody has a human heavy chain and light chain constant region. In certain embodiments, the heavy chain constant region comprises a CH1 domain and a hinge region. In some embodiments, the heavy chain constant region comprises a CH3 domain. If the heavy chain constant region includes substitutions, such substitutions modify the properties of the antibody (e.g., increase or decrease one or more of: Fc receptor binding, antibody glycosylation, the number of cysteine residues, effector cell function, or complement function). In certain embodiments, the antibody is an IgG antibody. In specific embodiments, the antibody is selected from the group consisting of IgG1, IgG2, IgG3, and IgG4. In certain embodiments, the antibody includes a human Fc region that binds FcγRIIa (CD32a) with an EC50 of 7 to 15 µg/mL. In certain embodiments, the antibody includes a human Fc region that binds FcγRIIa (CD32a) with an EC50 of 10 µg/mL. In certain embodiments, the antibody includes a human Fc region that binds FcγRIIa (CD32a) with an EC50 of 11 µg/mL. In certain embodiments, the antibody includes a human Fc region that binds FcγRIIa (CD32a) with an EC50 of 12 µg/mL.

In another aspect, the disclosure features an isolated antibody or antigen-binding fragment thereof that selectively binds to the ectodomain of human BDCA2 (SEQ ID NO:1), and comprises a heavy chain CDR1, a heavy chain CDR2, and a heavy chain CDR3. The heavy chain CDR1 comprises or consists of the amino acid sequence GFTFSTYTMS (SEQ ID NO:9) or the amino acid sequence set forth in SEQ ID NO:9 with a substitution at one, two, three, or four amino acid positions. The heavy chain CDR2 comprises or consists of the amino acid sequence TISPGDSFGYYYPDSVQG (SEQ ID NO:10) or the amino acid sequence set forth in SEQ ID NO:10 with a substitution at one, two, three, or four amino acid positions. The heavy chain CDR3 comprises or consists of the amino acid sequence DIYYNYGAWFAY (SEQ ID NO:11) or the amino acid sequence set forth in SEQ ID NO:11 with a substitution at one, two, three, or four amino acid positions. In another aspect, the antibody or antigen-binding fragment thereof comprises a heavy chain CDR1 consisting of the amino acid sequence set forth in SEQ ID NO:89 with a substitution at one, two, three, or four amino acid positions; a heavy chain CDR2 consisting of the amino acid sequence set forth in SEQ ID NO:91 with a substitution at one, two, three, or four amino acid positions; and a heavy chain CDR3 consisting of the amino acid sequence set forth in SEQ ID NO:11 with a substitution at one, two, three, or four amino acid positions. In another aspect, the antibody or antigen-binding fragment thereof comprises a heavy chain CDR1 consisting of the amino acid sequence set forth in SEQ ID NO:9 with a substitution at one, two, three, or four amino acid positions; a heavy chain CDR2 consisting of the amino acid sequence set forth in SEQ ID NO:92 with a substitution at one, two, three, or four amino acid positions; and a heavy chain CDR3 consisting of the amino acid sequence set forth in SEQ ID NO:11 with a substitution at one, two, three, or four amino acid positions. In another aspect, the antibody or antigen-binding fragment thereof comprises a heavy chain CDR1 consisting of the amino acid sequence set forth in SEQ ID NO:90 with a substitution at one, two, three, or four amino acid positions; a heavy chain CDR2 consisting of the amino acid sequence set forth in SEQ ID NO:93 with a substitution at one, two, three, or four amino acid positions; and a heavy chain CDR3 consisting of the amino acid sequence set forth in SEQ ID NO:94 with a substitution at one, two, three, or four amino acid positions. These antibodies (i) bind human or cynomolgus monkey BDCA2 but do not significantly bind BDCA2 from phylogenetic species below primates; and/or (ii) inhibit TLR7/TLR9-induced type I interferon and other cytokine or chemokine production by human pDCs; and/or (iii) mediate internalization of BDCA2 from the surface of pDCs; and/or (iv) downregulate CD32a and/or CD62L from the surface of pDCs; and/or (v) deplete pDCs in vitro by ADCC or CDC. In certain embodiments of this aspect, the antibody has a human heavy chain and light chain constant region.

In certain embodiments, the isolated antibody or antigen-binding fragment thereof that specifically binds human BDCA2 has a heavy chain CDR1 that comprises or consists of the amino acid sequence GFTFSTYTMS (SEQ ID NO:9) or the amino acid sequence set forth in SEQ ID NO:9 with a substitution at one or two amino acid positions; a heavy chain CDR2 that comprises or consists of the amino acid sequence TISPGDSFGYYYPDSVQG (SEQ ID NO:10) or the amino acid sequence set forth in SEQ ID NO:10 with a substitution at one or two amino acid positions; and a heavy chain CDR3 that comprises or consists of the amino acid sequence DIYYNYGAWFAY (SEQ ID NO:11) or the amino acid sequence set forth in SEQ ID NO:11 with a substitution at one or two amino acid positions. In other embodiments of this aspect, the isolated antibody or antigen-binding fragment has a heavy chain CDR1 that comprises or consists of the amino acid sequence GFTFSTYTMS (SEQ ID NO:9); a heavy chain CDR2 comprises or consists of the amino acid sequence TISPGDSFGYYYPDSVQG (SEQ ID NO:10); and a heavy chain CDR3 comprises or consists of the amino acid sequence DIYYNYGAWFAY (SEQ ID NO:11). In other embodiments of this aspect, the isolated antibody or antigen-binding fragment comprises a light chain CDR1, a light chain CDR2, and a light chain CDR3. The light chain CDR1 comprises or consists of the amino acid sequence KASQSVDYDGDSYMN (SEQ ID NO:5) or the amino acid sequence set forth in SEQ ID NO:5 with a substitution at one, two, three, or four amino acid positions. The light chain CDR2 comprises or consists of the amino acid sequence AASTLES (SEQ ID NO:6) or the amino acid sequence set forth in SEQ ID NO:6 with a substitution at one, two, three, or four amino acid positions. The light chain CDR3 comprises or consists of the amino acid sequence QQANEDPRT (SEQ ID NO:7) or the amino acid sequence set forth in SEQ ID NO:7 with a substitution at one, two, three, or four amino acid positions. In certain embodiments, the light chain CDR1 comprises or consists of the amino acid sequence KASQSVDYDGDSYMN (SEQ ID NO:5) or the amino acid sequence set forth in SEQ ID NO:5 with a substitution at one or two amino acid positions; the light chain CDR2 comprises or consists of the amino acid sequence AASTLES (SEQ ID NO:6) or the amino acid sequence set forth in SEQ ID NO:6 with a substitution at one or two amino acid positions; and the light chain CDR3 comprises or consists of the amino acid sequence QQANEDPRT (SEQ ID NO:7) or the amino acid sequence set forth in SEQ ID NO:7 with a substitution at one or two amino acid positions. In other embodiments, the isolated antibody or antigen-binding fragment thereof has a heavy chain CDR1 that comprises or consists of the amino acid sequence GFTFSTYTMS (SEQ ID NO:9); a heavy chain CDR2 that comprises or consists of the amino acid sequence TISPGDSFGYYYPDSVQG (SEQ ID NO:10); a heavy chain CDR3 that comprises or consists of the amino acid sequence DIYYNYGAWFAY (SEQ ID NO:11); a light chain CDR1 that comprises or consists of the amino acid sequence KASQSVDYDGDSYMN (SEQ ID NO:5); a light chain CDR2 comprises or consists of the amino acid sequence AASTLES (SEQ ID NO:6); and a light chain CDR3 that comprises or consists of the amino acid sequence QQANEDPRT (SEQ ID NO:7).

In certain embodiments, the isolated antibody or antigen-binding fragment thereof that selectively binds human BDCA2 comprises a heavy chain CDR1 that comprises or consists of the amino acid sequence TYTMS (SEQ ID NO:8) or the amino acid sequence set forth in SEQ ID NO:8 with a substitution at one or two amino acid positions; a heavy chain CDR2 that comprises or consists of the amino acid sequence TISPGDSFGYYYPDSVQG (SEQ ID NO:10) or the amino acid sequence set forth in SEQ ID NO:10 with a substitution at one or two amino acid positions; and a heavy chain CDR3 that comprises or consists of the amino acid sequence DIYYNYGAWFAY (SEQ ID NO:11) or the amino acid sequence set forth in SEQ ID NO:11 with a substitution at one or two amino acid positions. In other embodiments of this aspect, the isolated antibody or antigen-binding fragment has a heavy chain CDR1 that comprises or consists of the amino acid sequence TYTMS (SEQ ID NO:8); a heavy chain CDR2 comprises or consists of the amino acid sequence TISPGDSFGYYYPDSVQG (SEQ ID NO:10); and a heavy chain CDR3 comprises or consists of the amino acid sequence DIYYNYGAWFAY (SEQ ID NO:11). In other embodiments of this aspect, the isolated antibody or antigen-binding fragment comprises a light chain CDR1, a light chain CDR2, and a light chain CDR3. The light chain CDR1 comprises or consists of the amino acid sequence KASQSVDYDGDSYMN (SEQ ID NO:5) or the amino acid sequence set forth in SEQ ID NO:5 with a substitution at one, two, three, or four amino acid positions. The light chain CDR2 comprises or consists of the amino acid sequence AASTLES (SEQ ID NO:6) or the amino acid sequence set forth in SEQ ID NO:6 with a substitution at one, two, three, or four amino acid positions. The light chain CDR3 comprises or consists of the amino acid sequence QQANEDPRT (SEQ ID NO:7) or the amino acid sequence set forth in SEQ ID NO:7 with a substitution at one, two, three, or four amino acid positions. In certain embodiments, the light chain CDR1 comprises or consists of the amino acid sequence KASQSVDYDGDSYMN (SEQ ID NO:5) or the amino acid sequence set forth in SEQ ID NO:5 with a substitution at one or two amino acid positions; the light chain CDR2 comprises or consists of the amino acid sequence AASTLES (SEQ ID NO:6) or the amino acid sequence set forth in SEQ ID NO:6 with a substitution at one or two amino acid positions; and the light chain CDR3 comprises or consists of the amino acid sequence QQANEDPRT (SEQ ID NO:7) or the amino acid sequence set forth in SEQ ID NO:7 with a substitution at one or two amino acid positions. In other embodiments, the isolated antibody or antigen-binding fragment thereof has a heavy chain CDR1 that comprises or consists of the amino acid sequence TYTMS (SEQ ID NO:8); a heavy chain CDR2 that comprises or consists of the amino acid sequence TISPGDSFGYYYPDSVQG (SEQ ID NO:10); a heavy chain CDR3 that comprises or consists of the amino acid sequence DIYYNYGAWFAY (SEQ ID NO:11); a light chain CDR1 that comprises or consists of the amino acid sequence KASQSVDYDGDSYMN (SEQ ID NO:5); a light chain CDR2 comprises or consists of the amino acid sequence AASTLES (SEQ ID NO:6); and a light chain CDR3 that comprises or consists of the amino acid sequence QQANEDPRT (SEQ ID NO:7).

In certain embodiments, the isolated antibody or antigen-binding fragment thereof that selectively binds human BDCA2 comprises a heavy chain CDR1 that comprises or consists of the amino acid sequence GFTFSTY (SEQ ID NO:89) or the amino acid sequence set forth in SEQ ID NO:89 with a substitution at one or two amino acid positions; a heavy chain CDR2 that comprises or consists of the amino acid sequence SPGDSFG (SEQ ID NO:91) or the amino acid sequence set forth in SEQ ID NO:91 with a substitution at one or two amino acid positions; and a heavy chain CDR3 that comprises or consists of the amino acid sequence DIYYNYGAWFAY (SEQ ID NO:11) or the amino acid sequence set forth in SEQ ID NO:11 with a substitution at one or two amino acid positions. In other embodiments of this aspect, the isolated antibody or antigen-binding fragment has a heavy chain CDR1 that comprises or consists of the amino acid sequence GFTFSTY (SEQ ID NO:89); a heavy chain CDR2 comprises or consists of the amino acid sequence SPGDSFG (SEQ ID NO:91); and a heavy chain CDR3 comprises or consists of the amino acid sequence DIYYNYGAWFAY (SEQ ID NO:11). In other embodiments of this aspect, the isolated antibody or antigen-binding fragment comprises a light chain CDR1, a light chain CDR2, and a light chain CDR3. The light chain CDR1 comprises or consists of the amino acid sequence KASQSVDYDGDSYMN (SEQ ID NO:5) or the amino acid sequence set forth in SEQ ID NO:5 with a substitution at one, two, three, or four amino acid positions. The light chain CDR2 comprises or consists of the amino acid sequence AASTLES (SEQ ID NO:6) or the amino acid sequence set forth in SEQ ID NO:6 with a substitution at one, two, three, or four amino acid positions. The light chain CDR3 comprises or consists of the amino acid sequence QQANEDPRT (SEQ ID NO:7) or the amino acid sequence set forth in SEQ ID NO:7 with a substitution at one, two, three, or four amino acid positions. In certain embodiments, the light chain CDR1 comprises or consists of the amino acid sequence KASQSVDYDGDSYMN (SEQ ID NO:5) or the amino acid sequence set forth in SEQ ID NO:5 with a substitution at one or two amino acid positions; the light chain CDR2 comprises or consists of the amino acid sequence AASTLES (SEQ ID NO:6) or the amino acid sequence set forth in SEQ ID NO:6 with a substitution at one or two amino acid positions; and the light chain CDR3 comprises or consists of the amino acid sequence QQANEDPRT (SEQ ID NO:7) or the amino acid sequence set forth in SEQ ID NO:7 with a substitution at one or two amino acid positions. In other embodiments, the isolated antibody or antigen-binding fragment thereof has a heavy chain CDR1 that comprises or consists of the amino acid sequence GFTFSTY (SEQ ID NO:89); a heavy chain CDR2 that comprises or consists of the amino acid sequence SPGDSFG (SEQ ID NO:91); a heavy chain CDR3 that comprises or consists of the amino acid sequence DIYYNYGAWFAY (SEQ ID NO:11); a light chain CDR1 that comprises or consists of the amino acid sequence KASQSVDYDGDSYMN (SEQ ID NO:5); a light chain CDR2 comprises or consists of the amino acid sequence AASTLES (SEQ ID NO:6); and a light chain CDR3 that comprises or consists of the amino acid sequence QQANEDPRT (SEQ ID NO:7).

In certain embodiments, the isolated antibody or antigen-binding fragment thereof that selectively binds human BDCA2 comprises a heavy chain CDR1 that comprises or consists of the amino acid sequence GFTFSTYTMS (SEQ ID NO:9) or the amino acid sequence set forth in SEQ ID NO:9 with a substitution at one or two amino acid positions; a heavy chain CDR2 that comprises or consists of the amino acid sequence TISPGDSFGYY (SEQ ID NO:92) or the amino acid sequence set forth in SEQ ID NO:92 with a substitution at one or two amino acid positions; and a heavy chain CDR3 that comprises or consists of the amino acid sequence DIYYNYGAWFAY (SEQ ID NO:11) or the amino acid sequence set forth in SEQ ID NO:11 with a substitution at one or two amino acid positions. In other embodiments of this aspect, the isolated antibody or antigen-binding fragment has a heavy chain CDR1 that comprises or consists of the amino acid sequence GFTFSTYTMS (SEQ ID NO:9); a heavy chain CDR2 comprises or consists of the amino acid sequence TISPGDSFGYY (SEQ ID NO:92); and a heavy chain CDR3 comprises or consists of the amino acid sequence DIYYNYGAWFAY (SEQ ID NO:11). In other embodiments of this aspect, the isolated antibody or antigen-binding fragment comprises a light chain CDR1, a light chain CDR2, and a light chain CDR3. The light chain CDR1 comprises or consists of the amino acid sequence KASQSVDYDGDSYMN (SEQ ID NO:5) or the amino acid sequence set forth in SEQ ID NO:5 with a substitution at one, two, three, or four amino acid positions. The light chain CDR2 comprises or consists of the amino acid sequence AASTLES (SEQ ID NO:6) or the amino acid sequence set forth in SEQ ID NO:6 with a substitution at one, two, three, or four amino acid positions. The light chain CDR3 comprises or consists of the amino acid sequence QQANEDPRT (SEQ ID NO:7) or the amino acid sequence set forth in SEQ ID NO:7 with a substitution at one, two, three, or four amino acid positions. In certain embodiments, the light chain CDR1 comprises or consists of the amino acid sequence KASQSVDYDGDSYMN (SEQ ID NO:5) or the amino acid sequence set forth in SEQ ID NO:5 with a substitution at one or two amino acid positions; the light chain CDR2 comprises or consists of the amino acid sequence AASTLES (SEQ ID NO:6) or the amino acid sequence set forth in SEQ ID NO:6 with a substitution at one or two amino acid positions; and the light chain CDR3 comprises or consists of the amino acid sequence QQANEDPRT (SEQ ID NO:7) or the amino acid sequence set forth in SEQ ID NO:7 with a substitution at one or two amino acid positions. In other embodiments, the isolated antibody or antigen-binding fragment thereof has a heavy chain CDR1 that comprises or consists of the amino acid sequence GFTFSTYTMS (SEQ ID NO:9); a heavy chain CDR2 that comprises or consists of the amino acid sequence TISPGDSFGYY (SEQ ID NO:92); a heavy chain CDR3 that comprises or consists of the amino acid sequence DIYYNYGAWFAY (SEQ ID NO:11); a light chain CDR1 that comprises or consists of the amino acid sequence KASQSVDYDGDSYMN (SEQ ID NO:5); a light chain CDR2 comprises or consists of the amino acid sequence AASTLES (SEQ ID NO:6); and a light chain CDR3 that comprises or consists of the amino acid sequence QQANEDPRT (SEQ ID NO:7).

In certain embodiments, the isolated antibody or antigen-binding fragment thereof that selectively binds human BDCA2 comprises a heavy chain CDR1 that comprises or consists of the amino acid sequence STYTMS (SEQ ID NO:90) or the amino acid sequence set forth in SEQ ID NO:90 with a substitution at one or two amino acid positions; a heavy chain CDR2 that comprises or consists of the amino acid sequence WVATISPGDSFGYY (SEQ ID NO:93) or the amino acid sequence set forth in SEQ ID NO:93 with a substitution at one or two amino acid positions; and a heavy chain CDR3 that comprises or consists of the amino acid sequence TRDIYYNYGAWFA (SEQ ID NO:94) or the amino acid sequence set forth in SEQ ID NO:94 with a substitution at one or two amino acid positions. In other embodiments of this aspect, the isolated antibody or antigen-binding fragment has a heavy chain CDR1 that comprises or consists of the amino acid sequence STYTMS (SEQ ID NO:90); a heavy chain CDR2 comprises or consists of the amino acid sequence WVATISPGDSFGYY (SEQ ID NO:93); and a heavy chain CDR3 comprises or consists of the amino acid sequence TRDIYYNYGAWFA (SEQ ID NO:94). In other embodiments of this aspect, the isolated antibody or antigen-binding fragment comprises a light chain CDR1, a light chain CDR2, and a light chain CDR3. The light chain CDR1 comprises or consists of the amino acid sequence DYDGDSYMNWY (SEQ ID NO:95) or the amino acid sequence set forth in SEQ ID NO:95 with a substitution at one, two, three, or four amino acid positions. The light chain CDR2 comprises or consists of the amino acid sequence LLIYAASTLE (SEQ ID NO:96) or the amino acid sequence set forth in SEQ ID NO:96 with a substitution at one, two, three, or four amino acid positions. The light chain CDR3 comprises or consists of the amino acid sequence QQANEDPR (SEQ ID NO:97) or the amino acid sequence set forth in SEQ ID NO:97 with a substitution at one, two, three, or four amino acid positions. In certain embodiments, the light chain CDR1 comprises or consists of the amino acid sequence DYDGDSYMNWY (SEQ ID NO:95) or the amino acid sequence set forth in SEQ ID NO:95 with a substitution at one or two amino acid positions; the light chain CDR2 comprises or consists of the amino acid sequence LLIYAASTLE (SEQ ID NO:96) or the amino acid sequence set forth in SEQ ID NO:96 with a substitution at one or two amino acid positions; and the light chain CDR3 comprises or consists of the amino acid sequence QQANEDPR (SEQ ID NO:97) or the amino acid sequence set forth in SEQ ID NO:97 with a substitution at one or two amino acid positions. In other embodiments, the isolated antibody or antigen-binding fragment thereof has a heavy chain CDR1 that comprises or consists of the amino acid sequence STYTMS (SEQ ID NO:90); a heavy chain CDR2 that comprises or consists of the amino acid sequence WVATISPGDSFGYY (SEQ ID NO:93); a heavy chain CDR3 that comprises or consists of the amino acid sequence TRDIYYNYGAWFA (SEQ ID NO:94); a light chain CDR1 that comprises or consists of the amino acid sequence DYDGDSYMNWY (SEQ ID NO:95); a light chain CDR2 comprises or consists of the amino acid sequence LLIYAASTLE (SEQ ID NO:96); and a light chain CDR3 that comprises or consists of the amino acid sequence QQANEDPR (SEQ ID NO:97).

In certain embodiments of the above aspects, the antibody has a human heavy chain and light chain constant region. In certain embodiments, the heavy chain constant region comprises a CH1 domain and a hinge region. In some embodiments, the heavy chain constant region comprises a CH3 domain. If the heavy chain constant region includes substitutions, such substitutions modify the properties of the antibody (e.g., increase or decrease one or more of: Fc receptor binding, antibody glycosylation, the number of cysteine residues, effector cell function, or complement function). In certain embodiments, the antibody is an IgG antibody. In specific embodiments, the antibody is selected from the group consisting of IgG1, IgG2, IgG3, and IgG4. In certain embodiments, the antibody includes a human Fc region that binds FcγRIIa (CD32a) with an EC50 of 7 to 15 μg/mL. In certain embodiments, the antibody includes a human Fc region that binds FcγRIIa (CD32a) with an EC50 of 10 μg/mL. In certain embodiments, the antibody includes a human Fc region that binds FcγRIIa (CD32a) with an EC50 of 11 μg/mL. In certain embodiments, the antibody includes a human Fc region that binds FcγRIIa (CD32a) with an EC50 of 12 μg/mL.

In another aspect, the disclosure features an isolated antibody or antigen-binding fragment thereof that selectively binds to the ectodomain of human BDCA2 (SEQ ID NO:1), and comprises a heavy chain CDR1, a heavy chain CDR2, and a heavy chain CDR3 of the VH set forth in any one of SEQ ID NOs: 40, 42, 44, 46, 49, or 52. In some embodiments of this aspect, isolated antibody or antigen-binding fragment thereof comprises a light chain CDR1, a light chain CDR2, and a light chain CDR3 of the VL set forth in any one of SEQ ID NOs: 54, 56, or 58. The CDRs can be the Kabat CDRs or any of the alternate CDRs. In certain embodiments, the antibody has a human heavy chain and light chain constant region. In certain embodiments, the heavy chain constant region comprises a CH1 domain and a hinge region. In some embodiments, the heavy chain constant region comprises a CH3 domain. If the heavy chain constant region includes substitutions, such substitutions modify the properties of the antibody (e.g., increase or decrease one or more of: Fc receptor binding, antibody glycosylation, the number of cysteine residues, effector cell function, or complement function). In certain embodiments, the antibody is an IgG antibody. In specific embodiments, the antibody is selected from the group consisting of IgG1, IgG2, IgG3, and IgG4. In certain embodiments, the antibody includes a human Fc region that binds FcγRIIa (CD32a) with an EC50 of 7 to 15 μg/mL. In certain embodiments, the antibody includes a human Fc region that binds FcγRIIa (CD32a) with an EC50 of 10 μg/mL. In certain embodiments, the antibody includes a human Fc region that binds FcγRIIa (CD32a) with an EC50 of 11 μg/mL. In certain embodiments, the antibody includes a human Fc region that binds FcγRIIa (CD32a) with an EC50 of 12 μg/mL. In another aspect, the disclosure features an isolated antibody or antigen-binding fragment thereof that selectively binds to the ectodomain of human BDCA2 (SEQ ID NO:1) and comprises a variable heavy chain (VH) domain that is at least 80% identical to the amino acid sequence of the VH domain of BIIB059 (SEQ ID NO:24), or the VH domain set forth in any one of SEQ ID NOs: 40, 42, 44, 46, 49, or 52. These antibodies (i) bind human or cynomolgus monkey BDCA2 but do not significantly bind BDCA2 from phylogenetic species below primates; and/or (ii) inhibit TLR7/TLR9-induced type I interferon and other cytokine or chemokine production by human pDCs; and/or (iii) mediate internalization of BDCA2 from the surface of pDCs; and/or (iv) downregulate CD32a and/or CD62L from the surface of pDCs; and/or (v) deplete pDCs in vitro by ADCC or CDC.

In certain embodiments of this aspect, the antibody or antibody fragment thereof comprises or consists of a VH domain that is at least 90% identical to the amino acid sequence of the VH domain of BIIB059 (SEQ ID NO:24), or the VH domain set forth in any one of SEQ ID NOs: 40, 42, 44, 46, 49, or 52. In some embodiments of this aspect, the antibody or antibody fragment thereof comprises or consists of a VH domain that is at least 95% identical to the amino acid sequence of the VH domain of BIIB059 (SEQ ID NO:24), or the VH domain set forth in any one of SEQ ID NOs: 40, 42, 44, 46, 49, or 52. In other embodiments of this aspect, the VH domain of the isolated antibody or antigen-binding fragment is identical to the amino acid sequence of the VH domain of BIIB059 (SEQ ID NO:24), or the VH domain set forth in any one of SEQ ID NOs: 40, 42, 44, 46, 49, or 52. In certain embodiments, the heavy chain comprises or consists of the amino acid sequence set forth in SEQ ID NO:4. In certain embodiments of this aspect, the antibody or antigen-binding fragment thereof comprises or consists of a variable light chain (VL) domain that is at least 80% identical to the amino acid sequence of the VL domain of BIIB059 (SEQ ID NO:23), or the VL domain set forth in any one of SEQ ID NOs: 54, 56, or 58. In some embodiments of this aspect, the antibody or antigen-binding fragment thereof comprises or consists of a VL domain that is at least 90% identical to the amino acid sequence of the VL domain of BIIB059 (SEQ ID NO:23), or the VL domain set forth in any one of SEQ ID NOs: 54, 56, or 58. In some embodiments of this aspect, the antibody or antigen-binding fragment thereof comprises or consists of a VL domain that is at least 95% identical to the amino acid sequence of the VL domain of BIIB059 (SEQ ID NO:23), or the VL domain set forth in any one of SEQ ID NOs: 54, 56, or 58. In some embodiments of this aspect, the antibody or antigen-binding fragment thereof comprises or consists of a VH domain that is identical to the amino acid sequence of the VH domain of BIIB059 (SEQ ID NO:24) and a VL domain that is identical to the amino acid sequence of the VL domain of BIIB059 (SEQ ID NO:23). In some embodiments of this aspect, the antibody or antigen-binding fragment thereof comprises or consists of a VH domain that is identical to the amino acid sequence of a VH domain set forth in any one of SEQ ID NOs: 40, 42, 44, 46, 49, or 52 and a VL domain set forth in any one of SEQ ID NOs: 54, 56, or 58. In a particular embodiment, the antibody or antigen-binding fragment thereof comprises or consists of a heavy chain that comprises or consists of the amino acid sequence set forth in SEQ ID NO:4 and a light chain that comprises or consists of the amino acid sequence set forth in SEQ ID NO:3. These embodiments relate to all of the above aspects and their embodiments. In certain embodiments, the antibody or antigen-binding fragment thereof is a humanized antibody. In some embodiments, the antibody or antigen-binding fragment thereof is a monoclonal antibody. In some embodiments, the antibody or antigen-binding fragment thereof is a single chain antibody. In other embodiments, the antibody or antigen-binding fragment is a polyclonal antibody, a chimeric antibody, an $F_{ab}$ fragment, an $F_{(ab')2}$ fragment, an $F_{ab'}$ fragment, an $F_{sc}$ fragment, an $F_v$ fragment, an scFv, an sc(Fv)$_2$, or a diabody. In some embodiments, the antibody has an IgG1 heavy chain constant region.

In another aspect, the disclosure provides an isolated antibody or antigen binding fragment thereof that selectively binds to the ectodomain of human BDCA2 (SEQ ID NO:1) and comprises a heavy chain CDR1, a heavy chain CDR2, and a heavy chain CDR3 of the antibody produced by the hybridoma deposited at the ATCC with the designation number PTA-13450. In certain embodiments of this aspect, the antibody or antigen binding fragment thereof further comprises a light chain CDR1, a light chain CDR2, and a light chain CDR3 of the antibody produced by the hybridoma deposited at the ATCC with the designation number PTA-13450. In certain embodiments of this aspect, the antibody has a human heavy chain and light chain constant region. In certain embodiments, the heavy chain constant region comprises a CH1 domain and a hinge region. In some embodiments, the heavy chain constant region comprises a CH3 domain. If the heavy chain constant region includes substitutions, such substitutions modify the properties of the antibody (e.g., increase or decrease one or more of: Fc receptor binding, antibody glycosylation, the number of cysteine residues, effector cell function, or complement function). In certain embodiments, the antibody is an IgG antibody. In specific embodiments, the antibody is selected from the group consisting of IgG1, IgG2, IgG3, and IgG4. In certain embodiments, the antibody includes a human Fc region that binds FcγRIIa (CD32a) with an EC50 of 7 to 15 µg/mL. In certain embodiments, the antibody includes a human Fc region that binds FcγRIIa (CD32a) with an EC50 of 10 µg/mL. In certain embodiments, the antibody includes a human Fc region that binds FcγRIIa (CD32a) with an EC50 of 11 µg/mL. In certain embodiments, the antibody includes a human Fc region that binds FcγRIIa (CD32a) with an EC50 of 12 µg/mL. In another aspect, the disclosure provides an isolated antibody or antigen binding fragment thereof that selectively binds to the ectodomain of human BDCA2 (SEQ ID NO:1) and comprises variant heavy chain CDR1, heavy chain CDR2, and heavy chain CDR3 of the antibody produced by the hybridoma deposited at the ATCC with the designation number PTA-13450, wherein the variant heavy chain CDR1, CDR2, and CDR3 includes one, two, or three amino acid substitutions compared to the heavy chain CDR1, CDR2, and CDR3, respectively, of the antibody produced by the hybridoma deposited at the ATCC with the designation number PTA-13450. In certain embodiments of this aspect, the antibody or antigen binding fragment thereof further comprises variant light chain CDR1, light chain CDR2, and light chain CDR3 of the antibody produced by the hybridoma deposited at the ATCC with the designation number PTA-13450, wherein the variant light chain CDR1, CDR2, and CDR3 includes one, two, or three amino acid substitutions compared to the light chain CDR1, CDR2, and CDR3, respectively, of the antibody produced by the hybridoma deposited at the ATCC with the designation number PTA-13450. In certain embodiments of this aspect, the antibody has a human heavy chain and light chain constant region. In certain embodiments, the heavy chain constant region comprises a CH1 domain and a hinge region. In some embodiments, the heavy chain constant region comprises a CH3 domain. If the heavy chain constant region includes substitutions, such substitutions modify the properties of the antibody (e.g., increase or decrease one or more of: Fc receptor binding, antibody glycosylation, the number of cysteine residues, effector cell function, or complement function). In certain embodiments, the antibody is an IgG antibody. In specific embodiments, the antibody is selected from the group consisting of IgG1, IgG2, IgG3, and IgG4. In certain embodiments, the antibody includes a human Fc region that binds FcγRIIa (CD32a) with an EC50 of 7 to 15 µg/mL. In certain embodiments, the antibody includes a human Fc region that binds FcγRIIa (CD32a) with an EC50 of 10 µg/mL. In certain embodiments, the antibody includes a human Fc region that binds FcγRIIa (CD32a) with an EC50 of 11 µg/mL. In certain embodiments, the antibody includes a human Fc region that binds FcγRIIa (CD32a) with an EC50 of 12 µg/mL. In another aspect, the disclosure features an isolated antibody or antigen binding fragment thereof that selectively binds to the ectodomain of human BDCA2 (SEQ ID NO:1) and crossblocks binding of the antibody produced by the hybridoma deposited at the ATCC with the designation number PTA-13450. In certain embodiments, the antibody is an IgG antibody. In specific embodiments, the antibody is selected from the group consisting of IgG1, IgG2, IgG3, and IgG4. In certain embodiments, the antibody includes a human Fc region that binds FcγRIIa (CD32a) with an EC50 of 7 to 15 µg/mL. In certain embodiments, the antibody includes a human Fc region that binds FcγRIIa (CD32a) with an EC50 of 10 µg/mL. In certain embodiments, the antibody includes a human Fc region that binds FcγRIIa (CD32a) with an EC50 of 11 µg/mL. In certain embodiments, the antibody includes a human Fc region that binds FcγRIIa (CD32a) with an EC50 of 12 µg/mL. In yet another aspect, the disclosure features an isolated antibody or antigen binding fragment thereof that selectively binds to the ectodomain of human BDCA2 (SEQ ID NO:1) at the same epitope as the antibody produced by the hybridoma deposited at the ATCC with the designation number PTA-13450. In certain embodiments, the antibody is an IgG antibody. In specific embodiments, the antibody is selected from the group consisting of IgG1, IgG2, IgG3, and IgG4. In certain embodiments, the antibody includes a human Fc region that binds FcγRIIa (CD32a) with an EC50 of 7 to 15 µg/mL. In certain embodiments, the antibody includes a human Fc region that binds FcγRIIa (CD32a) with an EC50 of 10 µg/mL. In certain embodiments, the antibody includes a human Fc region that binds FcγRIIa (CD32a) with an EC50 of 11 µg/mL. In certain embodiments, the antibody includes a human Fc region that binds FcγRIIa (CD32a) with an EC50 of 12 µg/mL. In a further aspect, the disclosure features an isolated antibody or antigen binding fragment thereof that selectively binds to the ectodomain of human BDCA2 (SEQ ID NO:1) and comprises a VH domain that is at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, or at least 98%, identical to the VH domain of the antibody produced by the hybridoma deposited at the ATCC with the designation number PTA-13450. In certain embodiments of this aspect, the isolated antibody or antigen binding fragment thereof comprises a VL domain that is at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, or at least 98%, identical to the VL domain of the antibody produced by the hybridoma deposited at the ATCC with the designation number PTA-13450.

In all of the above five aspects, the antibody or antigen binding fragment thereof further: (i) inhibits secretion of type I interferons and/or type III interferons in addition to other cytokines and chemokines from plasmacytoid dendritic cells; or (ii) induces or enhances depletion of plasmacytoid dendritic cells in vitro. In some embodiments of the above five aspects, the antibody downregulates CD32a and/or CD62L on a pDC (relative to a pDC that is not contacted with an anti-BDCA2 antibody). In certain embodiments, the antibody mediates internalization of BDCA2 from the surface of pDCs. In some embodiments of the above five aspects, the antibody or antigen-binding fragment thereof binds to cynomolgus BDCA2 (SEQ ID NO:72) and rhesus BDCA2 (SEQ ID NO:72). In certain embodiments of the above five aspects, the isolated antibody or antigen-binding fragment thereof inhibits secretion or production of type I interferon, interleukin-6 (IL-6), tumor necrosis factor-α (TNF-α), type III interferon, macrophage inflammatory protein-1 (MIP-1)-α/CCL3, MIP-1β/CCL4, chemokine (C—C motif) ligand 5 (CCL5/RANTES), or interferon γ-induced protein-10 (IP-10/CXCL10). In certain embodiments of the above five aspects, the antibody or antigen-binding fragment thereof is a humanized antibody. In some embodiments of the above five aspects, the antibody or antigen-binding fragment thereof is a monoclonal antibody. In some embodiments of the above five aspects, the antibody or antigen-binding fragment thereof is a single chain antibody. In other embodiments of the above five aspects, the antibody or antigen-binding fragment is a polyclonal antibody, a chimeric antibody, an $F_{ab}$ fragment, an $F_{(ab')2}$ fragment, an $F_{ab'}$ fragment, an $F_{sc}$ fragment, an $F_v$ fragment, an scFv, an $sc(Fv)_2$, or a diabody. In some embodiments of the above five aspects, the antibody has an IgG1 heavy chain constant region. In some embodiments of the above five aspects, the antibody has an IgG2 heavy chain constant region. In some embodiments of the above five aspects, the antibody has an IgG4 heavy chain constant region. In some embodiments of the above five aspects, the antibody is a hybrid of the IgG1 and IgG4 heavy chain constant regions.

In certain embodiments, the disclosure provides an isolated cell that produces any of the above-described antibodies or antigen-binding fragments thereof.

In other embodiments, the disclosure provides a pharmaceutical composition comprising any of the above-described antibodies or antigen-binding fragments thereof and a pharmaceutically acceptable carrier. In some embodiments, the pharmaceutical composition comprises any of the above described antibodies or antigen-binding fragments thereof formulated in a composition comprising 10-25 mM citrate, 100-200 mM sodium chloride, and a pH of 5.5-6.5. In certain embodiments the pharmaceutical composition optionally includes Tween-80 (0.01 to 0.3%, e.g., 0.03%). In yet other embodiments, the pharmaceutical composition comprises any of the above described antibodies or antigen-binding fragments thereof formulated in a composition comprising 20 mM sodium citrate, 150 mM sodium chloride, and a pH of 6.0.

In another aspect, the disclosure provides a method for making an anti-BDCA2 antibody. The method involves providing a cell comprising a heavy chain and/or a light chain of the BDCA2 antibody, incubating the cell under conditions that permit the expression of the antibody and isolating the antibody. The method optionally comprises purifying the antibody. In certain embodiments, the cell is a CHO cell. In other embodiments the cell is a 293 cell. In a particular embodiment, the anti-BDCA2 antibody is BIIB059. In one embodiment, the anti-BDCA2 antibody or antigen-binding fragment thereof has a heavy chain and light chain, wherein the heavy chain comprises or consists of the sequence set forth in SEQ ID NO:4, and the light chain comprises or consists of the sequence set forth in SEQ ID NO:3. In another embodiment, the anti-BDCA2 antibody or antigen-binding fragment thereof comprises or consists of a VH CDR1 comprising or consisting of the amino acid sequence of SEQ ID NO:9, a VH CDR2 comprising or consisting of the amino acid sequence of SEQ ID NO:10, and a VH CDR3 comprising or consisting of the amino acid sequence of SEQ ID NO:11. In a further embodiment, the anti-BDCA2 antibody or antigen-binding fragment thereof comprises or consists of a VH CDR1 comprising or consisting of the amino acid sequence of SEQ ID NO:9, a VH CDR2 comprising or consisting of the amino acid sequence of SEQ ID NO:10, a VH CDR3 comprising or consisting of the amino acid sequence of SEQ ID NO:11, a VL CDR1 comprising or consisting of the amino acid sequence of SEQ ID NO:5, a VL CDR2 comprising or consisting of the amino acid sequence of SEQ ID NO:6, and a VL CDR3 comprising or consisting of the amino acid sequence of SEQ ID NO:7.

In another aspect, the disclosure provides a method for detecting the presence of a plasmacytoid dendritic cell in a tissue. The method comprises contacting the tissue with an anti-BDCA2 antibody. In certain embodiments, the tissue is a skin biopsy from a subject having systemic lupus erythematosus. In certain embodiments, the tissue is a skin biopsy from a subject having scleroderma. In certain embodiments, the tissue is a skin biopsy from a subject having morphea. In certain embodiments, the tissue is a skin biopsy from a subject having rheumatoid arthritis. In certain embodiments, the tissue is a skin biopsy from a subject having psoriasis. In certain embodiments, the tissue is a skin biopsy from a subject having dermatomyositis. In certain embodiments, the tissue is a skin biopsy from a subject having polymyositis. In certain embodiments, the tissue is a skin biopsy from a subject having inflammatory bowel disease. In specific embodiments, the systemic lupus erythematosus is cutaneous lupus, discoid lupus, or lupus nephritis. The anti-BDCA2 antibody or antigen-binding fragment thereof may be labeled, e.g., with a fluorophore (e.g., Alexa Fluor 647). In certain embodiments, the anti-BDCA2 antibody is BIIB059. In other embodiments, the anti-BDCA2 antibody is clone 124B3.13 (Dendritics). In certain embodiments, the method further comprises contacting the tissue with an anti-CD123 antibody.

In another aspect, the disclosure provides a method of inducing death of a plasmacytoid dendritic cell in a subject in need thereof. The method involves administering to the subject, or contacting a plasmacytoid dendritic cell that expresses BDCA2 with, any of the antibodies or antigen-binding fragments thereof described herein.

In another aspect, the disclosure features a method of reducing production of inflammatory cytokines or chemokines by a plasmacytoid dendritic cell in a subject in need thereof. The method comprises administering to the subject, or contacting a plasmacytoid dendritic cell that expresses BDCA2 with, an effective amount of any of the antibodies or antigen-binding fragments thereof described herein. In certain embodiments, the inflammatory cytokines or chemokines are selected from the group consisting of: type I interferon, IL-6, or TNF-α, type III interferon, MIP-1α/CCL3, MIP-1β/CCL4, CCL5/RANTES, and IP-10/CXCL10.

In another aspect, the disclosure features a method of downregulating expression of CD32a on the surface of a plasmacytoid dendritic cell. The method comprises contacting the plasmacytoid dendritic cell with an anti-BDCA2 antibody described herein. In certain embodiments, the anti-BDCA2 antibody has an IgG1 heavy chain constant region. In some embodiments, the antibody has an IgG2 heavy chain constant region. In some embodiments, the antibody has an IgG4 heavy chain constant region. In some embodiments, the antibody is a hybrid of the IgG1 and IgG4 heavy chain constant regions. In certain embodiments, the antibody is aglycosylated. In a specific embodiment, the antibody is an aglycosylated hybrid of the IgG1 and IgG4 heavy chain constant regions.

In another aspect, the disclosure features a method of downregulating expression of CD32a (FcγRIIa) on the surface of a plasmacytoid dendritic cell in a human subject in need thereof. The method comprises administering to the human subject an effective amount of an anti-BDCA2 antibody described herein. In certain embodiments, the anti-BDCA2 antibody has an IgG1 heavy chain constant region. In some embodiments, the antibody has an IgG2 heavy chain constant region. In some embodiments, the antibody has an IgG4 heavy chain constant region. In some embodiments, the antibody is a hybrid of the IgG1 and IgG4 heavy chain constant regions. In certain embodiments, the antibody is aglycosylated. In a specific embodiment, the antibody is an aglycosylated hybrid of the IgG1 and IgG4 heavy chain constant regions.

In another aspect, the disclosure features a method of inhibiting stimulation of a plasmacytoid dendritic cell by immune complexes in a human subject in need thereof. The method comprises administering to the human subject an effective amount of an anti-BDCA2 antibody described herein. In some embodiments, the administration reduces the level of CD32a on the surface of pDCs. In some embodiments, the subject has Type III hypersensitivity. In one embodiment, the human subject has SLE. In another embodiment, the human subject has rheumatoid arthritis. In yet another embodiment, the subject has Sjögren's syndrome. In certain embodiments, the anti-BDCA2 antibody has an IgG1 heavy chain constant region. In some embodiments, the antibody has an IgG2 heavy chain constant region. In some embodiments, the antibody has an IgG4 heavy chain constant region. In some embodiments, the antibody is a hybrid of the IgG1 and IgG4 heavy chain constant regions.

In another aspect, the disclosure features a method of downregulating expression (or shedding) of CD62L (L-selectin) on the surface of a plasmacytoid dendritic cell in a human subject in need thereof. The method comprises administering to the human subject an effective amount of an anti-BDCA2 antibody or antigen-binding fragment described herein. In specific embodiments, the administration of the anti-BDCA2 antibody or antigen-binding fragment increases the level of one or more metalloproteinases. In certain embodiments, the downregulation of CD62L occurs through cleavage by a metalloproteinase. In certain embodiments, the anti-BDCA2 antibody has an IgG1 heavy chain constant region. In some embodiments of the above five aspects, the antibody has an IgG2 heavy chain constant region. In some embodiments of the above five aspects, the antibody has an IgG4 heavy chain constant region. In some embodiments of the above five aspects, the antibody is a hybrid of the IgG1 and IgG4 heavy chain constant regions.

In a further aspect, the disclosure features a method of treating an inflammatory disorder in a subject in need thereof. The method involves administering to the subject in need thereof an effective amount of any of the anti-BDCA2 antibodies or antigen-binding fragments thereof described herein. In some embodiments, the inflammatory disorder is selected from the group consisting of systemic lupus erythematosus (SLE), cutaneous lupus, discoid lupus, lupus nephritis, rheumatoid arthritis, inflammatory bowel disease, systemic sclerosis, morphea, psoriasis, type I diabetes, dermatomyositis, polymyositis, and Sjogren's disease. In one particular embodiment, the inflammatory disorder is SLE. In another particular embodiment, the inflammatory disorder is discoid lupus. In yet another particular embodiment, the inflammatory disorder is lupus nephritis. In another particular embodiment, the inflammatory disorder is cutaneous lupus. In certain embodiments, the subject has general SLE. In certain embodiments, the subject has moderate SLE. In certain embodiments, the subject has moderate SLE without severe active CNS and/or severe active renal involvement. In certain embodiments, the subject has moderate SLE with severe active CNS and/or severe active renal involvement. In certain embodiments, the subject has cutaneous manifestations of SLE (e.g., malar or discoid rash). In certain embodiments, the subject has severe SLE. In certain embodiments, the subject has severe SLE without severe active CNS and/or severe active renal involvement. In certain embodiments, the subject has severe SLE with severe active CNS and/or severe active renal involvement. Moderate or severe lupus is a staging of lupus (see, e.g., Guidelines for Referral and Management of Systemic Lupus Erythematosus in Adults, *Arthritis & Rheumatism*, 42(9): 1785-1795 (1999); Gladman, Prognosis and treatment of systemic lupus erythematosus, *Curr. Opin. Rheumatol.*, 8:430-437 (1996); Kalunian et al., Definition, classification, activity and damage indices. In: Dubois' lupus eyrthematosus. $5^{th}$ ed., Baltimore: Williams and Wilkins; pp. 19-30 (1997)).

In another aspect, the disclosure features a method of treating an autoimmune disease in a subject in need thereof. The method involves administering to the subject in need thereof an effective amount of any of the anti-BDCA2 antibodies or antigen-binding fragments thereof described herein.

In any of the above aspects related to methods, in certain embodiments, the subject is a human. In any of the above aspects related to methods, in certain embodiments, the anti-BDCA2 antibody or antigen binding fragment is administered in combination with at least one of: an antimalarial (e.g., hydroxychloroquine), a TLR7 signaling inhibitor, a TLR9 signaling inhibitor, or a corticosteroid. In a specific embodiment, the anti-BDCA2 antibody comprises the heavy and light chain CDRs of BIIB059. In one embodiment, the anti-BDCA2 antibody comprises the heavy chain CDR1, CDR2, and CDR3 set forth in SEQ ID NOs. 8, 10, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 89, 91, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 9, 92, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 90, 93, and 94, respectively and light chain CDR1, CDR2, and CDR3 set forth in SEQ ID NOs. 95, 96, and 97, respectively. In certain embodiments, the anti-BDCA2 antibody further comprises an Fc region which binds to CD32a with an EC50 of at least about 7 to 15 µg/mL (e.g., 10, 11, 12 µg/mL). In a specific embodiment, the anti-BDCA2 antibody is BIIB059.

In another aspect, the disclosure features a combination comprising an antimalarial (e.g., hydroxychloroquine) and an anti-BDCA2 antibody or antigen binding fragment thereof. In a specific embodiment, the anti-BDCA2 antibody comprises heavy chain CDRs (or alternate CDRs) of SEQ ID NO:24. In another embodiment, the anti-BDCA2 antibody comprises light chain CDRs (or alternate CDRs) of SEQ ID NO:23. In a specific embodiment, the anti-BDCA2 antibody comprises the heavy and light chain CDRs of BIIB059. In one embodiment, the anti-BDCA2 antibody comprises the heavy chain CDR1, CDR2, and CDR3 set forth in SEQ ID NOs. 8, 10, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 89, 91, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 9, 92, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 90, 93, and 94, respectively and light chain CDR1, CDR2, and CDR3 set forth in SEQ ID NOs. 95, 96, and 97, respectively. In certain embodiments, the anti-BDCA2 antibody further comprises an Fc region which binds to CD32a with an EC50 of at least about 7 to 15 µg/mL (e.g., 9, 10, 11, 12, 13, 14 µg/mL). In a specific embodiment, the anti-BDCA2 antibody is BIIB059.

In another aspect, the disclosure features a combination comprising a TLR7 and/or TLR9 signaling inhibitor and an anti-BDCA2 antibody or antigen binding fragment thereof. In a specific embodiment, the anti-BDCA2 antibody comprises heavy chain CDRs (or alternate CDRs) of SEQ ID NO:24. In another embodiment, the anti-BDCA2 antibody comprises light chain CDRs (or alternate CDRs) of SEQ ID NO:23. In a specific embodiment, the anti-BDCA2 antibody comprises the heavy and light chain CDRs of BIIB059. In one embodiment, the anti-BDCA2 antibody comprises the heavy chain CDR1, CDR2, and CDR3 set forth in SEQ ID NOs. 8, 10, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 89, 91, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 9, 92, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 90, 93, and 94, respectively and light chain CDR1, CDR2, and CDR3 set forth in SEQ ID NOs. 95, 96, and 97, respectively. In certain embodiments, the anti-BDCA2 antibody further comprises an Fc region which binds to CD32a with an EC50 of at least about 7 to 15 µg/mL (e.g., 10, 11, 12 µg/mL). In a specific embodiment, the anti-BDCA2 antibody is BIIB059.

In a further aspect, the disclosure features a combination comprising a corticosteroid and an anti-BDCA2 antibody or antigen binding fragment thereof. In a specific embodiment, the anti-BDCA2 antibody comprises heavy chain CDRs (or alternate CDRs) of SEQ ID NO:24. In another embodiment, the anti-BDCA2 antibody comprises light chain CDRs (or alternate CDRs) of SEQ ID NO:23. In a specific embodiment, the anti-BDCA2 antibody comprises the heavy and light chain CDRs of BIIB059. In one embodiment, the anti-BDCA2 antibody comprises the heavy chain CDR1, CDR2, and CDR3 set forth in SEQ ID NOs. 8, 10, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 89, 91, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 9, 92, and 11, respectively and light chain CDR1, CDR2, and CDR3 set forth in SEQ ID NOs. 5, 6, and 7, respectively. In another embodiment, the anti-BDCA2 antibody comprises the heavy chain CDR1, CDR2, and CDR3 set forth in SEQ ID NOs. 90, 93, and 94, respectively and light chain CDR1, CDR2, and CDR3 set forth in SEQ ID NOs. 95, 96, and 97, respectively. In certain embodiments, the anti-BDCA2 antibody further comprises an Fc region which binds to CD32a with an EC50 of at least about 7 to 15 µg/mL (e.g., 9, 10, 11, 12, 13, 14 µg/mL). In a specific embodiment, the anti-BDCA2 antibody is BIIB059.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 3 is a graph showing hu24F4 Hx/L1 variants binding to cynomolgus BDCA2.

FIG. 13 is a graph showing the results of Octet binding of BIIB059 to human and cynomolgus monkey BDCA2 ectodomains.

FIG. 14 is a graph showing that BIIB059 potently inhibits IFNα from PBMCs stimulated with TLR9 agonist. Each symbol represents $IC_{50}$ from an independent experiment and vertical lines depict the SEM.

FIG. 15A-C provide a series of graphs showing that BIIB059 potently inhibits cytokines and chemokines from whole blood stimulated with TLR9 ligand. FIG. 15A shows inhibition of IFNα using heparinized venous blood from healthy donors. FIG. 15B shows inhibition of IFNα using whole blood from two SLE patients (upper panels) compared to results using whole blood from 2 healthy donors (bottom panels). FIG. 15C provides a series of bar graphs showing that BIIB059 treatment led to inhibition of a large array of cytokines and chemokines.

FIG. 20 is a series of line graphs showing BIIB059 binding to Fcγ receptors.

FIG. 22A-D are a series of graphs showing that BIIB059 mediates cell killing through ADCC. The CHO cell line (EAG2456 T1F2 Clone 34.16.7) was used as the target cell. Expression level of BDCA2 on the surface of CHO cells was determined by FACS using an APC-labeled anti-BDCA2 mAb (clone AC144, Miltenyi). NK cells were used as the effector cells. ADCC was evaluated using the Vybrant Cytotoxicity Assay kit (Invitrogen), following the manufacturer's instructions. The assay detects G6PD from damaged cells based on the G6PD-dependent reduction of resazurin which emits fluorescence at 590 nm after excitation at 530 nm. The ADCC assay depicted in FIG. 22A was performed using high BDCA2 expressing CHO cells (FIG. 22C) while the ADCC assay in FIG. 22B used CHO cells with lower BDCA2 expression (FIG. 22D).

FIG. 24 is a series of graphs used to determine EC50 of BIIB059 binding ("direct") and competitive BIIB059-A647 binding ("indirect") on cynomolgus monkey pDCs. Prior to in vivo injection of BIIB059, blood was drawn from twelve cynomolgus monkeys once a week for three weeks total. Flow cytometry was used to determine the EC50 of BIIB059 binding to BDCA2 on the pDC cell surface ("direct" method), and the amount of available BDCA2 receptor available in the presence of BIIB059 ("indirect" method). Blood was incubated with a six-point titration of BIIB059 at a range of 40-0.04 μg/mL. pDCs were identified by flow cytometry as CD20–CD14–CD123+HLA-DR+, and treated with either an anti-human IgG PE labeled secondary, or BIIB059-A647 labeled at 10 ug/mL. The MFI of PE (open symbols, graphed on the left y-axis) or A647 (closed symbols, graphed on the right y-axis) was calculated in FlowJo software, and graphed using GraphPad Prism software (four-parameter nonlinear regression curve fit of log-transformed data). Representative graphs from four of the twelve cynomolgus monkeys are shown here.

FIG. 25 is a representative graph presenting plateau binding of the anti-BDCA2 antibody BIIB059 to cell surface BDCA2 on pDCs in cynomolgus monkey whole blood. Blood was incubated with a six-point titration of BIIB059 at a range of 40-0.04 μg/mL. pDCs were identified by flow cytometry as CD20–CD14–CD123+HLA-DR+, and treated with an anti-human IgG PE labeled secondary. The MFI of PE was calculated in FlowJo software, and the percent of maximal binding, using the 40 μg/mL point as 100%, was computed. Each line represents one individual cynomolgus monkey, for a total of twelve cynomolgus monkeys, and graphed using GraphPad Prism software (four-parameter nonlinear regression curve fit of log-transformed data). Staining was repeated once a week for three weeks total. Dashed lines demonstrate that a concentration of 10 μg/mL of BIIB059 saturates BDCA2 receptor binding for all cynomolgus monkeys.

FIG. 26A-C addresses the levels of bound BIIB059 and free BDCA2 staining on vehicle treated cynomolgus monkeys. FIG. 26A is a series of FACS histograms showing background PE staining on vehicle treated cynomolgus monkeys. Cynomolgus monkeys 1, 4 and 12 were administered a single IV injection of vehicle control (sodium citrate) at time 0. After 1 hour, whole blood was drawn, and pDCs were identified by flow cytometry as CD20-CD14–CD123+HLA-DR+, and treated with anti-human IgG PE (open histograms) or FACS buffer as PE fluorescence minus one (FMO) control (solid histograms). FIG. 26B is a graph of PE staining on pDCs from blood draws from the three vehicle treated cynomolgus monkeys at the indicated time points. The MFI of PE was calculated in FlowJo software, and graphed using GraphPad Prism software. FIG. 26C is a graph of A647 staining on pDCs from blood draws from the three vehicle treated cynomolgus monkeys at the indicated time points. BIIB059-A647 at 10 μg/mL was added to the blood draws from the three vehicle treated cynomolgus monkeys at each of the indicated time points, and assayed for A647 staining on pDCs. The MFI of A647 was calculated in FlowJo software, and graphed using GraphPad Prism software.

FIG. 27A-C show that bound BIIB059 and BDCA2 receptor are no longer available on pDC cell surface after a single dose of BIIB059 10 mg/kg in cynomolgus monkey. FIG. 27A is a series of FACS histograms showing BIIB059 staining on BIIB059 10 mg/kg treated cynomolgus monkeys. Cynomolgus monkeys 3, 8 and 10 were administered a single IV injection of BIIB059 at 10 mg/kg at time 0. After 1 hour, whole blood was drawn, and pDCs were identified as CD20–CD14–CD123+HLA-DR+, and treated with anti-human IgG PE (open histograms) or FACS buffer as PE FMO control (solid histograms). FIG. 27B is a graph of PE staining on pDCs from blood draws from the three BIIB059 treated cynomolgus monkeys at the indicated time points. The MFI of PE was calculated in FlowJo software, and graphed using GraphPad Prism software. FIG. 27C is a graph of A647 staining on pDCs from blood draws from the three BIIB059 treated cynomolgus monkeys at the indicated time points. BIIB059-A647 at 10 µg/mL was added to the blood draws from the three BIIB059 treated cynomolgus monkeys at each of the indicated time points, and assayed for A647 staining on pDCs. The MFI of A647 was calculated in FlowJo software, and graphed using GraphPad Prism software.

FIG. 28A is a series of FACS histograms showing BIIB059 staining on BIIB059 1 mg/kg treated cynomolgus monkeys. Cynomolgus monkeys 3, 8 and 10 were administered a single IV injection of BIIB059 at 1 mg/kg at time 0. After 1 hour, whole blood was drawn, and pDCs were identified as CD20–CD14–CD123+HLA-DR+, and treated with anti-human IgG PE (open histograms) or FACS buffer as PE FMO control (solid histograms). FIG. 28B is a graph of PE staining on pDCs from blood draws from the three BIIB059 treated cynomolgus monkeys at the indicated time points. The MFI of PE was calculated in FlowJo software, and graphed using GraphPad Prism software. FIG. 28C is a graph of A647 staining on pDCs from blood draws from the three BIIB059 treated cynomolgus monkeys at the indicated time points. BIIB059-A647 at 10 µg/mL was added to the blood draws from the three BIIB059 treated cynomolgus monkeys at each of the indicated time points, and assayed for A647 staining on pDCs. The MFI of A647 was calculated in FlowJo software, and graphed using GraphPad Prism software.

FIG. 29A-C show that bound BIIB059 and BDCA2 receptor are no longer available on pDC cell surface after a single subcutaneous (SC) dose of BIIB059 0.2 mg/kg in cynomolgus monkey. FIG. 29A is a series of FACS histograms showing BIIB059 staining on SC 0.2 mg/kg BIIB059 treated cynomolgus monkeys. Cynomolgus monkeys 4, 6 and 12 were administered a single SC injection of BIIB059 at 0.2 mg/kg at time 0. After 1 hour, whole blood was drawn, and pDCs were identified as CD20⁻CD14⁻CD123⁺HLA-DR⁺, and treated with anti-human IgG PE (open histograms) or FACS buffer as PE FMO control (solid histograms). FIG. 29B is a graph of PE staining on pDCs from blood draws from the three BIIB059 treated cynomolgus monkeys at the indicated time points. The MFI of PE was calculated in FlowJo software, and graphed using GraphPad Prism software. FIG. 29C is a graph of A647 staining on pDCs from blood draws from the three BIIB059 treated cynomolgus monkeys at the indicated time points. BIIB059-A647 at 10 µg/mL was added to the blood draws from the three BIIB059 treated cynomolgus monkeys at each of the indicated time points, and assayed for A647 staining on pDCs. The MFI of A647 was calculated in FlowJo software, and graphed using GraphPad Prism software.

FIG. 30A-C are a series of graphs showing the observed PK/PD correlations for cynomolgus monkeys that received BIIB059 IV at 1 mg/kg, and cynomolgus monkeys that received BIIB059 IV at 10 mg/kg. For each graph in this figure, BIIB059 serum concentration is plotted on the left y-axis (open symbols), and BDCA2 receptor density is plotted on the right y-axis (solid symbols). The accelerated clearance observed in cynomolgus monkey 5 was likely due to immunogenicity to BIIB059.

FIG. 31A-B are a series of graphs showing the observed PK/PD correlations for cynomolgus monkeys that received BIIB059 SC at 0.2 mg/kg. For each graph in this figure, BIIB059 serum concentration is plotted on the left y-axis (open symbols), and BDCA2 receptor density is plotted on the right y-axis (solid symbols).

FIG. 36A shows BIIB059-mediated dose dependent inhibition of TLR9-induced IFNα from one representative whole blood assay out of 12 tested. Each symbol represents the mean and standard deviation (SD) for duplicate wells. FIG. 36B shows IC50 values for BIIB059 inhibition of TLR9-induced IFNα production in whole blood assays compared with PBMC assays. Each symbol represents an individual donor and vertical lines depicts the SD.

FIG. 37 PBMC from healthy human donors were stimulated with 1 µM of the TLR3 ligand (Poly I:C) and treated with concentrations of BIIB059 ranging from 10 µg/mL to 0.5 ng/mL in a total assay volume of 250 µL/well in a 96 well plate. The plates were incubated overnight (18 hours) at 37° C. and 5% CO2. 200 µL of the supernatants were collected for evaluation of IFNα levels by ELISA. Each symbol represents the average IFNα levels produced at each treatment condition. Data from two independent donors are shown. Vertical lines depict the standard deviation (SD).

FIG. 38A shows dose dependent BIIB059-mediated BDCA2 internalization from a representative healthy human donor. Circles represent MFI of 2D6 staining at the various doses of BIIB059. Triangle represents the MFI of 2D6 in presence of the isotype control (maximum staining). Diamond represents the MFI of FMO control (background staining). FIG. 38B shows EC50 of BIIB059-induced BDCA2 internalization on pDCs in whole blood assays from healthy human donors (closed circles; n=10 donors). The average EC50 was 0.017±0.005 µg/mL.

FIG. 39 is a graphical depiction of mean fluorescence intensity (MFI) values of 2D6-FITC staining of gated CD14−CD20−HLA-DR+CD123+pDCs. Isotype (iso) represents the maximum staining, FMO (fluorescence minus one control) consisted of the FACS staining cocktail minus 2D6-FITC represent background staining. Shown in this figure is a representative experiment of 4 independent experiments performed.

FIG. 44A is a histogram from a representative experiment of whole blood treated with 10 µg/mL of BIIB059 (tinted histogram), 10 µg/mL isotype control (dotted line) or whole blood stimulated with the TLR9 ligand, CpG-A (solid line). FIG. 44B is a graphical depiction of the effect of BIIB059 treatment of whole blood resulted on shedding of CD62L (closed squares). The open square represents the isotype treatment (10 µg/mL). This figure is representative of 3 independent experiments.

FIG. 45 is a graphical depiction of the surface expression of CD62L was assayed by flow cytometry. CD62L expression was measured in the presence of BIIB059 alone, and with increasing concentrations of GM6001 (circles). The open square represents the isotype treated control (10 µg/mL). Inverted triangle represents BIIB059 treated DMSO control. This figure is representative of 2 independent experiments.

FIG. 58 is a schematic representation of the Cynomolgus Monkey PK/PD Experimental Design. Nine Cynomolgus monkeys completed the intravenous (IV) dose study. Cynomolgus monkeys were bled before and after IV administration of vehicle, 1 mg/kg BIIB059, or 10 mg/kg BIIB059 according to the bleeding schedule shown. Following the completion of this study, 3 cynomolgus monkeys went on to complete a subcutaneous (SC) dose study, where they received a single SC injection of 0.2 mg/kg BIIB059. At each bleeding time point, a whole blood assay was performed where whole blood from the cynomolgus monkeys was diluted 1:4 with complete RPMI 1640 and stimulated with CPG-A to a final concentration of 200 µg/ml in a 96 well round bottom tissue culture plate and incubated at 37° C. 5% CO2 for 18-20 hours. At the end of the culture, the stimulated whole blood was centrifuged to harvest serum. In the MxA bioassay, A549 cells were stimulated with the harvested serum for 19-20 hours at 37° C. 5% CO2 to induce MxA protein. After 20 hours, A549 cells were lysed and a sandwich ELISA was performed to detect concentrations of MxA protein. IFNα levels (units/mL) were back calculated from a standard curve generated by treating A549 cells with increasing doses of rIFNα.

FIG. 61 is a graphical depiction of the decreased TLR9-induced IFNα production in an ex vivo Whole Blood Assay from cynomolgus monkeys treated subcutaneously with BIIB059. Whole blood from cynomolgus monkeys treated with a single subcutaneous dose of 0.2 mg/kg BIIB059 was diluted 1:4 with complete RPMI 1640 and stimulated with CPG-A (2216) to a final concentration of 200 μg/ml in a 96 well round bottom tissue culture plate and incubated at 37° C. 5% CO2 for 18-20 hours. At the end of the culture, the stimulated whole blood was centrifuged to harvest serum. A549 cells were stimulated with the harvested serum for 19-20 hours at 37° C. 5% CO2 to induce MxA protein. After 20 hours, A549 cells were lysed and a sandwich ELISA was performed to detect concentrations of MxA protein. IFNα levels (units/mL) were back calculated from a standard curve generated by treating A549 cells with increasing doses of rIFNα. A one-way analysis of variance (ANOVA) with random effects was fit to log 10 values of the calculated concentrations of IFNα. IFNα values are plotted (on log 10 scale) versus day of bleed for each animal. Vertical lines denote groupings of bleed days into pre-dose, post-dose up to 33 days, and post-dose greater than 33-days. Bleed days later than day 33 were not used in the analysis. The model-based estimates of geometric mean IFNα values are represented by thick black horizontal lines within the pre- and post-dose regions of each panel. Graph and statistical analysis were calculated using the R language for statistical computing.

DETAILED DESCRIPTION

BIIB059 is an exemplary monoclonal antibody that specifically binds to human BDCA2. The anti-BDCA2 antibodies described herein inhibit pDC production and/or secretion of inflammatory cytokines and chemokines. Furthermore, anti-BDCA2 antibodies described herein can downregulate levels of CD32a and/or CD62L on the surface of pDCs. Also, the anti-BDCA2 antibodies of this disclosure can mediate internalization of BDCA2 from the surface of pDCs. In addition, the anti-BDCA2 antibodies described herein can be used to deplete pDCs by ADCC or CDC and can be used to treat or prevent immunological disorders such as inflammatory and autoimmune conditions. This disclosure also shows that combining an antimalarial with an anti-BDCA2 antibody described herein can yield improved effects compared to treatment with either agent alone.

BDCA2

Figure 1:
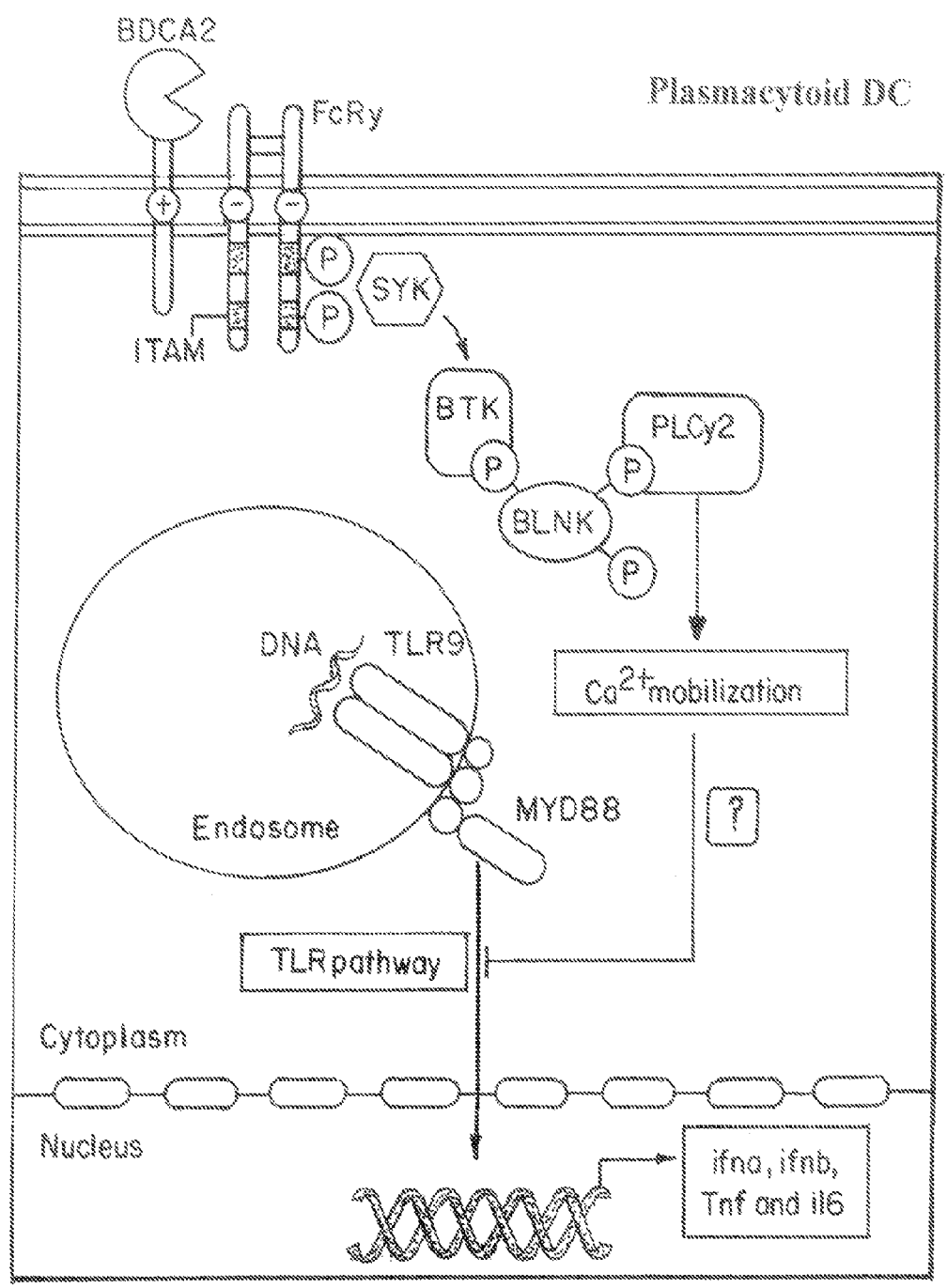
FIG. 1 is a schematic depiction of BDCA2 signaling in a plasmacytoid dendritic cell (see, Geijtenbeek et al., *Nature Reviews Immunology*, 9:465-479 (2009)).

BDCA2 is a type II C-type lectin that is specifically expressed on pDCs. BDCA2 consists of a single extracellular carbohydrate recognition domain (CRD) at its C-terminus, a transmembrane region, and a short cytoplasmic tail at its N-terminus that does not harbor a signaling motif. BDCA2 transmits intracellular signals through an associated transmembrane adaptor, FcεRIγ (see FIG. 1). Antibody-mediated ligation of BDCA2 leads to recruitment of spleen tyrosine kinase (SYK) to phosphorylated immunoreceptor tyrosine-based activation motif (ITAM) of FcεRIγ. Syk activation leads to the activation of B cell linker (Blnk), Bruton's tyrosine kinase (BTK), and phospholipase Cγ2 (PLCγ2), leading to Ca2+ mobilization.

The amino acid sequence of the human BDCA2 protein (GenBank® Accession No. NP_569708.1) is shown below (the transmembrane domain is italicized; the ectodomain is underlined).

```
                                            (SEQ ID NO: 1)
  1 MVPEEEPQDR EKGLWWFQLK VWSMAVVSIL LLSVCFTVSS

VVPHNFMYSK

51 TVKRLSKLRE YQQYHPSLTC VMEGKDIEDW SCCPTPWTSF

QSSCYFISTG

101 MQSWTKSQKN CSVMGADLVV INTREEQDFI IQNLKRNSSY

FLGLSDPGGR

151 RHWQWVDQTP YNENVTFWHS GEPNNLDERC AIINFRSSEE

WGWNDIHCHV

201 PQKSICKMKK IYI*
```

The amino acid sequence of the human FcεRIγ (GenBank® Accession No. NP_004097.1) is shown below.

```
                                            (SEQ ID NO: 2)
  1 MIPAVVLLLL LLVEQAAALG EPQLCYILDA ILFLYGIVLT

LLYCRLKIQV

51 RKAAITSYEK SDGVYTGLST RNQETYETLK HEKPPQ*
```

The closest rat BDCA2 homolog, rat Clec4b2 (GenBank® Accession No. NM_001005896), shares only 51.0% identity with human BDCA2. In contrast, the cynomolgus and rhesus monkey BDCA2 share 90.6% identity with human BDCA2. In addition, cynomolgus and rhesus monkey FcεRIγ protein sequence, which are identical to each other, shares 98.9% identity with human FcεRIγ protein.

The human, cynomolgus, and rhesus monkey BDCA2 proteins can be used as immunogens to prepare anti-BDCA2 antibodies. To prepare human anti-BDCA2 antibodies, the human BDCA2 protein can be used as the immunogen. Anti-human BDCA2 antibodies can then be screened to identify antibodies having one or more of the features described herein (e.g., reducing production/secretion of one or more of type I or type III interferons, IL-6, TNF-α, MIP-1-α, MIP-1β, CCL5, and IP-10/CXCL10; depleting pDCs; competing for binding to the extracellular domain of BDCA2 with BIIB059; selectively binding the ectodomain of human, cynomolgus and rhesus BDCA2 but not binding rat Clec4b2; inhibition of disease development in a human psoriatic xenograft model).

Anti-BDCA2 Antibodies

This disclosure includes the sequences of a monoclonal antibody, BIIB059, which binds to human, cynomolgus, and rhesus BDCA2, but not to rat Clec4b2. BIIB059 does not bind to or does not show significant binding to BDCA2 from phylogenetic species below primates.

BIIB059

BIIB059 is a humanized IgG1 antibody that specifically recognizes BDCA2 on the surface of plasmacytoid dendritic cells. It was derived from a murine antibody (24F4) that binds BDCA2 as follows. A plasmid encoding full-length human BDCA2 was injected into mice with a gene gun. Splenocytes from this mouse were fused to myeloma cells and the resulting hybridoma produced the 24F4 antibody. The 24F4 antibody was engineered into a wild-type human IgG1 framework to maintain full effector function. The predicted amino acid sequences of the mature BIIB059 heavy and light chains are shown below. Complementarity-determining regions (CDRs) 1, 2, and 3 of the variable light chain (VL) and the variable heavy chain (VH) are shown in that order from N to the C-terminus of the mature VL and VH sequences and are both underlined and boldened. An antibody consisting of the mature heavy chain (SEQ ID NO: 4) and the mature light chain (SEQ ID NO: 3) listed below is termed BIIB059.

Mature BIIB059 Light Chain (LC)

```
                                           (SEQ ID NO: 3)
DIQLTQSPSS LSASVGDRVT ITCKASQSVD YDGDSYMNWY

QQKPGKAPKL LIYAASTLES GVPSRFSGSG SGTDFTLTIS

SLQPEDFATY YCQQANEDPR TFGQGTKVEI KRTVAAPSVF

IFPPSDEQLK SGTASVVCLL NNFYPREAKV QWKVDNALQS

GNSQESVTEQ DSKDSTYSLS STLTLSKADY EKHKVYACEV

THQGLSSPVT KSFNRGEC
```

Mature BIIB059 Heavy Chain (HC)

```
                                           (SEQ ID NO: 4)
DVQLVESGGG LVKPGGSLRL SCAASGFTFS TYTMSWVRQA

PGKGLEWVAT ISPGDSFGYY YPDSVQGRFT ISRDNAKNSL

YLQMNSLRAE DTAVYYCTRD IYYNYGAWFA YWGQGTLVTV

SSASTKGPSV FPLAPSSKST SGGTAALGCL VKDYFPEPVT

VSWNSGALTS GVHTFPAVLQ SSGLYSLSSV VTVPSSSLGT
```

```
-continued
QTYICNVNHK PSNTKVDKKV EPKSCDKTHT CPPCPAPELL

GGPSVFLFPP KPKDTLMISR TPEVTCVVVD VSHEDPEVKF

NWYVDGVEVH NAKTKPREEQ YNSTYRVVSV LTVLHQDWLN

GKEYKCKVSN KALPAPIEKT ISKAKGQPRE PQVYTLPPSR

DELTKNQVSL TCLVKGFYPS DIAVEWESNG QPENNYKTTP

PVLDSDGSFF LYSKLTVDKS RWQQGNVFSC SVMHEALHNH

YTQKSLSLSP G
```

The variable light chain (VL) of BIIB059 has the following amino acid sequence:

```
                                           (SEQ ID NO: 23)
DIQLTQSPSS LSASVGDRVT ITCKASQSVD YDGDSYMNWY

QQKPGKAPKL LIYAASTLES GVPSRFSGSG SGTDFTLTIS

SLQPEDFATY YCQQANEDPR TFGQGTKVEI K
```

The variable heavy chain (VH) of BIIB059 has the following amino acid sequence:

```
                                           (SEQ ID NO: 24)
DVQLVESGGG LVKPGGSLRL SCAASGFTFS TYTMSWVRQA

PGKGLEWVAT ISPGDSFGYY YPDSVQGRFT ISRDNAKNSL

YLQMNSLRAE DTAVYYCTRD IYYNYGAWFA YWGQGTLVTV SS
```

The amino acid sequences of VL CDRs of BII059 are listed below:

```
                                           (SEQ ID NO: 5)
    VL CDR1: KASQSVDYDGDSYMN;

(SEQ ID NO: 6)
    VL CDR2: AASTLES;
    and (SEQ ID NO: 7)
    VL CDR3: QQANEDPRT.
```

The amino acid sequences of the VH CDRs of BII059 are listed below:

```
                                           (SEQ ID NO: 8)
    VH CDR1: TYTMS (Kabat CDR1) or (SEQ ID NO: 9)
    GFTFSTYTMS (enhanced Chothia/AbM CDR1);

(SEQ ID NO: 10)
    VH CDR2: TISPGDSFGYYYPDSVQG;

(SEQ ID NO: 11)
    VH CDR3: DIYYNYGAWFAY
```

As indicated above, the enhanced Chothia/AbM CDR definition of the VH CDR1 is 5 amino acids longer than the Kabat definition of this CDR. The five additional amino acids of the enhanced Chothia/AbM VH CDR1 are GFTFS (SEQ ID NO:12).

The anti-BDCA2 antibodies of this disclosure can also comprise "alternate CDRs" of BIIB059. By "alternate" CDRs are meant CDRs (CDR1, CDR2, and CDR3) defined according to any one of the Chothia, from Abysis, enhanced Chothia/AbM CDR, or the contact definitions. These alternate CDRs can be obtained, e.g., by using the AbYsis database (www.bioinf.org.uk/abysis/sequence_input/key_annotation/key_annotation.cgi). The amino acid sequences of "alternate" CDRs 1, 2, and 3 of the heavy chain variable region and the light chain variable region of BIIB059 are compared with the CDRs defined according to Kabat in the Table below.

includes a human Fc region that binds FcγRII (CD32a) with an EC50 of 10 µg/mL. In certain embodiments, the antibody includes a human Fc region that binds FcγRIIa (CD32a) with an EC50 of 11 µg/mL. In certain embodiments, the antibody includes a human Fc region that binds FcγRIIa (CD32a) with an EC50 of 12 µg/mL. Table 1 provides a list of the properties of the BIIB059 antibody.

| Domain | Kabat | Chothia, from Abysis | Enhanced Chothia/AbM | Contact |
|---|---|---|---|---|
| VH CDR1 | TYTMS (SEQ ID NO: 8) | GFTFSTY (SEQ ID NO: 89) | GFTFSTYTMS (SEQ ID NO: 9) | STYTMS (SEQ ID NO: 90) |
| VH CDR2 | TISPGDSFGYYYPDSVQG (SEQ ID NO: 10) | SPGDSFG (SEQ ID NO: 91) | TISPGDSFGYY (SEQ ID NO: 92) | WVATISPGDSFGYY (SEQ ID NO: 93) |
| VH CDR3 | DIYYNYGAWFAY (SEQ ID NO: 11) | DIYYNYGAWFAY (SEQ ID NO: 11) | DIYYNYGAWFAY (SEQ ID NO: 11) | TRDIYYNYGAWFA (SEQ ID NO: 94) |
| VL CDR1 | KASQSVDYDGDSYMN (SEQ ID NO: 5) | KASQSVDYDGDSYMN (SEQ ID NO: 5) | KASQSVDYDGDSYMN (SEQ ID NO: 5) | DYDGDSYMNWY (SEQ ID NO: 95) |
| VL CDR2 | AASTLES (SEQ ID NO: 6) | AASTLES (SEQ ID NO: 6) | AASTLES (SEQ ID NO: 6) | LLIYAASTLE (SEQ ID NO: 96) |
| VL CDR3 | QQANEDPRT (SEQ ID NO: 7) | QQANEDPRT (SEQ ID NO: 7) | QQANEDPRT (SEQ ID NO: 7) | QQANEDPR (SEQ ID NO: 97) |

The anti-BDCA2 antibodies can encompass the heavy chain and light chain CDR 1, CDR2, and CDR3 according to the Kabat definition, the Chothia from Abysis definition, the enhanced Chothia/AbM CDR definition, or the contact definition. These antibodies can have, e.g., 1, 2 or 3 substitutions within one or more (i.e., 1, 2, 3, 4, 5 or 6) of the CDRs. These antibodies (i) bind human or cynomolgus monkey BDCA2 but do not significantly bind BDCA2 from phylogenetic species below primates; and/or (ii) inhibit TLR7/TLR9-induced type I interferon and other cytokine or chemokine production by human pDCs; and/or (iii) mediate internalization of BDCA2 from the surface of pDCs; and/or (iv) downregulate CD32a and/or CD62L from the surface of pDCs; and/or (v) deplete pDCs in vitro by ADCC or CDC.

Human IgG antibodies are tetrameric molecules containing two light chains and two heavy chains. Each light chain of BIIB059 is covalently linked to a heavy chain through an interchain disulfide bond (LC Cys 218-HC Cys 225) and the heavy chains are paired to each other by two interchain disulfides (HC Cys 231-Cys 231 and Cys 234-Cys 234). All other cysteines form intramolecular disulfides that stabilize the constant and variable domains.

In certain embodiments, the anti-BDCA2 antibodies include a human heavy chain and light chain constant region. In certain embodiments, the heavy chain constant region comprises a CH1 domain and a hinge region. In some embodiments, the heavy chain constant region comprises a CH3 domain. If the heavy chain constant region includes substitutions, such substitutions modify the properties of the antibody (e.g., increase or decrease one or more of: Fc receptor binding, antibody glycosylation, the number of cysteine residues, effector cell function, or complement function). In certain embodiments, the antibody is an IgG antibody. In specific embodiments, the antibody is selected from the group consisting of IgG1, IgG2, IgG3, and IgG4. In certain embodiments, the antibody includes a human Fc region that binds FcγRIIa (CD32a) with an affinity of 7 µg/mL to 15 µg/mL. In certain embodiments, the antibody

TABLE 1

| | |
|---|---|
| Molecular Mass (estimated/deglycosylated actual) | 146,348.2 Da/146,352 Da |
| Molecular Mass (deglycosylated heavy chain, expected/actual) | 49,425.8 Da/49,424 Da |
| Molecular Mass (light chain, expected/actual) | 23,764.3 Da/23,765 Da |
| Molecular Mass (SDS-PAGE) | 150,000 Da |
| Extinction Coefficient (1 mg/mL) | 1.46 mL/mg/cm at 280 nm |
| Absorbance Maximum | 275 nm |
| pI (calculated) | 7.26 |
| pI (IEF) | Major component 7.01<br>Minor components 6.90, 6.81, 6.78, 7.09 |
| $EC_{50}$ human BDCA2 (FACS) | 7 nM |
| $EC_{50}$ cyno BDCA2 (FACS) | 7 nM |
| Tm by DSC: | CH2: 72° C.<br>Fab: 68.6° C., 75.9° C.<br>CH3: 85° C. |
| Free SH | 0.4/mole (1.1%) |
| Glycation | 0.1 mole/mole BIIB059 |
| N-linked glycosylation RRS2 | G0 (69.2%)<br>G1 (23.9%)<br>G2 (2.2%)<br>Aglycosylated (1%) |
| Exemplary Formulation Buffer | 20 mM sodium citrate, 150 mM NaCl pH 6.0 |
| Solubility in formulation buffer | >150 mg/mL |
| Aggregation (SEC) | 0.2% |
| Aggregation (AUC) | 0.3% (primarily dimers) |
| $T_{1/2}$ | 7.3 days in rats |
| Endotoxin | <0.05 EU/mg protein |

BIIB059 exhibits suitable physicochemical properties for an antibody therapeutic. This antibody shows low levels of aggregation. The wild-type IgG1 framework contains a single N-linked glycosylation site in the molecule and BIIB059 and binds to Fc receptors with affinities typical of this class of molecules. The calculated pI of 7.26 is somewhat low for an antibody. Charge heterogeneity detected in BIIB059 suggests that a significant fraction of BIIB059 contains modifications. Glycation levels of up to about 10% detected in purified batches of BIIB059 account at least in part for this charge heterogeneity. The folding Tm for the BIIB059 is at the lower end of typical values observed for antibodies, while those for the CH2 and CH3 domains are typical for a fully glycosylated IgG1 mAb. Based on differential scanning fluorimetry and viscosity measurements the BIIB059 can be formulated, e.g., at 50 mg/mL in 20 mM sodium citrate, 150 mM NaCl, pH 6.0. This antibody can also be formulated at much higher concentrations, such as 150-300 mg/mL (e.g., 150 mg/mL, 200 mg/mL, 250 mg/mL, 300 mg/mL).

BIIB059 is a fully humanized, Fc function-competent IgG1 mAb that exhibits high affinity for BDCA2 and binds equally well to native human and cynomolgus BDCA2. BIIB059 is a potent inhibitor of all TLR9-induced type I IFNs as well as other cytokines and chemokines by pDCs. BIIB059 is equally potent at inhibiting TLR9-induced type I interferon by pDCs from healthy human donors and SLE patients. BIIB059 specifically inhibits TLR9-induced type I IFN by pDCs and does not impact IFN production by other cell types triggered with different TLR ligand. BIIB059 leads to rapid internalization of BDCA2 from the cell surface. Upon stimulation, BDCA2 colocalize with TLR9 in the endosomal/lysosomal compartment which appears to be necessary for its inhibition of TLR9 signaling. BIIB059 was found to cause CD62L shedding from the surface of human pDCs which might impact their homing to target organs. In vitro antibody-dependent cell-mediated cytotoxicity (ADCC) and complement-dependent cytotoxicity (CDC) studies suggest that BIIB059 may have cell depletion activity in cell lines overexpressing BDCA2. However, the fact that BIIB059 leads to rapid and complete internalization of BDCA2 from the surface of pDCs makes it less likely that BIIB059 would effect sustained depletion pDCs in vivo. Combination of BIIB059 and hydroxychloroquine (HCQ) led to an additive inhibitory effect on TLR7 and TLR9-induced IFNα production by PBMC from healthy human donors. These data highlight the potential additive therapeutic benefit of BIIB059 when administered with antimalarial compounds such as HCQ.

Antibodies, such as BIIB059, can be made, for example, by preparing and expressing synthetic genes that encode the recited amino acid sequences or by mutating human germline genes to provide a gene that encodes the recited amino acid sequences. Moreover, this antibody and other anti-BDCA2 antibodies can be obtained, e.g., using one or more of the following methods.

Methods of Obtaining Anti-BDCA2 Antibodies

Numerous methods are available for obtaining antibodies, particularly human antibodies. One exemplary method includes screening protein expression libraries, e.g., phage or ribosome display libraries. Phage display is described, for example, in U.S. Pat. No. 5,223,409; Smith, Science 228: 1315-1317 (1985); WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667, 988; and 5,885,793.

In addition to the use of display libraries, other methods can be used to obtain a BDCA2-binding antibody. For example, the BDCA2 protein or a peptide thereof can be used as an antigen in a non-human animal, e.g., a rodent, e.g., a mouse, hamster, or rat. In addition, cells transfected with a cDNA encoding BDCA2 can be injected into a non-human animal as a means of producing antibodies that effectively bind the cell surface BDCA2 protein.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al., Nature Genetics 7:13-21 (1994), U.S. 2003-0070185, WO 96/34096, and WO 96/33735.

In another embodiment, a monoclonal antibody is obtained from the non-human animal, and then modified, e.g., humanized or deimmunized. Winter describes an exemplary CDR-grafting method that may be used to prepare humanized antibodies described herein (U.S. Pat. No. 5,225, 539). All or some of the CDRs of a particular human antibody may be replaced with at least a portion of a non-human antibody. It may only be necessary to replace the CDRs required for binding or binding determinants of such CDRs to arrive at a useful humanized antibody that binds to BDCA2.

Humanized antibodies can be generated by replacing sequences of the Fv variable region that are not directly involved in antigen binding with equivalent sequences from human Fv variable regions. General methods for generating humanized antibodies are provided by Morrison, S. L., Science, 229:1202-1207 (1985), by Oi et al., BioTechniques, 4:214 (1986), and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, I. A. et al., J. Mol. Biol., 227:776-798 (1992); Cook, G. P. et al., Immunol. Today, 16: 237-242 (1995); Chothia, D. et al., J. Mol. Bio. 227:799-817 (1992); and Tomlinson et al., EMBO J., 14:4628-4638 (1995). The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

A non-human BDCA2-binding antibody may also be modified by specific deletion of human T cell epitopes or "deimmunization" by the methods disclosed in WO 98/52976 and WO 00/34317. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made. Often, but not exclusively, an amino acid common to a position in human germline antibody sequences may be used. After the deimmunizing changes are identified, nucleic acids encoding $V_H$ and $V_L$ can be constructed by mutagenesis or other synthetic methods (e.g., de novo synthesis, cassette replacement, and so forth). A mutagenized variable sequence can, optionally, be fused to a human constant region, e.g., human IgG1 or kappa constant regions.

In some cases, a potential T cell epitope will include residues known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs can be eliminated by substitutions outside the CDRs. In some cases, an alteration within a CDR is the only option, and thus variants with and without this substitution can be tested. In other cases, the substitution required to remove a potential T cell epitope is at a residue position within the framework that might be critical for antibody binding. In these cases, variants with and without this substitution are tested. Thus, in some cases several variant deimmunized heavy and light chain variable regions are designed and various heavy/light chain combinations are tested to identify the optimal deimmunized antibody. The choice of the final deimmunized antibody can then be made by considering the binding affinity of the different variants in conjunction with the extent of deimmunization, particularly, the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693,762; 5,693,761; 5,585,089; 5,530,101; and 6,407,213; Tempest et al. (1991) *Biotechnology* 9:266-271. Still another method is termed "humaneering" and is described, for example, in U.S. 2005-008625.

The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237 (based on Kabat numbering). Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. Antibodies may also have mutations that stabilize the disulfide bond between the two heavy chains of an immunoglobulin, such as mutations in the hinge region of IgG4, as disclosed in the art (e.g., Angal et al. (1993) *Mol. Immunol.* 30:105-08). See also, e.g., U.S. 2005-0037000.

Affinity Maturation

In one embodiment, an anti-BDCA2 antibody or antigen-binding fragment thereof is modified, e.g., by mutagenesis, to provide a pool of modified antibodies. The modified antibodies are then evaluated to identify one or more antibodies having altered functional properties (e.g., improved binding, improved stability, reduced antigenicity, or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used.

In some implementations, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

Calculations of "sequence identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit. Rev. Biochem.*, 22:259-306. Removal of any carbohydrate moieties present on the antibodies may be accomplished chemically or enzymatically as described in the art (Hakimuddin et al. (1987) *Arch. Biochem. Biophys.*, 259:52; Edge et al. (1981) *Anal. Biochem.*, 118:131; and Thotakura et al. (1987) *Meth. Enzymol.*, 138:350). See, e.g., U.S. Pat. No. 5,869,046 for a modification that increases in vivo half life by providing a salvage receptor binding epitope.

In one embodiment, an antibody has CDR sequences (e.g., a Chothia or Kabat CDR) that differ from those of the BIIB059 monoclonal antibody. CDR sequences that differ from those of the BIIB059 monoclonal antibody include amino acid changes, such as substitutions of 1, 2, 3, or 4 amino acids if a CDR is 5-7 amino acids in length, or substitutions of 1, 2, 3, 4, 5, 6, or 7 of amino acids in the sequence of a CDR if a CDR is 10 amino acids or greater in length. The amino acid that is substituted can have similar charge, hydrophobicity, or stereochemical characteristics. In some embodiments, the amino acid substitution(s) is a conservative substitution. In other embodiments, the amino acid substitution(s) is a non-conservative substitution. Such substitutions are within the ordinary skill of an artisan. The antibody or antibody fragments thereof that contain the substituted CDRs can be screened to identify antibodies having one or more of the features described herein (e.g., reducing production/secretion of type I or type III interferons, IL-6, TNF-α, MIP-1-α/CCL3, MIP-1β/CCL4, CCL5/RANTES, IP-10/CXCL10; depleting pDCs; competing for binding to the extracellular domain of BDCA2 with BIIB059; selectively binding the ectodomain of human, cynomolgus and rhesus BDCA2 but not binding rat Clec4b2 or binding to rat Clec4b2 with a lower binding affinity than to human, cynomolgus or rhesus BDCA2; inhibition of disease development in a human psoriatic xenograft model).

Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al., *J. Immun.*, 147:2657-62 (1991); Morgan et al., *Immunology*, 86:319-24 (1995)), or changing the species from which the constant region is derived.

The anti-BDCA2 antibodies can be in the form of full length antibodies, or in the form of low molecular weight forms (e.g., biologically active antibody fragments or minibodies) of the anti-BDCA2 antibodies, e.g., Fab, Fab', F(ab')$_2$, Fv, Fd, dAb, scFv, and sc(Fv)2. Other anti-BDCA2 antibodies encompassed by this disclosure include single domain antibody (sdAb) containing a single variable chain such as, VH or VL, or a biologically active fragment thereof. See, e.g., Moller et al., *J. Biol. Chem.*, 285(49): 38348-38361 (2010); Harmsen et al., *Appl. Microbiol. Biotechnol.*, 77(1):13-22 (2007); U.S. 2005/0079574 and Davies et al. (1996) *Protein Eng.*, 9(6):531-7. Like a whole antibody, a sdAb is able to bind selectively to a specific antigen. With a molecular weight of only 12-15 kDa, sdAbs are much smaller than common antibodies and even smaller than Fab fragments and single-chain variable fragments.

Provided herein are compositions comprising a mixture of an anti-BDCA2 antibody or antigen-binding fragment thereof and one or more acidic variants thereof, e.g., wherein the amount of acidic variant(s) is less than about 80%, 70%, 60%, 60%, 50%, 40%, 30%, 30%, 20%, 10%, 5% or 1%. Also provided are compositions comprising an anti-BDCA2 antibody or antigen-binding fragment thereof comprising at least one deamidation site, wherein the pH of the composition is from about 5.0 to about 6.5, such that, e.g., at least about 90% of the anti-BDCA2 antibodies are not deamidated (i.e., less than about 10% of the antibodies are deamidated). In certain embodiments, less than about 5%, 3%, 2% or 1% of the antibodies are deamidated. The pH may be from 5.0 to 6.0, such as 5.5 or 6.0. In certain embodiments, the pH of the composition is 5.5, 5.6, 5.7, 5.8, 5.9, 6.0, 6.1, 6.2, 6.3, 6.4 or 6.5.

An "acidic variant" is a variant of a polypeptide of interest which is more acidic (e.g. as determined by cation exchange chromatography) than the polypeptide of interest. An example of an acidic variant is a deamidated variant.

A "deamidated" variant of a polypeptide molecule is a polypeptide wherein one or more asparagine residue(s) of the original polypeptide have been converted to aspartate, i.e. the neutral amide side chain has been converted to a residue with an overall acidic character.

The term "mixture" as used herein in reference to a composition comprising an anti-BDCA2 antibody or antigen-binding fragment thereof, means the presence of both the desired anti-BDCA2 antibody or antigen-binding fragment thereof and one or more acidic variants thereof. The acidic variants may comprise predominantly deamidated anti-BDCA2 antibody, with minor amounts of other acidic variant(s).

In certain embodiments, the binding affinity ($K_D$), on-rate ($K_D$ on) and/or off-rate ($K_D$ off) of the antibody that was mutated to eliminate deamidation is similar to that of the wild-type antibody, e.g., having a difference of less than about 5 fold, 2 fold, 1 fold (100%), 50%, 30%, 20%, 10%, 5%, 3%, 2% or 1%.

In certain embodiments, an anti-BDCA2 antibody or antigen-binding fragment thereof or low molecular weight antibodies thereof bind to BDCA2 on pDCs and inhibit or reduce the production and/or secretion by pDCs of type I and type III IFNs, IL-6, TNF-α, and other inflammatory cytokines and chemokines (e.g., MIP-1α/CCL3, MIP-1β/CCL4, CCL5, and IP-10/CXCL10); and/or depletes pDCs by ADCC or CDC or apoptosis; and/or reduces the severity of symptoms when administered to human patients having one or more of, or animal models of: systemic lupus erythematosus, cutaneous lupus, discoid lupus, lupus nephritis, scleroderma, morphea, rheumatoid arthritis, polymyositis-dermatomyositis, psoriasis, Sjogren's syndrome, vasculitis, and Type I diabetes. In one embodiment, the anti-BDCA2 antibody or antigen-binding fragment thereof or low molecular weight antibodies thereof inhibit disease development in a human psoriatic xenograft model (Nestle et al., *J. Exp. Med.*, 202(1):135-143 (2005)). These features of an anti-BDCA2 antibody or antigen-binding fragment thereof or low molecular weight antibodies thereof can be measured according to the methods described in the Examples as well as by other methods known in the art.

Antibody Fragments

Antibody fragments (e.g., Fab, Fab', F(ab')2, Facb, and Fv) may be prepared by proteolytic digestion of intact antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., *J. Immunol.*, 152:2968-2976 (1994); Better, M. and Horwitz, A. H., *Methods in Enzymology*, 178:476-496 (1989); Plueckthun, A. and Skerra, A., *Methods in Enzymology*, 178:476-496 (1989); Lamoyi, E., *Methods in Enzymology*, 121:652-663 (1989); Rousseaux, J. et al., *Methods in Enzymology*, (1989) 121: 663-669 (1989); and Bird, R. E. et al., *TIBTECH*, 9:132-137 (1991)). Antibody fragments can be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab)2 fragments (Carter et al., *Bio/Technology*, 10:163-167 (1992)). According to another approach, F(ab')2 fragments can be isolated directly from recombinant host cell culture. Fab and F(ab') 2 fragment with increased in vivo half-life comprising a salvage receptor binding epitope residues are described in U.S. Pat. No. 5,869,046.

Minibodies

Minibodies of anti-BDCA2 antibodies include diabodies, single chain (scFv), and single-chain (Fv)2 (sc(Fv)2).

A "diabody" is a bivalent minibody constructed by gene fusion (see, e.g., Holliger, P. et al., *Proc. Natl. Acad. Sci. U.S.A.*, 90:6444-6448 (1993); EP 404,097; WO 93/11161). Diabodies are dimers composed of two polypeptide chains. The VL and VH domain of each polypeptide chain of the diabody are bound by linkers. The number of amino acid residues that constitute a linker can be between 2 to 12 residues (e.g., 3-10 residues or five or about five residues). The linkers of the polypeptides in a diabody are typically too short to allow the VL and VH to bind to each other. Thus, the VL and VH encoded in the same polypeptide chain cannot form a single-chain variable region fragment, but instead form a dimer with a different single-chain variable region fragment. As a result, a diabody has two antigen-binding sites.\

An scFv is a single-chain polypeptide antibody obtained by linking the VH and VL with a linker (see e.g., Huston et al., *Proc. Natl. Acad. Sci. U.S.A.*, 85:5879-5883 (1988); and Plickthun, "The Pharmacology of Monoclonal Antibodies" Vol. 113, Ed Resenburg and Moore, Springer Verlag, New York, pp. 269-315, (1994)). The order of VHs and VLs to be linked is not particularly limited, and they may be arranged in any order. Examples of arrangements include: [VH] linker [VL]; or [VL] linker [VH]. The H chain V region and L chain V region in an scFv may be derived from any anti-BDCA2 antibody or antigen-binding fragment thereof described herein.

An sc(Fv)2 is a minibody in which two VHs and two VLs are linked by a linker to form a single chain (Hudson, et al., *J. Immunol. Methods*, (1999) 231: 177-189 (1999)). An sc(Fv)2 can be prepared, for example, by connecting scFvs with a linker. The sc(Fv)2 of the present invention include antibodies preferably in which two VHs and two VLs are arranged in the order of: VH, VL, VH, and VL ([VH] linker [VL] linker [VH] linker [VL]), beginning from the N terminus of a single-chain polypeptide; however the order of the two VHs and two VLs is not limited to the above arrangement, and they may be arranged in any order. Examples of arrangements are listed below:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

Normally, three linkers are required when four antibody variable regions are linked; the linkers used may be identical or different. There is no particular limitation on the linkers that link the VH and VL regions of the minibodies. In some embodiments, the linker is a peptide linker. Any arbitrary single-chain peptide comprising about three to 25 residues (e.g., 5, 6, 7, 8, 9, 10, 11, 12, 13, 14, 15, 16, 17, 18) can be used as a linker. Examples of such peptide linkers include: Ser; Gly Ser; Gly Gly Ser; Ser Gly Gly; Gly Gly Gly Ser (SEQ ID NO:13); Ser Gly Gly Gly (SEQ ID NO:14); Gly Gly Gly Gly Ser (SEQ ID NO:15); Ser Gly Gly Gly Gly (SEQ ID NO: 16); Gly Gly Gly Gly Gly Ser (SEQ ID NO: 17); Ser Gly Gly Gly Gly Gly (SEQ ID NO: 18); Gly Gly Gly Gly Gly Ser (SEQ ID NO: 19); Ser Gly Gly Gly Gly Gly Gly (SEQ ID NO: 20); (Gly Gly Gly Gly Ser (SEQ ID NO: 21)$_n$, wherein n is an integer of one or more; and (Ser Gly Gly Gly Gly (SEQ ID NO: 22)$_n$, wherein n is an integer of one or more.

In certain embodiments, the linker is a synthetic compound linker (chemical cross-linking agent). Examples of cross-linking agents that are available on the market include N-hydroxysuccinimide (NHS), disuccinimidylsuberate (DSS), bis(sulfosuccinimidyl)suberate (BS3), dithiobis(succinimidylpropionate) (DSP), dithiobis(sulfosuccinimidyl-propionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis [2-(succinimidooxycarbonyloxy)ethyl]sulfone (BSOCOES), and bis[2-(sulfosuccinimidooxycarbonyloxy)ethyl] sulfone (sulfo-BSOCOES).

The amino acid sequence of the VH or VL in the minibodies may include modifications such as substitutions, deletions, additions, and/or insertions. For example, the modification may be in one or more of the CDRs of the anti-BDCA2 antibody or antigen-binding fragment thereof (e.g., BIIB059). In certain embodiments, the modification involves one, two, or three amino acid substitutions in one or more CDRs of the VH and/or VL domain of the anti-BDCA2 minibody. Such substitutions are made to improve the binding and/or functional activity of the anti-BDCA2 minibody. In other embodiments, one, two, or three amino acids of the CDRs of the anti-BDCA2 antibody or antigen-binding fragment thereof (e.g., BIIB059) may be deleted or added as long as there is BDCA2 binding and/or functional activity when VH and VL are associated.

Bispecific Antibodies

Bispecific antibodies are antibodies that have binding specificities for at least two different epitopes. Exemplary bispecific antibodies may bind to two different epitopes of the BDCA2 protein. Other such antibodies may combine a BDCA2 binding site with a binding site for another protein. Bispecific antibodies can be prepared as full length antibodies or low molecular weight forms thereof (e.g., F(ab')$_2$ bispecific antibodies, sc(Fv)2 bispecific antibodies, diabody bispecific antibodies).

Traditional production of full length bispecific antibodies is based on the co-expression of two immunoglobulin heavy chain-light chain pairs, where the two chains have different specificities (Millstein et al., *Nature*, 305:537-539 (1983)). In a different approach, antibody variable domains with the desired binding specificities are fused to immunoglobulin constant domain sequences. DNAs encoding the immunoglobulin heavy chain fusions and, if desired, the immunoglobulin light chain, are inserted into separate expression vectors, and are co-transfected into a suitable host cell. This provides for greater flexibility in adjusting the proportions of the three polypeptide fragments. It is, however, possible to insert the coding sequences for two or all three polypeptide chains into a single expression vector when the expression of at least two polypeptide chains in equal ratios results in high yields.

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods.

The "diabody" technology provides an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites.

Multivalent Antibodies

A multivalent antibody may be internalized (and/or catabolized) faster than a bivalent antibody by a cell expressing an antigen to which the antibodies bind. The antibodies describe herein can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. An exemplary dimerization domain comprises (or consists of) an Fc region or a hinge region. A multivalent antibody can comprise (or consist of) three to about eight (e.g., four) antigen binding sites. The multivalent antibody optionally comprises at least one polypeptide chain (e.g., at least two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is a polypeptide chain of an Fc region, X1 and X2 represent an amino acid or peptide spacer, and n is 0 or 1.

Conjugated Antibodies

The antibodies disclosed herein may be conjugated antibodies which are bound to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g. $^{90}$Y, $^{131}$I) fluorescent substances, luminescent substances, haptens, enzymes, metal chelates, drugs, and toxins (e.g., calcheamicin, *Pseudomonas* exotoxin A, ricin (e.g. deglycosylated ricin A chain)).

In one embodiment, to improve the cytotoxic actions of anti-BDCA2 antibodies and consequently their therapeutic effectiveness, the antibodies are conjugated with highly toxic substances, including radioisotopes and cytotoxic agents. These conjugates can deliver a toxic load selectively to the target site (i.e., cells expressing the antigen recognized by the antibody) while cells that are not recognized by the antibody are spared. In order to minimize toxicity, conjugates are generally engineered based on molecules with a short serum half-life (thus, the use of murine sequences, and IgG3 or IgG4 isotypes).

In certain embodiments, an anti-BDCA2 antibody or antigen-binding fragment thereof are modified with a moiety that improves its stabilization and/or retention in circulation, e.g., in blood, serum, or other tissues, e.g., by at least 1.5, 2, 5, 10, or 50 fold. For example, the anti-BDCA2 antibody or antigen-binding fragment thereof can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the anti-BDCA2 antibody or antigen-binding fragment thereof can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

The above-described conjugated antibodies can be prepared by performing chemical modifications on the antibodies or the lower molecular weight forms thereof described herein. Methods for modifying antibodies are well known in the art (e.g., U.S. Pat. No. 5,057,313 and U.S. Pat. No. 5,156,840).

Methods of Producing Antibodies

Antibodies may be produced in bacterial or eukaryotic cells. Some antibodies, e.g., Fab's, can be produced in bacterial cells, e.g., *E. coli* cells. Antibodies can also be produced in eukaryotic cells such as transformed cell lines (e.g., CHO, 293E, COS). In addition, antibodies (e.g., scFv's) can be expressed in a yeast cell such as *Pichia* (see, e.g., Powers et al., *J Immunol Methods.* 251:123-35 (2001)), *Hanseula*, or *Saccharomyces*. To produce the antibody of interest, a polynucleotide encoding the antibody is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341:544-546 (1989), araB promoter (Better et al., *Science*, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., *J. Bacteriol.,* 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, and NIH3T3 cells, the expression vector includes a promoter necessary for expression in these cells, for example, an SV40 promoter (Mulligan et al., *Nature*, 277:108 (1979)), MMLV-LTR promoter, EF1α promoter (Mizushima et al., *Nucleic Acids Res.*, 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including dhfr⁻ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of an anti-BDCA2 antibody (e.g., BIIB059) is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Antibodies can also be produced by a transgenic animal. For example, U.S. Pat. No. 5,849,992 describes a method of expressing an antibody in the mammary gland of a transgenic mammal A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly. Animals are also provided comprising one or more of the nucleic acids described herein.

The antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Characterization of the Antibodies

The BDCA2-binding properties of the antibodies described herein may be measured by any standard method, e.g., one or more of the following methods: OCTET®, Surface Plasmon Resonance (SPR), BIACORE™ analysis, Enzyme Linked Immunosorbent Assay (ELISA), EIA (enzyme immunoassay), RIA (radioimmunoassay), and Fluorescence Resonance Energy Transfer (FRET).

The binding interaction of a protein of interest (an anti-BDCA2 antibody) and a target (e.g., BDCA2) can be analyzed using the OCTET® systems. In this method, one of several variations of instruments (e.g., OCTET® $QK^e$ and QK), made by the ForteBio company are used to determine protein interactions, binding specificity, and epitope mapping. The OCTET® systems provide an easy way to monitor real-time binding by measuring the changes in polarized light that travels down a custom tip and then back to a sensor.

The binding interaction of a protein of interest (an anti-BDCA2 antibody) and a target (e.g., BDCA2) can be analyzed using Surface Plasmon Resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Information from SPR can be used to provide an accurate and quantitative measure of the equilibrium dissociation constant ($K_d$), and kinetic parameters, including $K_{on}$ and $K_{off}$, for the binding of a biomolecule to a target.

Epitopes can also be directly mapped by assessing the ability of different antibodies to compete with each other for binding to human BDCA2 using BIACORE chromatographic techniques (Pharmacia BIAtechnology Handbook, "Epitope Mapping", Section 6.3.2, (May 1994); see also Johne et al. (1993) *J. Immunol. Methods,* 160:191-198).

When employing an enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Additional general guidance for evaluating antibodies, e.g., Western blots and immunoprecipitation assays, can be found in *Antibodies: A Laboratory Manual*, ed. by Harlow and Lane, Cold Spring Harbor press (1988)).

Deposits

A hybridoma producing the anti-BDCA2 monoclonal antibody designated murine hybridoma BDCA2-1P24F4.1.1.1 has been deposited with the American Type Culture Collection (ATCC) under the terms of the Budapest Treaty on the International Recognition of the Deposit of Microorganisms for the Purpose of Patent Procedure on Jan. 15, 2013, and bears the accession number PTA-13450. Applicants acknowledge their duty to replace the deposits should the depository be unable to furnish a sample when requested due to the condition of the deposit before the end of the term of a patent issued hereon. Applicants also acknowledge their responsibility to notify the ATCC of the issuance of such a patent, at which time the deposit will be made available to the public. Prior to that time, the deposit will be made available to the Commissioner of Patents under the terms of 37 C.F.R. §1.14 and 35 U.S.C. §112.

Antibodies with Altered Effector Function

The interaction of antibodies and antibody-antigen complexes with cells of the immune system triggers a variety of responses, referred to herein as effector functions. Immune-mediated effector functions include two major mechanisms: antibody-dependent cell-mediated cytotoxicity (ADCC) and complement-dependent cytotoxicity (CDC). Both of them are mediated by the constant region of the immunoglobulin protein. The antibody Fc domain is, therefore, the portion that defines interactions with immune effector mechanisms.

IgG antibodies activate effector pathways of the immune system by binding to members of the family of cell surface Fcγ receptors and to C1q of the complement system. Ligation of effector proteins by clustered antibodies triggers a variety of responses, including release of inflammatory cytokines, regulation of antigen production, endocytosis, and cell killing. In some clinical applications these responses are crucial for the efficacy of a monoclonal antibody. In others they provoke unwanted side effects such as inflammation and the elimination of antigen-bearing cells. Accordingly, the present invention further relates to BDCA2-binding proteins, including antibodies, with altered, e.g., increased or reduced effector functions.

Effector function of an anti-BDCA2 antibody of the present invention may be determined using one of many known assays. The anti-BDCA2 antibody's effector function may be increased or reduced relative to a second anti-BDCA2 antibody. In some embodiments, the second anti-BDCA2 antibody may be any antibody that binds BDCA2 specifically. In other embodiments, the second BDCA2-specific antibody may be any of the antibodies of the invention, such as BIIB059. In other embodiments, where the anti-BDCA2 antibody of interest has been modified to increase or reduce effector function, the second anti-BDCA2 antibody may be the unmodified or parental version of the antibody.

Effector functions include antibody-dependent cell-mediated cytotoxicity (ADCC), whereby antibodies bind Fc receptors on cytotoxic T cells, natural killer (NK) cells, or macrophages leading to cell death, and complement-dependent cytotoxicity (CDC), which is cell death induced via activation of the complement cascade (reviewed in Daeron, *Annu. Rev. Immunol.,* 15:203-234 (1997); Ward and Ghetie, *Therapeutic Immunol.,* 2:77-94 (1995); and Ravetch and Kinet, *Annu. Rev. Immunol.* 9:457-492 (1991)). Such effector functions generally require the Fc region to be combined with a binding domain (e.g. an antibody variable domain) and can be assessed using standard assays that are known in the art (see, e.g., WO 05/018572, WO 05/003175, and U.S. Pat. No. 6,242,195).

Effector functions can be avoided by using antibody fragments lacking the Fc domain such as Fab, Fab'2, or single chain Fv. An alternative is to use the IgG4 subtype antibody, which binds to FcγRI but which binds poorly to C1q and FcγRII and RIII. The IgG2 subtype also has reduced binding to Fc receptors, but retains significant binding to the H131 allotype of FcγRIIa and to C1q. Thus, additional changes in the Fc sequence are required to eliminate binding to all the Fc receptors and to C1q.

Several antibody effector functions, including ADCC, are mediated by Fc receptors (FcRs), which bind the Fc region of an antibody. The affinity of an antibody for a particular FcR, and hence the effector activity mediated by the antibody, may be modulated by altering the amino acid sequence and/or post-translational modifications of the Fc and/or constant region of the antibody.

FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16). Both FcγRII and FcγRIII have two types: FcγRIIa (CD32a) and FcγRIIB (CD32b); and FcγRIIIA (CD16a) and FcγRIIIB (CD16b). Because each FcγR subclass is encoded by two or three genes, and alternative RNA splicing leads to multiple transcripts, a broad diversity in FcγR isoforms exists. For example, FcγRII (CD32) includes the isoforms IIa, IIb1, IIb2 IIb3, and IIc.

The binding site on human and murine antibodies for FcγR has been previously mapped to the so-called "lower hinge region" consisting of residues 233-239 (EU index numbering as in Kabat et al., Sequences of Proteins of Immunological Interest, 5th Ed. Public Health Service, National Institutes of Health, Bethesda, Md. (1991), Woof et al., *Molec. Immunol.* 23:319-330 (1986); Duncan et al., *Nature* 332:563 (1988); Canfield and Morrison, *J. Exp. Med.* 173:1483-1491 (1991); Chappel et al., *Proc. Natl. Acad. Sci USA* 88:9036-9040 (1991)). Of residues 233-239, P238 and S239 are among those cited as possibly being involved in binding. Other previously cited areas possibly involved in binding to FcγR are: G316-K338 (human IgG) for human FcγRI (Woof et al., *Mol. Immunol.*, 23:319-330 (1986)); K274-R301 (human IgG1) for human FcγRIII (Sarmay et al., *Molec. Immunol.* 21:43-51 (1984)); and Y407-R416 (human IgG) for human FcγRIII (Gergely et al., *Biochem. Soc. Trans.* 12:739-743 (1984) and Shields et al., *J Biol Chem* 276: 6591-6604 (2001), Lazar G A et al., *Proc Natl Acad Sci* 103: 4005-4010 (2006). These and other stretches or regions of amino acid residues involved in FcR binding may be evident to the skilled artisan from an examination of the crystal structures of Ig-FcR complexes (see, e.g., Sondermann et al. 2000 *Nature* 406(6793):267-73 and Sondermann et al. 2002 *Biochem Soc Trans.* 30(4):481-6). Accordingly, the anti-BDCA2 antibodies of the present invention include modifications of one or more of the aforementioned residues (to increase or decrease effector function as needed).

Another approach for altering monoclonal antibody effector function include mutating amino acids on the surface of the monoclonal antibody that are involved in effector binding interactions (Lund, J., et al. (1991) *J. Immunol.* 147(8): 2657-62; Shields, R. L. et al. (2001) *J Biol. Chem.* 276(9): 6591-604).

Methods of increasing effector function of antibodies are well known in the art (see, e.g., Kelley et al., *Methods Mol. Biol.*, 901:277-93 (2012); Natsume et al., *Drug Des Devel Ther.*, 3:7-16 (2009); U.S. Pat. No. 8,188,231, U.S. Pat. No. 7,960,512). In one embodiment, the BDCA2 antibodies have one, two, three, four, five, six, seven, or more amino acid substitutions at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein the numbering of the residues in the Fc region is that of the EU index as in Kabat. In certain embodiments, the BDCA2 antibodies have one, two, three, four, five, six, seven, or more of the amino acid substitutions selected from the group consisting of: D221K, D221Y, K222E, K222Y, T223E, T223K, H224E, H224Y, T225E, T225K, T225W, P227E, P227G, P227K, P227Y, P228E, P228G, P228K, P228Y, P230A, P230E, P230G, P230Y, A231E, A231G, A231K, A231P, A231Y, P232E, P232G, P232K, P232Y, E233A, E233D, E233F, E233G, E233H, E233I, E233K, E233L, E233M, E233N, E233Q, E233R, E233S, E233T, E233V, E233W, E233Y, L234A, L234D, L234E, L234F, L234G, L234H, L234I, L234K, L234M, L234N, L234P, L234Q, L234R, L234S, L234T, L234V, L234W, L234Y, L235A, L235D, L235E, L235F, L235G, L235H, L235I, L235K, L235M, L235N, L235P, L235Q, L235R, L235S, L235T, L235V, L235W, L235Y, G236A, G236D, G236E, G236F, G236H, G236I, G236K, G236L, G236M, G236N, G236P, G236Q, G236R, G236S, G236T, G236V, G236W, G236Y, G237D, G237E, G237F, G237H, G237I, G237K, G237L, G237M, G237N, G237P, G237Q, G237R, G237S, G237T, G237V, G237W, G237Y, P238D, P238E, P238F, P238G, P238H, P238I, P238K, P238L, P238M, P238N, P238Q, P238R, P238S, P238T, P238V, P238W, P238Y, S239D, S239E, S239F, S239G, S239H, S239I, S239K, S239L, S239M, S239N, S239P, S239Q, S239R, S239T, S239V, S239W, S239Y, V240A, V240I, V240M, V240T, F241D, F241E, F241L, F241R, F241S, F241W, F241Y, F243E, F243H, F243L, F243Q, F243R, F243W, F243Y, P244H, P245A, K246D, K246E, K246H, K246Y, P247G, P247V, D249H, D249Q, D249Y, R255E, R255Y, E258H, E258S, E258Y, T260D, T260E, T260H, T260Y, V262A, V262E, V262F, V262I, V262T, V263A, V263I, V263M, V263T, V264A, V264D, V264E, V264F, V264G, V264H, V264I, V264K, V264L, V264M, V264N, V264P, V264Q, V264R, V264S, V264T, V264W, V264Y, D265F, D265G, D265H, D265I, D265K, D265L, D265M, D265N, D265P, D265Q, D265R, D265S, D265T, D265V, D265W, D265Y, V266A, V266I, V266M, V266T, S267D, S267E, S267F, S267H, S267I, S267K, S267L, S267M, S267N, S267P, S267Q, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, K274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278G, Y278H, Y278I, Y278K, Y278L, Y278M, Y278N, Y278P, Y278Q, Y278R, Y278S, Y278T, Y278V, Y278W, D280G, D280K, D280L, D280P, D280W, G281D, G281E, G281K, G281N, G281P, G281Q, G281Y, V282E, V282G, V282K, V282P, V282Y, E283G, E283H, E283K, E283L, E283P, E283R, E283Y, V284D, V284E, V284L, V284N, V284Q, V284T, V284Y, H285D, H285E, H285K, H285Q, H285W, H285Y, N286E, N286G, N286P, N286Y, K288D, K288E, K288Y, K290D, K290H, K290L, K290N, K290W, P291D, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296A, Y296D, Y296E, Y296G, Y296H, Y296I, Y296K, Y296L, Y296M, Y296N, Y296Q, Y296R, Y296S, Y296T, Y296V, N297D, N297E, N297F, N297G, N297H, N297I, N297K, N297L, N297M, N297P, N297Q, N297R, N297S, N297T, N297V, N297W, N297Y, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320V, K320W, K320Y, K322D, K322F, K322G, K322H, K322I, K322P, K322S, K322T, K322V, K322W, K322Y, V323I, S324D, S324F, S324G, S324H, S324I, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328E, L328F, L328G, L328H, L328I, L328K, L328M, L328N, L328P, L328Q, L328R, L328S, L328T, L328V, L328W, L328Y, P329D, P329E, P329F, P329G, P329H, P329I, P329K, P329L, P329M, P329N, P329Q, P329R, P329S, P329T, P329V, P329W, P329Y, A330E, A330F, A330G, A330H, A330I, A330L, A330M, A330N, A330P, A330R, A330S, A330T, A330V, A330W, A330Y, P331D, P331F, P331H, P331I, P331L, P331M, P331Q, P331R, P331T, P331V, P331W, P331Y, I332A, I332D, I332E, I332F, I332H, I332K, I332L, I332M, I332N, I332P, I332Q, I332R, I332S, I332T, I332V, I332W, I332Y, E333F, E333H, E333I, E333L, E333M, E333P, E333T, E333Y, K334F, K334I, K334L, K334P, K334T, T335D, T335F, T335G, T335H, T335I, T335L, T335M, T335N, T335P, T335R, T335S, T335V, T335W, T335Y, I336E, I336K, I336Y, S337E, S337H, and S337N, wherein the numbering of the residues in the Fc region is that of the EU index as in Kabat. In a particular embodiment, the BDCA2 antibodies comprise one, two, or three of the following mutations: S239D, S239D/I332E, S239D/I332E/A330L, S239D/I332E/G236A, S298A, A330L I332E, E333A, and K334A.

The presence of oligosaccharides—specifically, the N-linked oligosaccharide at asparigine-297 in the CH2 domain of IgG1—is important for binding to FcγR as well as C1q. Reducing the fucose content of antibodies improves effector function (see, e.g., U.S. Pat. No. 8,163,551). In certain embodiments the BDCA2 antibodies have reduced fucosylation and amino acid substitutions that increase effector function (e.g., one, two, or three of the following mutations: S298A; E333A, and K334A). Effector function can also be achieved by preparing and expressing the anti-BDCA2 antibodies described herein in the presence of alpha-mannosidase I inhibitors (e.g., kifunensine) at a concentration of the inhibitor of about 60-200 ng/mL (e.g., 60 ng/mL, 75 ng/mL, 100 ng/mL, 150 g/ml). Antibodies expressed in the presence of alpha-mannosidase I inhibitors contain mainly oligomannose-type glycans and generally demonstrate increased ADCC activity and affinity for FcγRIIIA, but reduced C1q binding.

Anti-BDCA2 antibodies of the present disclosure with increased effector function include antibodies with increased binding affinity for one or more Fc receptors (FcRs) relative to a parent or non-variant anti-BDCA2 antibody. Accordingly, anti-BDCA2 antibodies with increased FcR binding affinity includes anti-BDCA2 antibodies that exhibit a 1.5-fold, 2-fold, 2.5-fold, 3-fold, 4-fold, or 5-fold or higher increase in binding affinity to one or more Fc receptors compared to a parent or non-variant anti-BDCA2 antibody. In some embodiments, an anti-BDCA2 antibody with increased effector function binds to an FcR with about 10-fold greater affinity relative to a parent or non-variant antibody. In other embodiments, an anti-BDCA2 antibody with increased effector function binds to an FcR with about 15-fold greater affinity or with about 20-fold greater affinity relative to a parent or non-variant antibody. The FcR receptor may be one or more of FcγRI (CD64), FcγRII (CD32), and FcγRIII, and isoforms thereof, and FcεR, FcμR, FcδR, and/or an FcαR. In particular embodiments, an anti-BDCA2 antibody with increased effector function exhibits a 1.5-fold, 2-fold, 2.5-fold, 3-fold, 4-fold, or 5-fold or higher increase in binding affinity to FcγRIIa.

To reduce effector function, one can use combinations of different subtype sequence segments (e.g., IgG2 and IgG4 combinations) to give a greater reduction in binding to Fcγ receptors than either subtype alone (Armour et al., *Eur. J. Immunol.*, 29:2613-1624 (1999); *Mol. Immunol.*, 40:585-593 (2003)). In addition, sites of N-linked glycosylation can be removed as a means of reducing effector function. A large number of Fc variants having altered and/or reduced affinities for some or all Fc receptor subtypes (and thus for effector functions) are known in the art. See, e.g., US 2007/0224188; US 2007/0148171; US 2007/0048300; US 2007/0041966; US 2007/0009523; US 2007/0036799; US 2006/0275283; US 2006/0235208; US 2006/0193856; US 2006/0160996; US 2006/0134105; US 2006/0024298; US 2005/0244403; US 2005/0233382; US 2005/0215768; US 2005/0118174; US 2005/0054832; US 2004/0228856; US 2004/132101; US 2003/158389; see also U.S. Pat. Nos. 7,183,387; 6,737,056; 6,538,124; 6,528,624; 6,194,551; 5,624,821; 5,648,260.

Anti-BDCA2 antibodies of the present invention with reduced effector function include antibodies with reduced binding affinity for one or more Fc receptors (FcRs) relative to a parent or non-variant anti-BDCA2 antibody. Accordingly, anti-BDCA2 antibodies with reduced FcR binding affinity includes anti-BDCA2 antibodies that exhibit a 1.5-fold, 2-fold, 2.5-fold, 3-fold, 4-fold, or 5-fold or higher decrease in binding affinity to one or more Fc receptors compared to a parent or non-variant anti-BDCA2 antibody. In some embodiments, an anti-BDCA2 antibody with reduced effector function binds to an FcR with about 10-fold less affinity relative to a parent or non-variant antibody. In other embodiments, an anti-BDCA2 antibody with reduced effector function binds to an FcR with about 15-fold less affinity or with about 20-fold less affinity relative to a parent or non-variant antibody. The FcR receptor may be one or more of FcγRI (CD64), FcγRII (CD32), and FcγRIII, and isoforms thereof, and FcεR, FcμR, FcδR, and/or an FcαR. In particular embodiments, an anti-BDCA2 antibody with reduced effector function exhibits a 1.5-fold, 2-fold, 2.5-fold, 3-fold, 4-fold, or 5-fold or higher decrease in binding affinity to FcγRIIa.

In CDC, the antibody-antigen complex binds complement, resulting in the activation of the complement cascade and generation of the membrane attack complex. Activation of the classical complement pathway is initiated by the binding of the first component of the complement system (C1q) to antibodies (of the appropriate subclass) which are bound to their cognate antigen; thus the activation of the complement cascade is regulated in part by the binding affinity of the immunoglobulin to C1q protein. To activate the complement cascade, it is necessary for C1q to bind to at least two molecules of IgG1, IgG2, or IgG3, but only one molecule of IgM, attached to the antigenic target (Ward and Ghetie, *Therapeutic Immunology* 2:77-94 (1995) p. 80). To assess complement activation, a CDC assay, e.g. as described in Gazzano-Santoro et al., *J. Immunol. Methods,* 202:163 (1996), may be performed.

It has been proposed that various residues of the IgG molecule are involved in binding to C1q including the Glu318, Lys320 and Lys322 residues on the CH2 domain, amino acid residue 331 located on a turn in close proximity to the same beta strand, the Lys235 and Gly237 residues located in the lower hinge region, and residues 231 to 238 located in the N-terminal region of the CH2 domain (see e.g., Xu et al., *J. Immunol.* 150:152A (Abstract) (1993), WO94/29351; Tao et al, *J. Exp. Med.*, 178:661-667 (1993); Brekke et al., *Eur. J. Immunol.,* 24:2542-47 (1994); Burton et al; *Nature,* 288:338-344 (1980); Duncan and Winter, *Nature* 332:738-40 (1988); Idusogie et al *J Immunol* 164: 4178-4184 (2000; U.S. Pat. No. 5,648,260, and U.S. Pat. No. 5,624,821).

Ant-BDCA2 antibodies with improved C1q binding can comprise an amino acid substitution at one, two, three, or four of amino acid positions 326, 327, 333 and 334 of the human IgG Fc region, where the numbering of the residues in the IgG Fc region is that of the EU index as in Kabat. In one embodiment, the anti-BDCA2 antibodies include the following amino acid substitutions: K326W/E333S, which are known to increase binding of an IgG1 antibody to C1q (Steurer W. et al., *J Immunol.,* 155(3):1165-74 (1995)).

Ant-BDCA2 antibodies with reduced C1q binding can comprise an amino acid substitution at one, two, three, or four of amino acid positions 270, 322, 329 and 331 of the human IgG Fc region, where the numbering of the residues in the IgG Fc region is that of the EU index as in Kabat. As an example in IgG1, two mutations in the COOH terminal region of the CH2 domain of human IgG1—K322A and P329A—do not activate the CDC pathway and were shown to result in more than a 100 fold decrease in C1q binding (U.S. Pat. No. 6,242,195).

Accordingly, in certain embodiments, an anti-BDCA2 antibody of the present invention exhibits increased or reduced binding to a complement protein relative to a second anti-BDCA2 antibody. In certain embodiments, an anti-BDCA2 antibody of the invention exhibits increased or reduced binding to C1q by a factor of about 1.5-fold or more, about 2-fold or more, about 3-fold or more, about 4-fold or more, about 5-fold or more, about 6-fold or more, about 7-fold or more, about 8-fold or more, about 9-fold or more, about 10-fold or more, or about 15-fold or more, relative to a second anti-BDCA2 antibody.

Thus, in certain embodiments of the invention, one or more of these residues may be modified, substituted, or removed or one or more amino acid residues may be inserted so as to increase or decrease CDC activity of the anti-BDCA2 antibodies provided herein.

In certain other embodiments, the present invention provides an anti-BDCA2 antibody that exhibits reduced binding to one or more FcR receptors but that maintains its ability to bind complement (e.g., to a similar or, in some embodiments, to a lesser extent than a native, non-variant, or parent anti-BDCA2 antibody). Accordingly, an anti-BDCA2 antibody of the present invention may bind and activate complement while exhibiting reduced binding to an FcR, such as, for example, FcγRIIa (e.g., FcγRIIa expressed on platelets). Such an antibody with reduced or no binding to FcγRIIa (such as FcγRIIa expressed on platelets, for example) but that can bind C1q and activate the complement cascade to at least some degree will reduce the risk of thromboembolic events while maintaining perhaps desirable effector functions. In alternative embodiments, an anti-BDCA2 antibody of the present invention exhibits reduced binding to one or more FcRs but maintains its ability to bind one or more other FcRs. See, for example, US 2007-0009523, 2006-0194290, 2005-0233382, 2004-0228856, and 2004-0191244, which describe various amino acid modifications that generate antibodies with reduced binding to FcRI, FcRII, and/or FcRIII, as well as amino acid substitutions that result in increased binding to one FcR but decreased binding to another FcR.

Accordingly, effector functions involving the constant region of an anti-BDCA2 antibody may be modulated by altering properties of the constant region, and the Fc region in particular. In certain embodiments, the anti-BDCA2 antibody having increased or decreased effector function is compared with a second antibody with effector function and which may be a non-variant, native, or parent antibody comprising a native constant or Fc region that mediates effector function.

A native sequence Fc or constant region comprises an amino acid sequence identical to the amino acid sequence of a Fc or constant chain region found in nature. Preferably, a control molecule used to assess relative effector function comprises the same type/subtype Fc region as does the test or variant antibody. A variant or altered Fc or constant region comprises an amino acid sequence which differs from that of a native sequence heavy chain region by virtue of at least one amino acid modification (such as, for example, post-translational modification, amino acid substitution, insertion, or deletion). Accordingly, the variant constant region may contain one or more amino acid substitutions, deletions, or insertions that results in altered post-translational modifications, including, for example, an altered glycosylation pattern. A parent antibody or Fc region is, for example, a variant having normal effector function used to construct a constant region (i.e., Fc) having altered, e.g., increased effector function.

Antibodies with altered (e.g., increased) effector function(s) may be generated by engineering or producing antibodies with variant constant, Fc, or heavy chain regions. Recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g. glycosylation patterns, may be achieved by manipulating the host cell and cell culture and expression conditions by which the antibody is produced.

Certain embodiments of the present invention relate to an anti-BDCA2 antibody comprising one or more heavy chain CDR sequences selected from VH CDR1 of SEQ ID NO:9, VH CDR2 of SEQ ID NO:10, and VH CDR3 of SEQ ID NO:11; or one or more heavy chain alternate CDR sequences selected from: VH CDR1 of SEQ ID NO:8, VH CDR2 of SEQ ID NO:10, and VH CDR3 of SEQ ID NO:11; or one or more heavy chain alternate CDR sequences selected from: VH CDR1 of SEQ ID NO:89, VH CDR2 of SEQ ID NO:91, and VH CDR3 of SEQ ID NO:11; or one or more heavy chain alternate CDR sequences selected from: VH CDR1 of SEQ ID NO:9, VH CDR2 of SEQ ID NO:92, and VH CDR3 of SEQ ID NO:11; or one or more heavy chain alternate CDR sequences selected from: VH CDR1 of SEQ ID NO:90, VH CDR2 of SEQ ID NO:93, and VH CDR3 of SEQ ID NO:94, wherein the antibody further comprises a variant Fc region that confers increased or reduced effector function compared to a native or parental Fc region. In further embodiments, the anti-BDCA2 antibody comprises at least two of the CDRs (or alternate CDRs), and in other embodiments the antibody comprises all three of the heavy chain CDR sequences (or alternate CDRs). These anti-BDCA2 antibodies i) inhibit secretion of type I interferons and/or type III interferons in addition to other cytokines and chemokines from plasmacytoid dendritic cells; and/or (ii) induce or enhance depletion of plasmacytoid dendritic cells in vitro.

Other embodiments of the present invention relate to an anti-BDCA2 antibody comprising one or more light chain CDR sequences selected from VL CDR1 of SEQ ID NO:5, VL CDR2 of SEQ ID NO:6, and VL CDR3 of SEQ ID NO:7; or one or more light chain alternate CDR sequences selected from VL CDR1 of SEQ ID NO:95, VL CDR2 of SEQ ID NO:96, and VL CDR3 of SEQ ID NO:97, the antibody further comprising a variant Fc region that confers increased or reduced effector function compared to a native or parental Fc region. In further embodiments, the anti-BDCA2 antibody comprises at least two of the light chain CDRs (or alternate CDRs), and in other embodiments the antibody comprises all three of the light chain CDR sequences (or alternate CDRs). These anti-BDCA2 antibodies i) inhibit secretion of type I interferons and/or type III interferons in addition to other cytokines and chemokines from plasmacytoid dendritic cells; and/or (ii) induce or enhance depletion of plasmacytoid dendritic cells in vitro.

In further embodiments of the present invention, the anti-BDCA2 antibody with increased or reduced effector function comprises all three light chain CDR sequences or alternate light chain CDRs of SEQ ID NO:3 and comprises all three heavy chain CDR sequences or alternate heavy chain CDRs of SEQ ID NO:4

In other embodiments, the invention relates to an anti-BDCA2 antibody comprising a VL sequence comprising SEQ ID NO:23, the antibody further comprising a variant Fc region that confers reduced effector function compared to a native or parental Fc region. In yet other embodiments, the invention relates to an anti-BDCA2 antibody comprising a VH sequence comprising SEQ ID NO:24, the antibody further comprising a variant Fc region that confers reduced effector function compared to a native or parental Fc region.

Methods of generating any of the aforementioned anti-BDCA2 antibody variants comprising amino acid substitutions are well known in the art. These methods include, but are not limited to, preparation by site-directed (or oligonucleotide-mediated) mutagenesis, PCR mutagenesis, and cassette mutagenesis of a prepared DNA molecule encoding the antibody or at least the constant region of the antibody. Site-directed mutagenesis is well known in the art (see, e.g., Carter et al., *Nucleic Acids Res.*, 13:4431-4443 (1985) and Kunkel et al., *Proc. Natl. Acad. Sci. USA*, 82:488 (1987)). PCR mutagenesis is also suitable for making amino acid sequence variants of the starting polypeptide. See Higuchi, in PCR Protocols, pp. 177-183 (Academic Press, 1990); and Vallette et al., *Nuc. Acids Res.* 17:723-733 (1989). Another method for preparing sequence variants, cassette mutagenesis, is based on the technique described by Wells et al., *Gene*, 34:315-323 (1985).

Anti-BDCA2 Antibodies with Altered Glycosylation

Different glycoforms can profoundly affect the properties of a therapeutic, including pharmacokinetics, pharmacodynamics, receptor-interaction and tissue-specific targeting (Graddis et al., 2002, *Curr Pharm Biotechnol.* 3: 285-297). In particular, for antibodies, the oligosaccharide structure can affect properties relevant to protease resistance, the serum half-life of the antibody mediated by the FcRn receptor, phagocytosis and antibody feedback, in addition to effector functions of the antibody (e.g., binding to the complement complex C1, which induces CDC, and binding to FcγR receptors, which are responsible for modulating the ADCC pathway) (Nose and Wigzell, 1983; Leatherbarrow and Dwek, 1983; Leatherbarrow et al., 1985; Walker et al., 1989; Carter et al., 1992, *PNAS,* 89: 4285-4289).

Accordingly, another means of modulating effector function of antibodies includes altering glycosylation of the antibody constant region. Altered glycosylation includes, for example, a decrease or increase in the number of glycosylated residues, a change in the pattern or location of glycosylated residues, as well as a change in sugar structure(s). The oligosaccharides found on human IgGs affects their degree of effector function (Raju, T. S. *BioProcess International* April 2003. 44-53); the microheterogeneity of human IgG oligosaccharides can affect biological functions such as CDC and ADCC, binding to various Fc receptors, and binding to C1q protein (Wright A. & Morrison S L. TIBTECH 1997, 15 26-32; Shields et al. *J Biol Chem.* 2001 276(9):6591-604; Shields et al. *J Biol Chem.* 2002; 277(30): 26733-40; Shinkawa et al. *J Biol Chem.* 2003 278(5):3466-73; Umana et al. *Nat Biotechnol.* 1999 February; 17(2): 176-80). For example, the ability of IgG to bind C1q and activate the complement cascade may depend on the presence, absence or modification of the carbohydrate moiety positioned between the two CH2 domains (which is normally anchored at Asn297) (Ward and Ghetie, *Therapeutic Immunology* 2:77-94 (1995).

Glycosylation sites in an Fc-containing polypeptide, for example an antibody such as an IgG antibody, may be identified by standard techniques. The identification of the glycosylation site can be experimental or based on sequence analysis or modeling data. Consensus motifs, that is, the amino acid sequence recognized by various glycosyl transferases, have been described. For example, the consensus motif for an N-linked glycosylation motif is frequently NXT or NXS, where X can be any amino acid except proline. Several algorithms for locating a potential glycosylation motif have also been described. Accordingly, to identify potential glycosylation sites within an antibody or Fc-containing fragment, the sequence of the antibody is examined, for example, by using publicly available databases such as the website provided by the Center for Biological Sequence Analysis (see NetNGlyc services for predicting N-linked glycosylation sites and NetOGlyc services for predicting O-linked glycosylation sites).

In vivo studies have confirmed the reduction in the effector function of aglycosyl antibodies. For example, an aglycosyl anti-CD8 antibody is incapable of depleting CD8-bearing cells in mice (Isaacs, 1992 *J. Immunol.* 148: 3062) and an aglycosyl anti-CD3 antibody does not induce cytokine release syndrome in mice or humans (Boyd, 1995 supra; Friend, 1999 *Transplantation* 68:1632). Aglycosylated forms of the BDCA2 antibody also have reduced effector function.

Importantly, while removal of the glycans in the CH2 domain appears to have a significant effect on effector function, other functional and physical properties of the antibody remain unaltered. Specifically, it has been shown that removal of the glycans had little to no effect on serum half-life and binding to antigen (Nose, 1983 supra; Tao, 1989 supra; Dorai, 1991 supra; Hand, 1992 supra; Hobbs, 1992 *Mol. Immunol.* 29:949).

The anti-BDCA2 antibodies of the present invention may be modified or altered to elicit increased or decreased effector function(s) (compared to a second BDCA2-specific antibody). Methods for altering glycosylation sites of antibodies are described, e.g., in U.S. Pat. No. 6,350,861 and U.S. Pat. No. 5,714,350, WO 05/18572 and WO 05/03175; these methods can be used to produce anti-BDCA2 antibodies of the present invention with altered, reduced, or no glycosylation.

Indications

An anti-BDCA2 antibody described herein can be used to treat or prevent a variety of immunological disorders, such as inflammatory and autoimmune disorders. Anti-BDCA2 antibodies are useful to treat or prevent such disorders at least because they disable or deplete pDCs, and/or inhibit inflammatory cytokines and chemokines produced by pDCs, and/or downregulate CD32a, and/or inhibiting immune complex stimulation of pDCs, and/or downregulate or cause shedding of CD62L. The anti-BDCA2 antibodies of this disclosure can be combined with an antimalarial agent (e.g., HCQ) for improved therapeutic effects in the treatment of inflammatory and autoimmune disorders. Anti-BDCA2 antibodies can be used to reduce levels of cytokines and chemokines such as: type I interferons, type III interferons, IL-6, TNF-α, MIP1-α and MIP1-β, CCL5, and IP-10. Type I IFNs constitute a multiple-member family of cytokines, including 13 IFN-α subtypes, IFN-β, -ε, -κ, -ω, -δ and -τ. (Theofilopoulos, *Annu. Rev. Immunol.*, 23:307-36 (2005)). Type III interferons consist of three IFN-λ, molecules called IFN-λ1, IFN-λ2 and IFN-λ3 (also referred to as IL29, IL28A and IL28B, respectively). By depleting and/or dampening pDC function, the anti-BDCA2 antibodies described herein provide a more robust treatment approach than treatments attempting to reduce specific IFN subtypes with neutralizing antibodies. In addition, the pDC-focused treatment approach of the anti-BDCA2 antibodies is more selective and potentially safer than global blockade of the IFN response. For example, anti-BDCA2 antibodies described herein effectively eliminate pDC-derived type I IFNs while maintaining other sources of IFN that could be necessary in the event of viral infections.

The term "treating" refers to administering a composition described herein in an amount, manner, and/or mode effective to improve a condition, symptom, or parameter associated with a disorder or to prevent progression or exacerbation of the disorder (including secondary damage caused by the disorder) to either a statistically significant degree or to a degree detectable to one skilled in the art.

Diseases or conditions that can be treated with an anti-BDCA2 antibody described herein include, e.g., systematic lupus erythematosus (SLE) (e.g., moderate or severe lupus), cutaneous lupus, discoid lupus, lupus nephritis, systemic sclerosis (scleroderma), morphea, psoriasis, rheumatoid arthritis, inflammatory bowel disease (IBD), deratomyositis, polymyositis, and type I diabetes.

SLE is a chronic autoimmune disease where multiple organs are damaged by immune complexes and tissue-binding autoantibodies (see, Guidelines for Referral and Management of Systemic Lupus Erythematosus in Adults, *Arthritis & Rheumatism*, 42(9):1785-1795 (1999)). Autoantibodies are present in SLE and may precede the development of the clinical disease (Arbuckle et al., *N Engl. J. Med.*, 349(16):1526-33 (2003)). Internalization of the autoantibody containing immune complexes through Fc receptors leads to the production of type I interferon which in turn promotes loss of tolerance, perpetuating the vicious cycle of autoimmunity (Means et al., *Ann N Y Acad Sci.*, 1062:242-51 (2005)). SLE is heterogeneous with regard to its clinical presentation, course, prognosis and genetics. African Americans share an increased risk for SLE that is often more severe as compared to white patients. Complement deficiencies were recognized early as risk factors for the development of SLE. More recently, genetic polymorphisms associated with type I interferon pathways have been described to confer susceptibility. For example, anti-double stranded DNA and anti-Ro autoantibodies were associated with a certain haplotype of the transcription factor interferon regulatory factor 5 (IRF5). The haplotype also predicted high levels of IFN-α in the serum of SLE patients (Niewold et al., *Ann. Rheum. Dis.*, 71(3):463-8 (2012)). Higher IFN-α levels have been correlated with a greater extent of multiple organ involvement in SLE patients (Bengtsson et al., *Lupus*, 9(9): 664-71 (2000)). Furthermore, the so called "interferon signature" seems to be prominent in SLE. Interferon signature represents an mRNA expression pattern of interferon inducible genes. A type-I interferon signature is found in more than half of SLE patients and is associated with greater disease activity (Baechler et al., *Proc. Natl. Acad. Sci USA*, 100(5):2610-5 (2003)). IFN-α monoclonal antibodies have now entered the clinics and phase 1 results of sifalimumab and rontalizumab have demonstrated a dose-dependent reduction in type I IFN signature in the whole blood of SLE patients (McBride et al., *Arthritis Rheum.*, 64(11):3666-76 (2012); Yao et al., *Arthritis Rheum.*, (6):1785-96 (2009)). Validated indices have been developed for the assessment of disease activity and disease severity (e.g., moderate, severe) (see, e.g., Gladman, Prognosis and treatment of systemic lupus erythematosus, *Curr. Opin. Rheumatol.*, 8:430-437 (1996); Kalunian et al., Definition, classification, activity and damage indices. In: Dubois' lupus eyrthematosus. 5th ed., Baltimore: Williams and Wilkins; pp. 19-30 (1997)).

Systemic sclerosis or systemic scleroderma is a systemic autoimmune disease or systemic connective tissue disease that is a subtype of scleroderma. It is characterized by deposition of collagen in the skin and, less commonly, in the kidneys, heart, lungs & stomach. The female to male ratio for this disease is 4:1. The peak age of onset of the disease is between 30-50 years.

Psoriasis is an autoimmune disease that affects the skin. It occurs when the immune system mistakes the skin cells as a pathogen, and sends out faulty signals that speed up the growth cycle of skin cells. Psoriasis has been linked to an increased risk of stroke, and treating high blood lipid levels may lead to improvement. There are five types of psoriasis: plaque, guttate, inverse, pustular, and erythrodermic. The most common form, plaque psoriasis, is commonly seen as red and white hues of scaly patches appearing on the top first layer of the epidermis. However, some patients have no dermatological signs or symptoms.

Rheumatoid arthritis is a chronic inflammatory disorder that affects many tissues and organs, but principally attacks flexible joints. The process involves an inflammatory response of the capsule around the joints secondary to swelling of synovial cells, excess synovial fluid, and the development of fibrous tissue (pannus) in the synovium. The pathology of the disease process often leads to the destruction of articular cartilage and ankylosis of the joints. Rheumatoid arthritis can also produce diffuse inflammation in the lungs, membrane around the heart (pericardium), the membranes of the lung (pleura), and white of the eye (sclera), and also nodular lesions, most common in subcutaneous tissue. Although the cause of rheumatoid arthritis is unknown, autoimmunity plays a pivotal role in both its chronicity and progression, and RA is considered a systemic autoimmune disease. Over expression of TNFα and other proinflammatory cytokines has been observed in patients with arthritis (Feldmann et. al., *Prog Growth Factor Res.*, 4:247-55 (1992)). Furthermore, transgenic animals that over express human TNFα develop an erosive polyarthritis with many characteristics associated with the disease (Keffer et. al., *EMBO J.*, 10(13):4025-31 (1991)). Analgesia and anti-inflammatory drugs, including steroids, are used to suppress the symptoms, while disease-modifying antirheumatic drugs (DMARDs) are required to inhibit or halt the underlying immune process and prevent long-term damage. More recently, anti-TNFα antibody therapy (Rituximab) has been used to manage the disease (Edwards, et. al., *N. Engl. J. Med.*, 350(25): 2572-81 (2004)).

Inflammatory bowel disease (IBD) is a group of inflammatory conditions of the colon and small intestine. The major types of IBD are Crohn's disease and ulcerative colitis (UC). The main difference between Crohn's disease and UC is the location and nature of the inflammatory changes: Crohn's disease can affect any part of the gastrointestinal tract, from mouth to anus (skip lesions), although a majority of the cases start in the terminal ileum; whereas, UC is restricted to the colon and the rectum. Depending on the level of severity, IBD may require immunosuppression to control the symptom, such as prednisone, TNF inhibition, azathioprine (Imuran), methotrexate, or 6-mercaptopurine. More commonly, treatment of IBD requires a form of mesalazine.

Dermatomyositis (DM) is a type of autoimmune connective-tissue disease related to polymyositis (PM) that is characterized by inflammation of the muscles and the skin. While DM most frequently affects the skin and muscles, it is a systemic disorder that may also affect the joints, the esophagus, the lungs, and, less commonly, the heart.

Polymyositis (PM) ("inflammation of many muscles") is a type of chronic inflammation of the muscles (inflammatory myopathy) related to dermatomyositis and inclusion body myositis.

Type I diabetes is a form of diabetes mellitus that results from autoimmune destruction of insulin-producing beta cells of the pancreas. The subsequent lack of insulin leads to increased blood and urine glucose. The classical symptoms are polyuria, polydipsia, polyphagia, and weight loss.

Examples of other diseases suitable for treatment with an anti-BDCA2 antibodies described herein include asthma, Behcet's disease, CREST syndrome, Crohn's disease, dermatomyositis, juvenile dermatomyositis, diabetes mellitus, discoid lupus erythematosus, pulmonary fibrosis, autoimmune glomerulonephritis, membranous glomerulopathy, juvenile rheumatoid arthritis (juvenile chronic arthritis), mixed connective tissue disease, multiple sclerosis, nephrotic syndrome, panniculitis, pemphigoid, *pemphigus, pemphigus erythematosus, pemphigus foliaceus, pemphigus vulgaris*, rheumatic polymyalgia, systemic sclerosis, progressive systemic sclerosis (scleroderma), morphea (localized scleroderma), multiple sclerosis, psoriasis, psoriatic arthritis, pulmonary fibrosis, Raynaud's phenomenon/syndrome, Sjogren's syndrome, and ulcerative colitis.

A subject who is at risk for, diagnosed with, or who has one of these disorders can be administered an anti-BDCA2 antibody in an amount and for a time to provide an overall therapeutic effect. The anti-BDCA2 antibody can be administered alone (monotherapy) or in combination with other agents (combination therapy). In one embodiment, the agent for use in combination therapy with an anti-BDCA2 antibody described herein is an antimalarial agent. In one embodiment, the agent for use in combination therapy with an anti-BDCA2 antibody described herein is a TLR7 and/or TLR9 signaling inhibitor. In another embodiment, the agent for use in combination therapy with an anti-BDCA2 antibody described herein is a corticosteroid. In certain embodiments, the agent for use in combination therapy with an anti-BDCA2 antibody described herein is an anti-malarial drug and/or a kinase inhibitor (e.g., BTK inhibitor (e.g., ibrutinib (PCI-32765), AVI-292, ONO-WG-307), JAK1 inhibitor, JAK2 inhibitor, JAK3 inhibitor, Tyk2 inhibitor). In a specific embodiment, the agent for use in combination therapy with an anti-BDCA2 antibody described herein is hydroxychloroquine. The amounts and times of administration for combination therapies can be those that provide, e.g., an additive or a synergistic therapeutic effect. Further, the administration of the anti-BDCA2 antibody (with or without the second agent) can be used as a primary, e.g., first line treatment, or as a secondary treatment, e.g., for subjects who have an inadequate response to a previously administered therapy (i.e., a therapy other than one with an anti-BDCA2 antibody). In some embodiments, the combination therapy includes the use of an anti-BDCA2 antibody and one or more of the following agents: glucocorticoid, NSAID, prednisone, hydroxychloroquine, chloroquine, amodiaquine, pyrimethamine, proguanil, mefloquine, dapsone, primaquine, methotrexate, mycophenolate mofetil, azathioprine, thalidomide, cyclophosphamide, cyclosporine A, rapamycin, prostacyclin, phosphodiesterase inhibitor, endothelin antagonists, statin, ACE inhibitor, and calcium channel blockers. In other embodiments, the combination therapy includes the use of an anti-BDCA2 antibody and any one or more of: sulfasalazine, doxycycline, minocycline, penicillamine, tofacitinib, and leflunomide.

Pharmaceutical Compositions

An anti-BDCA2 antibody or antigen-binding fragment thereof described herein can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) *J. Pharm. Sci.* 66:1-19).

Pharmaceutical formulation is a well-established art, and is further described, e.g., in Gennaro (ed.), *Remington: The Science and Practice of Pharmacy*, 20$^{th}$ ed., Lippincott, Williams & Wilkins (2000) (ISBN: 0683306472); Ansel et al., *Pharmaceutical Dosage Forms and Drug Delivery Systems*, 7$^{th}$ Ed., Lippincott Williams & Wilkins Publishers (1999) (ISBN: 0683305727); and Kibbe (ed.), *Handbook of Pharmaceutical Excipients American Pharmaceutical Association*, 3$^{rd}$ ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, an anti-BDCA2 antibody described herein is formulated with excipient materials, such as sodium chloride, sodium citrate, sodium dibasic phosphate heptahydrate, sodium monobasic phosphate, Tween-80, and a stabilizer. It can be provided, for example, in a buffered solution at a suitable concentration and can be stored at 2-8° C. In some other embodiments, the pH of the composition is between about 5.8 and 6.6 (e.g., 5.8, 5.9, 6.0, 6.1, 6.2, 6.3, 6.4, 6.5, 6.6).

The pharmaceutical compositions can also include agents that reduce aggregation of the BDCA2 antibody or antigen-binding fragment thereof when formulated. Examples of aggregation reducing agents include one or more amino acids selected from the group consisting of methionine, arginine, lysine, aspartic acid, glycine, and glutamic acid. These amino acids may be added to the formulation to a concentration of about 0.5 mM to about 145 mM (e.g., 0.5 mM, 1 mM, 2 mM, 5 mM, 10 mM, 25 mM, 50 mM, 100 mM). The pharmaceutical compositions can also include a sugar (e.g., sucrose, trehalose, mannitol, sorbitol, or xylitol) and/or a tonicity modifier (e.g., sodium chloride, mannitol, or sorbitol) and/or a surfactant (e.g., polysorbate-20 or polysorbate-80).

Such compositions can be administered by a parenteral mode (e.g., intravenous, subcutaneous, intraperitoneal, or intramuscular injection). In one embodiment, the anti-BDCA2 antibody or antigen-binding fragment thereof compositions are administered subcutaneously. In one embodiment, the anti-BDCA2 antibody or antigen-binding fragment thereof compositions are administered intravenously. The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the anti-BDCA2 antibody or antigen-binding fragment thereof may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York (1978).

In one embodiment, the pharmaceutical formulation comprises an anti-BDCA2 antibody or antigen-binding fragment thereof (e.g., BIIB059) at a concentration of about 0.5 mg/mL to 300 mg/mL (e.g., 1 mg/mL, 5 mg/mL, 10 mg/mL, 25 mg/mL, 50 mg/mL, 75 mg/mL, 100 mg/mL, 125 mg/mL, 150 mg/mL, 175 mg/mL, 200 mg/mL, 250 mg/mL), formulated with sodium citrate, sodium chloride and optionally Tween-80 (0.01-0.1%, e.g., 0.03%, 0.05%, or 0.7%). The pH of the formulation may be between 5.5 and 7.5 (e.g., 5.6, 5.7, 5.8, 5.9, 6.0, 6.1, 6.2 6.3, 6.4 6.5, 6.6 6.7, 6.8, 6.9 7.0, 7.1, 7.3).

Administration

The anti-BDCA2 antibody or antigen-binding fragment thereof can be administered to a subject, e.g., a subject in need thereof, for example, a human subject, by a variety of methods. For many applications, the route of administration is one of: intravenous injection or infusion (IV), subcutaneous injection (SC), intraperitoneally (IP), or intramuscular injection. It is also possible to use intra-articular delivery. Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection. In some cases, administration can be oral.

The route and/or mode of administration of the antibody or antigen-binding fragment thereof can also be tailored for the individual case, e.g., by monitoring the subject, e.g., using tomographic imaging, e.g., to visualize a tumor.

The antibody or antigen-binding fragment thereof can be administered as a fixed dose, or in a mg/kg dose. The dose can also be chosen to reduce or avoid production of antibodies against the anti-BDCA2 antibody. Dosage regimens are adjusted to provide the desired response, e.g., a therapeutic response or a combinatorial therapeutic effect. Generally, doses of the anti-BDCA2 antibody (and optionally a second agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, 0.1-10 mg/kg, or 1-10 mg/kg can be administered. Other doses can also be used. In specific embodiments, a subject in need of treatment with an anti-BDCA2 antibody is administered the antibody at a dose 2 mg/kg, 4 mg/kg, 5 mg/kg, 10 mg/kg, 15 mg/kg, 20 mg/kg, 30 mg/kg, 35 mg/kg, or 40 mg/kg.

A composition may comprise about 1 mg/mL to 100 mg/ml or about 10 mg/mL to 100 mg/ml or about 50 to 250 mg/mL or about 100 to 150 mg/ml or about 100 to 250 mg/ml of anti-BDCA2 antibody or antigen-binding fragment thereof.

In certain embodiments, the anti-BDCA2 antibody or antigen-binding fragment thereof in a composition is predominantly in monomeric form, e.g., at least about 90%, 92%, 94%, 96%, 98%, 98.5% or 99% in monomeric form. Certain anti-BDCA2 antibody or antigen-binding fragment thereof compositions may comprise less than about 5, 4, 3, 2, 1, 0.5, 0.3 or 0.1% aggregates, as detected, e.g., by UV at A280 nm. Certain anti-BDCA2 antibody or antigen-binding fragment thereof compositions comprise less than about 5, 4, 3, 2, 1, 0.5, 0.3, 0.2 or 0.1% fragments, as detected, e.g., by UV at A280 nm.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Single or multiple dosages may be given. Alternatively, or in addition, the antibody may be administered via continuous infusion.

An anti-BDCA2 antibody or antigen-binding fragment thereof dose can be administered, e.g., at a periodic interval over a period of time (a course of treatment) sufficient to encompass at least 2 doses, 3 doses, 5 doses, 10 doses, or more, e.g., once or twice daily, or about one to four times per week, or preferably weekly, biweekly (every two weeks), every three weeks, monthly, e.g., for between about 1 to 12 weeks, preferably between 2 to 8 weeks, more preferably between about 3 to 7 weeks, and even more preferably for about 4, 5, or 6 weeks. Factors that may influence the dosage and timing required to effectively treat a subject, include, e.g., the severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments.

If a subject is at risk for developing an immunological disorder described herein, the antibody can be administered before the full onset of the immunological disorder, e.g., as a preventative measure. The duration of such preventative treatment can be a single dosage of the antibody or the treatment may continue (e.g., multiple dosages). For example, a subject at risk for the disorder or who has a predisposition for the disorder may be treated with the antibody for days, weeks, months, or even years so as to prevent the disorder from occurring or fulminating.

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

In certain embodiments, the anti-BDCA2 antibody or antigen-binding fragment thereof is administered subcutaneously at a concentration of about 1 mg/mL to about 300 mg/mL (e.g., 1 mg/mL, 5 mg/mL, 10 mg/mL, 25 mg/mL, 50 mg/mL, 75 mg/mL, 100 mg/mL, 125 mg/mL, 150 mg/mL, 175 mg/mL, 200 mg/mL, 250 mg/mL). In one embodiment, the anti-BDCA2 antibody or antigen-binding fragment thereof is administered subcutaneously at a concentration of 50 mg/mL. In another embodiment, the anti-BDCA2 antibody or antigen-binding fragment thereof is administered intravenously at a concentration of about 1 mg/mL to about 300 mg/mL. In a particular embodiment, the anti-BDCA2 antibody or antigen-binding fragment thereof is administered intravenously at a concentration of 50 mg/mL.

Devices and Kits for Therapy

Pharmaceutical compositions that include the anti-BDCA2 antibody or antigen-binding fragment thereof can be administered with a medical device. The device can be designed with features such as portability, room temperature storage, and ease of use so that it can be used in emergency situations, e.g., by an untrained subject or by emergency personnel in the field, removed from medical facilities and other medical equipment. The device can include, e.g., one or more housings for storing pharmaceutical preparations that include anti-BDCA2 antibody or antigen-binding fragment thereof, and can be configured to deliver one or more unit doses of the antibody. The device can be further configured to administer a second agent, e.g., a chemotherapeutic agent, either as a single pharmaceutical composition that also includes the anti-BDCA2 antibody or antigen-binding fragment thereof or as two separate pharmaceutical compositions.

The pharmaceutical composition may be administered with a syringe. The pharmaceutical composition can also be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

An anti-BDCA2 antibody or antigen-binding fragment thereof can be provided in a kit. In one embodiment, the kit includes (a) a container that contains a composition that includes anti-BDCA2 antibody, and optionally (b) informational material. The informational material can be descriptive, instructional, marketing or other material that relates to the methods described herein and/or the use of the agents for therapeutic benefit.

In an embodiment, the kit also includes a second agent for treating a disorder described herein (e.g., BTK inhibitor, an anti-malarial, glucocorticoid, NSAID, prednisone, hydroxychloroquine, amodiaquine, pyrimethamine, proguanil, sulfonamides, mefloquine, atovaquone, primaquine, artemisinin and derivatives, halofantrine, doxycycline, clindamycin, methotrexate, mycophenolate mofetil, azathioprine, cyclophosphamide, sulfasalazine or leflunomide). For example, the kit includes a first container that contains a composition that includes the anti-BDCA2 antibody, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the anti-BDCA2 antibody or antigen-binding fragment thereof, e.g., in a suitable dose, dosage form, or mode of administration (e.g., a dose, dosage form, or mode of administration described herein), to treat a subject who has had or who is at risk for an immunological disorder described herein. The information can be provided in a variety of formats, include printed text, computer readable material, video recording, or audio recording, or information that provides a link or address to substantive material, e.g., on the internet.

In addition to the antibody, the composition in the kit can include other ingredients, such as a solvent or buffer, a stabilizer, or a preservative. The antibody can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the anti-BDCA2 antibody or antigen-binding fragment thereof and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Diagnostic Uses

Anti-BDCA2 antibodies or antigen-binding fragments thereof can be used in a diagnostic method for detecting the presence of BDCA2, in vitro (e.g., a biological sample, such as tissue, biopsy) or in vivo (e.g., in vivo imaging in a subject). For example, human or effectively human anti-BDCA2 antibodies can be administered to a subject to detect BDCA2 within the subject. For example, the antibody can be labeled, e.g., with an MRI detectable label or a radiolabel. The subject can be evaluated using a means for detecting the detectable label. For example, the subject can be scanned to evaluate localization of the antibody within the subject. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{33}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, can also be employed. The protein ligand can be labeled with such reagents using known techniques. For example, see Wensel and Meares (1983) *Radioimmunoimaging and Radioimmunotherapy*, Elsevier, New York for techniques relating to the radiolabeling of antibodies and Colcher et al. (1986) *Meth. Enzymol.* 121: 802-816.

The subject can be "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP0 502 814 A. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents, paramagnetic agents (which primarily alter T1) and ferromagnetic or superparamagnetic agents (which primarily alter T2 response). Chelates (e.g., EDTA, DTPA and NTA chelates) can be used to attach (and reduce toxicity) of some paramagnetic substances (e.g., $Fe^{3+}$, $Mn^{2+}$, $Gd^{3+}$). Other agents can be in the form of particles, e.g., less than 10 µm to about 10 nm in diameter). Particles can have ferromagnetic, antiferromagnetic or superparamagnetic properties. Particles can include, e.g., magnetite ($Fe_3O_4$), $\gamma$-$Fe_2O_3$, ferrites, and other magnetic mineral compounds of transition elements. Magnetic particles may include one or more magnetic crystals with and without nonmagnetic material. The nonmagnetic material can include synthetic or natural polymers (such as sepharose, dextran, dextrin, starch and the like).

The anti-BDCA2 antibodies or antigen-binding fragments thereof can also be labeled with an indicating group containing the NMR-active $^{19}$F atom, or a plurality of such atoms inasmuch as (i) substantially all of naturally abundant fluorine atoms are the $^{19}$F isotope and, thus, substantially all fluorine-containing compounds are NMR-active; (ii) many chemically active polyfluorinated compounds such as trifluoroacetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) *Scientific American*, 246:78-88 to locate and image BDCA2 distribution.

In another aspect, the disclosure provides a method for detecting the presence of BDCA2 in a sample in vitro (e.g., a biological sample, such as serum, plasma, tissue, biopsy). The subject method can be used to diagnose a disorder, e.g., an autoimmune disorder (e.g., SLE) or a to detect levels of pDCs in a sample. The method includes: (i) contacting the sample or a control sample with the anti-BDCA2 antibody; and (ii) evaluating the sample for the presence of BDCA2, e.g., by detecting formation of a complex between the anti-BDCA2 antibody and BDCA2, or by detecting the presence of the antibody or BDCA2. For example, the antibody can be immobilized, e.g., on a support, and retention of the antigen on the support is detected, and/or vice versa. The antibody used may be labeled e.g., with a fluorophore. A control sample can be included. The positive control can be a sample known to have the disease or disorder being assessed, and a negative control can be a sample from a subject who does not have the disease or disorder being assessed. A statistically significant change in the formation of the complex in the sample relative to the control sample can be indicative of the presence of BDCA2 in the sample. Generally, an anti-BDCA2 antibody can be used in applications that include fluorescence polarization, microscopy, ELISA, centrifugation, chromatography, and cell sorting (e.g., fluorescence activated cell sorting). In certain embodiments, the anti-BDCA2 antibody is BIIB059 or Dendritics clone 124B3.13. In some embodiments, the method further involves immunostaining a tissue sample with an anti-CD123 antibody. The tissue sample can be, e.g., skin biopsies from human patients with autoimmune conditions, e.g., SLE.

The following are examples of the practice of the invention. They are not to be construed as limiting the scope of the invention in any way.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Cloning of the Heavy and Light Chains of Murine Anti-BDCA2 Antibody

The 24F4 murine hybridoma (IgG1, kappa) was derived from a Balb/c mouse immunized by Gene Gun with the plasmid pEAG2456, a mammalian expression vector which co-expresses full-length human BDCA2 and FcεRIγcDNAs (see Example 17).

Total cellular RNA from the 24F4 murine hybridoma cells was prepared using a Qiagen RNeasy mini kit following the manufacturer's recommended protocol. cDNAs encoding the variable regions of the heavy and light chains were cloned by RT-PCR from total cellular RNA using the GE Healthcare First Strand cDNA Synthesis kit following the manufacturer's recommended protocol using random hexamers for priming.

For PCR amplification of the murine immunoglobulin variable domains with intact signal sequences, a cocktail of degenerate forward primers hybridizing to multiple murine immunoglobulin gene family signal sequences and a single back primer specific for 5' end of the murine constant domain as described in Current Protocols in Immunology (Wiley and Sons, 1999) were used. The 24F4 heavy chain variable domain was amplified with the following primers: 5' ACT AGT CGA CAT GRA CTT TGG GYT CAG CTT GRT TT 3' (R=A/G and Y=C/T) (SEQ ID NO:25) and 5' AGG TCT AGA AYC TCC ACA CAC AGG RRC CAG TGG ATA GAC 3' (R=A/G and Y=C/T) (SEQ ID NO:26). The 24F4 light chain variable domain with its signal sequence was amplified with the following primers: 5' ACT AGT CGA CAT GGA GWC AGA CAC ACT CCT GYT ATG GGT 3' (W=A/T and Y=C/T) (SEQ ID NO: 27) and 5' GCG TCT AGA ACT GGA TGG TGG GAG ATG GA 3' (SEQ ID NO:28).

The PCR products were gel-purified using a Qiagen Qiaquick gel extraction kit following the manufacturer's recommended protocol. Purified PCR products were subcloned into Invitrogen's pCR2.1TOPO vector using their TOPO cloning kit following the manufacturer's recommended protocol. Inserts from multiple independent subclones were sequenced to establish a consensus sequence (from heavy chain clone designated pYL647 and light chain clone pYL651).

The variation in the sequences amongst the clones was consistent with the primers' positions of degeneracy. BLAST analysis of the variable domain sequences confirmed their immunoglobulin identity. The deduced mature light and heavy chain N-terminal sequences match those of the authentic 24F4 chains derived from Edman degradation data. Deduced intact masses from hypothetical sequences assembled by adding deduced constant domain sequences from cloned Balb/c IgG1 heavy chain and kappa light chain cDNAs to the deduced mature variable domain sequences were consistent with those of the purified hybridoma-derived 24F4 determined by mass spectroscopy.

The murine 24F4 heavy chain variable domain (VH) is a member of murine subgroup III(D). The sequence of the murine 24F4 mature heavy chain variable domain with CDR H1, CDR H2, and CDR H3 underlined in that order is shown below:

(SEQ ID NO: 29)
1 DVKLVESGGG LVKPGGSLKL SCAAS<u>GFTFS TYTMS</u>WVRQT

PEKRLEWVA<u>T</u>

51 <u>ISPGDSFGYY YPDSVQGRFT</u> ISRDNAKNTL FLQMSSLKSE

DTAMYYCTR<u>D</u>

101 <u>IYYNYGAWFA Y</u>WGQGTLVTV SA

The murine 24F4 light chain variable domain (VL) is a member of murine kappa subgroup III. The sequence of the murine 24F4 mature light chain variable domain with CDR L1, CDR L2, and CDR L3 underlined in that order is shown below:

(SEQ ID NO: 30)
1 DIVLTQSPAS LAVSLGQRAT ISC<u>KASQSVD YDGDSYMN</u>WY

QQKPGQPPKL

51 LIY<u>AASTLES</u> GVPARFSGSG SGTDFTLNIH PVEEEDAATY

YC<u>QQCNEDPR</u>

101 <u>T</u>FGGGTKLEI K

An unpaired cysteine is present at residue 95 in CDRL3 in the murine 24F4 VL sequence above (in Kabat nomenclature this Cys is residue 91).

Example 2. Chimerization of the Murine 24F4 Antibody cDNAs encoding the murine 24F4 variable domains were used to construct vectors for expression of murine-human chimeras (ch24F4) in which the mu24F4 variable regions were linked to human IgG1 and kappa constant regions.

The variable domains were first engineered by PCR to add a 5' Kozak sequence and to introduce human sequences and new restriction sites at the FR4/constant domain junctions for fusion to human immunoglobulin constant domains. The variable region cDNA sequences in the resultant plasmids were confirmed by DNA sequencing. The heavy chain variable domain in plasmid pYL647 was used as template for PCR with the primers 5' GAT CCG CGG CCG CAC CAT GGA CTT TGG GTT CAG CTT G 3' (SEQ ID NO:31) (adds NotI site and Kozak sequence) and 5' GAT GGG CCC TTG GTG GAA GCT GCA GAG ACA GTG ACC AGA G 3' (SEQ ID NO:32) (adds human IgG1 CH1 sequences at FR4/constant domain junction and an ApaI site), amplifying a 0.45 kb fragment that was purified and subcloned into the Invitrogen pCRBluntIITOPO cloning vector, generating pYL668. For construction of the heavy chain chimera, the 0.45 kb NotI-ApaI fragment from the 24F4 heavy chain variable domain construct pYL668 and the 0.98 kb ApaI-BamHI fragment from pEAG1325 (a plasmid containing a sequence-confirmed huIgG1 heavy chain constant domain cDNA (with the IgG1 C-terminal lysine residue genetically removed) were subcloned into the vector backbone of the expression vector pV90 (in which heterologous gene expression is controlled by a CMV-IE promoter and a human growth hormone polyadenylation signal and which carries a dhfr selectable marker, see U.S. Pat. No. 7,494,805), to produce the expression vector pYL672. The heavy chain cDNA sequence in the resultant plasmid pYL672 was confirmed by DNA sequencing. The deduced mature ch24F4-huIgG1 heavy chain protein sequence encoded by pYL672 is shown below:

```
                                          (SEQ ID NO: 33)
  1 DVKLVESGGG LVKPGGSLKL SCAASGFTFS TYTMSWVRQT

PEKRLEWVAT

51 ISPGDSFGYY YPDSVQGRFT ISRDNAKNTL FLQMSSLKSE

DTAMYYCTRD

101 IYYNYGAWFA YWGQGTLVTV SAASTKGPSV FPLAPSSKST

SGGTAALGCL

151 VKDYFPEPVT VSWNSGALTS GVHTFPAVLQ SSGLYSLSSV

VTVPSSSLGT

201 QTYICNVNHK PSNTKVDKKV EPKSCDKTHT CPPCPAPELL

GGPSVFLFPP

251 KPKDTLMISR TPEVTCVVVD VSHEDPEVKF NWYVDGVEVH

NAKTKPREEQ

301 YNSTYRVVSV LTVLHQDWLN GKEYKCKVSN KALPAPIEKT

ISKAKGQPRE

351 PQVYTLPPSR DELTKNQVSL TCLVKGFYPS DIAVEWESNG

QPENNYKTTP

401 PVLDSDGSFF LYSKLTVDKS RWQQGNVFSC SVMHEALHNH

YTQKSLSLSP

451 G
```

An aglycosyl low effector function form of ch24F4 was also constructed by subcloning the 0.45 kb NotI-ApaI fragment from the 24F4 heavy chain variable domain construct pYL668 and the 0.98 kb ApaI-BamHI fragment from pEAG2412 (a plasmid containing a sequence-confirmed S228P/N299Q huIgG4/IgG1 hybrid heavy chain constant domain cDNA with the IgG1 C-terminal lysine residue genetically removed) were subcloned into the vector backbone of expression vector pV90, generating plasmid pYL670. The heavy chain cDNA sequence in the resultant plasmid pYL670 was confirmed by DNA sequencing. The deduced mature agly ch24F4-huIgG4/G1 hybrid heavy chain protein sequence encoded by pYL670 is shown below:

```
                                          (SEQ ID NO: 34)
  1 DVKLVESGGG LVKPGGSLKL SCAASGFTFS TYTMSWVRQT

PEKRLEWVAT

51 ISPGDSFGYY YPDSVQGRFT ISRDNAKNTL FLQMSSLKSE

DTAMYYCTRD

101 IYYNYGAWFA YWGQGTLVTV SAASTKGPSV FPLAPCSRST

SESTAALGCL

151 VKDYFPEPVT VSWNSGALTS GVHTFPAVLQ SSGLYSLSSV

VTVPSSSLGT

201 KTYTCNVDHK PSNTKVDKRV ESKYGPPCPP CPAPEFLGGP

SVFLFPPKPK

251 DTLMISRTPE VTCVVVDVSQ EDPEVQFNWY VDGVEVHNAK

TKPREEQFQS

301 TYRVVSVLTV LHQDWLNGKE YKCKVSNKGL PSSIEKTISK

AKGQPREPQV

351 YTLPPSRDEL TKNQVSLTCL VKGFYPSDIA VEWESNGQPE

NNYKTTPPVL

401 DSDGSFFLYS KLTVDKSRWQ QGNVFSCSVM HEALHNHYTQ

KSLSLSPG
```

The kappa light chain variable domain in plasmid pYL651 was used as template for PCR with the primers 5' GAT CCG CGG CCG CCA CCA TGG AGA CAG ACA CAC TCC TG 3' (SEQ ID NO:35) (adds a 5' NotI site and Kozak sequence) and 5' CCA CCG TAC GTT TGA TTT CCA GCT TGG TGC 3' (SEQ ID NO:36) (adds human kappa constant domain sequences at FR4/constant domain junction and a 3' BsiWI site), amplifying a 0.4 kb fragment that was purified and subcloned into the Invitrogen pCR-BluntIITOPO cloning vector, generating pYL669. The variable region cDNA sequences in plasmid pYL669 were confirmed by DNA sequencing. For construction of the light chain chimera, the 0.4 kb NotI-BsiWI light chain variable domain fragment from pYL669 and the 0.34 kb BsiWI-BamHI fragment from the plasmid pEAG1572 (containing a sequence-confirmed human kappa light chain constant domain cDNA) were subcloned into the vector backbone of pV100 (in which heterologous gene expression is controlled by a CMV-IE promoter and a human growth hormone polyadenylation signal and which carries a neomycin selectable marker), to produce the expression vector pYL671. The light chain cDNA sequence in the resultant plasmid pYL671 was confirmed by DNA sequencing. The deduced mature ch24F4-human kappa light chain protein sequence encoded by pYL671 is shown below:

```
                                            (SEQ ID NO: 37)
  1 DIVLTQSPAS LAVSLGQRAT ISCKASQSVD YDGDSYMNWY

QQKPGQPPKL

51 LIYAASTLES GVPARFSGSG SGTDFTLNIH PVEEEDAATY

YCQQCNEDPR

101 TFGGGTKLEI KRTVAAPSVF IFPPSDEQLK SGTASVVCLL

NNFYPREAKV

151 QWKVDNALQS GNSQESVTEQ DSKDSTYSLS STLTLSKADY

EKHKVYACEV

201 THQGLSSPVT KSFNRGEC
```

Expression vectors (ch24F4 heavy chain vectors pYL670 or pYL672 and ch24F4 light chain vector pYL671) were co-transfected into 293-EBNA cells and transfected cells were tested for antibody secretion and specificity (empty vector- and a molecularly cloned irrelevant mAb vector-transfected cells served as controls). Western blot analysis (developed with anti-human heavy and light chain antibodies) of conditioned medium indicated that ch24F4-transfected cells synthesized and efficiently secreted heavy and light chains. Direct FACS binding to surface human BDCA2 confirmed the specificity of ch24F4. The EC50 binding of both variants of ch24F4 was equivalent to that of the murine 24F4 mAb by direct binding to surface expressed human BDCA2 by dilution titration FACS assay. Stable CHO cell lines secreting ch24F4-huIgG1, kappa mAb and agly ch24F4-huIgG4/G1 hybrid kappa mAb were produced by co-transfection with pYL672/pYL671 and pYL670/pYL671, respectively.

Example 3. Removal of an Unpaired Cysteine Residue in CDRL3 of the Chimeric 24F4 Antibody As unpaired cysteines in an exposed CDR can produce product heterogeneity or instability, ch24F4 variants C95S and C95T were constructed by site-directed mutagenesis using the ch24F4 light chain expression vector plasmid pYL671 as template.

Site-directed mutagenesis was performed using Agilent's QuikChange II mutagenesis kit following the manufacturer's recommended protocol. The C95S variant was constructed using the mutagenic primer 5' GCA ACC TAT TAC TGT CAA CAA AGT AAT GAG GAT CCT CGG AC 3' (SEQ ID NO: 38) and its reverse complement, which introduced a new HincII site, producing plasmid pEAG2678. The C95T variant was constructed using the mutagenic primer 5' CAA CCT ATT ACT GTC AGC AAA CTA ATG AAG ATC CTC GGA CGT TCG 3' (SEQ ID NO: 39) and its reverse complement, which removed a BamHI site, producing plasmid pEAG2679. Mutated plasmids were identified by screening for the introduced restriction site changes. The full-length light chain cDNA sequences in the resultant plasmids were confirmed by DNA sequencing. Wildtype ch24F4 and the C95S and C95T variant mAbs were expressed transiently in 293E cells by co-transfection of pYL672 and pYL671, pEAG2678 or pEAG2679. Conditioned medium was harvested at 2 days post-transfection. Titers (assayed by Octet on anti-human Fc tips) of both variants were similar to that of wildtype ch24F4, and Western blots of nonreducing SDS-PAGE indicated no gross aggregation or obvious clipping relative to wildtype ch24F4 mAb. Direct binding by FACS on surface BDCA2 indicated that while the apparent EC50 for binding by the C95S variant was equivalent to that of wildtype ch24F4, the EC50 binding of the C95T variant was reduced by several-fold. Conditioned medium containing ch24F4 and the C95 variant mAbs was assayed by Octet for binding to human BDCA2 ectodomain. Antibodies from conditioned medium from transiently transfected cells were bound to anti-human Fc tips, then monomeric huBDCA2 was flowed over the Octet tips, to examine binding and dissociation. Octet binding and dissociation kinetics for wildtype ch24F4 and the C95S variant were equivalent, while the off-rate of the C95T variant was faster than that of wildtype ch24F4. Based upon these results, C95S was incorporated into the humanized 24F4 light chain CDRL3.

Example 4. Exemplary Humanized 24F4 Heavy and Light Chains

Examples of seven humanized (hu) 24F4 heavy chains (huIGHV3-21*01 framework/24F4 VH CDRs) and their corresponding DNA sequences are shown below. CDRs 1, 2, and 3 in each heavy chain are underlined in that order. Framework backmutations are shown in lowercase bold font. Changes to CDR residues from murine 24F4 are shown by shading within the CDR sequences. CDR1 of the variable heavy chain (CDR H1) is defined according to the Chothia definition, which is 5 amino acids longer than the Kabat definition; the italicized residues in CDR H1 identify the additional 5 amino acids (i.e., GFTFS (SEQ ID NO:12)) that form the Chothia CDR H1. The N-terminal most amino acid (i.e., glutamic acid in versions H0, H1, H2, and H3 and aspartic acid in versions H4, H5, and H6) of the variable heavy chain domain may contact antigen directly and affect binding affinity. The buried residue at Kabat position 49 may affect the conformation of CDR2 of the heavy chain (serine in versions H0, H1, H2, and H3; and alanine in versions H4, H5 and H6). The residue at Kabat position 93 may have an effect on heavy-light chain pairing (alanine in versions H0, H1, H2, and H3; and threonine in versions H4, H5 and H6. The amino acid residues in the CDR H1, H2, and H3 regions that differ from the murine 24F4 CDR H1, H2, and H3 are shaded.

```
Version H0
                                                   (SEQ ID NO: 40)
EVQLVESGGGLVKPGGSLRLSCAAS GFTFS TYTMS WVRQAPGKGLEWVS AISGSGGSTYYADSVKGRFTISRDNA

KNSLYLQMNSLRAEDTAVYYCAR DIYYNYGAWFAY WGQGTLVTVSS
```

-continued (SEQ ID NO: 41)
GAAGTGCAGCTGGTGGAGTCTGGGGGAGGCTTAGTGAAGCCTGGAGGGTCCCTGAGACTCTCCTGTGCAGCCTCT

GGATTCACTTTCAGTACCTATACCATGTCTTGGGTTCGCCAAGCACCGGGCAAGGGACTGGAGTGGGTCTCTGCT

ATTAGTGGTAGCGGAGGTAGTACATACTATGCAGACAGTGTGAAGGGCCGATTCACCATCTCCAGAGACAATGCC

AAGAACAGTCTGTACCTGCAAATGAACAGTCTGAGGGCAGAGGACACAGCCGTGTATTACTGTGCTCGAGATATC

TACTATAATTACGGAGCCTGGTTTGCTTACTGGGGCCAAGGGACTCTGGTCACTGTCTCTAGC (pYL742)
Version H1

(SEQ ID NO: 42)
EVQLVESGGGLVKPGGSLRLSCAAS*GFTFS*TYTMSWVRQAPGKGLEWVSTISPGDSFGYYPDSVKGRFTISRDNA

KNSLYLQMNSLRAEDTAVYYCARDIYYNYGAWFAYWGQGTLVTVSS (SEQ ID NO: 43)
GAAGTGCAGCTGGTGGAGTCTGGGGGAGGCTTAGTGAAGCCTGGAGGGTCCCTGAGACTCTCCTGTGCAGCCTCT

GGATTCACTTTCAGTACCTATACCATGTCTTGGGTTCGCCAAGCACCGGGCAAGGGACTGGAGTGGGTCTCTACC

ATTAGTCCAGGAGACAGTTTCGGATACTATCCAGACAGTGTGAAGGGCCGATTCACCATCTCCAGAGACAATGCC

AAGAACAGTCTGTACCTGCAAATGAACAGTCTGAGGGCAGAGGACACAGCCGTGTATTACTGTGCTCGAGATATT

TACTATAATTACGGAGCCTGGTTTGCTTACTGGGGCCAAGGGACTCTGGTCACTGTCTCTAGC (pYL743)
Version H2

(SEQ ID NO: 44)
EVQLVESGGGLVKPGGSLRLSCAAS*GFTFS*TYTMSWVRQAPGKGLEWVSTISPGDSSTIYYADSVKGRFTISRDN

AKNSLYLQMNSLRAEDTAVYYCARDIYYNYGAWFAYWGQGTLVTVSS (SEQ ID NO: 45)
GAAGTGCAGCTGGTGGAGTCTGGGGGAGGCTTAGTGAAGCCTGGAGGGTCCCTGAGACTCTCCTGTGCAGCCTCT

GGATTCACTTTCAGTACCTATACCATGTCTTGGGTTCGCCAAGCACCGGGCAAGGGACTGGAGTGGGTCTCTACC

ATTAGTCCAGGAGACAGTAGCACTATCTACTATGCAGACAGTGTGAAGGGCCGATTCACCATCTCCAGAGACAAT

GCCAAGAACAGTCTGTACCTGCAAATGAACAGTCTGAGGGCAGAGGACACAGCCGTGTATTACTGTGCCCGAGAT

ATTTACTATAATTACGGAGCCTGGTTTGCTTACTGGGGCCAAGGGACTCTGGTCACTGTCTCTAGC (pYL744)
Version H3

(SEQ ID NO: 46)
EVQLVESGGGLVKPGGSLRLSCAAS*GFTFS*TYTMSWVRQAPGKGLEWVSTISPGDSFGYYPDSVQGRFTISRDN

AKNSLYLQMNSLRAEDTAVYYCARDIYYNYGAWFAYWGQGTLVTVSS (SEQ ID NO: 47)
GAAGTGCAGCTGGTGGAGTCTGGGGGAGGCTTAGTGAAGCCTGGAGGGTCCCTGAGACTCTCCTGCGCAGCCTCT

GGATTCACTTTCAGTACCTATACCATGTCTTGGGTTCGCCAAGCACCGGGCAAGGGACTGGAGTGGGTCTCTACC

ATTAGTCCAGGAGACAGTTTCGGCTACTACTATCCAGACAGTGTGCAGGGCCGATTCACCATCTCCAGAGACAAT

GCCAAGAACAGTCTGTACCTGCAAATGAACAGTCTGAGGGCAGAGGACACAGCCGTGTATTACTGTGCCCGAGAT

ATTTACTATAATTACGGAGCCTGGTTTGCTTACTGGGGCCAAGGGACTCTGGTCACTGTCTCTAGC (pYL745)
Version H4

(SEQ ID NO: 24)
dVQLVESGGGLVKPGGSLRLSCAAS*GFTFS*TYTMSWVRQAPGKGLEWVaTISPGDSFGYYPDSVQGRFTISRDN

AKNSLYLQMNSLRAEDTAVYYCtRDIYYNYGAWFAYWGQGTLVTVSS (SEQ ID NO: 48)
GACGTCCAGCTGGTGGAGTCTGGGGGAGGCTTAGTGAAGCCTGGAGGGTCCCTGAGACTCTCCTGCGCAGCCTCT

GGATTCACTTTCAGTACCTATACCATGTCTTGGGTTCGCCAAGCACCGGGCAAGGGACTGGAGTGGGTCGCAACC

ATTAGTCCAGGAGACAGTTTCGGCTACTACTATCCAGACAGTGTCCAGGGCCGATTCACCATCTCCAGAGACAAT

GCCAAGAACAGTCTGTACCTGCAAATGAACAGTCTGAGGGCAGAGGACACAGCCGTGTATTACTGTACCCGAGAT

-continued

```
ATTTACTATAATTACGGAGCCTGGTTTGCTTACTGGGGCCAAGGGACTCTGGTCACTGTCTCTAGC (pYL746)
Version H5
                                                         (SEQ ID NO: 49)
dVQLVqSGGGLVKPGGSLRLSCAAS GFTFS TYTMSWVRQAPGKGLEWVaTISPGDSFGYYYPDSVQGRFTISRDN AKNSLYLQMNrLRAEDTAVYYCtRDIYYNYGAWFAYWGrGTLVTVSS (SEQ ID NO: 50)
GACGTCCAGCTGGTGCAGTCTGGGGGAGGCTTAGTGAAGCCTGGAGGGTCCCTGAGACTCTCCTGCGCAGCCTCT

GGATTCACTTTCAGTACCTATACCATGTCTTGGGTTCGCCAAGCACCGGGCAAGGGACTGGAGTGGGTCGCAACC

ATTAGTCCAGGAGACAGTTTCGGCTACTACTATCCAGACAGTGTCCAGGGCCGATTCACCATCTCCAGAGACAAT

GCCAAGAACAGTCTGTACCTGCAAATGAACAGGCTGAGGGCAGAGGACACAGCCGTGTATTACTGTACCCGAGAT

ATTTACTATAATTACGGAGCCTGGTTTGCTTACTGGGGCAGAGGGACTCTGGTCACTGTCTCTAGC (pYL747)
Version H6
                                                         (SEQ ID NO: 52)
dVQLVESGGGLVKPGGSLRLSCAAS GFTFS TYTMSWVRQAPGKGLEWVaTISgGnnyGYsYPDSVkGRFTISRDN AKNSLYLQMNSLRAEDTAVYYCtRDIYYNYGAWFAYWGQGTLVTVSS (SEQ ID NO: 53)
GACGTCCAGCTGGTGGAGTCTGGGGGAGGCTTAGTGAAGCCTGGAGGGTCCCTGAGACTCTCCTGCGCAGCCTCT

GGATTCACTTTCAGTACCTATACCATGTCTTGGGTTCGCCAAGCACCGGGCAAGGGACTGGAGTGGGTCGCAACC

ATTAGTGGCGGAAATAACTACGGCTACTCCTATCCAGACAGTGTCAAGGGCCGATTCACCATCTCTAGAGACAAT

GCCAAGAACAGTCTGTACCTGCAAATGAACTCCCTGAGGGCAGAGGACACAGCCGTGTATTACTGTACCCGAGAT

ATTTACTATAATTACGGAGCCTGGTTTGCTTACTGGGGCCAGGGGACTCTGGTCACTGTCTCTAGC (pYL748)
```

An alignment of the amino acid sequences of versions H0 to H6 is shown below:

```
H0 EVQLVESGGGLVKPGGSLRLSCAASGFTESTYTMSWVRQAPGKGLEWVSAIS-GSGGSTY

H1 EVQLVESGGGLVKPGGSLRLSCAASGFTESTYTMSWVRQAPGKGLEWVSTISPGDSFG-Y

H2 EVQLVESGGGLVKPGGSLRLSCAASGFTESTYTMSWVRQAPGKGLEWVSTISPGDSSTIY

H3 EVQLVESGGGLVKPGGSLRLSCAASGFTESTYTMSWVRQAPGKGLEWVSTISPGDSFGYY

H4 DVQLVESGGGLVKPGGSLRLSCAASGFTFSTYTMSWVRQAPGKGLEWVATISPGDSFGYY

H5 DVQLVQSGGGLVKPGGSLRLSCAASGFTFSTYTMSWVRQAPGKGLEWVATISPGDSFGYY

H6 DVQLVESGGGLVKPGGSLRLSCAASGFTFSTYTMSWVRQAPGKGLEWVATISGGNNYGYS
   :****:***************************************::** *..
                                                         (SEQ ID NO: 40)
H0 YADSVKGRFTISRDNAKNSLYLQMNSLRAEDTAVYYCARDIYYNYGAWFAYWGQGTLVTVSS (SEQ ID NO: 42)
H1 YPDSVKGRFTISRDNAKNSLYLQMNSLRAEDTAVYYCARDIYYNYGAWFAYWGQGTLVTVSS (SEQ ID NO: 44)
H2 YADSVKGRFTISRDNAKNSLYLQMNSLRAEDTAVYYCARDIYYNYGAWFAYWGQGTLVTVSS (SEQ ID NO: 46)
H3 YPDSVQGRFTISRDNAKNSLYLQMNSLRAEDTAVYYCARDIYYNYGAWFAYWGQGTLVTVSS (SEQ ID NO: 24)
H4 YPDSVQGRFTISRDNAKNSLYLQMNSLRAEDTAVYYCTRDIYYNYGAWFAYWGQGTLVTVSS (SEQ ID NO: 49)
H5 YPDSVQGRFTISRDNAKNSLYLQMNRLRAEDTAVYYCTRDIYYNYGAWFAYWGRGTLVTVSS
```

(SEQ ID NO: 52)
```
H6 YPDSVKGRFTISRDNAKNSLYLQMNSLRAEDTAVYYCTRDIYYNYGAWFAYWGQGTLVTVSS
   *:***.*******************.***********:*****************:*******
```

Examples of three humanized 24F4 light chains (hu-IGKV1-13*02 framework/24F4 VL CDRs) and their corresponding DNA sequences are shown below. CDRs 1, 2, and 3 in each light chain are underlined in that order. Ser91 (according to Kabat numbering), which has been substituted for Cys91 in all light chains, is highlighted. The N-terminal most amino acid (i.e., alanine in version L0 and aspartic acid in versions L1 and L2) of the variable light chain domain may contact antigen directly and affect binding affinity. Framework backmutations are shown in lowercase bold font. The first version (L0) contains the fewest backmutations and the third version (L2) contains the most backmutations (i.e., the least "humanized").

```
Version L0
                                                            (SEQ ID NO: 54)
AIQLTQSPSSLSASVGDRVTITCKASQSVDYDGDSYMNWYQQKPGKAPKLLIYAASTLESGVPSRFSGSGSGTDF

TLTISSLQPEDFATYYCQQSNEDPRTFGQGTKVEIK (SEQ ID NO: 55)
GCTATTCAGCTGACCCAATCTCCATCCTCTTTGTCCGCCTCTGTGGGGGACAGGGTCACCATCACCTGCAAGGCC

AGCCAAAGTGTTGATTATGATGGTGATAGTTATATGAACTGGTATCAACAGAAACCAGGGAAGGCTCCCAAACTC

CTCATCTACGCTGCATCCACTCTCGAGTCTGGGGTCCCATCCAGGTTTAGTGGCAGTGGGTCTGGGACAGACTTC

ACCCTCACAATCAGCTCACTCCAGCCAGAGGATTTCGCAACCTATTACTGTCAGCAAAGCAACGAGGATCCTCGG

ACGTTCGGTCAGGGCACCAAAGTGGAAATCAAG (pYL729)

Version L1
                                                            (SEQ ID NO: 56)
dIQLTQSPSSLSASVGDRVTITCKASQSVDYDGDSYMNWYQQKPGKAPKLLIYAASTLESGVPSRFSGSGSGTDF

TLTISSLQPEDFATYYCQQSNEDPRTFGQGTKVEIK (SEQ ID NO: 57)
GACATTCAGCTGACCCAATCTCCATCCTCTTTGTCCGCCTCTGTGGGGGACAGGGTCACCATCACCTGCAAGGCC

AGCCAAAGTGTTGATTATGATGGTGATAGTTATATGAACTGGTATCAACAGAAACCAGGGAAGGCTCCCAAACTC

CTCATCTACGCTGCATCCACTCTCGAGTCTGGGGTCCCATCCAGGTTTAGTGGCAGTGGGTCTGGGACAGACTTC

ACCCTCACAATCAGCTCACTCCAGCCAGAGGATTTCGCAACCTATTACTGTCAGCAAAGCAACGAGGATCCTCGG

ACGTTCGGTCAGGGCACCAAAGTGGAAATCAAG (pYL730)

Version L2
                                                            (SEQ ID NO: 58)
dIQLTQSPSSLSvSVGDRaTIsCKASQSVDYDGDSYMNWYQQKPGKAPKLLIYAASTLESGVPSRFSGSGSGTDF TLTISSvQPEDFATYYCQQSNEDPRTFGQGTKVEIK (SEQ ID NO: 59)
GACATTCAGCTGACCCAATCTCCATCCTCTTTGTCCGTCTCTGTGGGGGACAGGGCAACCATCTCCTGCAAGGCC

AGCCAAAGTGTTGATTATGATGGTGATAGTTATATGAACTGGTATCAACAGAAACCAGGGAAGGCTCCCAAACTC

CTCATCTACGCTGCATCCACTCTTGAGTCTGGGGTCCCATCCAGGTTTAGTGGCAGTGGGTCTGGGACAGACTTC

ACCCTCACAATCAGCTCAGTGCAGCCAGAGGATTTCGCAACCTATTACTGTCAGCAAAGCAACGAGGATCCTCGG

ACGTTCGGTCAGGGCACCAAAGTGGAAATCAAG (pYL731)
```

An alignment of the amino acid sequences of versions L0 to L2 is shown below:

```
L0 AIQLTQSPSSLSASVGDRVTITCKASQSVDYDGDSYMNWYQQKPGKAPKLLIYAASTLES

L1 DIQLTQSPSSLSASVGDRVTITCKASQSVDYDGDSYMNWYQQKPGKAPKLLIYAASTLES

L2 DIQLTQSPSSLSVSVGDRATISCKASQSVDYDGDSYMNWYQQKPGKAPKLLIYAASTLES
   .***********.*****.**:**************************************
```

-continued

```
L0  GVPSRFSGSGSGTDFTLTISSLQPEDFATYYCQQSNEDPRTFGQGTKVEIK       (SEQ ID NO: 54)

L1  GVPSRFSGSGSGTDFTLTISSLQPEDFATYYCQQSNEDPRTFGQGTKVEIK       (SEQ ID NO: 56)

L2  GVPSRFSGSGSGTDFTLTISSVQPEDFATYYCQQSNEDPRTFGQGTKVEIK       (SEQ ID NO: 58)
    *********************:****************************
```

The humanized VH and VL amino acid sequences above do not contain any potential N-linked glycosylation sites or Asn-Gly deamidation sites. The methionines in both the VH and VL domains are observed in germline sequences, and are not surface exposed, so the risk of methionine oxidation appears to be minimal.

Solubility of proteins can correlate with their pI. The pI's of the designed constructs were calculated using pK's of amino acids in Bjellqvist et al. (*Electrophoresis*, 14:1023-31 (1993); *Electrophoresis*, 15:529-39 (1994)). The values shown below were calculated using human IgG1 heavy chains. Each of the humanized antibodies has a pI significantly above 7 and is therefore expected to have a significant positive charge at neutral pH. Each entry in the table is the calculated pI value of the full combined antibody, with the net charge in parentheses.

| Molecule | Calculated pI (net charge) |
| --- | --- |
| Chimeric 24F4 | 6.94 (−2) |
| Humanized H4L1 | 7.26 (0) |

Example 5. Binding of Hx/L1 to BDCA2

All 21 possible variants of hu24F4 heavy and light chains (described in Example 4) and ch24F4 were expressed transiently in 293E cells by co-transfection of heavy chain and light chain plasmids. All versions of hu24F4 were assembled and secreted, with titers exceeding that of ch24F4 (determined by quantitation of mAb in conditioned medium by Octet binding to anti-human Fc tips). Western blots of non-reducing SDS-PAGE analysis of chimeric and humanized 24F4 mAbs showed no evidence of gross aggregation or obvious clipping relative to ch24F4.

Figures 2, 60:
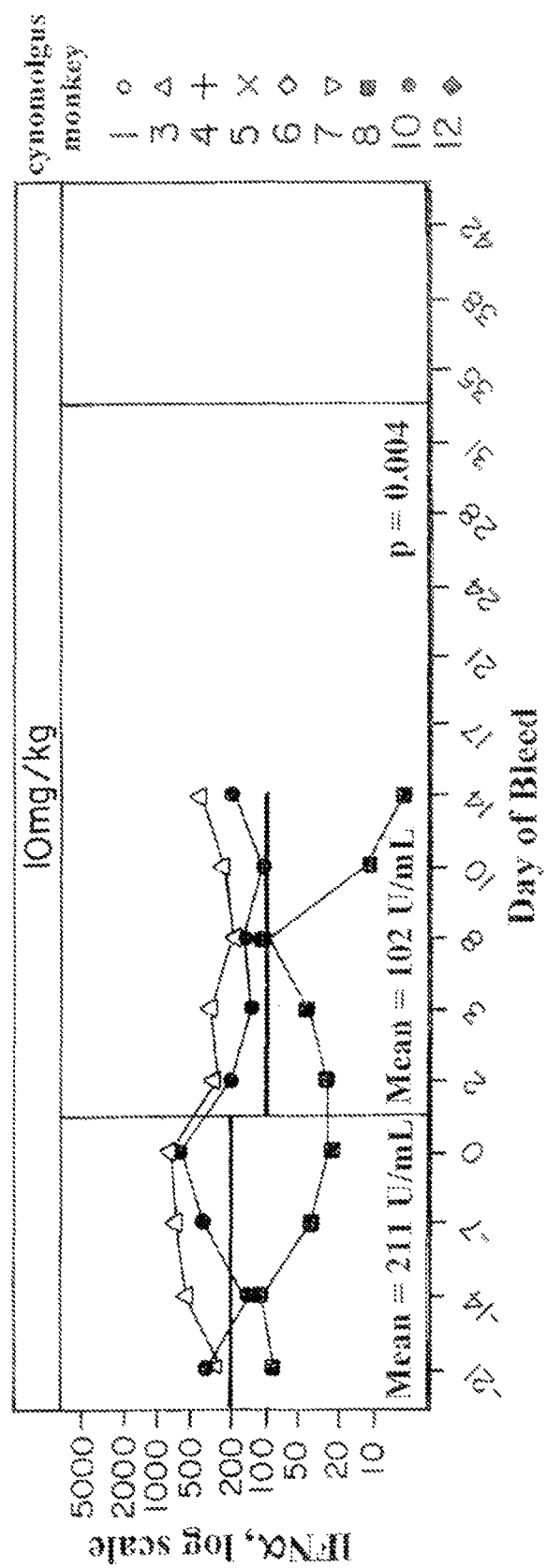
FIG. 2 is a graph showing hu24F4 Hx/L1 variants binding to human BDCA2.
FIG. 60 is a graphical depiction of the decreased TLR9-Induced IFNα production in an ex vivo Whole Blood Assay from cynomolgus monkeys treated intravenously with BIIB059. Whole blood from cynomolgus monkeys treated with a single intravenous dose of vehicle (top panel), 1 mg/kg BIIB059 (middle panel), or 10 mg/kg BIIB059 (bottom panel) was diluted 1:4 with complete RPMI 1640 and stimulated with CPG-A (2216) to a final concentration of 200 μg/ml in a 96 well round bottom tissue culture plate and incubated at 37° C. 5% CO2 for 18-20 hours. At the end of the culture, the stimulated whole blood was centrifuged to harvest serum. A549 cells were stimulated with the harvested serum for 19-20 hours at 37° C. 5% CO2 to induce MxA protein. After 20 hours, A549 cells were lysed and a sandwich ELISA was performed to detect concentrations of MxA protein. IFNα levels (Units/mL) were back calculated from a standard curve generated by treating A549 cells with increasing doses of rIFNα. A two-way mixed effects analysis of variance (ANOVA) was fit to log 10 values of the calculated concentrations of IFNα. IFNα values are plotted (on log 10 scale) versus day of bleed for each animal within each dose group. Vertical lines denote groupings of bleed days into pre-dose, post-dose up to 31 days, and post-dose greater than 31-days. Bleed days later than day 31 were not used in the analysis. The model-based estimates of geometric mean IFNα values are represented by thick black horizontal lines within the pre- and post-dose regions of each panel. Graph and statistical analysis were calculated using the R language for statistical computing.

Conditioned medium was assayed by direct binding FACS on stably transfected DG44 CHO cells co-expressing full-length BDCA2 and FcεRIγ cDNAs (human or cynomolgus monkey), (relevant expression vectors are human BDCA2/FcεRIγ: pEAG2456, cyno BDCA2/FcεRIγ: pEAG2668). In direct binding to surface human or cynomolgus monkey BDCA2, a complete loss in binding was observed for the H0, H1 and H2 series of hu24F4, a significant loss of binding affinity was observed for the H3 series of hu24F4, good retention of affinity for both the H4 and H5 series of hu24F4 and a moderate loss of binding for the H6 series of hu24F4 variants (FIGS. 2 and 3). Based upon titer and apparent EC50 values in direct binding FACS analysis, H4/L1 and H5/L1 were determined as the "best" variants of hu24F4.

Conditioned medium containing ch24F4 and all hu24F4 variant mAbs was assayed by Octet for binding to human BDCA2 ectodomain. The monomeric huBDCA2 ectodomain was prepared by proteolytic cleavage from the purified muIgG2a Fc-huBDCA2 fusion protein (relevant plasmid: pEAG2423). Antibodies from conditioned medium from transiently transfected cells were bound to anti-human Fc tips, and then monomeric huBDCA2 was flowed over the Octet tips, to examine binding and dissociation. The H4 and H5 series of hu24F4 variants showed the best affinities for huBDCA2.

| Sample name | KD (M) | kon (1/Ms) | kdis (1/s) |
| --- | --- | --- | --- |
| H6/L0 | 5.00E−09 | 2.73E+05 | 1.37E−03 |
| H0/L1 | 9.50E−11 | 1.00E+05 | 9.50E−06 |
| H1/L1 | 5.03E−11 | 1.00E+05 | 5.03E−06 |
| H2/L1 | 3.35E−11 | 1.00E+05 | 3.35E−06 |
| H3/L1 | 1.30E−08 | 4.52E+05 | 5.86E−03 |
| H4/L1 | 7.44E−10 | 5.49E+05 | 4.08E−04 |
| ch24F4 | 2.17E−09 | 1.61E+06 | 3.49E−03 |
| 5C8 control | 2.51E−14 | 1.00E+05 | 2.51E−09 |

Example 6. Enhancing hu24F4 Affinity

To explore the possibility of enhancing hu24F4 affinity by substitution at the position of the 24F4 version L1 CDR L3 unpaired cysteine (C95S in hu24F4 light chain expression vector pYL740), a number of version L1 variants were constructed by site-directed mutagenesis. Backmutation to the unpaired cysteine, i.e., S95C, was constructed by site-directed mutagenesis producing plasmid pYL749. Variants S95T, S95A, and S95V were constructed by site-directed mutagenesis producing plasmids pYL750, pYL751, and pYL752, respectively. The full-length light chain cDNA sequences in the resultant plasmids were confirmed by DNA sequencing. C95 variant hu24F4 mAbs were expressed transiently in 293E cells by co-transfection of hu24F4 H4 heavy chain pYL746 or hu24F4 H5 heavy chain pYL747 with hu24F4 L1 variant light chains C95S pYL740, S95C pYL749, S95T pYL750, S95A pYL751 or S95V pYL752 plasmids. Conditioned medium was harvested at 2 days post-transfection. Titers (assayed by Octet on anti-human Fc tips) of all variants were similar, and Western blots of nonreducing SDS-PAGE indicated no gross aggregation or obvious clipping. Conditioned medium containing the C95 variant mAbs was assayed by Octet for binding to human BDCA2 ectodomain. Antibodies from conditioned medium from transiently transfected cells were bound to anti-human Fc tips, then monomeric huBDCA2 was flowed over the Octet tips, to examine binding and dissociation. C95A variants had the slowest off-rates.

| Sample name | KD (M) | kon (1/Ms) | kdis (1/s) |
| --- | --- | --- | --- |
| 24F4-H4/L1 (YL740/YL746) | 5.48E−10 | 7.27E+05 | 3.98E−04 |
| H4-L1-S95C (YL749/YL746) | 2.89E−10 | 9.67E+05 | 2.79E−04 |
| H4-L1-C95T (YL750/YL746) | 3.92E−10 | 9.44E+05 | 3.70E−04 |
| H4-L1-C95A (YL751/YL746) | 2.61E−10 | 8.84E+05 | 2.30E−04 |
| H4-L1-C95V (YL752/YL746) | 3.23E−10 | 9.33E+05 | 3.01E−04 |

Based upon these results, stable CHO cell lines were produced for the hu24F4 H4/L1 C95T and C95A variants and H5/L1 C95T and C95A variants, which had the slowest apparent off-rates. Octet binding studies were repeated for purified hu24F4 mAbs. The hu24F4 H4/L1 C95A variant was selected as the lead candidate. Sequences of plasmids pYL746 (hu 24F4 H4 heavy chain) and pYL751 ((hu 24F4 L1 light chain) were used for recoding and construction of expression vectors for CHO production cell line generation.

The deduced mature hu24F4 L1 C95A light chain amino acid sequence encoded by pYL751 is shown below (CDR L1, CDR L2, and CDR L3 are underlined):

```
                                                  (SEQ ID NO: 3)
  1  DIQLTQSPSS LSASVGDRVT ITCKASQSVD YDGDSYMNWY QQKPGKAPKL

51  LIYAASTLES GVPSRFSGSG SGTDFTLTIS SLQPEDFATY YCQQANEDPR

101  TFGQGTKVEI KRTVAAPSVF IFPPSDEQLK SGTASVVCLL NNFYPREAKV

151  QWKVDNALQS GNSQESVTEQ DSKDSTYSLS STLTLSKADY EKHKVYACEV

201  THQGLSSPVT KSFNRGEC
```

The deduced mature hu24F4 H4-huIgG1 heavy chain amino acid sequence encoded by pYL746 is shown below (CDR H1; CDR H2, and CDR H3 are underlined):

```
                                                  (SEQ ID NO: 4)
  1  DVQLVESGGG LVKPGGSLRL SCAASGFTFS TYTMSWVRQA PGKGLEWVAT

51  ISPGDSFGYY YPDSVQGRFT ISRDNAKNSL YLQMNSLRAE DTAVYYCTRD

101  IYYNYGAWFA YWGQGTLVTV SSASTKGPSV FPLAPSSKST SGGTAALGCL

151  VKDYFPEPVT VSWNSGALTS GVHTFPAVLQ SSGLYSLSSV VTVPSSSLGT

201  QTYICNVNHK PSNTKVDKKV EPKSCDKTHT CPPCPAPELL GGPSVFLFPP

251  KPKDTLMISR TPEVTCVVVD VSHEDPEVKF NWYVDGVEVH NAKTKPREEQ

301  YNSTYRVVSV LTVLHQDWLN GKEYKCKVSN KALPAPIEKT ISKAKGQPRE

351  PQVYTLPPSR DELTKNQVSL TCLVKGFYPS DIAVEWESNG QPENNYKTTP

401  PVLDSDGSFF LYSKLTVDKS RWQQGNVFSC SVMHEALHNH YTQKSLSLSP

451  G
```

An antibody consisting of the mature heavy chain (SEQ ID NO: 4) and the mature light chain (SEQ ID NO: 3) listed above is termed BIIB059.

Example 7. Recoding the Heavy and Light Chain Genes

To potentially improve expression, the nucleotide sequence of the light and heavy chain genes were recoded without changing the amino acid sequence. The modified DNA sequence for the anti-BDCA2 light chain gene is shown below. Amino acids 1-240 contain the light chain sequence Amino acids 1-22 (nucleotides in lower case) contain the native light chain signal peptide. The mature N-terminus begins with amino acid 23 (D).

```
1    atg gac atg agg gtc ccc gct cag ctc ctg ggg
1>   M   D   M   R   V   P   A   Q   L   L   G ctc ctt ctg ctc tgg ctc cct gga gca cga tgt
     L   L   L   L   W   L   P   G   A   R   C 67   GAC ATT CAG CTG ACC CAA TCT CCA TCC TCT TTG
23>  D   I   Q   L   T   Q   S   P   S   S   L TCC GCC TCT GTG GGG GAC AGG GTC ACC ATC ACC
     S   A   S   V   G   D   R   V   T   I   T 133  TGC AAG GCC AGC CAA AGT GTT GAT TAT GAT GGT
45>  C   K   A   S   Q   S   V   D   Y   D   G GAT AGT TAT ATG AAC TGG TAT CAA CAG AAA CCA
     D   S   Y   M   N   W   Y   Q   Q   K   P 199  GGG AAG GCT CCC AAA CTC CTC ATC TAC GCT GCA
67>  G   K   A   P   K   L   L   I   Y   A   A TCC ACT CTC GAG TCT GGG GTC CCA TCC AGG TTT
     S   T   L   E   S   G   V   P   S   R   F 265  AGT GGC AGT GGG TCT GGG ACA GAC TTC ACC CTC
89>  S   G   S   G   S   G   T   D   F   T   L ACA ATC AGC TCA CTC CAG CCA GAG GAT TTC GCA
     T   I   S   S   L   Q   P   E   D   F   A 331  ACC TAT TAC TGT CAA CAA GCC AAC GAA GAT CCT
111> T   Y   Y   C   Q   Q   A   N   E   D   P CGG ACC TTC GGT CAG GGC ACC AAA GTG GAA ATC
     R   T   F   G   Q   G   T   K   V   E   I 397  AAG CGG ACC GTG GCT GCA CCA TCT GTC TTC ATC
133> K   R   T   V   A   A   P   S   V   F   I TTC CCT CCA TCT GAT GAG CAG TTG AAA TCT GGA
     F   P   P   S   D   E   Q   L   K   S   G 463  ACT GCC TCT GTT GTG TGC CTG CTG AAT AAC TTC
155> T   A   S   V   V   C   L   L   N   N   F TAT CCC AGA GAG GCC AAA GTG CAG TGG AAG GTG
     Y   P   R   E   A   K   V   Q   W   K   V 529  GAT AAC GCC CTC CAA TCT GGC AAC TCC CAG GAG
177> D   N   A   L   Q   S   G   N   S   Q   E AGT GTC ACA GAG CAG GAC AGC AAG GAC AGC ACC
     S   V   T   E   Q   D   S   K   D   S   T 595  TAC AGC CTC AGC AGC ACC CTG ACC CTG AGC AAA
199> Y   S   L   S   S   T   L   T   L   S   K
```

```
          GCA GAC TAC GAG AAA CAC AAA GTC TAC GCC TGC
           A   D   Y   E   K   H   K   V   Y   A   C

661  GAA GTC ACC CAT CAG GGC CTG AGC TCT CCC GTC
     221>  E   V   T   H   Q   G   L   S   S   P   V

ACA AAG AGC TTC AAC AGG GGA GAG TGT TGA
           T   K   S   F   N   R   G   E   C   *

(SEQ ID NO: 60)
          (SEQ ID NO: 61)
```

The modified DNA sequence for the anti-BDCA2 heavy chain gene is shown below. Amino acids 1-470 contain the heavy chain sequence. Amino acids 1-19 (nucleotides in lower case) contain the native heavy chain signal peptide. The mature N-terminus begins with amino acid 20 (D).

```
     1    atg ggt tgg agc ctc atc ttg ctc ttc ctt gtc
     1>    M   G   W   S   L   I   L   L   F   L   V gct gtt gct acc cgg gtc ctg tcc GAC GTC CAG
           A   V   A   T   R   V   L   S   D   V   Q 67   CTG GTG GAG TCT GGG GGA GGC CTG GTG AAG CCT
     23>   L   V   E   S   G   G   G   L   V   K   P GGA GGG TCC CTG AGA CTC TCC TGC GCA GCC TCT
           G   G   S   L   R   L   S   C   A   A   S 133  GGA TTC ACT TTC AGT ACC TAT ACC ATG TCT TGG
     45>   G   F   T   F   S   T   Y   T   M   S   W GTT CGC CAA GCA CCT GGC AAG GGA CTG GAG TGG
           V   R   Q   A   P   G   K   G   L   E   W 199  GTC GCA ACC ATT AGT CCA GGA GAC AGT TTC GGC
     67>   V   A   T   I   S   P   G   D   S   F   G TAC TAC TAT CCA GAC AGT GTC CAG GGC CGA TTC
           Y   Y   Y   P   D   S   V   Q   G   R   F 265  ACC ATC TCC AGA GAC AAT GCC AAG AAC AGT CTG
     89>   T   I   S   R   D   N   A   K   N   S   L TAC CTG CAA ATG AAC AGT CTG AGG GCA GAG GAC
           Y   L   Q   M   N   S   L   R   A   E   D 331  ACA GCC GTG TAT TAC TGT ACC CGA GAT ATT TAC
     111>  T   A   V   Y   Y   C   T   R   D   I   Y TAT AAT TAC GGA GCC TGG TTT GCT TAC TGG GGC
           Y   N   Y   G   A   W   F   A   Y   W   G 397  CAA GGG ACT CTG GTC ACT GTC TCT AGC GCT TCC
     133>  Q   G   T   L   V   T   V   S   S   A   S ACC AAG GGC CCA TCC GTC TTC CCC CTG GCA CCC
           T   K   G   P   S   V   F   P   L   A   P 463  TCC TCC AAG AGC ACC TCT GGG GGC ACA GCT GCC
     155>  S   S   K   S   T   S   G   G   T   A   A CTG GGC TGC CTG GTC AAG GAC TAC TTC CCC GAA
           L   G   C   L   V   K   D   Y   F   P   E 529  CCC GTG ACC GTG TCC TGG AAC TCA GGC GCC CTG
     177>  P   V   T   V   S   W   N   S   G   A   L ACC AGC GGC GTG CAC ACC TTC CCC GCT GTC CTG
           T   S   G   V   H   T   F   P   A   V   L 595  CAA TCC TCA GGA CTC TAC TCC CTC TCC AGC GTG
     199>  Q   S   S   G   L   Y   S   L   S   S   V GTG ACC GTG CCC TCC AGC AGC TTG GGC ACC CAG
           V   T   V   P   S   S   S   L   G   T   Q 661  ACC TAC ATC TGC AAC GTG AAT CAC AAG CCC AGC
     221>  T   Y   I   C   N   V   N   H   K   P   S AAC ACC AAG GTG GAC AAG AAA GTT GAG CCC AAA
           N   T   K   V   D   K   K   V   E   P   K 727  TCT TGT GAC AAG ACT CAC ACA TGC CCA CCT TGC
     243>  S   C   D   K   T   H   T   C   P   P   C CCA GCA CCT GAA CTC CTG GGG GGA CCT TCA GTC
           P   A   P   E   L   L   G   G   P   S   V 793  TTC CTC TTC CCC CCA AAA CCC AAG GAC ACC CTC
     265>  F   L   F   P   P   K   P   K   D   T   L ATG ATC TCC CGG ACC CCT GAG GTC ACA TGC GTG
           M   I   S   R   T   P   E   V   T   C   V 859  GTG GTG GAC GTG AGC CAC GAA GAC CCT GAG GTC
     287>  V   V   D   V   S   H   E   D   P   E   V AAG TTC AAC TGG TAT GTT GAC GGC GTG GAG GTC
           K   F   N   W   Y   V   D   G   V   E   V 925  CAT AAT GCC AAG ACA AAG CCT CGG GAG GAG CAG
     309>  H   N   A   K   T   K   P   R   E   E   Q TAC AAC AGC ACC TAC CGG GTG GTC AGC GTC CTC
           Y   N   S   T   Y   R   V   V   S   V   L 991  ACC GTC CTG CAC CAA GAC TGG CTG AAT GGC AAG
     331>  T   V   L   H   Q   D   W   L   N   G   K GAG TAC AAG TGC AAG GTC TCC AAC AAA GCC CTC
           E   Y   K   C   K   V   S   N   K   A   L 1057 CCA GCC CCC ATC GAG AAA ACC ATC TCC AAA GCC
     353>  P   A   P   I   E   K   T   I   S   K   A AAA GGG CAG CCC CGA GAA CCA CAG GTG TAC ACC
           K   G   Q   P   R   E   P   Q   V   Y   T 1123 CTG CCC CCA TCC CGG GAT GAG CTG ACC AAG AAC
     375>  L   P   P   S   R   D   E   L   T   K   N CAA GTC AGC CTG ACC TGC CTG GTC AAA GGC TTC
           Q   V   S   L   T   C   L   V   K   G   F 1189 TAT CCC AGC GAC ATC GCC GTG GAG TGG GAG AGC
     397>  Y   P   S   D   I   A   V   E   W   E   S AAT GGG CAG CCT GAG AAC AAC TAC AAG ACC ACA
           N   G   Q   P   E   N   N   Y   K   T   T 1255 CCT CCC GTG TTG GAC TCC GAC GGC TCC TTC TTC
     419>  P   P   V   L   D   S   D   G   S   F   F CTC TAC TCC AAG CTC ACC GTG GAC AAG AGC AGG
           L   Y   S   K   L   T   V   D   K   S   R 1321 TGG CAG CAG GGG AAC GTC TTC TCA TGC TCC GTG
     441>  W   Q   Q   G   N   V   F   S   C   S   V ATG CAT GAG GCT CTG CAC AAC CAC TAC ACC CAG
           M   H   E   A   L   H   N   H   Y   T   Q 1387 AAG AGC CTC TCC CTG TCT CCC GGT TGA
          (SEQ ID NO: 62)
     463>  K   S   L   S   L   S   P   G   *
          (SEQ ID NO: 63)
```

Example 8. Expression Cassettes and Vectors

The heavy chain gene and the light chain genes were excised and ligated into separate expression vectors. Each gene is under transcriptional control of the human cytomegalovirus immediate-early promoter and the human growth hormone gene polyadenylation sequence.

Figure 4:
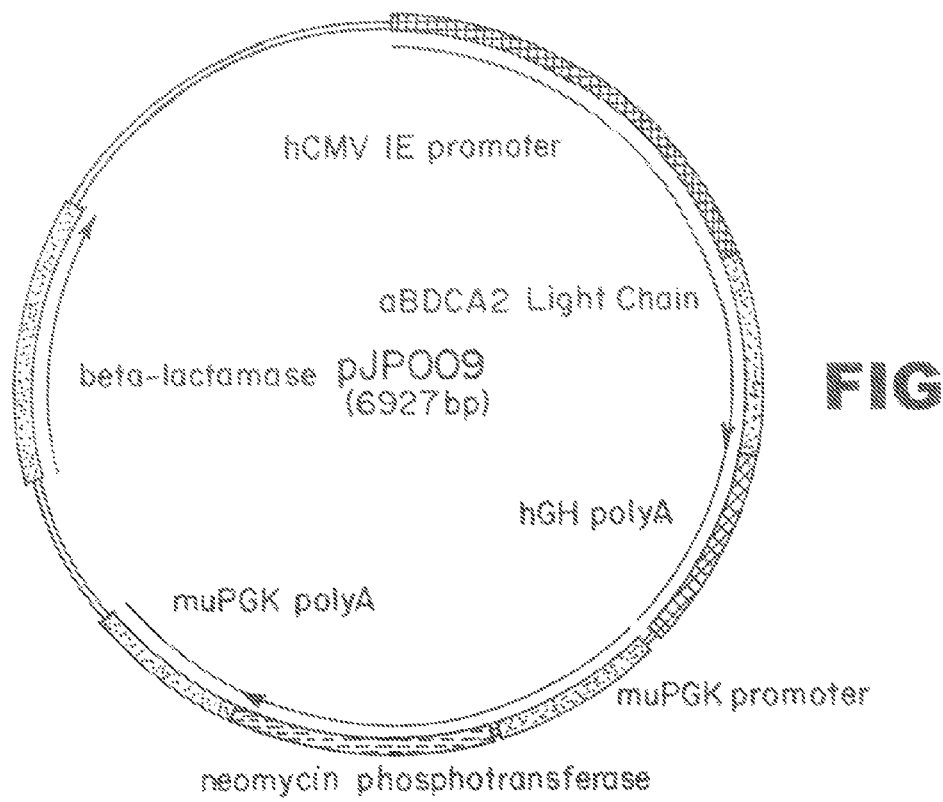
FIG. 4 is a schematic map of plasmid pJP009 that encodes the anti-BDCA2 light chain. The anti-BDCA2 light chain nucleic acid sequence is under transcriptional control of the hCMV IE promoter and the hGH polyadenylation sequences. The gene for aminoglycoside phosphotransferase (neomycin resistance) is under transcriptional control of the murine phosphoglycerine kinase (muPGK) promoter and polyadenylation sequences. The remaining sequences, including the gene for beta-lactamase are for propagation and selection in *E. coli*.

The plasmid expressing the light chain, pJP009, also contains an expression cassette for the neomycin phosphotransferase gene (neo) containing the murine phosphoglycerate kinase (muPGK) early promoter and the muPGK polyadenylation sequence (FIG. 4). The plasmid expressing the heavy chain, pJP010, also contains an expression cassette for the dhfr gene which was used as a selectable and methotrexate-amplifiable marker. The key features of plasmids pJP009 and pJP010 are summarized below.

| Plasmid Name | Promoters | Signal Peptides | Mature Polypeptide Chain | Poly-adenylation | Selectable Markers |
|---|---|---|---|---|---|
| pJP009 | hCMV IE muPGK | Native human kappa subgroup I | Light chain 218 aa | hGH muPGK | Neomycin phosphotransferase: (G418) beta-lactamase: (ampicillin) |
| pJP010 | hCMV IE SV40E | Synthetic signal peptide sequence | Heavy chain 451 aa | hGH SV40E | DHFR: (alpha-nucleosides) beta-lactamase: (ampicillin) |

Abbreviations:
human cytomegalovirus immediate early (hCMV IE),
early simian virus 40 (SV40E),
murine phosphoglycerate kinase (muPGK),
human growth hormone (hGH),
neomycin phosphotransferase gene (G418 resistance),
dihydrofolate reductase gene (dhfr),
bacterial gene for resistance to ampicillin (beta-lactamase).

The complete nucleotide sequence of plasmid pJP009 is shown below. The three open reading frames are the 24F4 light chain, neomycin phosphotransferase, and beta-lactamase.

```
   1   TTGACATTGATTATTGACTAGTTATTAATAGTAATCAATTACGGGGTCATTAGTTCATAGCCCATATATGGAGTTCCGCGTTACATAACTTA

93   CGGTAAATGGCCCGCCTGGCTGACCGCCCAACGACCCCCGCCCATTGACGTCAATAATGACGTATGTTCCCATAGTAACGCCAATAGGGACT

185   TTCCATTGACGTCAATGGGTGGAGTATTTACGGTAAACTGCCCACTTGGCAGTACATCAAGTGTATCATATGCCAAGTACGCCCCCTATTGA

277   CGTCAATGACGGTAAATGGCCCGCCTGGCATTATGCCCAGTACATGACCTTATGGGACTTTCCTACTTGGCAGTACATCTACGTATTAGTCA

369   TCGCTATTACCATGGTGATGCGGTTTTGGCAGTACATCAATGGGCGTGGATAGCGGTTTGACTCACGGGGATTTCCAAGTCTCCACCCCATT

461   GACGTCAATGGGAGTTTGTTTTGGCACCAAAATCAACGGGACTTTCCAAAATGTCGTAACAACTCCGCCCCATTGACGCAAATGGGCGGTAG

553   GCGTGTACGGTGGGAGGTCTATATAAGCAGAGCTCGTTTAGTGAACCGTCAGATCGCCTGGAGACGCCATCCACGCTGTTTTGACCTCCATA

645   GAAGACACCGGGACCGATCCAGCCTCCGCGGCCGGGAACGGTGCATTGGAACGCGGATTCCCCGTGCCAAGAGTGACGTAAGTACCGCCTAT

737   AGAGTCTATAGGCCCACCCCCTTGGCTTCTTATGCATGCTATACTGTTTTTGGCTTGGGGTCTATACACCCCCGCTTCCTCATGTTATAGGT

829   GATGGTATAGCTTAGCCTATAGGTGTGGGTTATTGACCATTATTGACCACTCCCCTATTGGTGACGATACTTTCCATTACTAATCCATAACA

921   TGGCTCTTTGCCACAACTCTCTTTATTGGCTATATGCCAATACACTGTCCTTCAGAGACTGACACGGACTCTGTATTTTTACAGGATGGGGT

1013   CTCATTTATTATTTACAAATTCACATATACAACACCACCGTCCCCAGTGCCCGCAGTTTTTATTAAACATAACGTGGGATCTCCACGCGAAT

1105   CTCGGGTACGTGTTCCGGAACGGTGGAGGGCAGTGTAGTCTGAGCAGTACTCGTTGCTGCCGCGCGCGCCACCAGACATAATAGCTGACAGA

1197   CTAACAGACTGTTCCTTTCCATGGGTCTTTTCTGCAGTCACCGTCCTTGACACGGGATCCGCCACC ATG GAC ATG AGG GTC CCC
                                                                         > M   D   M   R   V   P

1281   GCT CAG CTC CTG GGG CTC CTT CTG CTC TGG CTC CCT GGA GCA CGA TGT GAC ATT CAG CTG ACC CAA TCT
       > A   Q   L   L   G   L   L   L   L   W   L   P   G   A   R   C   D   I   Q   L   T   Q   S

1350   CCA TCC TCT TTG TCC GCC TCT GTG GGG GAC AGG GTC ACC ATC ACC TGC AAG GCC AGC CAA AGT GTT GAT
       > P   S   S   L   S   A   S   V   G   D   R   V   T   I   T   C   K   A   S   Q   S   V   D

1419   TAT GAT GGT GAT AGT TAT ATG AAC TGG TAT CAA CAG AAA CCA GGG AAG GCT CCC AAA CTC CTC ATC TAC
       > Y   D   G   D   S   Y   M   N   W   Y   Q   Q   K   P   G   K   A   P   K   L   L   I   Y

1488   GCT GCA TCC ACT CTC GAG TCT GGG GTC CCA TCC AGG TTT AGT GGC AGT GGG TCT GGG ACA GAC TTC ACC
       > A   A   S   T   L   E   S   G   V   P   S   R   F   S   G   S   G   S   G   T   D   F   T

1557   CTC ACA ATC AGC TCA CTC CAG CCA GAG GAT TTC GCA ACC TAT TAC TGT CAA CAA GCC AAC GAA GAT CCT
       > L   T   I   S   S   L   Q   P   E   D   F   A   T   Y   Y   C   Q   Q   A   N   E   D   P
```

-continued

```
1626 CGG ACC TTC GGT CAG GGC ACC AAA GTG GAA ATC AAG CGG ACC GTG GCT GCA CCA TCT GTC TTC ATC TTC
    > R   T   F   G   Q   G   T   K   V   E   I   K   R   T   V   A   A   P   S   V   F   I   F

1695 CCT CCA TCT GAT GAG CAG TTG AAA TCT GGA ACT GCC TCT GTT GTG TGC CTG CTG AAT AAC TTC TAT CCC
    > P   P   S   D   E   Q   L   K   S   G   T   A   S   V   V   C   L   L   N   N   F   Y   P

1764 AGA GAG GCC AAA GTG CAG TGG AAG GTG GAT AAC GCC CTC CAA TCT GGC AAC TCC CAG GAG AGT GTC ACA
    > R   E   A   K   V   Q   W   K   V   D   N   A   L   Q   S   G   N   S   Q   E   S   V   T

1833 GAG CAG GAC AGC AAG GAC AGC ACC TAC AGC CTC AGC AGC ACC CTG ACC CTG AGC AAA GCA GAC TAC GAG
    > E   Q   D   S   K   D   S   T   Y   S   L   S   S   T   L   T   L   S   K   A   D   Y   E

1902 AAA CAC AAA GTC TAC GCC TGC GAA GTC ACC CAT CAG GGC CTG AGC TCT CCC GTC ACA AAG AGC TTC AAC
    > K   H   K   V   Y   A   C   E   V   T   H   Q   G   L   S   S   P   V   T   K   S   F   N

1971 AGG GGA GAG TGT TGA GGATCCCTGCCCGGGTGGCATCCCTGTGACCCCTCCCAGTGCCTCTCCTGGTCGTGGAAGGTGCTACTCCA
    > R   G   E   C   •  (SEQ ID NO: 64)

2058 GTGCCCACCAGCCTTGTCCTAATAAAATTAAGTTGCATCATTTTGTTTGACTAGGTGTCCTTGTATAATATTATGGGGTGGAGGCGGGTGGT

2150 ATGGAGCAAGGGGCAGGTTGGGAAGACAACCTGTAGGGCCTTCAGGGTCTATTGGGAACCAGGCTGGAGTGCAGTGGCACGATCTTGGCTCG

2242 CTGCAATCTCCGCCTCCTGGGTTCAAGCGATTCTCCTGCCTCAGTCTCCCGAATAGTTGGGATTCCAGGCATGCACGACCAGGCTCAGCTAA

2334 TTTTTGTATTTTTGGTAGAGACGGGGTTTCACCATATTGGCCAGTCTGGTCTCCATCTCCTGACCTCAGGTAATCCGCCCGCCTCGGCCTCC

2426 CAAATTGCTGGGATTACAGGTATGAGCCACTGGGCCCTTCCCTGTCCTGTGATTTTAAAATAATTATACCAGCAGAAGGACGTCCAGACACA

2518 GCATGGGCTACCTGGCCATGCCCAGCCAGTTGGACATTTGAGTTGTTTGCTTGGCACTGTCCTCTCATGAATTCCTGCAGGATTCGAGGGCC

2610 CCTGCAGGTCAATTCTACCGGGTAGGGAGGCGCTTTTCCCAAGGCAGTCTGGAGCATGCGCTTTAGCAGCCCCGCTGGGCACTTGGCGCTA

2702 CACAAGTGGCCTCTGGCCTCGCACACATTCCACATCCACCGGTAGGCGCCAACCGGCTCCGTTCTTTGGTGGCCCCTTCGCGCCACCTTCTA

2794 CTCCTCCCCTAGTCAGGAAGTTCCCCCCCGCCCCGCAGCTCGCGTCGTCAGGACGTGACAAATGGAAGTAGCACGTCTCACTAGTCTCGTG

2886 CAGATGGACAGCACCGCTGAGCAATGGAAGCGGGTAGGCCTTTGGGGCAGCGGCCAATAGCAGCTTTGCTCCTTCGCTTTCTGGGCTCAGAG

2978 GCTGGGAAGGGGTGGGTCCGGGGGCGGGCTCAGGGGCGGGCTCAGGGGCGGGCGGGCGCCCGAAGGTCCTCCGGAGGCCCGGCATTCTGCA

3070 CGCTTCAAAAGCGCACGTCTGCCGCGCTGTTCTCCTCTTCCTCATCTCCGGGCCTTTCGACCTGCAGCCAATATGGGATCGGCCATTGAACA
                                                                                > M   G   S   A   I   E   Q

3162 AGATGGATTGCACGCAGGTTCTCCGGCCGCTTGGGTGGAGAGGCTATTCGGCTATGACTGGGCACAACAGACAATCGGCTGCTCTGATGCCG
    > D   G   L   H   A   G   S   P   A   A   W   V   E   R   L   F   G   Y   D   W   A   Q   Q   T   I   G   C   S   D   A

3254 CCGTGTTCCGGCTGTCAGCGCAGGGGCGCCCGGTTCTTTTTGTCAAGACCGACCTGTCCGGTGCCCTGAATGAACTGCAGGACGAGGCAGCG
    >A  V   F   R   L   S   A   Q   G   R   P   V   L   F   V   K   T   D   L   S   G   A   L   N   E   L   Q   D   E   A   A

3346 CGGCTATCGTGGCTGGCCACGACGGGCGTTCCTTGCGCAGCTGTGCTCGACGTTGTCACTGAAGCGGGAAGGGACTGGCTGCTATTGGGCGA
    >R   L   S   W   L   A   T   T   G   V   P   C   A   A   V   L   D   V   V   T   E   A   G   R   D   W   L   L   L   G   E

3438 AGTGCCGGGGCAGGATCTCCTGTCATCTCACCTTGCTCCTGCCGAGAAAGTATCCATCATGGCTGATGCAATGCGGCGGCTGCATACGTTG
    > V   P   G   Q   D   L   L   S   S   H   L   A   P   A   E   K   V   S   I   M   A   D   A   M   R   R   L   H   T   L

3530 ATCCGGCTACCTGCCCATTCGACCACCAAGCGAAACATCGCATCGAGCGAGCACGTACTCGGATGGAAGCCGGTCTTGTCGATCAGGATGAT
    >D   P   A   T   C   P   F   D   H   Q   A   K   H   R   I   E   R   A   R   T   R   M   E   A   G   L   V   D   Q   D   D

3622 CTGGACGAAGAGCATCAGGGGCTCGCGCCAGCCGAACTGTTCGCCAGGCTCAAGGCGCGCATGCCCGACGGCGATGATCTCGTCGTGACCCA
    > L   D   E   E   H   Q   G   L   A   P   A   E   L   F   A   R   L   K   A   R   M   P   D   G   D   D   L   V   V   T   H

3714 TGGCGATGCCTGCTTGCCGAATATCATGGTGGAAAATGGCCGCTTTTCTGGATTCATCGACTGTGGCCGGCTGGGTGTGGCGGACCGCTATC
    > G   D   A   C   L   P   N   I   M   V   E   N   G   R   F   S   G   F   I   D   C   G   R   L   G   V   A   D   R   Y

3806 AGGACATAGCGTTGGCTACCCGTGATATTGCTGAAGAGCTTGGCGGCGAATGGGCTGACCGCTTCCTCGTGCTTTACGGTATCGCCGCTCCC
    >Q   D   I   A   L   A   T   R   D   I   A   E   E   L   G   G   E   W   A   D   R   F   L   V   L   Y   G   I   A   A   P

3898 GATTCGCAGCGCATCGCCTTCTATCGCCTTCTTGACGAGTTCTTCTGAGGGGATCGATCCGCTGTAAGTCTGCAGAAATTGATGATCTATTA
    > D   S   Q   R   I   A   F   Y   R   L   L   D   E   F   F   •  (SEQ ID NO: 65)

3990 AACAATAAAGATGTCCACTAAAATGGAAGTTTTTCCTGTCATACTTTGTTAAGAAGGGTGAGAACAGAGTACCTACATTTTGAATGGAAGGA

4082 TTGGAGCTACGGGGGTGGGGGTGGGTGGGATTAGATAAATGCCTGCTCTTTACTGAAGGCTCTTTACTATTGCTTTATGATAATGTTTCAT

4174 AGTTGGATATCATAATTTAAACAAGCAAAACCAAATTAAGGGCCAGCTCATTCCTCCCACTCATGATCTATAGATCTATAGATCTCTCGTGG

4266 GATCATTGTTTTTCTCTTGATTCCCACTTTGTGGTTCTAAGTACTGTGGTTTCCAAATGTGTCAGTTTCATAGCCTGAAGAACGAGATCAGC

4358 AGCCTCTGTTCCACATACACTTCATTCTCAGTATTGTTTTGCCAAGTTCTAATTCCATCAGAAGCTGACTCTAGATCTGGATCGATGAATTC
```

-continued
```
4450 GGCGCCTGATGCGGTATTTTCTCCTTACGCATCTGTGCGGTATTTCACACCGCATATGGTGCACTCTCAGTACAATCTGCTCTGATGCCGCA 4542 TAGTTAAGCCAGCCCCGACACCCGCCAACACCCGCTGACGCGCCCTGACGGGCTTGTCTGCTCCCGGCATCCGCTTACAGACAAGCTGTGAC 4634 CGTCTCCGGGAGCTGCATGTGTCAGAGGTTTTCACCGTCATCACCGAAACGCGCGAGACGAAAGGGCCTCGTGATACGCCTATTTTTATAGG 4726 TTAATGTCATGATAATAATGGTTTCTTAGACGTCAGGTGGCACTTTTCGGGGAAATGTGCGCGGAACCCCTATTTGTTTATTTTTCTAAATA 4818 CATTCAAATATGTATCCGCTCATGAGACAATAACCCTGATAAATGCTTCAATAATATTGAAAAAGGAAGAGTATGAGTATTCAACATTTCCG
                                                                    >  M  S  I  Q  H  F  R 4910 TGTCGCCCTTATTCCCTTTTTTGCGGCATTTTGCCTTCCTGTTTTTGCTCACCCAGAAACGCTGGTGAAAGTAAAAGATGCTGAAGATCAGT
     >  V  A  L  I  P  F  F  A  A  F  C  L  P  V  F  A  H  P  E  T  L  V  K  V  K  D  A  E  D  Q 5002 TGGGTGCACGAGTGGGTTACATCGAACTGGATCTCAACAGCGGTAAGATCCTTGAGAGTTTTCGCCCCGAAGAACGTTTTCCAATGATGAGC
     >L  G  A  R  V  G  Y  I  E  L  D  L  N  S  G  K  I  L  E  S  F  R  P  E  E  R  F  P  M  M  S 5094 ACTTTTAAAGTTCTGCTATGTGGCGCGGTATTATCCCGTATTGACGCCGGGCAAGAGCAACTCGGTCGCCGCATACACTATTCTCAGAATGA
     >  T  F  K  V  L  L  C  G  A  V  L  S  R  I  D  A  G  Q  E  Q  L  G  R  R  I  H  Y  S  Q  N  D 5186 CTTGGTTGAGTACTCACCAGTCACAGAAAAGCATCTTACGGATGGCATGACAGTAAGAGAATTATGCAGTGCTGCCATAACCATGAGTGATA
     >  L  V  E  Y  S  P  V  T  E  K  H  L  T  D  G  M  T  V  R  E  L  C  S  A  A  I  T  M  S  D 5278 ACACTGCGGCCAACTTACTTCTGACAACGATCGGAGGACCGAAGGAGCTAACCGCTTTTTTGCACAACATGGGGGATCATGTAACTCGCCTT
     >N  T  A  A  N  L  L  L  T  T  I  G  G  P  K  E  L  T  A  F  L  H  N  M  G  D  H  V  T  R  L 5370 GATCGTTGGGAACCGGAGCTGAATGAAGCCATACCAAACGACGAGCGTGACACCACGATGCCTGTAGCAATGGCAACAACGTTGCGCAAACT
     >  D  R  W  E  P  E  L  N  E  A  I  P  N  D  E  R  D  T  T  M  P  V  A  M  A  T  T  L  R  K  L 5462 ATTAACTGGCGAACTACTTACTCTAGCTTCCCGGCAACAATTAATAGACTGGATGGAGGCGGATAAAGTTGCAGGACCACTTCTGCGCTCGG
     >  L  T  G  E  L  L  T  L  A  S  R  Q  Q  L  I  D  W  M  E  A  D  K  V  A  G  P  L  L  R  S 5554 CCCTTCCGGCTGGCTGGTTTATTGCTGATAAATCTGGAGCCGGTGAGCGTGGGTCTCGCGGTATCATTGCAGCACTGGGGCCAGATGGTAAG
     >A  L  P  A  G  W  F  I  A  D  K  S  G  A  G  E  R  G  S  R  G  I  I  A  A  L  G  P  D  G  K 5646 CCCTCCCGTATCGTAGTTATCTACACGACGGGGAGTCAGGCAACTATGGATGAACGAAATAGACAGATCGCTGAGATAGGTGCCTCACTGAT
     >  P  S  R  I  V  V  I  Y  T  T  G  S  Q  A  T  M  D  E  R  N  R  Q  I  A  E  I  G  A  S  L  I 5738 TAAGCATTGGTAACTGTCAGACCAAGTTTACTCATATATACTTTAGATTGATTTAAAACTTCATTTTTAATTTAAAAGGATCTAGGTGAAGA
     >  K  H  W  •  (SEQ ID NO: 66)

5830 TCCTTTTTGATAATCTCATGACCAAAATCCCTTAACGTGAGTTTTCGTTCCACTGAGCGTCAGACCCCGTAGAAAAGATCAAAGGATCTTCT

5922 TGAGATCCTTTTTTTCTGCGCGTAATCTGCTGCTTGCAAACAAAAAAACCACCGCTACCAGCGGTGGTTTGTTTGCCGGATCAAGAGCTACC

6014 AACTCTTTTTCCGAAGGTAACTGGCTTCAGCAGAGCGCAGATACCAAATACTGTTCTTCTAGTGTAGCCGTAGTTAGGCCACCACTTCAAGA

6106 ACTCTGTAGCACCGCCTACATACCTCGCTCTGCTAATCCTGTTACCAGTGGCTGCTGCCAGTGGCGATAAGTCGTGTCTTACCGGGTTGGAC

6198 TCAAGACGATAGTTACCGGATAAGGCGCAGCGGTCGGGCTGAACGGGGGGTTCGTGCACACAGCCCAGCTTGGAGCGAACGACCTACACCGA

6290 ACTGAGATACCTACAGCGTGAGCTATGAGAAAGCGCCACGCTTCCCGAAGGGAGAAAGGCGGACAGGTATCCGGTAAGCGGCAGGGTCGGAA

6382 CAGGAGAGCGCACGAGGGAGCTTCCAGGGGGAAACGCCTGGTATCTTTATAGTCCTGTCGGGTTTCGCCACCTCTGACTTGAGCGTCGATTT

6474 TTGTGATGCTCGTCAGGGGGGCGGAGCCTATGGAAAAACGCCAGCAACGCGGCCTTTTTACGGTTCCTGGCCTTTTGCTGGCCTTTTGCTCA

6566 CATGTTCTTTCCTGCGTTATCCCCTGATTCTGTGGATAACCGTATTACCGCCTTTGAGTGAGCTGATACCGCTCGCCGCAGCCGAACGACCG

6658 AGCGCAGCGAGTCAGTGAGCGAGGAAGCGGAAGAGCGCCCAATACGCAAACCGCCTCTCCCCGCGCGTTGGCCGATTCATTAATGCAGCTGG

6750 CACGACAGGTTTCCCGACTGGAAAGCGGGCAGTGAGCGCAACGCAATTAATGTGAGTTAGCTCACTCATTAGGCACCCCAGGCTTTACACTT

6842 TATGCTTCCGGCTCGTATGTTGTGTGGAATTGTGAGCGGATAACAATTTCACACAGGAAACAGCTATGACCATGATTACGCCAAGC
     (SEQ ID NO: 67)
```

Figure 5:
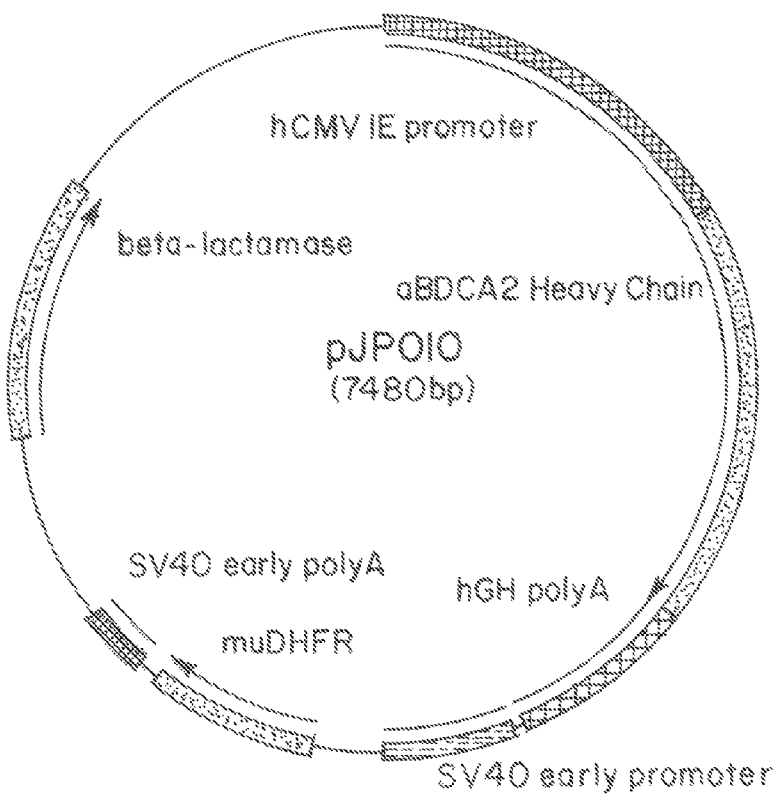
FIG. 5 is a schematic map of plasmid pJP010 that encodes the anti-BDCA2 heavy chain. The anti-BDCA2 heavy chain nucleic acid sequence is under transcriptional control of the hCMV IE promoter and human growth hGH polyadenylation sequences. The gene for dihydrofolate reductase (dhfr) is under transcriptional control of the SV40E promoter and polyadenylation sequences. The remaining sequences, including the gene for beta-lactamase are for propagation and selection in *E. coli*.

The complete nucleotide sequence of plasmid pJP010 (FIG. 5) is shown below. The three open reading frames are the 24F4 heavy chain, murine dihydrofolate reductase, and beta-lactamase.

```
  1 TTGACATTGATTATTGACTAGTTATTAATAGTAATCAATTACGGGGTCATTAGTTCATAGCCCATATATGGAGTTCCGCGTTACATAACTTA

93 CGGTAAATGGCCCGCCTGGCTGACCGCCCAACGACCCCCGCCCATTGACGTCAATAATGACGTATGTTCCCATAGTAACGCCAATAGGGACT

185 TTCCATTGACGTCAATGGGTGGAGTATTTACGGTAAACTGCCCACTTGGCAGTACATCAAGTGTATCATATGCCAAGTACGCCCCCTATTGA

277 CGTCAATGACGGTAAATGGCCCGCCTGGCATTATGCCCAGTACATGACCTTATGGGACTTTCCTACTTGGCAGTACATCTACGTATTAGTCA
```

```
 369 TCGCTATTACCATGGTGATGCGGTTTTGGCAGTACATCAATGGGCGTGGATAGCGGTTTGACTCACGGGGATTTCCAAGTCTCCACCCCATT

461 GACGTCAATGGGAGTTTGTTTTGGCACCAAAATCAACGGGACTTTCCAAAATGTCGTAACAACTCCGCCCCATTGACGCAAATGGGCGGTAG

553 GCGTGTACGGTGGGAGGTCTATATAAGCAGAGCTCGTTTAGTGAACCGTCAGATCGCCTGGAGACGCCATCCACGCTGTTTTGACCTCCATA

645 GAAGACACCGGGACCGATCCAGCCTCCGCGGCCGGGAACGGTGCATTGGAACGCGGATTCCCCGTGCCAAGAGTGACGTAAGTACCGCCTAT

737 AGAGTCTATAGGCCCACCCCCTTGGCTTCTTATGCATGCTATACTGTTTTTGGCTTGGGGTCTATACACCCCCGCTTCCTCATGTTATAGGT

829 GATGGTATAGCTTAGCCTATAGGTGTGGGTTATTGACCATTATTGACCACTCCCCTATTGGTGACGATACTTTCCATTACTAATCCATAACA

921 TGGCTCTTTGCCACAACTCTCTTTATTGGCTATATGCCAATACACTGTCCTTCAGAGACTGACACGGACTCTGTATTTTTACAGGATGGGGT

1013 CTCATTTATTATTTACAAATTCACATATACAACACCACCGTCCCCAGTGCCCGCAGTTTTTATTAAACATAACGTGGGATCTCCACGCGAAT

1105 CTCGGGTACGTGTTCCGGAACGGTGGAGGGCAGTGTAGTCTGAGCAGTACTCGTTGCTGCCGCGCGCCACCAGACATAATAGCTGACAGA

1197 CTAACAGACTGTTCCTTTCCATGGGTCTTTTCTGCAGTCACCGTCCTTGACACGGGATCCGCCACC ATG GGT TGG AGC CTC ATC
                                                                    > M   G   W   S   L   I

1281 TTG CTC TTC CTT GTC GCT GTT GCT ACC CGG GTC CTG TCC GAC GTC CAG CTG GTG GAG TCT GGG GGA GGC
    > L   L   F   L   V   A   V   A   T   R   V   L   S   D   V   Q   L   V   E   S   G   G   G

1350 CTG GTG AAG CCT GGA GGG TCC CTG AGA CTC TCC TGC GCA GCC TCT GGA TTC ACT TTC AGT ACC TAT ACC
    > L   V   K   P   G   G   S   L   R   L   S   C   A   A   S   G   F   T   F   S   T   Y   T

1419 ATG TCT TGG GTT CGC CAA GCA CCT GGC AAG GGA CTG GAG TGG GTC GCA ACC ATT AGT CCA GGA GAC AGT
    > M   S   W   V   R   Q   A   P   G   K   G   L   E   W   V   A   T   I   S   P   G   D   S

1488 TTC GGC TAC TAC TAT CCA GAC AGT GTC CAG GGC CGA TTC ACC ATC TCC AGA GAC AAT GCC AAG AAC AGT
    > F   G   Y   Y   Y   P   D   S   V   Q   G   R   F   T   I   S   R   D   N   A   K   N   S

1557 CTG TAC CTG CAA ATG AAC AGT CTG AGG GCA GAG GAC ACA GCC GTG TAT TAC TGT ACC CGA GAT ATT TAC
    > L   Y   L   Q   M   N   S   L   R   A   E   D   T   A   V   Y   Y   C   T   R   D   I   Y

1626 TAT AAT TAC GGA GCC TGG TTT GCT TAC TGG GGC CAA GGG ACT CTG GTC ACT GTC TCT AGC GCT TCC ACC
    > Y   N   Y   G   A   W   F   A   Y   W   G   Q   G   T   L   V   T   V   S   S   A   S   T

1695 AAG GGC CCA TCC GTC TTC CCC CTG GCA CCC TCC TCC AAG AGC ACC TCT GGG GGC ACA GCT GCC CTG GGC
    > K   G   P   S   V   F   P   L   A   P   S   S   K   S   T   S   G   G   T   A   A   L   G

1764 TGC CTG GTC AAG GAC TAC TTC CCC GAA CCC GTG ACC GTG TCC TGG AAC TCA GGC GCC CTG ACC AGC GGC
    > C   L   V   K   D   Y   F   P   E   P   V   T   V   S   W   N   S   G   A   L   T   S   G

1833 GTG CAC ACC TTC CCC GCT GTC CTG CAA TCC TCA GGA CTC TAC TCC CTC TCC AGC GTG GTG ACC GTG CCC
    > V   H   T   F   P   A   V   L   Q   S   S   G   L   Y   S   L   S   S   V   V   T   V   P

1902 TCC AGC AGC TTG GGC ACC CAG ACC TAC ATC TGC AAC GTG AAT CAC AAG CCC AGC AAC ACC AAG GTG GAC
    > S   S   S   L   G   T   Q   T   Y   I   C   N   V   N   H   K   P   S   N   T   K   V   D

1971 AAG AAA GTT GAG CCC AAA TCT TGT GAC AAG ACT CAC ACA TGC CCA CCT TGC CCA GCA CCT GAA CTC CTG
    > K   K   V   E   P   K   S   C   D   K   T   H   T   C   P   P   C   P   A   P   E   L   L

2040 GGG GGA CCT TCA GTC TTC CTC TTC CCC CCA AAA CCC AAG GAC ACC CTC ATG ATC TCC CGG ACC CCT GAG
    > G   G   P   S   V   F   L   F   P   P   K   P   K   D   T   L   M   I   S   R   T   P   E

2109 GTC ACA TGC GTG GTG GTG GAC GTG AGC CAC GAA GAC CCT GAG GTC AAG TTC AAC TGG TAT GTT GAC GGC
    > V   T   C   V   V   V   D   V   S   H   E   D   P   E   V   K   F   N   W   Y   V   D   G

2178 GTG GAG GTC CAT AAT GCC AAG ACA AAG CCT CGG GAG GAG CAG TAC AAC AGC ACC TAC CGG GTG GTC AGC
    > V   E   V   H   N   A   K   T   K   P   R   E   E   Q   Y   N   S   T   Y   R   V   V   S

2247 GTC CTC ACC GTC CTG CAC CAA GAC TGG CTG AAT GGC AAG GAG TAC AAG TGC AAG GTC TCC AAC AAA GCC
    > V   L   T   V   L   H   Q   D   W   L   N   G   K   E   Y   K   C   K   V   S   N   K   A

2316 CTC CCA GCC CCC ATC GAG AAA ACC ATC TCC AAA GCC AAA GGG CAG CCC CGA GAA CCA CAG GTG TAC ACC
    > L   P   A   P   I   E   K   T   I   S   K   A   K   G   Q   P   R   E   P   Q   V   Y   T

2385 CTG CCC CCA TCC CGG GAT GAG CTG ACC AAG AAC CAA GTC AGC CTG ACC TGC CTG GTC AAA GGC TTC TAT
    > L   P   P   S   R   D   E   L   T   K   N   Q   V   S   L   T   C   L   V   K   G   F   Y

2454 CCC AGC GAC ATC GCC GTG GAG TGG GAG AGC AAT GGG CAG CCT GAG AAC AAC TAC AAG ACC ACA CCT CCC
    > P   S   D   I   A   V   E   W   E   S   N   G   Q   P   E   N   N   Y   K   T   T   P   P

2523 GTG TTG GAC TCC GAC GGC TCC TTC TTC CTC TAC TCC AAG CTC ACC GTG GAC AAG AGC AGG TGG CAG CAG
    > V   L   D   S   D   G   S   F   F   L   Y   S   K   L   T   V   D   K   S   R   W   Q   Q

2592 GGG AAC GTC TTC TCA TGC TCC GTG ATG CAT GAG GCT CTG CAC AAC CAC TAC ACC CAG AAG AGC CTC TCC
    > G   N   V   F   S   C   S   V   M   H   E   A   L   H   N   H   Y   T   Q   K   S   L   S
```

```
2661 CTG TCT CCC GGT TGA GGATCCCTGCCCGGGTGGCATCCCTGTGACCCCTCCCAGTGCCTCTCCTGGTCGTGGAAGGTGCTACTCCA
      > L   S   P   G   •  (SEQ ID NO: 68)

2748 GTGCCCACCAGCCTTGTCCTAATAAAATTAAGTTGCATCATTTTGTTTGACTAGGTGTCCTTGTATAATATTATGGGGTGGAGGCGGGTGGT

2840 ATGGAGCAAGGGGCAGGTTGGGAAGACAACCTGTAGGGCCTTCAGGGTCTATTGGGAACCAGGCTGGAGTGCAGTGGCACGATCTTGGCTCG

2932 CTGCAATCTCCGCCTCCTGGGTTCAAGCGATTCTCCTGCCTCAGTCTCCCGAATAGTTGGGATTCCAGGCATGCACGACCAGGCTCAGCTAA

3024 TTTTTGTATTTTTGGTAGAGACGGGGTTTCACCATATTGGCCAGTCTGGTCTCCATCTCCTGACCTCAGGTAATCCGCCCGCCTCGGCCTCC

3116 CAAATTGCTGGGATTACAGGTATGAGCCACTGGGCCCTTCCCTGTCCTGTGATTTTAAAATAATTATACCAGCAGAAGGACGTCCAGACACA

3208 GCATGGGCTACCTGGCCATGCCCAGCCAGTTGGACATTTGAGTTGTTTGCTTGGCACTGTCCTCTCATGAATTCGTCGACAGATCTGCGCAG

3300 CACCATGGCCTGAAATAACCTCTGAAAGAGGAACTTGGTTAGGTACCTTCTGAGGCGGAAAGAACCAGCTGTGGAATGTGTGTCAGTTAGGG

3392 TGTGGAAAGTCCCCAGGCTCCCCAGCAGGCAGAAGTATGCAAAGCATGCATCTCAATTAGTCAGCAACCAGGTGTGGAAAGTCCCCAGGCTC

3484 CCCAGCAGGCAGAAGTATGCAAAGCATGCATCTCAATTAGTCAGCAACCATAGTCCCGCCCCTAACTCCGCCCATCCCGCCCCTAACTCCGC

3576 CCAGTTCCGCCCATTCTCCGCCCCATGGCTGACTAATTTTTTTTATTTATGCAGAGGCCGAGGCCGCCTCGGCCTCTGAGCTATTCCAGAAG

3668 TAGTGAGGAGGCTTTTTTGGAGGCCTAGGCTTTTGCAAAAAGCTTGATTCTTCTGACACAACAGTCTCGAACTTAAGCTGCAGAAGTTGGTC

3760 GTGAGGCACTGGGCAGGTAAGTATCAAGGTTACAAGACAGGTTTAAGGAGACCAATAGAAACTGGGCTTGTCGAGACAGAGAAGACTCTTGC

3852 GTTTCTGATAGGCACCTATTGGTCTTACTGACATCCACTTTGCCTTTCTCTCCAGGTGTCCACTCCCAGTTCAATTACAGCTCTTAAGGC

3944 TAGAGTACTTAATACGACTCACTATAGGCTAGCATGGTTCGACCATTGAACTGCATCGTCGCCGTGTCCAAAATATGGGGATTGGCAAGAA
                                           > M   V   R   P   L   N   C   I   V   A   V   S   Q   N   M   G   I   G   K   N

4036 CGGAGACCTACCCTGGCCTCCGCTCAGGAACGAGTTCAAGTACTTCCAAAGAATGACCACAACCTCTTCAGTGGAAGGTAAACAGAATCTGG
      > G   D   L   P   W   P   P   L   R   N   E   F   K   Y   F   Q   R   M   T   T   T   S   S   V   E   G   K   Q   N   L

4128 TGATTATGGGTAGGAAAACCTGGTTCTCCATTCCTGAGAAGAATCGACCTTTAAAGGACAGAATTAATATAGTTCTCAGTAGAGAACTCAAA
      >V   I   M   G   R   K   T   W   F   S   I   P   E   K   N   R   P   L   K   D   R   I   N   I   V   L   S   R   E   L   K

4220 GAACCACCACGAGGAGCTCATTTTCTTGCCAAAAGTTTGGATGATGCCTTAAGACTTATTGAACAACCGGAATTGGCAAGTAAAGTAGACAT
      > E   P   P   R   G   A   H   F   L   A   K   S   L   D   D   A   L   R   L   I   E   Q   P   E   L   A   S   K   V   D   M

4312 GGTTTGGATAGTCGGAGGCAGTTCTGTTTACCAGGAAGCCATGAATCAACCAGGCCACCTCAGACTCTTTGTGACAAGGATCATGCAGGAAT
      > V   W   I   V   G   G   S   S   V   Y   Q   E   A   M   N   Q   P   G   H   L   R   L   F   V   T   R   I   M   Q   E

4404 TTGAAAGTGACACGTTTTTCCCAGAAATTGATTTGGGGAAATATAAACTTCTCCCAGAATACCCAGGCGTCCTCTCTGAGGTCCAGGAGGAA
      > F   E   S   D   T   F   F   P   E   I   D   L   G   K   Y   K   L   L   P   E   Y   P   G   V   L   S   E   V   Q   E   E

4496 AAAGGCATCAAGTATAAGTTTGAAGTCTACGAGAAGAAAGACTAACTCGAGAATTCACGCGTGGTACCTCTAGAGTCGACCCGGGCGGCCGG
      > K   G   I   K   Y   K   F   E   V   Y   E   K   K   D   •  (SEQ ID NO: 69)

4588 CCGCTTCGAGCAGACATGATAAGATACATTGATGAGTTTGGACAAACCACAACTAGAATGCAGTGAAAAAAATGCTTTATTTGTGAAATTTG

4680 TGATGCTATTGCTTTATTTGTAACCATTATAAGCTGCAATAAACAAGTTAACAACAACAATTGCATTCATTTTATGTTTCAGGTTCAGGGGG

4772 AGGTGTGGGAGGTTTTTTAAAGCAAGTAAAACCTCTACAAATGTGGTAAAATCGATAAGGATCTGTCGACGAATTCACTGGCCGTCGTTTTA

4864 CAACGTCGTGACTGGGAAAACCCTGGCGTTACCCAACTTAATCGCCTTGCAGCACATCCCCCTTTCGCCAGCTGGCGTAATAGCGAAGAGGC

4956 CCGCACCGATCGCCCTTCCCAACAGTTGCGCAGCCTGAATGGCGAATGGCGCCTGATGCGGTATTTTCTCCTTACGCATCTGTGCGGTATTT

5048 CACACCGCATATGGTGCACTCTCAGTACAATCTGCTCTGATGCCGCATAGTTAAGCCAGCCCCGACACCCGCCAACACCCGCTGACGCGCCC

5140 TGACGGGCTTGTCTGCTCCCGGCATCCGCTTACAGACAAGCTGTGACCGTCTCCGGGAGCTGCATGTGTCAGAGGTTTTCACCGTCATCACC

5232 GAAACGCGCGAGACGAAAGGGCCTCGTGATACGCCTATTTTTATAGGTTAATGTCATGATAATAATGGTTTCTTAGACGTCAGGTGGCACTT

5324 TTCGGGGAAATGTGCGCGGAACCCCTATTTGTTTATTTTTCTAAATACATTCAAATATGTATCCGCTCATGAGACAATAACCCTGATAAATG

5416 CTTCAATAATATTGAAAAAGGAAGAGTATGAGTATTCAACATTTCCGTGTCGCCCTTATTCCCTTTTTTGCGGCATTTTGCCTTCCTGTTTT
                                         > M   S   I   Q   H   F   R   V   A   L   I   P   F   F   A   A   F   C   L   P   V   F

5508 TGCTCACCCAGAAACGCTGGTGAAAGTAAAAGATGCTGAAGATCAGTTGGGTGCACGAGTGGGTTACATCGAACTGGATCTCAACAGCGGTA
      > A   H   P   E   T   L   V   K   V   K   D   A   E   D   Q   L   G   A   R   V   G   Y   I   E   L   D   L   N   S   G

5600 AGATCCTTGAGAGTTTTCGCCCCGAAGAACGTTTTCCAATGATGAGCACTTTTAAAGTTCTGCTATGTGGCGCGGTATTATCCCGTATTGAC
      >K   I   L   E   S   F   R   P   E   E   R   F   P   M   M   S   T   F   K   V   L   L   C   G   A   V   L   S   R   I   D

5692 GCCGGGCAAGAGCAACTCGGTCGCCGCATACACTATTCTCAGAATGACTTGGTTGAGTACTCACCAGTCACAGAAAAGCATCTTACGGATGG
      > A   G   Q   E   Q   L   G   R   R   I   H   Y   S   Q   N   D   L   V   E   Y   S   P   V   T   E   K   H   L   T   D   G
```

-continued

```
5784 CATGACAGTAAGAGAATTATGCAGTGCTGCCATAACCATGAGTGATAACACTGCGGCCAACTTACTTCTGACAACGATCGGAGGACCGAAGG
      >  M   T   V   R   E   L   C   S   A   A   I   T   M   S   D   N   T   A   A   N   L   L   L   T   T   I   G   G   P   K

5876 AGCTAACCGCTTTTTTGCACAACATGGGGGATCATGTAACTCGCCTTGATCGTTGGGAACCGGAGCTGAATGAAGCCATACCAAACGACGAG
     >E   L   T   A   F   L   H   N   M   G   D   H   V   T   R   L   D   R   W   E   P   E   L   N   E   A   I   P   N   D   E

5968 CGTGACACCACGATGCCTGTAGCAATGGCAACAACGTTGCGCAAACTATTAACTGGCGAACTACTTACTCTAGCTTCCCGGCAACAATTAAT
     >  R   D   T   T   M   P   V   A   M   A   T   T   L   R   K   L   L   T   G   E   L   L   T   L   A   S   R   Q   Q   L   I

6060 AGACTGGATGGAGGCGGATAAAGTTGCAGGACCACTTCTGCGCTCGGCCCTTCCGGCTGGCTGGTTTATTGCTGATAAATCTGGAGCCGGTG
     >  D   W   M   E   A   D   K   V   A   G   P   L   L   R   S   A   L   P   A   G   W   F   I   A   D   K   S   G   A   G

6152 AGCGTGGGTCTCGCGGTATCATTGCAGCACTGGGGCCAGATGGTAAGCCCTCCCGTATCGTAGTTATCTACACGACGGGGAGTCAGGCAACT
     >E   R   G   S   R   G   I   I   A   A   L   G   P   D   G   K   P   S   R   I   V   V   I   Y   T   T   G   S   Q   A   T

6244 ATGGATGAACGAAATAGACAGATCGCTGAGATAGGTGCCTCACTGATTAAGCATTGGTAACTGTCAGACCAAGTTTACTCATATATACTTTA
      >  M   D   E   R   N   R   Q   I   A   E   I   G   A   S   L   I   K   H   W   •   (SEQ ID NO: 70)

6336 GATTGATTTAAAACTTCATTTTTAATTTAAAAGGATCTAGGTGAAGATCCTTTTTGATAATCTCATGACCAAAATCCCTTAACGTGAGTTTT

6428 CGTTCCACTGAGCGTCAGACCCCGTAGAAAAGATCAAAGGATCTTCTTGAGATCCTTTTTTTCTGCGCGTAATCTGCTGCTTGCAAACAAAA

6520 AAACCACCGCTACCAGCGGTGGTTTGTTTGCCGGATCAAGAGCTACCAACTCTTTTTCCGAAGGTAACTGGCTTCAGCAGAGCGCAGATACC

6612 AAATACTGTTCTTCTAGTGTAGCCGTAGTTAGGCCACCACTTCAAGAACTCTGTAGCACCGCCTACATACCTCGCTCTGCTAATCCTGTTAC

6704 CAGTGGCTGCTGCCAGTGGCGATAAGTCGTGTCTTACCGGGTTGGACTCAAGACGATAGTTACCGGATAAGGCGCAGCGGTCGGGCTGAACG

6796 GGGGGTTCGTGCACACAGCCCAGCTTGGAGCGAACGACCTACACCGAACTGAGATACCTACAGCGTGAGCTATGAGAAAGCGCCACGCTTCC

6888 CGAAGGGAGAAAGGCGGACAGGTATCCGGTAAGCGGCAGGGTCGGAACAGGAGAGCGCACGAGGGAGCTTCCAGGGGGAAACGCCTGGTATC

6980 TTTATAGTCCTGTCGGGTTTCGCCACCTCTGACTTGAGCGTCGATTTTTGTGATGCTCGTCAGGGGGCGGAGCCTATGGAAAAACGCCAGC

7072 AACGCGGCCTTTTTACGGTTCCTGGCCTTTTGCTGGCCTTTTGCTCACATGTTCTTTCCTGCGTTATCCCCTGATTCTGTGGATAACCGTAT

7164 TACCGCCTTTGAGTGAGCTGATACCGCTCGCCGCAGCCGAACGACCGAGCGCAGCGAGTCAGTGAGCGAGGAAGCGGAAGAGCGCCCAATAC

7256 GCAAACCGCCTCTCCCCGCGCGTTGGCCGATTCATTAATGCAGCTGGCACGACAGGTTTCCCGACTGGAAAGCGGGCAGTGAGCGCAACGCA

7348 ATTAATGTGAGTTAGCTCACTCATTAGGCACCCCAGGCTTTACACTTTATGCTTCCGGCTCGTATGTTGTGTGGAATTGTGAGCGGATAACA

7440 ATTTCACACAGGAAACAGCTATGACCATGATTACGCCAAGC (SEQ ID NO: 71)
```

Example 9. Construction of Cell Line

The host cell used was a Chinese hamster ovary dihydrofolate reductase (dhfr) deficient host cell line, CHO-DG44. The DG44 host cell bank has been tested and found negative for the presence of adventitious agents prior to use. The DG44 host (CER-00-05-01) was used for the construction of cell lines expressing the anti-BDCA2.

Plasmids pJP009 and pJP010 expressing the recoded light chain and heavy chain of anti-BDCA2, respectively, were transfected into the host cell line by electroporation. Transfected cells expressing dhfr were selected using a medium deficient in a nucleosides. After selection in the αMEM nucleosides-free media described above, the transfected pool was enriched for high expressing cell lines using a combination of fluorescence activated cell sorting and the Genetix Clonepix FL instrument (CER-00-09-03). Cell colonies isolated by the ClonePix FL were picked from the semi-solid medium to 96-well plates. Individual wells were expanded and the productivity was assessed. The cell line showing the highest titer in shake flask fed-batch analysis (#49) was transferred to Research Animal Fermentation for growth in a 10 L bioreactor for generation of material for characterization.

Following the initial cell line screening, the highest producing cell lines were selected for amplification. The top cell lines were subjected to methotrexate (MTX) amplification. Amplified pools were subcloned using limiting dilution at a theoretical density of 0.5 cells per well into 384-well plates. Individual wells of 384-well plates were imaged using a Cellavista instrument (Innovatis) for the presence of a single cell per well and verified to be clonal.

The top four amplified, clonal cell lines were selected based on scale-down fed-batch shake flask and product quality analysis. Pre-Master Cell Banks (Pre-MCB) were made from these top 4 cell lines which are evaluated in bioreactors. One lead subclone was selected based on bioreactor performance and product quality analysis. A Pre-MCB vial of the lead cell line was transferred to Manufacturing for Master Cell Bank generation.

Example 10. Post-Translational Modifications of Anti-BDCA2 Antibody, BIIB059 a) Oxidation

Endo-Lys C peptide mapping of anti-BDCA2 BIIB059 antibody revealed that heavy chain Met-257, Met-433 and Trp-163 are susceptible sites to oxidation. Levels ranged from 4 to 7%. Experimental data indicate that much of the oxidation is related to sample preparation.

b) Deamidation

Analysis of the Endo-Lys-C peptide map of BIIB059 antibody showed that ~2.5% each of Asn-389, Asn-394 and Asn-395 in the heavy chain was deamidated (combined deamidation and succinimide formation), and that ~2.5% of Asn-320 in the heavy chain was deamidated (in a succinimide form). The total amount of succinimide forms for Asp-32 and Asp-34 in the light chain was ~3%. Combined isomerization of Asp-32 and Asp-34 in the light chain was ~5%. Similar to the oxidation, some of these modifications may be related to sample preparation.

c) Glycation

Glycation is a non-enzymatic modification caused by the reaction of amino groups on proteins with glucose, a component of the culture medium. Glycation is routinely detected in proteins and levels vary widely depending on cell culture conditions. In the BIIB059 antibody, the level of glycation, as measured by intact mass analysis of the non-reduced protein, was ~10%. Peptide mapping analysis revealed ~0.46% of the glycation on Lys-107 of the light chain, 0.28% on Lys-103 of the light chain and ~0.2% on Lys-295 of the heavy chain O-linked d) Glycosylation There was no detectable O-linked glycosylation of BIIB059.

e) Other Modifications (Eg. Hydroxylysine, Etc.)

Analyses showed that <1% of the heavy chain of BIIB059 antibody is in the aglycosyl form. Analysis showed no Asn-to-Ser substitutions in and there were no unknown modifications or mutations at a level of ≥1% in the antibody.

Figure 6A:
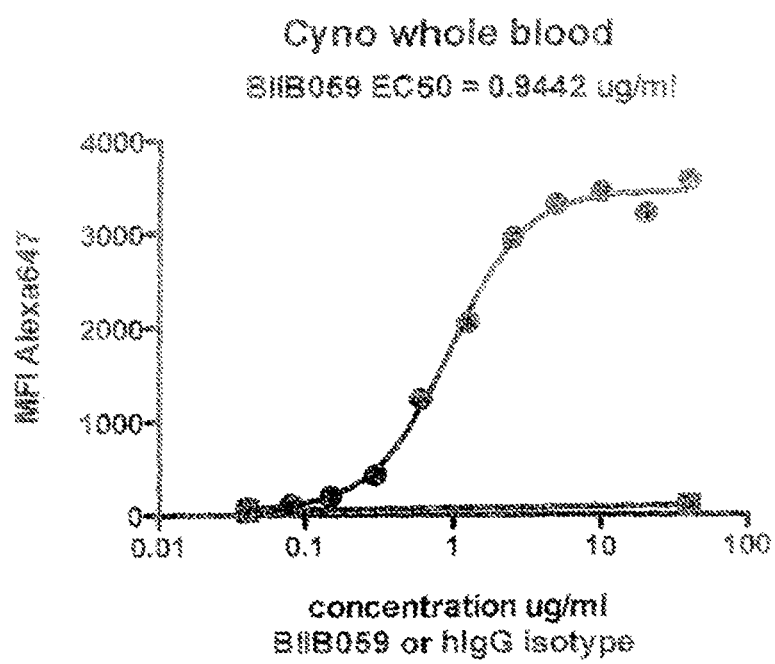
FIG. 6 is a line graph showing the binding of BIIB059 on cynomolgus (A) and human (B) plasmacytoid dendritic cells. Cynomologous monkey (A) or human (B) whole blood was incubated with varying concentrations of Alexa647 labeled BIIB059 antibody (circles), or a human IgG isotype (squares) on ice. Data was acquired using the LSRII-4 color FACS machine, and analyzed using FlowJo and GraphPad Prism software.
Figure 6B:
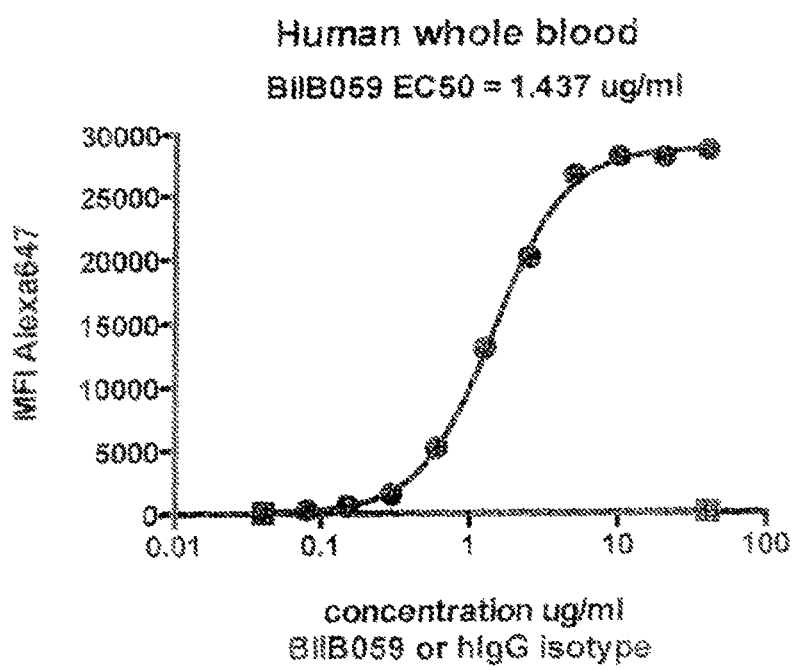

Example 11. Direct Binding of BIIB059 to the Cell Surface of Plasmacytoid Dendritic Cells A flow cytometric whole blood assay was developed to evaluate BIIB059 binding to BDCA2 on the human or cynomolgus plasmacytoid dendritic cells (pDC). Cynomolgus monkey (Toxikon, Inc, Bedford, Mass.) or human peripheral blood (Biogen Idec) were collected in sodium heparin collection tubes and maintained at room temperature. A FACS staining antibody cocktail for identifying pDCs was added to each whole blood aliquot, incorporating CD20, CD14, CD123 and HLA-DR antibodies. Alexa647 labeled BIIB059 (Biogen Idec, Lot#17073-057) or an Alexa647-labelled hIgG isotype control was added to the FACS staining cocktail, at a concentration of 0 to 40 μg/mL. Blood was incubated on ice, protected from light, for 30 min. After 30 min., each 500 μL aliquot of whole blood (cyno) or 100 μL (human) was treated with 10 mL (cyno) or 2 mL (human) of 1× Easy Lyse Buffer (Leinco Technologies) that had been incubated at 37° C. for at least one hour. After a 10-15 min. incubation at room temperature, samples were centrifuged at 1400 rpm for 5 min. The supernatant was decanted, leaving only a pellet of white blood cells (WBC). Each WBC pellet was washed with 5 mL of FACS buffer (1% BSA+0.002% NaAzide+1 mM CaCl$_2$+1 mM MgCl$_2$ in PBS), and centrifuged at 1400 rpm for 5 min. The supernatant was decanted, and each WBC pellet was resuspended in 200 μL of FACS buffer and transferred to a 96-well round bottom plate (Fisher Scientific). The plate was centrifuged at 1400 rpm for 5 min. The supernatant was dumped out of the plate, and each WBC pellet was washed with 200 μL of FACS buffer. The plate was centrifuged at 1400 rpm for 5 min, and the supernatant dumped out of the plate. Following washing (as above), WBCs were resuspended in 200 μL of 1% paraformaldehyde (PFA) in PBS, and fixed at 4° C. overnight, protected from light. Immediately prior to flow cytometry analysis, WBCs were filtered using a 60-micron nylon mesh filter plate (Millipore). Each pellet was then transferred to a new, 96-well round bottom plate and centrifuged at 1400 rpm for 5 min. Each WBC pellet was resuspended in 250 μL of FACS buffer and fluorescence intensity measured on a LSRII 4-color FACS machine. Single color compensation was acquired using anti-mouse Ig Compensation Particle beads set (BD Biosciences). Analysis was performed using FlowJo and GraphPad Prism software. BIIB059 bound cynomolgus and human cells similarly with $EC_{50}$ values of 1-2 μg/mL (7-13 nM) (FIG. 6).

Example 12. Assessing Self Association for BIIB059

The AlphaScreen assay is a homogeneous proximity assay utilizing glutathione donor and acceptor beads (Perkin Elmer) to bind human FcRIIa (CD32a) GST. Various concentrations of the antibodies to be tested were added in this mixture. Since the binding of the antibody to FcRIIa is monovalent, the only way for a signal to be generated is if donor and acceptor beads both have a bound antibody which then associates bringing the beads within 200 nm allowing for the production of singlet oxygen and consequent light emission. The level of emission detected by the Envision (Perkin Elmer) instrument is proportional to the degree of self-association.

Figure 7:
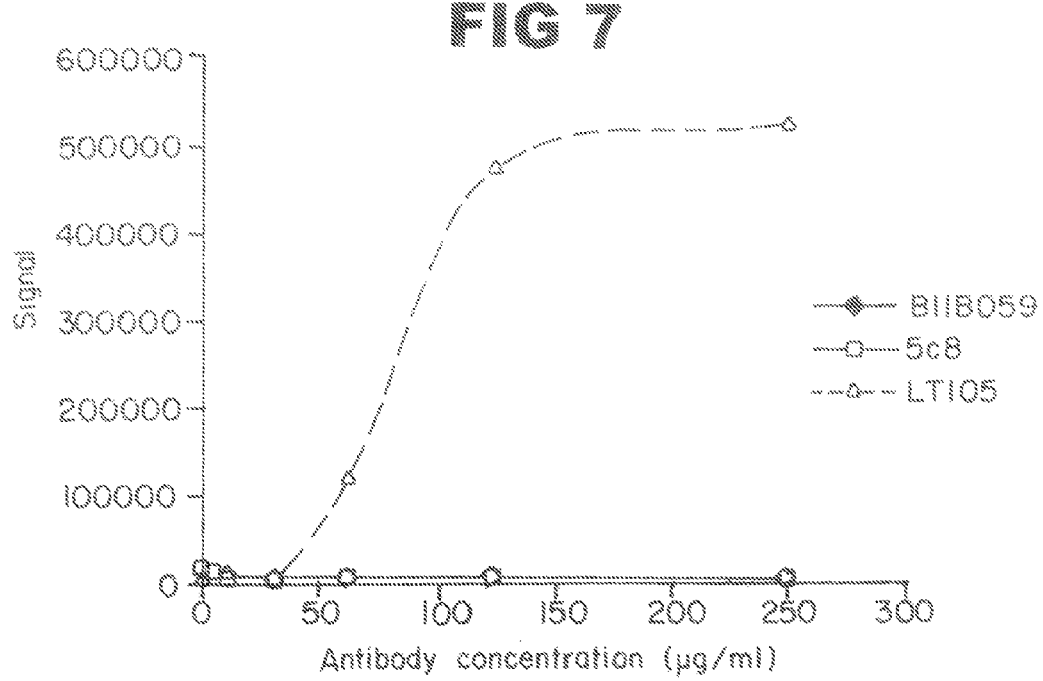
FIG. 7 is a line graph showing the results of an AlphaScreen assay for self-association. Key: diamond=BIIB059; square=5c8; and triangle=LT105.

FIG. 7 shows the results of the Alpha Screen for BIIB059 compared to 5c8 (negative control) and LT105 (positive control with strong self-association).

Example 13. Assessing Non-Specific Binding of BIIB059

Cross-interaction chromatography (CIC) is a high throughput method for preliminary assessment of the stickiness of mAb candidates (Jacobs et al., Pharm Res., 27(1): 65-71 (2010)). In this method, bulk polyclonal human IgG is chemically coupled to an NHS-activated chromatography resin. The retention times of BIIB059 on non-derivatized and IgG-derivatized columns were then compared to a control panel of well-behaved and poorly behaved mAbs. BIIB059 showed no evidence of non-specific binding by this method as evidenced by its low retention times and K' values.

CIC Data Showing Solubility and Non-Specific Binding

| Antibody | Solubility | Rt-Test | Rt-Blank | K' | |
|---|---|---|---|---|---|
| 5C8 | good | 9.3 | 9.46 | −0.017 | |
| Hu H0/L0 | bad | 14.1 | 10.4 | 0.356 | ← higher K' values |
| Li33 | bad | 10.8 | 9.2 | 0.174 | ← may indicate lower solubility |
| Herceptin | good | 9.5 | 9.4 | 0.011 | |
| 15F3 H4/L1 (1-3) | good | 9.3 | 9.2 | 0.011 | |
| 24F4 H4/L1 (1-5) | good | 9.3 | 9.1 | 0.022 | |
| 16A8 | good | 9.1 | 9 | 0.011 | |

Example 14. Assessing Stability of BIIB059

Figure 8:
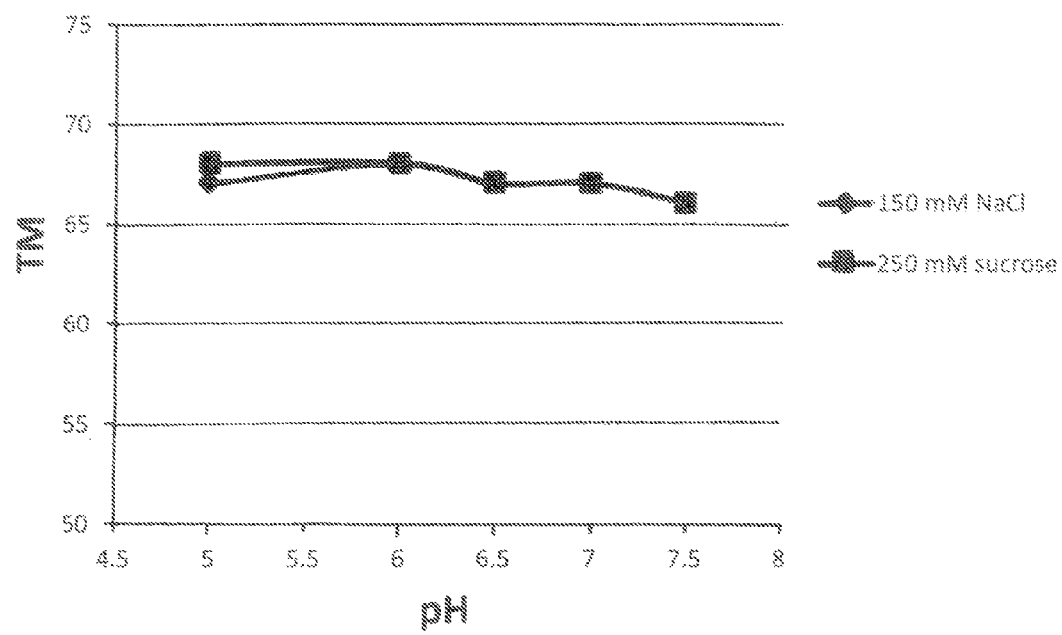
FIG. 8 is a line graph showing the results of a differential scanning fluorometry to test the stability of BIIB059 over different conditions. This graph shows data with 150 mM sodium chloride and 250 mM sucrose as a function of pH.

Differential scanning fluorometry was used to test the stability of BIIB059 over a range of buffer conditions for the initial research formulation. Protein unfolding was monitored on an Mx3005p real-time PCR system (Agilent Technologies) in a 96-well format using 10 μg of protein in 50 μL PBS (at pH 7.0) supplemented with SYPRO orange fluorophor at a final concentration of 10× (based on Invitrogen stock designation of 1000×). Samples were heated from 25° C. to 95° C. at 1° C./min with fluorescence intensity measured three times every 1° C. Fluorescence intensities were plotted as a function of temperature. Tm were derived from these curves by taking the negative derivative ("—R'(T)" in the Mx3005p software) and selecting the local minima of the derivative plots. Using a base buffer of 20 mM sodium citrate, the pH was varied from 5.0 to 7.5 and NaCl and sucrose concentrations were varied from 50 to 250 mM. Stability was similar throughout these buffer ranges. FIG. 8 shows data with 150 mM NaCl and 250 mM sucrose as a function of pH. 20 mM sodium citrate, 150 mM NaCl pH 6.0 was chosen as the research formulation over sucrose due to difficulty reaching high concentrations with sucrose using research centrifugal concentrators.

Example 15. Assessing Agitation Stability of BIIB059

Figure 9:
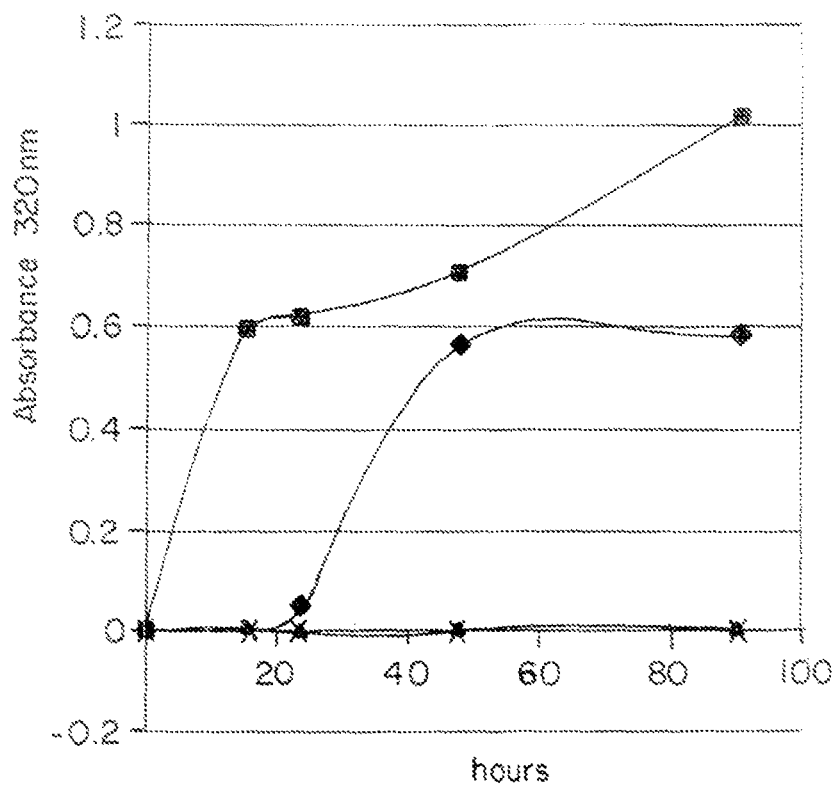
FIG. 9 is a line graph showing the effect of agitation on aggregation over time. Aggregation was suppressed with the addition of Tween 80.

A 0.2 mL volume of the BIIB059 mAb solution at 1 mg/mL in 20 mM sodium citrate, pH 6.0, 150 mM NaCl was subjected to reciprocal shaking at room temperature in 2 mL glass vials (Waters, WAT270946C) using a Lab-Line Instruments model 4626 Titer Plate Shaker set at 600 rpm. Aggregation was assessed by monitoring increases in turbidity at 320 nm using a Beckman DU640 spectrophotometer. BIIB059 displayed time-dependent aggregation. Normally wild type human IgG1 antibodies do not aggregate under these agitation conditions. As shown in FIG. 9, aggregation was completely suppressed by the addition of 0.03% Tween 80, a common formulation excipient. Agitation-induced aggregation can sometimes be highly pH dependent. The aglycosyl IgG4/IgG1 showed a more rapid and more extensive aggregation than BIIB059. Aggregation of aglycosyl IgG4/IgG1 was also suppressed with addition of Tween 80.

Example 16. Assessing Viscosity of BIIB059

The stability and viscosity of BIIB059 samples were measured at high concentrations of 150 mg/mL and greater, to support potential development of the product for subcutaneous administration. Solutions of BIIB059 were centrifuged in ultra-concentrator tubes to limit volumes and the concentrations achieved were determined by UV scans. Stability was determined by size exclusion chromatography after storage at 2-8° C. for one and two weeks. Protein concentrations of greater than 200 mg/mL were readily achieved for small amounts of protein in 20 mM citrate, pH 6, 150 mM NaCl buffer and aggregate remained low (0.68%) after two weeks at 2-8° C. Viscosity was measured using a Viscopro2000 instrument (Cambridge Viscosity). The viscosity at 150 mg/mL was only 8 cP in the citrate/saline buffer. These results demonstrate that a high-concentration formulation of BIIB059 should be achievable.

Example 17. Cloning the Human BDCA2 Gene

The full-length human BDCA2 (huBDCA2) cDNA was subcloned in Invitrogen's pCR4TOPO cloning vector from Open Biosystems: this plasmid was designated pEAG2367. DNA sequencing confirmed that its cDNA was identical to the full-length human BDCA2 cDNA in the reference GenBank® accession number NM_130441. The huBDCA2 full-length open reading frame encoded by pEAG2420 is shown below, with the TM-HMM-predicted transmembrane domain underlined:

```
                                                  (SEQ ID NO: 1)
  1 MVPEEEPQDR EKGLWWFQLK VWSMAVVSIL LLSVCFTVSS VVPHNFMYSK

51 TVKRLSKLRE YQQYHPSLTC VMEGKDIEDW SCCPTPWTSF QSSCYFISTG

101 MQSWTKSQKN CSVMGADLVV INTREEQDFI IQNLKRNSSY FLGLSDPGGR

151 RHWQWVDQTP YNENVTFWHS GEPNNLDERC AIINFRSSEE WGWNDIHCHV

201 PQKSICKMKK IYI*
```

The huFcεRIγ full-length open reading frame encoded by pEAG2413, which is identical to the reference sequence in GenBank® accession number NP_004097, is shown below:

```
                                                  (SEQ ID NO: 2)
  1 MIPAVVLLLL LLVEQAAALG EPQLCYILDA ILFLYGIVLT LLYCRLKIQV

51 RKAAITSYEK SDGVYTGLST RNQETYETLK HEKPPQ*
```

A CHO expression vector co-expressing both human BDCA2 and FcεRIγ cDNAs in tandem transcriptional units was constructed by subcloning the 2.11 kb SpeI fragment from pEAG2413 into the linearized, phosphatased 6.71 kb SpeI vector backbone of pEAG2420, resulting in a "univector" designated pEAG2456. The human BDCA2 and FcεRIγ cDNAs in pEAG2420 were sequence confirmed. A stable CHO cell line stably co-expressing BDCA2 and FcεRIγ cDNAs was produced by transfection with pEAG2456.

Example 18. Cloning the Cyno and Rhesus BDCA2 Gene

The deduced macaque BDCA2 open reading frame encoded by pEAG2384 and one of the SNP forms observed in pEAG2383 is shown below. This SNP form is referred to below as the E73 SNP form of cyno BDCA2. In the rhesus, a single sequence identical to the E73 SNP form of cyno BDCA2 was observed.

```
                                                 (SEQ ID NO: 72)
  1 MVPEEEPQDR EKGVWWFQLK VWSVAVVSIL LLCVCFTVSS VASHNFMYSK
```

```
 51 TVKRLSKLQE YQQYYPSLTC VMEGKDMEDW SCCPTPWTSF QSSCYFISTV

101 MQSWTKSQNN CSVMGADLVV INTKEEQDFI TQNLKINSAY FLGLSDPKGW

151 RHWQWVDQTP YNKNVTFWHS GEPNSPDERC AIINFRSEEW GWNDVHCHVP

201 QKSICKMKKI YI*
```

In a second SNP form of cyno BDCA2, residue 73 (GAA=Glu, E) highlighted above is Lysine (AAA=Lys, K). This second SNP form is referred to as the K73 SNP form of cynomolgus monkey BDCA2. In human BDCA2, residue 73 is Glutamic acid. The gapped alignment of the human (upper) and macaque (lower) BDCA2 sequences, which share 90.6% identity, is shown below. Potential N-linked glycosylation sites are shaded. Macaque BDCA2 lacks one potential N-linked glycosylation site present in human (NSS at 137-139 in human vs. NSA in macaque).

A CHO expression vector co-expressing both the cyno E73 SNP form of BDCA2 and FcεRIγ cDNAs in tandem transcriptional units was constructed by subcloning the 2.11 kb SpeI fragment from pCN652 into the linearized, phosphatased 6.72 kb SpeI vector backbone of pCN654, resulting in a "univector" designated pEAG2668. The cyno BDCA2 and FcεRIγcDNAs in pEAG2668 were sequence confirmed. A stable CHO cell line stably co-expressing BDCA2 and FcεRIγ cDNAs was produced by transfection with pEAG2668.

```
  1 MVPEEEPQDREKGLWWFQLKVWSMAVVSILLLSVCFTVSSVVPHNFMYSK  50
    ||||||||.||||:|||||||||||.|||||||||||||||||||||||
  1 MVPEEEPQDREKGVWWFQLKVWSVAVVSILLLCVCFTVSSVASHNFMYSK  50

51 TVKRLSKLREYQQYHPSLTCVMEGKDIEDWSCCPTPWTSFQSSCYFISTG 100
    ||||||||.||||:|||||||||||.|||||||||||||||||||||||
 51 TVKRLSKLQEYQQYYPSLTCVMEGKDMEDWSCCPTPWTSFQSSCYFISTV 100

101 MQSWTKSQKNCSVMGADLVVINTREEQDFIIQNLKRNSSYFLGLSDPGGR 101
    ||||||||.||||||||||||||:||||| |||| ||.:||||||||| |
101 MQSWTKSQNNCSVMGADLVVINTKEEQDFITQNLKINSAYFLGLSDPKGW 101

151 RHWQWVDQTPYNENVTFWHSGEPNNLDERCAIINFRSSEEWGWNDIHCHV 200
    |||||||||||.|||||||||||. ||||||||||.|||||||||:||||
151 RHWQWVDQTPYNKNVTFWHSGEPNSPDERCAIINFR.SEEWGWNDVHCHV 199

201 PQKSICKMKKIYI* 214   (SEQ ID NO: 1)
    ||||||||||||||
200 PQKSICKMKKIYI* 213   (SEQ ID NO: 72)
```

A consensus cynomolgus monkey FcεRIγ open reading frame is shown below:

```
                                          (SEQ ID NO: 73)
  1 MIPAVVLLLL LLVEQAAALG EPQLCYILDA ILFLYGIVLT LLYCRLKIQV

51 RKAAIASYEK SDGVYTGLST RNQETYETLK HEKPPQ
```

The cynomolgus monkey FcεRIγ cDNA sequence is a perfect match to that of the predicted rhesus cDNA (based upon genomic short reads) described in GenBank® accession number XM_001115585 and a cyno sequence deposited as GenBank® accession number AF485816 by scientists at Genentech. The cyno FcεRIγ protein sequence shares 98.9% identity with human FcεRIγ protein, differing by only a single, conservative substitution. The alignment between human (upper) and cyno (lower) FcεRIγ is shown below:

Example 19. Cross-Reactivity Between Human and Cyno BDCA2

To determine whether the cynomolgus monkey E73/K73 BDCA2 SNP affected anti-BDCA2 binding, 293E cells were co-transfected with expression vectors carrying an EGFP reporter (pEAG1458) and BDCA2 and FcεRIγ cDNAs (human BDCA2: pEAG2420 and FcεRIγ: pEAG2413; cyno E73 BDCA2: pCN652 or K73 BDCA2: pCN656 and cyno

```
  1 MIPAVVLLLLLLVEQAAALGEPQLCYILDAILFLYGIVLTLLYCRLKIQV  50
    ||||||||| |||||||||||||||||||||||||||||||||||||||
  1 MIPAVVLLLLLLVEQAAALGEPQLCYILDAILFLYGIVLTLLYCRLKIQV  50

51 RKAAITSYEKSDGVYTGLSTRNQETYETLKHEKPPQ* 87    (SEQ ID NO: 2)
    |||||  |||||||||||||||||||||||||||||
 51 RKAAIASYEKSDGVYTGLSTRNQETYETLKHEKPPQ* 87    (SEQ ID NO: 73)
```

Figure 10:
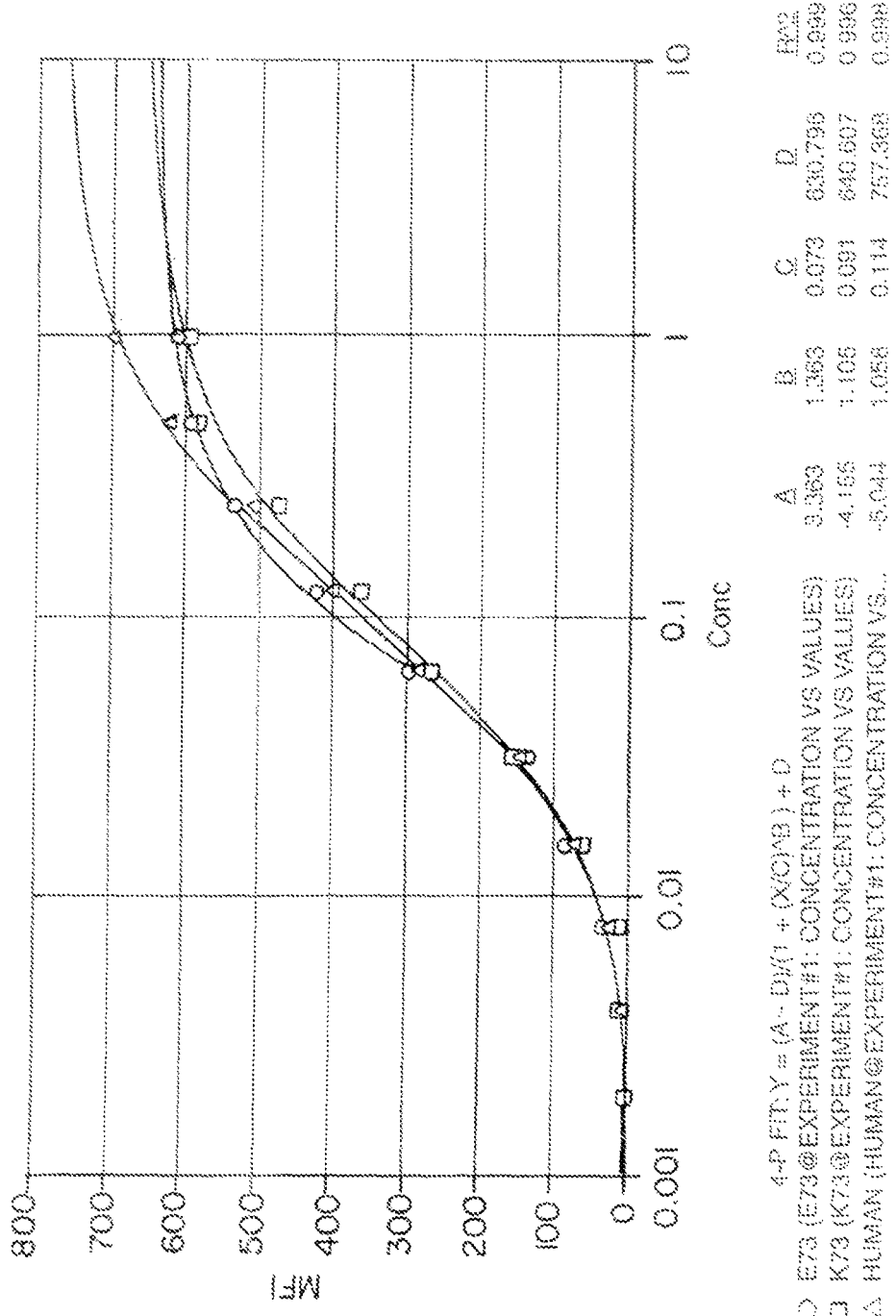
FIG. 10 is a line graph showing direct binding of AC144 to human and cynomolgus surface BDCA2.

FcεRIγ: pCN652) at 1:1:1 molar ratios. At 3 days post-transfection, cells were harvested and stained with PE-conjugated Miltenyi anti-human BDCA2 AC144 mAb (Miltenyi Biotec catalog number 130-090-511) in a direct binding dilution titration FACS, gating on green EGFP-positive cells. FIG. 10 shows the direct binding of AC144 to human and cyno surface BDCA2.

The apparent EC50's are essentially equivalent for human BDCA2 and both E73 and K73 SNP forms of cynomolgus monkey BDCA2. Given this result, CHO stable transfectants for surface full-length BDCA2 were generated using the human BDCA2/FcεRIγ expression vector pEAG2456 and the cyno E73 SNP BDCA2/FcεRIγ expression vector pEAG2668. These lines were used for triage of human/cyno cross-reactive anti-BDCA2 antibodies.

Example 20. Fc Fusion Constructs of Human and Cynomolgus BDCA2 Ectodomains

Five Fc fusion constructs of human and cyno BDCA2 ECD were engineered. In three of the constructs, BDCA2 is attached via a G4S linker sequence to the C-terminus of human IgG1 hinge and Fc. In two of the constructs, the G4S linker was replaced with a TEV protease cleavage site ENLYFQC.

As BDCA2 is a type II membrane protein (the C-terminus is outside the cell), the design of soluble Fc fusion proteins involved adding the C-terminal ectodomain of BDCA2 (residues 45-213 for human BDCA2) to the C-terminus of engineered IgG Fc's with secretion was driven by an in-frame murine kappa light chain signal sequence. The full-length huBDCA2 construct pEAG2367 was used as template for PCR with primers 5' CAG TGT CTG TTT CAC TCC CGG GGG TGG CGG TGG TAG CAA TTT TAT GTA TAG C 3' (SEQ ID NO:74) (to add a 5' XmaI (Pro-Gly) and Gly4Ser linker immediately before the huBDCA2 ectodomain's 5' end) and 5' CCA GGG AGA ATA GGA TCC TTA TAT GTA GAT CTT 3' (SEQ ID NO:75) (to add a 3' BamHI site immediately after the huBDCA2 terminator). The 0.56 kb PCR product was purified and subcloned into Invitrogen's pCRBluntIITOPO cloning vector, producing pEAG2417, whose insert cDNA sequence was confirmed. The 0.53 kb XmaI-BamHI fragment from pEAG2417 and the 0.75 kb NotI-XmaI fragment from pEAG1397 (carrying an engineered huIgG1 Fc whose secretion is driven by an in-frame engineered murine kappa light chain signal sequence) were ligated with the 1.89 kb BamHI-XbaI and 4.17 kb XbaI-NotI vector backbone fragments from the expression vector pV90, producing the huIgG1 Fc-huBDCA2 fusion protein expression vector pEAG2421, whose cDNA insert sequence was confirmed. The deduced open reading frame encoded by pEAG2421 is shown below:

```
                                                          (SEQ ID NO: 76)
  1 MKLPVRLLVL MFWIPASSSE PKSSDKTHTC PPCPAPELLG GPSVFLFPPK

51 PKDTLMISRT PEVTCVVVDV SHEDPEVKFN WYVDGVEVHN AKTKPREEQY

101 NSTYRVVSVL TVLHQDWLNG KEYKCKVSNK ALPAPIEKTI SKAKGQPREP

151 QVYTLPPSRD ELTKNQVSLT CLVKGFYPSD IAVEWESNGQ PENNYKTTPP

201 VLDSDGSFFL YSKLTVDKSR WQQGNVFSCS VMHEALHNHY TQKSLSLSPG

251 GGGGSNFMYS KTVKRLSKLR EYQQYHPSLT CVMEGKDIED WSCCPTPWTS

301 FQSSCYFIST GMQSWTKSQK NCSVMGADLV VINTREEQDF IIQNLKRNSS

351 YFLGLSDPGG RRHWQWVDQT PYNENVTFWH SGEPNNLDER CAIINFRSSE

401 EWGWNDIHCH VPQKSICKMK KIYI*
kappa light chain signal sequence: residues 1-19 above (italicized)
human IgG1 Fc: residues 20-250 above
G4S linker: residues 251-255 above (boldened)
huBDCA2 ectodomain: residues 256-424 above (underlined)
```

To construct an expression vector for a muIgG2a Fc-huBDCA2 fusion protein, the 0.53 kb XmaI-BamHI fragment from pEAG2417 and the 0.75 kb NotI-XmaI fragment from pEAG1442 (carrying an engineered murine IgG2a Fc whose secretion is driven by an in-frame engineered murine kappa light chain signal sequence) were ligated with the 1.89 kb BamHI-XbaI and 4.17 kb XbaI-NotI vector backbone fragments from the expression vector pV90, producing pEAG2423, whose cDNA insert sequence was confirmed. The deduced open reading frame encoded by pEAG2423 is shown below:

```
                                                          (SEQ ID NO: 77 )
  1 MKLPVRLLVL MFWIPASSSE PRGPTIKPSP PCKCPAPNLL GGPSVFIFPP

51 KIKDVLMISL SPIVTCVVVD VSEDDPDVQI SWFVNNVEVH TAQTQTHRED

101 YNSTLRVVSA LPIQHQDWMS GKEFKCKVNN KDLPAPIERT ISKPKGSVRA

151 PQVYVLPPPE EEMTKKQVTL TCMVTDFMPE DIYVEWTNNG KTELNYKNTE

201 PVLDSDGSYF MYSKLRVEKK NWVERNSYSC SVVHEGLHNH HTTKSFSRTP

251 GGGGGSNFMY SKTVKRLSKL REYQQYHPSL TCVMEGKDIE DWSCCPTPWT
```

```
301 SFQSSCYFIS TGMQSWTKSQ KNCSVMGADL VVINTREEQD FIIQNLKRNS

351 SYFLGLSDPG GRRHWQWVDQ TPYNENVTFW HSGEPNNLDE RCAIINFRSS

401 EEWGWNDIHC HVPQKSICKM KKIYI*
kappa light chain signal sequence: residues 1-19 above (italicized)
murine IgG2a Fc: residues 20-251 above
G4S linker: residues 252-256 above (boldened)
huBDCA2 ectodomain: residues 257-425 above (underlined)
```

Stable CHO cell lines producing the Fc-huBDCA2 fusion proteins were produced by transfection with expression vectors pEAG2421 and pEAG2423. These fusion proteins were used in ELISA and Octet binding assays for antibody triage during candidate screening.

To engineer cynomolgus (cyno) BDCA2 to make an Fc fusion protein protein, the full-length E73 SNP variant of cyno BDCA2 in construct pCN648 was subjected to site-directed mutagenesis with primers 5' CTC TGT GTC TGT TTC ACT CCC GGG GGT GGC GGT GGT AGC AAT TTT ATG TAT AGC 3' (SEQ ID NO:78) and its reverse complement, to add a 5' XmaI (Pro-Gly) and Gly4Ser linker immediately before the huBDCA2 ectodomain's 5' end, producing construct pEAG2675, whose cDNA insert sequence was confirmed. To construct an expression vector for a muIgG2a Fc-cyno BDCA2 fusion protein, the 0.53 kb XmaI-BamHI fragment from pEAG2675 and the 0.75 kb NotI-XmaI fragment from pEAG1442 (carrying an engineered murine IgG2a Fc whose secretion is driven by an in-frame engineered murine kappa light chain signal sequence) were ligated with the 1.89 kb BamHI-XbaI and 4.17 kb XbaI-NotI vector backbone fragments from the expression vector pV90, producing pEAG2677, whose cDNA insert sequence was confirmed. The deduced open reading frame encoded by pEAG2677 is shown below:

```
                                                (SEQ ID NO: 79)
  1 MKLPVRLLVL MFWIPASSSE PRGPTIKPSP PCKCPAPNLL GGPSVFIFPP

51 KIKDVLMISL SPIVTCVVVD VSEDDPDVQI SWFVNNVEVH TAQTQTHRED

101 YNSTLRVVSA LPIQHQDWMS GKEFKCKVNN KDLPAPIERT ISKPKGSVRA

151 PQVYVLPPPE EEMTKKQVTL TCMVTDFMPE DIYVEWTNNG KTELNYKNTE

201 PVLDSDGSYF MYSKLRVEKK NWVERNSYSC SVVHEGLHNH HTTKSFSRTP

251 GGGGGSNFMY SKTVKRLSKL QEYQQYYPSL TCVMEGKDME DWSCCPTPWT

301 SFQSSCYFIS TVMQSWTKSQ NNCSVMGADL VVINTKEEQD FITQNLKINS

351 AYFLGLSDPK GWRHWQWVDQ TPYNKNVTFW HSGEPNSPDE RCAIINFRSE

401 EWGWNDVHCH VPQKSICKMK KIYI*
kappa light chain signal sequence: residues 1-19 above (italicized)
murine IgG2a Fc: residues 20-251 above
G4S linker: residues 252-256 above (boldened)
cyno BDCA2 ectodomain: residues 257-424 above (underlined)
```

A stable CHO cell line producing the Fc-cyno BDCA2 fusion protein was produced by transfection with expression vector pEAG2677.

The muIgG2a Fc-BDCA2 fusion proteins were subjected to limited proteolysis, to isolate monomeric BDCA2 ectodomain proteins. To facilitate isolation of recombinant soluble BDCA2 ectodomain, new Fc fusion constructs were constructed in which a TEV protease cleavage site was inserted between the C-terminus of the Fc and the N-terminus of the BDCA2 ectodomain. Syngenes carrying engineered human or cyno BDCA2 ectodomains with a 5' XmaI site (Pro-Gly) for fusion to the Fc C-terminus followed by an in-frame TEV cleavage site (ENLYFQG) fused to residue 45 of the BDCA2 sequence and a 3' BamHI site following the BDCA2 terminator were designed and delivered by GeneWiz as XmaI-BamHI insert's in their proprietary pUC57-amp cloning vector. The sequences of the inserts in engineered XmaI-BamHI TEV-BDCA2 ectodomain cDNA constructs, pEAG2917 (human) and pEAG2918 (cyno), were confirmed. To construct pV90-IRES-dhfr-based CHO expression vectors for huIgG1 Fc-TEV-BDCA2 fusion proteins, the 0.75 kb NotI-XmaI fragment of pEAG1397 and the 0.54 kb XmaI-BamHI fragments from either pEAG2917 or pEAG2918 were subcloned into the 5.4 kb BglII-NotI vector backbone fragment of pXJC194, producing pEAG2937 (Fc-huBDCA2) or pEAG2938 (Fc-cyno BDCA2). The insert cDNAs in pEAG2937 and pEAG2938 were sequence confirmed. Stable CHO cell lines were generated by transfection with pEAG2937 and pEAG2938. The deduced open reading frame of the huFc-TEV-huBDCA2 fusion protein encoded by pEAG2937 is shown below:

```
                                                (SEQ ID NO: 80)
  1 MKLPVRLLVL MFWIPASSSE PKSSDKTHTC PPCPAPELLG GPSVFLFPPK

51 PKDTLMISRT PEVTCVVVDV SHEDPEVKFN WYVDGVEVHN AKTKPREEQY

101 NSTYRVVSVL TVLHQDWLNG KEYKCKVSNK ALPAPIEKTI SKAKGQPREP
```

```
151 QVYTLPPSRD ELTKNQVSLT CLVKGFYPSD IAVEWESNGQ PENNYKTTPP

201 VLDSDGSFFL YSKLTVDKSR WQQGNVFSCS VMHEALHNHY TQKSLSLSPG

251 ENLYFQGNFM YSKTVKRLSK LREYQQYHPS LTCVMEGKDI EDWSCCPTPW

301 TSFQSSCYFI STGMQSWTKS QKNCSVMGAD LVVINTREEQ DFIIQNLKRN

351 SSYFLGLSDP GGRRHWQWVD QTPYNENVTF WHSGEPNNLD ERCAIINFRS

401 SEEWGWNDIH CHVPQKSICK MKKIYI*
kappa light chain signal sequence: residues 1-19 above (italicized)
human IgG1 Fc: residues 20-250 above
TEV cleavage site: residues 251-257 above (boldened)
huBDCA2 ectodomain: residues 258-426 above
```

The deduced open reading frame of the huFc-TEV-cyno BDCA2 fusion protein encoded by pEAG2938 is shown below:

```
                                                       (SEQ ID NO: 81)
  1 MKLPVRLLVL MFWIPASSSE PKSSDKTHTC PPCPAPELLG GPSVFLFPPK

51 PKDTLMISRT PEVTCVVVDV SHEDPEVKFN WYVDGVEVHN AKTKPREEQY

101 NSTYRVVSVL TVLHQDWLNG KEYKCKVSNK ALPAPIEKTI SKAKGQPREP

151 QVYTLPPSRD ELTKNQVSLT CLVKGFYPSD IAVEWESNGQ PENNYKTTPP

201 VLDSDGSFFL YSKLTVDKSR WQQGNVFSCS VMHEALHNHY TQKSLSLSPG

251 ENLYFQGNFM YSKTVKRLSK LQEYQQYYPS LTCVMEGKDM EDWSCCPTPW

301 TSFQSSCYFI STVMQSWTKS QNNCSVMGAD LVVINTKEEQ DFITQNLKIN

351 SAYFLGLSDP KGWRHWQWVD QTPYNKNVTF WHSGEPNSPD ERCAIINFRS

401 EEWGWNDVHC HVPQKSICKM KKIYI*
kappa light chain signal sequence: residues 1-19 above (italicized)
human IgG1 Fc: residues 20-250 above
TEV cleavage site: residues 251-257 above (boldened)
cyno BDCA2 ectodomain: residues 258-425 above (underlined)
```

Example 21. BIIB059 Binding to BDCA2-Fc Fusion Proteins

Figure 11:
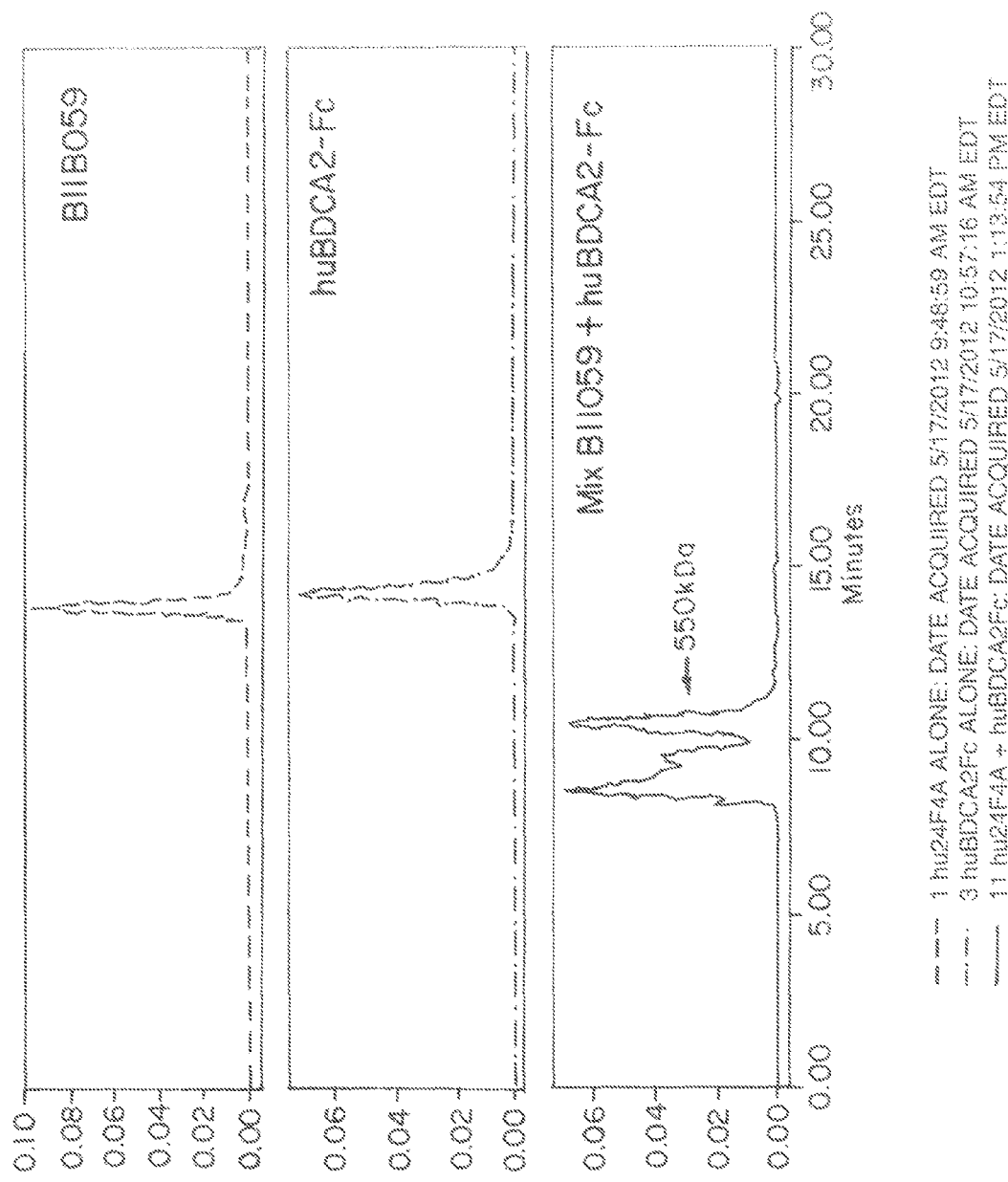
FIG. 11 is a series of graphs showing the results of size exclusion chromatography analysis of Fc fusion proteins.

The ability of BIIB059 to bind huBDCA2-Fc in solution was assessed by SEC (FIG. 11). When analyzed alone, BIIB059 (top panel) and huBDCA2 (middle panel) eluted as single sharp peaks with molecular masses of ~150 kDa. When BIIB059 and huBDCA2-Fc were mixed together and analyzed (bottom panel), there was a shift of BIIB059 and huBDCA2-Fc to higher masses of >550 kDa as evident from their elution at earlier positions in the chromatogram. The heterogeneity in the elution peak is presumably caused by the fact that both BIIIB059 and BDCA2-Fc each contain 2 binding sites and consequently a large number of complexes with different stoichiometries of BIIB059 and BDCA2 are formed.

The binding of cynoBDCA2 ECD to BIIB059 was also assessed by SEC and similarly led to a quantitative shift to higher molecular mass complexes.

Example 22. Calcium Enhances the Binding of BIIB059 to BDCA2

The binding of BIIB059 to human BDCA2 fused to murine Fc (huBDCA2-muFc) in the presence of calcium or EDTA was studied in an Octet binding assay. The huBDCA2-muFc protein was captured on an anti-murine Fc biosensor, followed by the association of BIIB059 and the dissociation step. All steps were run in 50 mM HEPES, pH 7, 100 mM NaCl, 1 mg/ml BSA, 0.02% Tween 20 and 0.001% azide containing either 10 mM CaCl2 or 10 mM EDTA.

Figure 12:
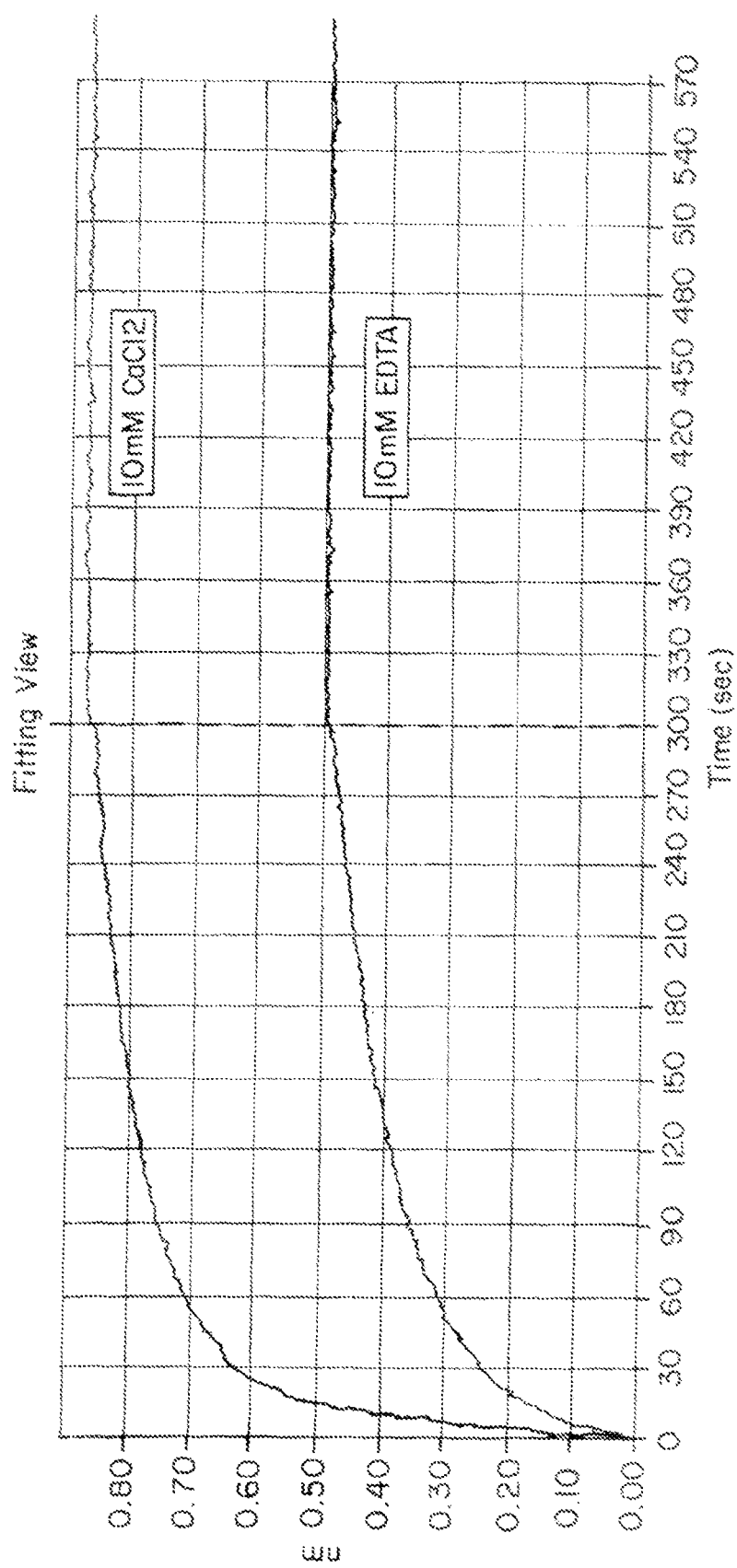
FIG. 12 is a graph showing the effect of calcium on BIIB059 binding to BDCA2. BIIB059 binding to BDCA2 is enhanced by the addition of calcium relative to EDTA giving about a 2-fold higher signal.

FIG. 12 shows that BIIB059 binding is enhanced by the addition of calcium relative to EDTA leading to about a 2-fold higher signal. Both association and dissociation rates were affected by calcium.

Example 23. Binding Measurements

Octet was used to monitor binding of BIIB059 to the BDCA2-Fc fusion protein and BDCA2 ECD. FIG. 13 shows an Octet experiment in which BIIB059 was loaded onto anti-human Fc Octet tips at a concentration of 20 µg/mL. For the association step, human and cynomolgus BDCA2 ECD was added at a concentration of 2 µg/mL. The buffer for this experiment was 50 mM HEPES, pH 7, 100 mM NaCl, 5 mM CaCl2, 1 mg/mL BSA, 0.02% Tween 20 and 0.001% azide. Under these conditions, binding of BIIB059 to human and cyno BDCA2 ECD was comparable

Example 24. PBMC Assay to Determine IC50 Value for BIIB059 for Inhibition of TLR9-Induced IFNα Production BDCA2 ligation has been shown to activate a BCR-like signaling cascade, which potently suppresses the ability of pDCs to produce type I IFNs and other cytokines in response to TLR ligands (Cao W. et al., *PLoS Biol.*, 5(10):e248 (2007)) Inhibition of TLR9-induced IFNα production by PBMC was used as the primary cellular assay for screening.

PBMCs from heparinized venous blood of healthy donors were isolated by discontinuous gradient centrifugation over Ficoll, washed in PBS and re-suspended in complete culture medium (RPMI with 3% FBS). $1\times10^6$ cells were seeded/well and stimulated with 10 μg/mL of the TLR9 ligand (CpG-A ODN 2216) in the presence of doses of BIIB059 and 24F4A-Agly (an Fc crippled version of BIIB059), or isotype control mAb ranging from 10 μg/mL to 1 pg/mL in a total assay volume of 200 μL/well. The plates were incubated overnight (18 hours) at 37° C., and the supernatants were collected for evaluation in IFNα ELISA assays (PBL InterferonSource). The assays were performed according to the manufacturer's protocol. The titrations of BIIB059 and 24F4A agly were tested to determine the $IC_{50}$ for inhibition of TLR9-induced IFNα production. A total of twelve independent experiments gave an average $IC_{50}$ of 0.001 μg/mL for BIIB059. The Aglycosylated mAb was less potent, with an average $IC_{50}$ of 0.007 μg/mL (FIG. 14).

Figure 18:
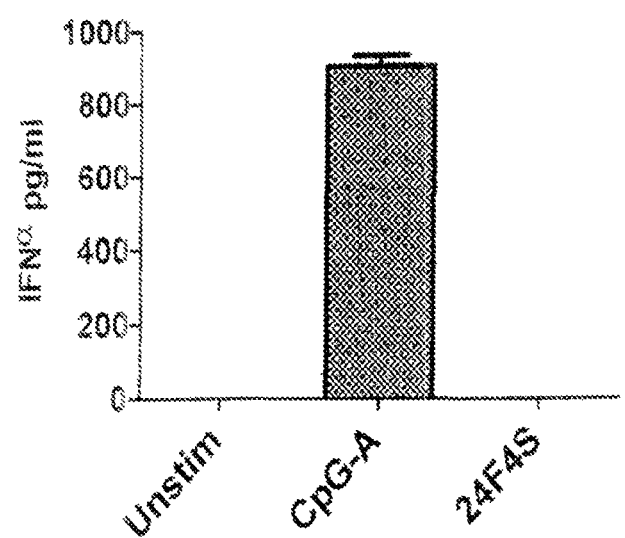
FIG. 18 is a bar graph showing that ligation of BDCA2 suppresses induction of IFN-α production in SLE serum stimulated pDCs.

The ability of anti-BDCA2 mAb to inhibit IFNα production following stimulation with a physiologically relevant ligand, namely, sera from patients with SLE was also tested. SLE sera are believed to induce type I IFN through complexes of anti-DNA autoantibodies and immunostimulatory hypomethylated DNA that stimulate TLR9. PBMCs were stimulated with sera from an SLE patient (provided by Dr. Gregg Silverman, NYU) and used at a final dilution of 1/5. Antibody 24F4S H4/L1C95S, which differs from BIIB059 by 1 amino acid residue, completely abrogated IFNα production from SLE sera stimulated pDCs (FIG. 18).

Example 25. TLR9-Induced IFNα Production in Whole Blood Assay

The activity of BIIB059 was also evaluated in a whole blood assay of TLR9-induced IFNα production.

Whole blood was drawn from heparinized venous blood of healthy donors. Doses of BIIB059 and 24F4A-Agly ranged from 10 μg/mL to 1 pg/mL in a total assay volume of 200 μl/well. CpG-A was added at 200 μg/mL, which was determined to be optimal for stimulation of IFNα production in whole blood. Plates were incubated for 18 hours at 37° C. and supernatants collected for use in IFNα ELISA assays (PBL InterferonSource). The assays were performed according to the manufacturer's protocol. Shown in FIG. 15A is a representative experiment of 6 independent experiments performed. The inhibitory potency of BIIB059 in the TLR9-induced IFNα assay in whole blood was similar to the potency seen in the PBMC assays. In addition to inhibiting pDC-derived cytokines (IFNα, IL-6), BIIB059 treatment also led to inhibition of a large array of cytokines and chemokines (FIG. 15C).

The following experiment was performed to determine if BIIB059 could inhibit TLR9-induced IFNα production in whole blood from SLE patients similarly to healthy volunteers. To this end, whole blood from 2 SLE patients or 2 healthy controls was stimulated with 200 μg/ml CpGA in the presence of 10 μg/ml BIIB059 and IFNα production was assessed by ELISA. Specifically, whole blood from 2 SLE patients or 2 healthy donors was provided by Bioreclamation LLC by overnight shipping. Upon arrival, blood was treated with 10 μg/mL BIIB059 or isotype control and stimulated with 200 μg/mL CpG-A and plated in 96 well plate. Plates were incubated for 18 hours at 37° C. and supernatants collected for use in IFNα ELISA assays (PBL Interferon-Source). The assays were performed according to the manufacturer's protocol.

Figure 15B:
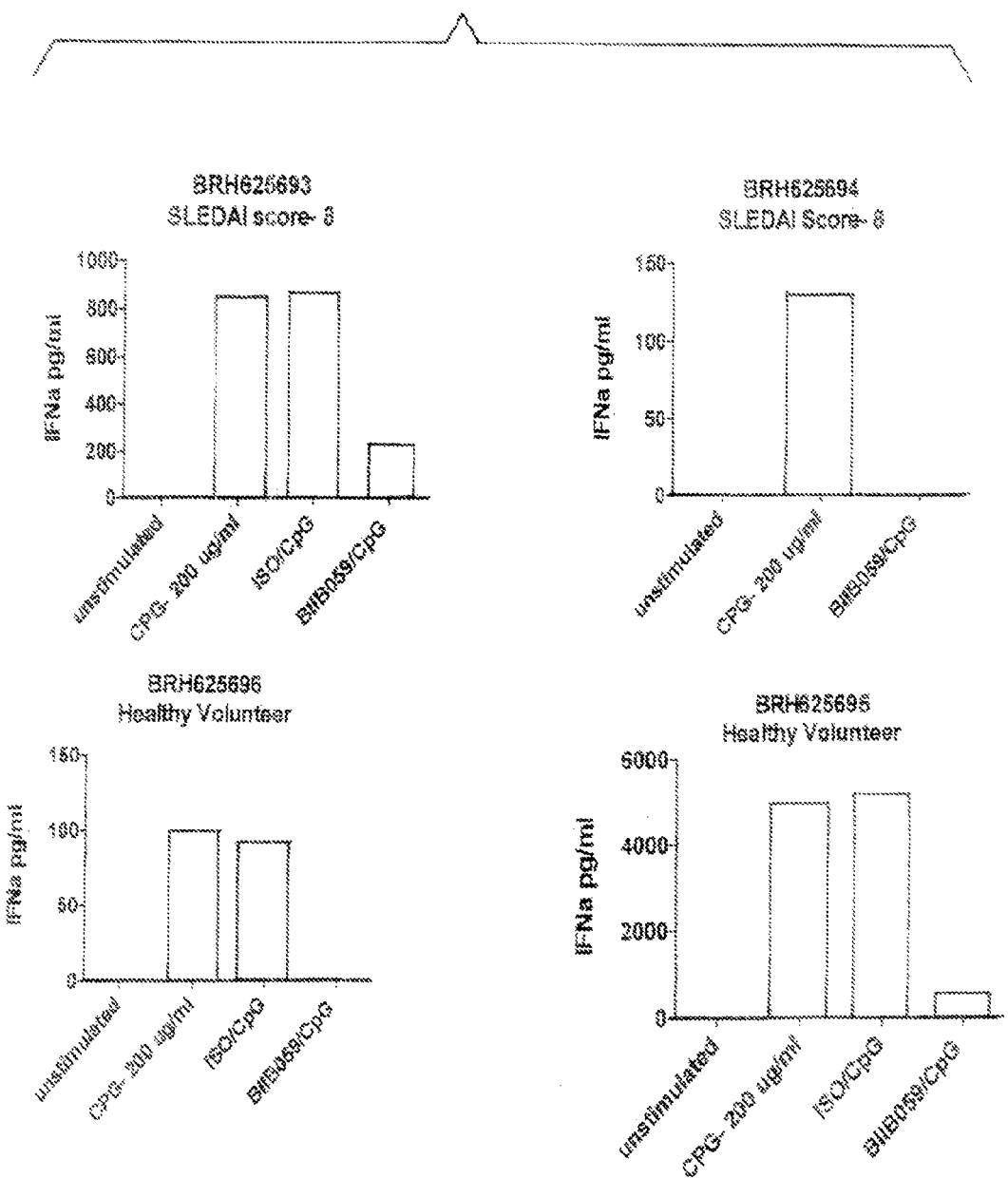

As shown in FIG. 15B, BIIB059 showed similar potency in whole blood from SLE patients as compared to healthy volunteers.

Example 26. Assessing BIIB059-Mediated Inhibition of Type I Interferons

The inhibitory activity of BIIB059 was also confirmed using purified pDCs stimulated with either synthetic TLR agonists (CpG-A) or the more physiologic stimulus (SLE sera). The inhibitory effect of BDCA2 cross-linking on other pDC derived cytokines (IL-6) was also determined. BIIB059 activity was confirmed using a variety of approaches such as qualitative polymerase chain reaction and ELISA.

a) Q-PCR

Thirteen IFNα subtypes and a single member of IFNβ exist in humans. Stimulation with TLR9 agonist results in upregulation of most type I IFNs (Ito T. et al., *Blood*, 107(6):2423-31 (2006)) Inhibition of individual type I IFN genes was evaluated using qualitative polymerase chain reaction (Q-PCR) assays.

pDCs were purified using a two-step magnetic bead separation procedure (MACS kit, Miltenyi Biotec). $5\times10^4$ pDCs/well were stimulated with 5 μM CPG-A in the presence or absence of increasing concentrations of BIIB059 or 10 μg/mL of isotype control. Total assay volume was 200 μl/well. Plates were incubated for 18 hours at 37° C., and RNA was extracted from cells using Trizol reagent (Invitrogen corporation) and further purified using an RNeasy mini column (Qiagen Sciences). All primers and probes were purchased from Applied Biosystems Inc. Relative transcript quantities were determined for each sample by comparison to the oligonucleotide standard curve using Sequence Detection Software (Applied Biosystems Inc.) and normalized to a control (GAPDH).

Treatment with BIIB059 inhibited transcription of all type I IFNs tested, thereby recapitulating previous data using anti-BDCA2 antibody clone AC144 (Cao W. et al., *PLoS Biol.*, 5(10):e248 (2007)).

b) ELISA

Figure 17:
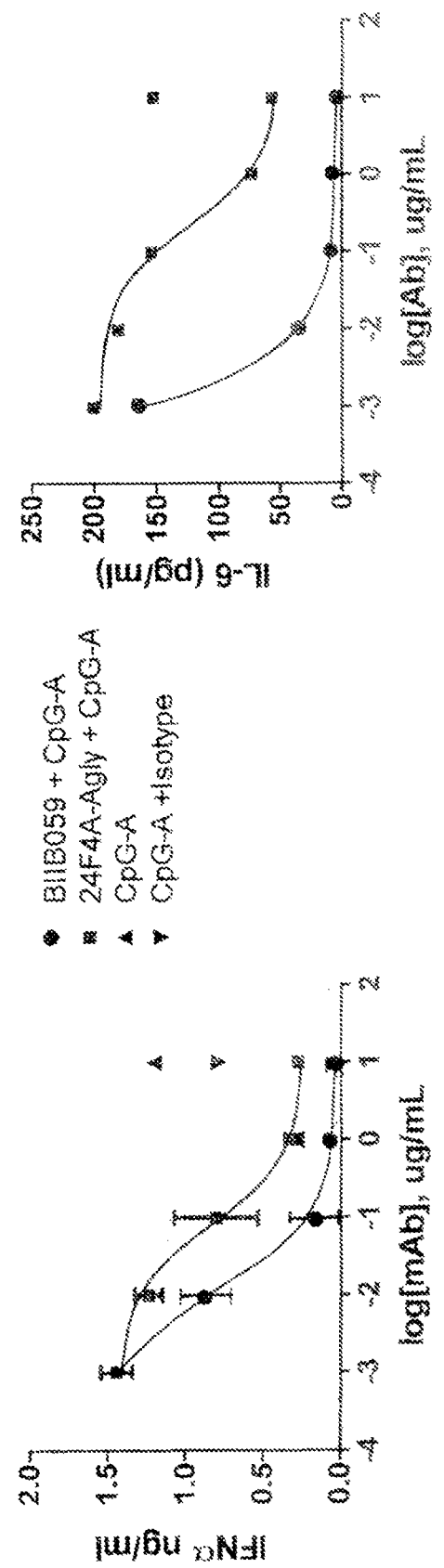
FIG. 17 includes two line graphs showing that ligation of BDCA2 with BIIB059 inhibits TLR9-induced cytokine production in purified pDCs.

The effect of BIIB059 on inhibition of pDC cytokines was tested at the protein level using ELISA. $5\times10^4$ purified pDCs/well were stimulated with 5 μM CPG-A in the presence or absence of increasing concentrations of BIIB059 or 10 μg/mL of isotype control. Shown in FIG. 17 are the amounts of secreted IFNα and IL-6 measured from a representative donor of three tested healthy donors.

BDCA2 ligation with BIIB059 potently inhibited IFNα production and greatly reduced the production of IL-6 induced by CpG-A stimulation.

Example 27. BIIB059-Mediated Receptor Internalization

Ligation of BDCA2 with anti-BDCA2 mAb (clone AC144, Miltenyi) has been shown to rapidly induce receptor internalization (Dzionek A. et al., *J. Immunol.*, 165(11): 6037-46 (2000)). The following experiment was directed at determining the kinetics of BIIB059-mediated BDCA2 internalization.

Figure 19A:
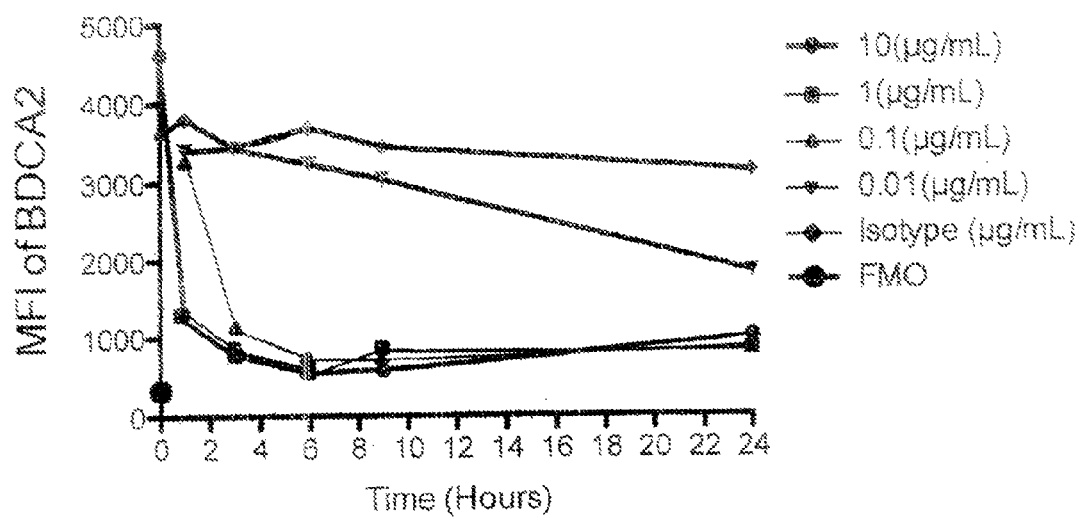
FIG. 19A is a line graph showing that BDCA2 is internalized after ligation with BIIB059.

Human whole blood was treated with 10, 1, 0.1 or 0.01 μg/mL of BIIB059 or an isotype control (10 μg/ml) at 37° C. for the periods indicated and then incubated for 30' at 4° C. with FITC-labeled non-cross blocking anti-BDCA2 mAb (clone 2D6), anti-HLADR, anti-CD123, anti-CD14 and anti-CD20. Red blood cells (RBCs) were lysed using 1× Easy-lyse buffer (BD Bioscience) and the remaining cells fixed. Shown in FIG. 19A are mean fluorescence intensity (MFI) values of 2D6-FITC staining of gated CD14−CD20−HLA-DR+CD123+pDCs. FMO (fluorescence minus one control) consisted of the FACS staining cocktail minus 2D6-FITC. The data in this figure is a representative experiment of 3 independent experiments performed.

As shown in FIG. 19A, upon incubation with BIIB059 at 1 µg/ml, the intensity of FITC-labeled 2D6 staining rapidly decreased reaching background levels within one hour of incubation at 37° C. Tenfold lower BIIB059 concentration (0.1 µg/ml) affected the kinetics of endocytosis delaying it by 2 hours. This demonstrates that BDCA2 is internalized upon ligation with BIIB059 with dose dependent kinetics.

Figure 19B:
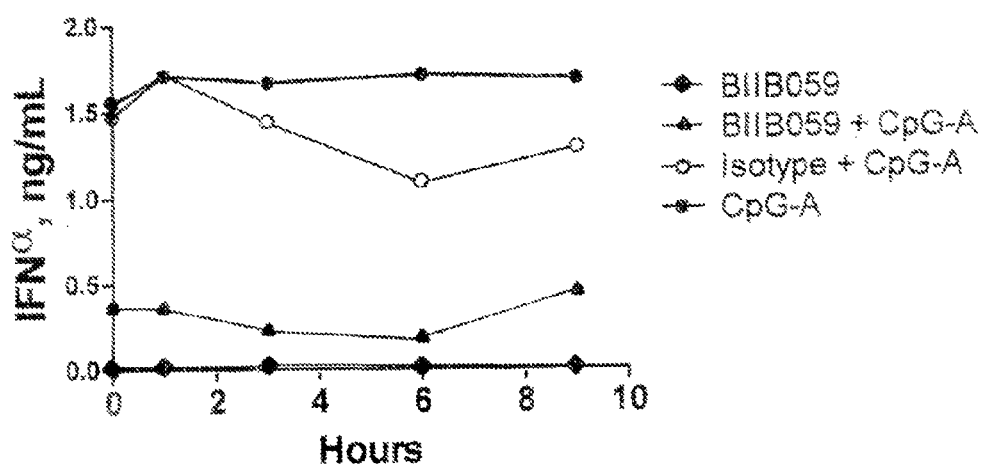
FIG. 19B is a line graph showing that internalization does not affect BIIB059-mediated inhibition of IFN-α production.

The following experiment was conducted to ascertain whether BIIB059-mediated receptor internalization affected IFN inhibition. Whole blood was collected from heparinized venous blood of healthy donors and pre-incubated with BIIB059 (to allow for receptor internalization) or isotype for the duration indicated. At each time point after pre-incubation, cells were challenged with 200 µg/mL CpGA and incubated for an additional 18 hours at 37° C. Supernatants were collected for use in IFNα ELISA assays (PBL InterferonSource). The assays were performed according to the manufacturer's protocol. FIG. 19B is a representative experiment of 3 independent experiments performed. As shown in FIG. 19B, after 9 hours preincubation with BIIB059 prior to stimulation—corresponding to maximal internalization—did not affect IFN inhibition suggesting that BDCA2 endocytosis and TLR9 inhibition are potentially linked. To test this hypothesis anti-BDCA2 mAbs were used that were incapable of mediating IFN inhibition and demonstrated lack of internalization. In addition, we have previously shown that bivalent binding was necessary for anti-BDCA2 mediated IFN inhibition. In fact, Fab fragment did not lead to internalization or IFN inhibition. Taken together, these data raise the possibility that BDCA2 mediated TLR9 inhibition requires endocytosis and localization into endosomal compartments containing TLR9. This hypothesis can be tested using live imaging to track BDCA2 internalization and trafficking in the cell after BIIB059 ligation.

Example 28. Antibody Effector Function

The Fc domain of BIIB059 is a fully glycosylated human IgG1, and is competent to bind both cellular Fcγ receptors and complement, and to induce cellular effector immune cell responses, both through antigen-dependent cytotoxicity (ADCC) and complement-dependent cytotoxicity (CDC). In order to confirm the binding of BIIB059 to Fc receptors, relative binding affinities were measured using the Amplified Luminescent Proximity Homogeneous Assay (ALPHA) technology from Perkin Elmer (FIG. 20). The assay was performed in a competitive format in which serial dilutions of test antibodies were incubated with the receptor-GST fusion proteins and anti-GST acceptor beads overnight at 4° C. in a 96-well plate. Streptavidin donor beads and biotinylated wild-type IgG1 were also incubated overnight at 4° C. in a separate tube and then added to the assay plate the next day. The plates were incubated at room temperature for 2 hr with gentle shaking and read in an Envision plate reader (Perkin Elmer). The data were plotted to a 4-parameter curve fit using Graphpad Prism software to calculate the IC50 values in order to determine the relative binding affinities.

IC50 values of BIIB059 for FcγR1: 0.03 µg/mL, FcγR11a: 11 µg/mL FcγR11b: 17 µg/mL FcγR111a: and 3 µg/mL were calculated. These values are in line with those observed for other human IgG1 antibodies in this assay. IC50 values for the G4P/G1 agly low effector function version of 24F4 used in the cyno were studies were also determined. As expected, no binding was detected to FcγR11a, FcγR11b, and FcγR111a and binding to FcγR1 was reduced by 100-fold. The 5c8 antibody both in IgG1 WT and G4P/G1 agly frameworks were included in the assays as comparators.

Example 29. Complement Fixation

Antibody coating of targets has been shown to mediate potent killing mechanisms via ADCC or CDC. These effector functions of antibodies are mediated by the antibody Fc region. This experiment was directed to testing the ability of BIIB059 to recruit complement by testing its binding to C1q by ELISA.

The C1q binding assay was conducted in a 96 well ELISA format using Maxisorb ELISA plates. The test antibody was coated in a 3-fold dilution series in PBS starting at 15 µg/mL overnight at 2-8° C. and the wells were then washed with PBS, 0.05% Tween 20 and blocked with 200 µl of 0.1 M Na Phosphate pH 7.2, 0.1 M NaCl, 0.1% gelatin, 0.05% Tween 20. Subsequently, 50 µl/well of 2 µg/mL of human C1q from Complement Technology (A099) diluted in block/diluent buffer was added and incubated for 2 h at room temperature. After aspirating and washing as above, 50 µl/well of chicken IgY anti-human C1q (custom production by Ayes Labs, Inc using Sigma human C1q, C0660) diluted 8,000-fold in block/diluent buffer, was added. After incubation for 1.5 h at room temperature the wells were aspirated and washed as above. Donkey F(ab') 2 anti-chicken IgY HRP conjugate (Jackson ImmunoResearch 703-030-155) diluted to 5,000-fold in block/diluent was then added at 50 µl/well and incubated for 1 h at room temperature. After aspirating and washing as above, 100 µl TMB substrate (420 µM TMB, 0.004% $H_2O_2$ in 0.1 M sodium acetate/citric acid buffer, pH 4.9) was added and incubated for 2 min before stopping with 100 µl 2 N sulfuric acid. The absorbance was read at 450 nm with a Softmax PRO instrument and Softmax software was used to determine the relative binding affinity (C value) with a 4-parameter fit.

Figure 21:
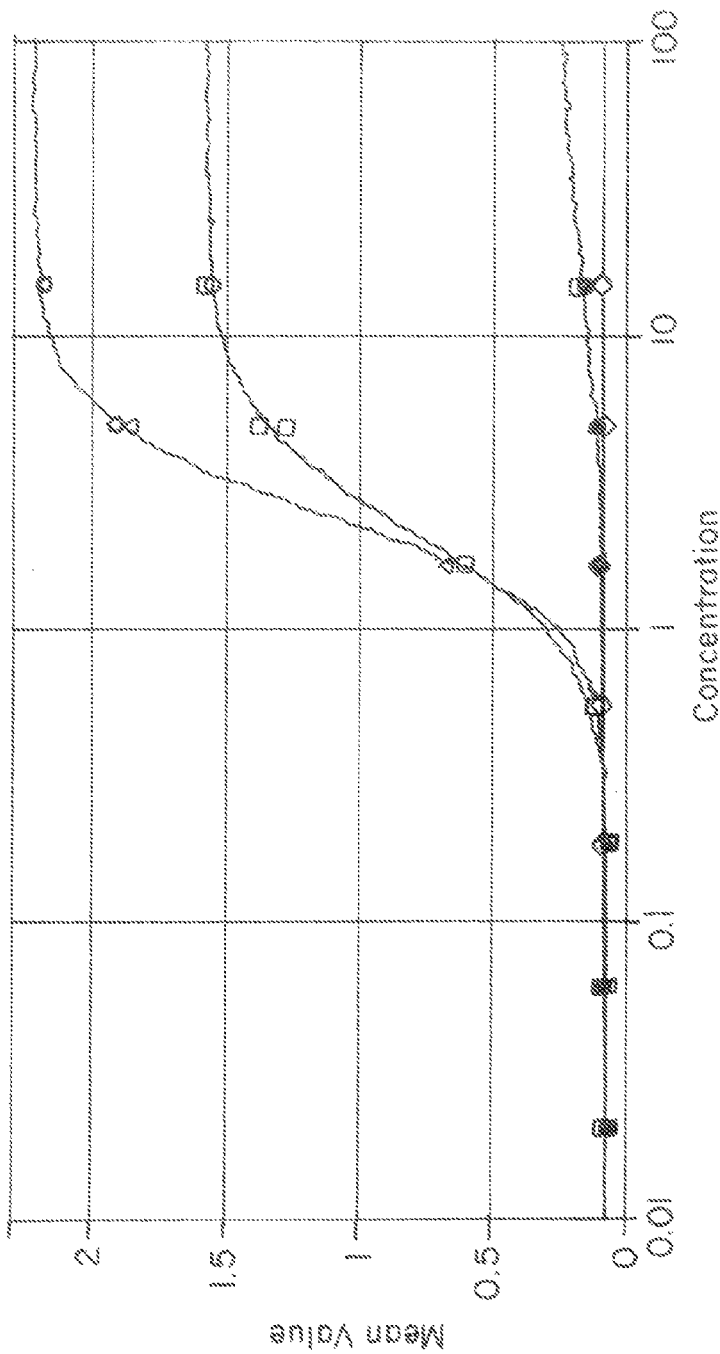
FIG. 21 provides the results of C1q ELISA showing binding of human C1q to increasing concentrations (0-15 μg/mL) of coated antibody.

FIG. 21 shows that while BIIB059 is capable of binding C1q, 24F4A IgG4.P/IgG1 agly is essentially devoid of C1q binding.

Example 30. Cell Depletion Studies

BIIB059 potently inhibits type I IFN and IL-6 production after BDCA2 ligation. In addition to its agonistic activity, these experiments were conducted to evaluate whether BIIB059 could deplete BDCA2 bearing pDCs by virtue of its functional Fc. To investigate the cytotoxic potency of BIIB059 its activity in ADCC and CDC assays was tested.

a) ADCC Assay

ADCC is a mechanism whereby an effector cell of the immune system actively lyses a target cell, whose surface receptors have been bound by antibodies (FIG. 22).

The CHO cell line (EAG2456 T1F2 Clone 34.16.7) was used as the target cell. Expression level of BDCA2 on the surface of CHO cells was determined by FACS using an APC-labeled anti-BDCA2 mAb (clone AC144, Miltenyi). NK cells were used as the effector cells and were separated from whole blood by negative selection using the RosetteSep™ Human NK Cell Enrichment Cocktail (Stem Cells Technologies). After a 20 minute incubation with the cocktail at room temperature, NK cells were isolated by discontinuous gradient centrifugation over ficoll. CHO cells and human NK cells were seeded at a ratio of 5:1 (NK:CHO) in the presence of effector competent anti-BDCA2 mAbs (24F4S and BIIB059), Fc crippled mAbs (24F4S-Agly and 24F4A-Agly) or IgG1 isotype control and incubated for 4 hours at 37° C. The negative control consisted of wells containing CHO and NK cells without antibodies. NK and CHO cells lysed with Tx-100 were used to determine maximal killing. ADCC was evaluated using the Vybrant Cytotoxicity Assay kit (Invitrogen), following the manufacturer's instructions. The assay detects G6PD from damaged cells based on the G6PD-dependent reduction of resazurin which emits fluorescence at 590 nm after excitation at 530 nm. The ADCC assay depicted in FIG. 22 panel A was performed using high BDCA2 expressing CHO cells (panel C) while the ADCC assay in FIG. 22 panel B used CHO cells with lower BDCA2 expression (panel D).

Figure 22C:
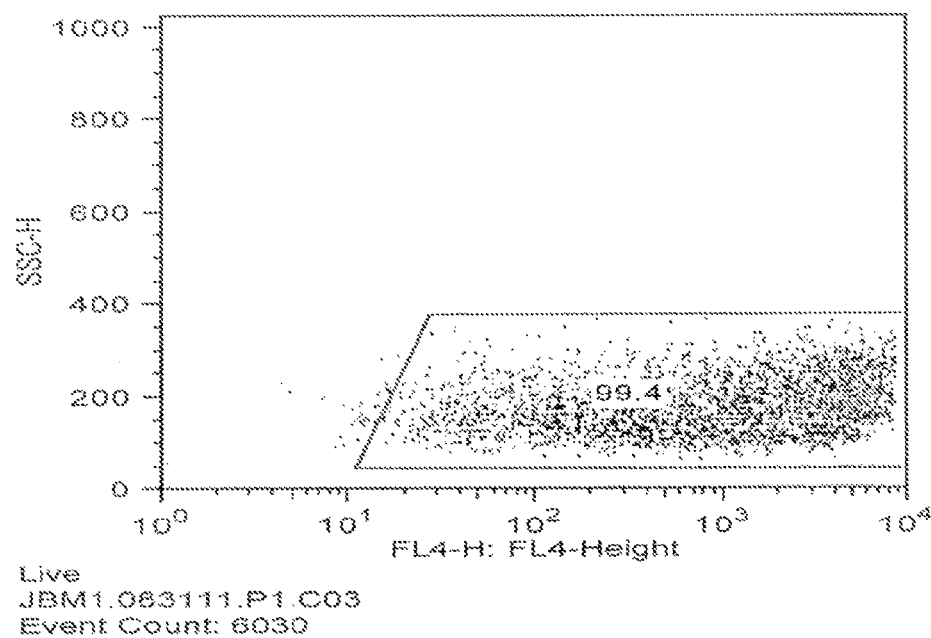
Figure 22D:
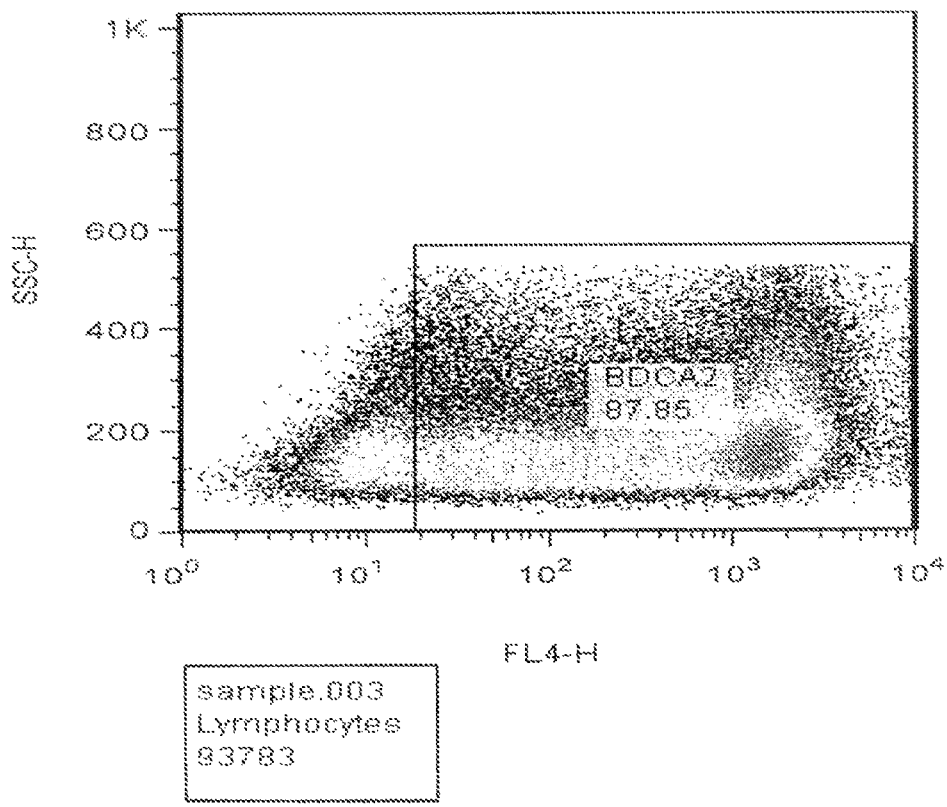

24F4S led to 100% killing of BDCA2 bearing CHO cells similar to triton X lysing. As expected the aglycosylated version of the mAb (24F4S-agly) did not lead to ADCC (FIG. 22A). When compared with 24F4S, BIIB059 had an identical ADCC activity (FIG. 22 B). Of note, the killing efficiency correlated with the level of BDCA2 expression on CHO cells (FIG. 22C and FIG. 22D).

b) CDC Assay

Figure 23:
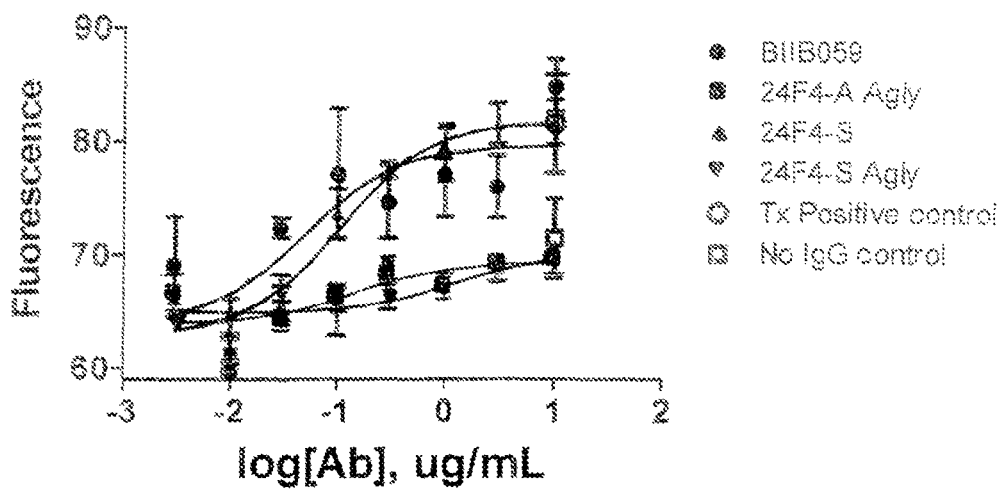
FIG. 23 is a line graph showing that BIIB059 mediates cell killing through CDC. CHO cells (EAG2456 T1F2 Clone 34.16.7) were seeded at $5 \times 10^4$ cells in 96 well Collagen black well plates and incubated at 370 C for 48 hrs. The plates were then washed and incubated with rabbit serum complement and propidium iodide (PI) in the presence of effector competent anti-BDCA2 mAbs (24F4S and BIIB059), effector function deficient mAbs (24F4S-Agly and 24F4A-Agly) or IgG1 isotype control for 1 h at 37° C. Negative control consisted of wells containing CHO cells, rabbit serum complement, PI, without antibodies.

In complement-dependent cytotoxicity (CDC), C1q binds the antibody triggering the complement cascade and leading to cell lysis (FIG. 23). As shown in section Example 29, BIIB059 can efficiently bind complement component C1q. This experiment was performed to confirm that BIIB059 can mediate CDC.

CHO-BDCA2/FceRIγ stable transfectant cells (EAG2456 T1F2 Clone 34.16.7) were seeded at 5×10⁴ cells in 96 well Collagen black well plates and incubated at 37° C. for 48 hrs. The plates were then washed and incubated with rabbit serum complement and propidium iodide (PI) in the presence of effector competent anti-BDCA2 mAbs (24F4S and BIIB059), effector function deficient mAbs (24F4S-Agly and 24F4A-Agly) or IgG1 isotype control for 1 h at 37° C. Negative control consisted of wells containing CHO cells, rabbit serum complement, and PI, without antibodies. NK and CHO cells lysed with T-100x were used to determine maximal killing. The plates were read using Cytoflour Fluorescence plate reader (ex530/em645). Anti-BDCA2 mAbs (BIIB059 and 24F4S) led to cell killing by CDC similar to Triton lysis. As expected effector-deficient aglycosylated mAbs (24F4S-Agly and 24F4A-Agly) did not mediate CDC (FIG. 23). BIIB059 has the potential to deplete BDCA2 bearing pDCs by virtue of its functional IgG1 Fc region. While BIIB059 is capable of cytotoxic activity in BDCA2 over-expressing cells it is not expected to deplete in vivo owing to the rapid, sustained and near-complete internalization of the receptor after BIIB059 ligation.

Example 31. Cloning of a Rat BDCA2 Homolog and Screening for Binding by BIIB059

When the human BDCA2 cDNA sequence is BLASTed against rat sequences in the NCBI database, the closest homolog is rat Clec4b2, described in GenBank® accession number NM_001005896. To determine whether the lead hu24F4 H4/L1 C95A mAb was capable of binding to a rat homolog of human BDCA2, cDNAs were cloned and constructed expression vectors for rat Clec4b2 and rat FceRIγ. The full-length rat Clec4b2 protein sequence shares only 51.0% identity with human BDCA2. The gapped alignment of human BDCA2 (upper) and rat Clec4b2 (lower) is shown below:

```
  1 MVPEEEPQDREKGLWWFQLKVWSMAVVSILLLSVCFTVSSVVPHNFMYSK   50
    |. |. ||    ||    |  |:.|| ||:|.|||| ||  .|| : || |
  1 MMQEKLPQG..KGGCW.TLRLWSAAVISMLLLSTCFIMSCVVTYQFMMEK   47

51 TVKRLSKLREYQQYHPSLTCVMEGKDIED..WSCCPTPWTSFQSSCYFIS   98
    :|||.|       |..  ||   :|      :      |||||   |  | | |||:.
 48 PNRRLSEL...HTYNSNFTCCSDGTMVSGKVWSCCPKDWKPFGSHCYFTT   94

99 TGMQSWTKSQKNCSVMGADLVVINTREEQDFIIQNLKRNSSYFLGLSDPG  148
    ..|  .|..   || |||  |.||...||||||      |    || ||||
 95 DFVANWNESKEKCSHMGAHLLVIHSQEEQDFINGILDTRWGYGTGLSDQ.  143

149 GRRHWQWVDQTPYNENVTFWHSGEPNNLDERCAIINFRSSEEWGWNDIHC  198
    |.   |||:|||||||.|||||   |||||   |:|  ||      ||||| : |
144 GQNQWQWIDQTPYNESVTFWHEDEPNNDYEKCVEINHHKDIGQGWNDVVC  193

199 HVPQKSICKMKKIYI  213    (SEQ ID NO: 1)
    ||||..||||:
194 SSEHKSICQVKKIYL  208    (SEQ ID NO: 82)
```

Rat Clec4b2 was cloned by RT-PCR from rat spleen first strand cDNA with primers 5' GAC CTT CTG AAT ATA TGC GGC CGC CAT GAT GCA GGA AAA AC 3' (SEQ ID NO: 83) (which adds a 5' NotI site and Kozak sequence immediately before the Clec4b2 initiator methionine) and 5' CCC ACA GCC ATG GAG GAC AGG ATC CTC ATA AGT ATA TTT TC 3' (SEQ ID NO: 84) (which adds a 3' BamHI site immediately after the Clec4b2 terminator). The 0.64 kb RT-PCR product was purified and subcloned into Invitrogen's pCR2.1TOPO cloning vector, producing the construct pCN815, whose insert was sequenced. Site-directed mutagenesis was performed on template pCN815 with primers 5' CAG GAT TTC ATC AAC GGA ATC CTA GAC ACT CGT TGG G 3' (SEQ ID NO:85) and its reverse complement, to correct a PCR error, resulting in the construct pCN822, whose Clec4b2 deduced protein sequence was confirmed to be identical to that in NM_001005896. A mammalian expression vector for rat Clec4b2 full-length cDNA was constructed by ligating the 0.64 kb NotI-BamHI fragment from pCN822 with the 1.89 kb BamHI-XbaI and 4.17 kb XbaI-NotI vector backbone fragments from the expression vector pV90, to produce the expression vector pCN834, whose cDNA insert sequence was confirmed.

The rat FcεRIγ cDNA is described in GenBank® accession number NM_001131001. The rat FcεRIγ protein sequence shares 90.7% identity with human FcεRIγ: the alignment, with human (upper) and rat (lower) is shown below:

```
 1 MIPAVVLLLLLLVEQAAALGEPQLCYILDAILFLYGIVLTLLYCRLKIQV 50
   |||||:| ||||||:|||||||||||||||||||||||||||||||||
 1 MIPAVILFLLLLVEEAAALGEPQLCYILDAILFLYGIVLTLLYCRLKIQV 50

51 RKAAITSYEKSDGVYTGLSTRNQETYETLKHEKPPQ 86    (SEQ ID NO: 2)
   ||| | | |||| |||||·|||||||||||||||||
51 RKADIASREKSDAVYTGLNTRNQETYETLKHEKPPQ 86    (SEQ ID NO: 86)
```

Rat FcεRIγ cDNA was cloned by RT-PCR from rat spleen first strand cDNA with primers 5' CCC AGC GCT GCA GCC CGC GGC CGC CAT GAT CCC AGC GGT 3' (SEQ ID NO: 87) (which adds a NotI site and Kozak sequence immediately before the FcεRIγ initiator methionine) and 5' GAA CAC GTG TTG GGA TCC TAT TGG GGT GGT TTC TC 3' (SEQ ID NO:88) (which adds a 3' BamHI site immediately after the FcεRIγ terminator). The 0.27 kb RT-PCR product was purified and subcloned into Invitrogen's pCR2.1TOPO cloning vector, producing the construct pCN816, whose insert was sequenced and confirmed to be identical to that in NM_001131001. The 0.27 kb NotI-BamHI fragment from pCN816 was ligated to the 0.66 kb BamHI-XhoI and 4.16 kb XhoI-NotI vector backbone fragments from pBHS103, to construct the mammalian expression vector pCN844, whose rat FcεRIγ cDNA insert sequence was confirmed.

To determine whether the lead hu24F4 H4/L1 C95A mAb was capable of binding to surface rat Clec4b2, 293E cells were transiently co-transfected with an EGFP reporter expression vector (pEAG1458) and either human BDCA2/FcεRIγ vectors (pEAG2420 and pEAG2413) or rat Clec4b2/FcεRIγ vectors (pCN834 and pCN844) at 1:1:1 molar ratios. At 3 days post-transfection cells were harvested and stained with the lead hu24F4 H4/L1 C95A mAb in a dilution titration direct FACS binding assay, gating on live EGFP-positive cells. Although high affinity binding by hu24F4 to surface human BDCA2 was observed, no binding to surface rat Clec4b2 was detected. This indicates that hu24F4 has no cross-reactivity to the closest rat homolog of human BDCA2.

Example 32. Administration of BIIB059 to Healthy Cynomolgus Monkeys Results in Loss of BDCA2 from the Plasmacytoid Dendritic Cell Surface, Likely Via Internalization In order to assess whether BDCA2 surface levels changed upon administration of BIIB059 to cynomolgus monkeys, two assays were used. The first assay, the so-called "direct" method, detects surface bound BIIB059 with an anti-human PE-labeled secondary antibody. Ideally, a non-cross blocking antibody to BDCA2 would be used to detect total BDCA2; however, such an antibody does not exist. Thus, in the second assay, the so-called "indirect" method, unoccupied BDCA2 is detected through the addition of BIIB059 conjugated to A647.

Prior to administration of any test articles, for each cynomolgus monkey, the maximal mean fluorescence intensity (MFI) for BIIB059 binding to the pDCs was established at 3 different time points (weeks −3, −2, and −1 prior to single injection of BIIB059). At each time point, titration of unlabeled BIIB059 (40 to 0.04 µg/mL final concentration) was added to aliquots of blood, and BIIB059 was detected using a PE-labeled secondary antibody ("direct" method), or free BDCA2 evaluated with BIIB059-A647 ("indirect" method). The maximal values were taken from the values at the plateau in each assay (FIGS. 24 and 25). Evaluation of the values revealed very modest fluctuation in the maximal MFI for each cynomolgus monkey, with more variation between cynomolgus monkeys, showing that the BDCA2 density on pDCs in cynomolgus monkey is variable (Table 2).

TABLE 2

Summary of average EC50 binding of BIIB059 to cell surface BDCA2 on pDCs in cynomolgus monkey whole blood Whole blood was drawn from twelve cynomolgus monkeys, once a week for three weeks total. Blood was incubated with various concentrations of BIIB059 human IgG1 (0.04 to 40 ug/mL, 6-point curve, 1:4 fold dilutions). pDCs were identified using flow cytometry as CD20−CD14−CD123+HLA-DR+, and treated with anti-human IgG PE labeled secondary to detect BIIB059 bound to the BDCA2 receptor on pDCs. MFI of PE was calculated with FlowJo software, and EC50 curves were generated in GraphPad Prism software.

| Cynomolgus monkey Donor | EC50 (ug/mL) |
|---|---|
| 1 | 0.81 |
| 2 | 1 |
| 3 | 0.95 |
| 4 | 1.7 |
| 5 | 0.71 |
| 6 | 1.3 |
| 7 | 1.1 |
| 8 | 1.2 |
| 9 | 1.4 |
| 10 | 1.2 |
| 11 | 1.4 |
| 12 | 1.6 |
| average | 1.2 |
| SD | 0.3 |

* average of 2-3 experiments

After administration of the vehicle, no BIIB059 was found as expected, and no significant change in BDCA2 levels was found as assessed by binding of BIIB059-A647 (10 µg/ml) (FIG. 26).

Figure 27A:
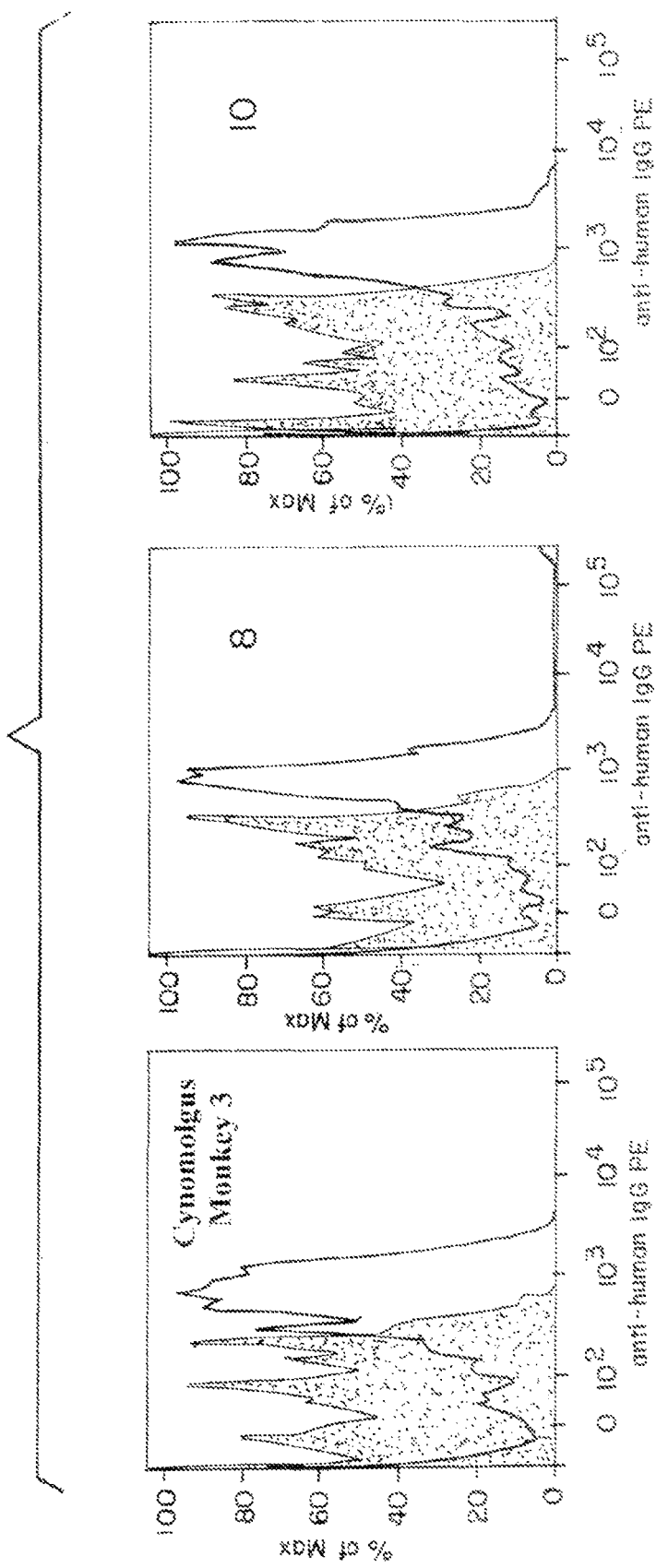
Figure 28A:
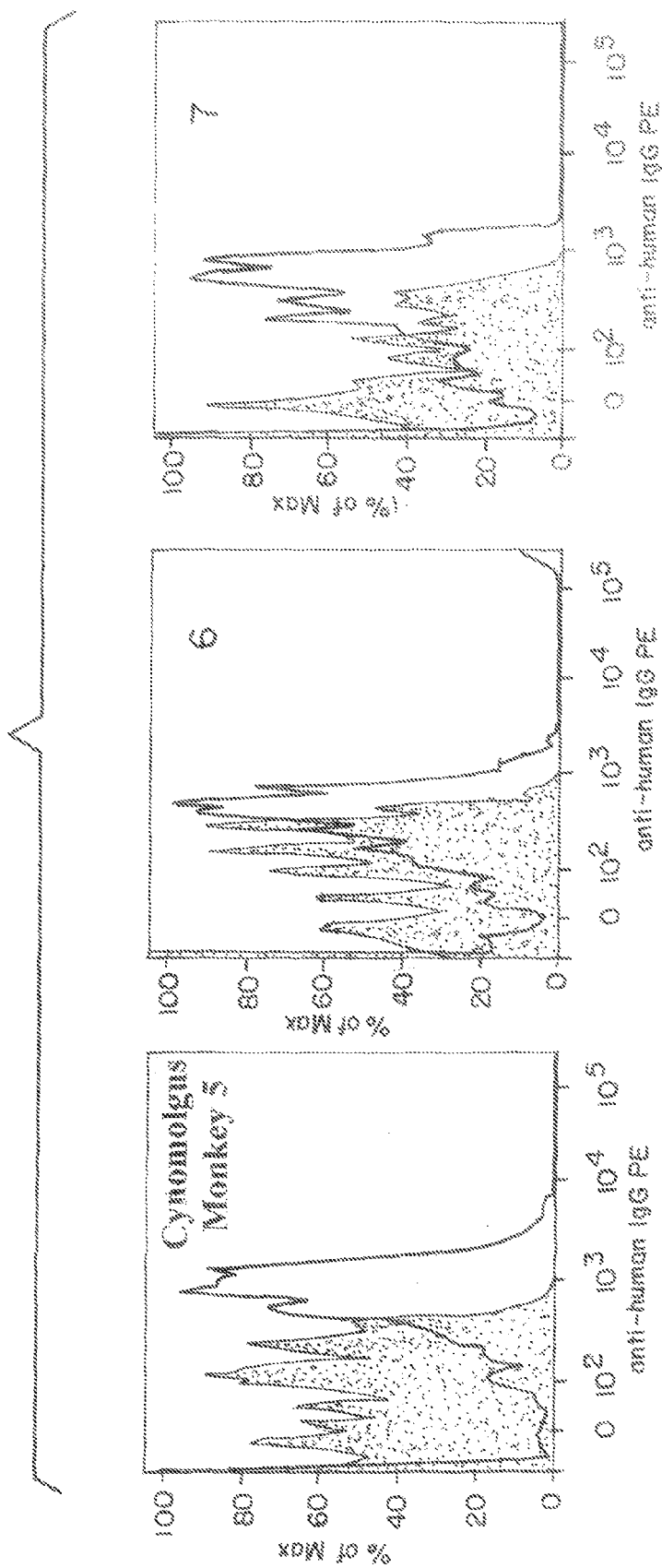
FIG. 28A-C show that bound BIIB059 and BDCA2 receptor are no longer available on pDC cell surface after a single dose of BIIB059 1 mg/kg in cynomolgus monkey.
Figure 28B:
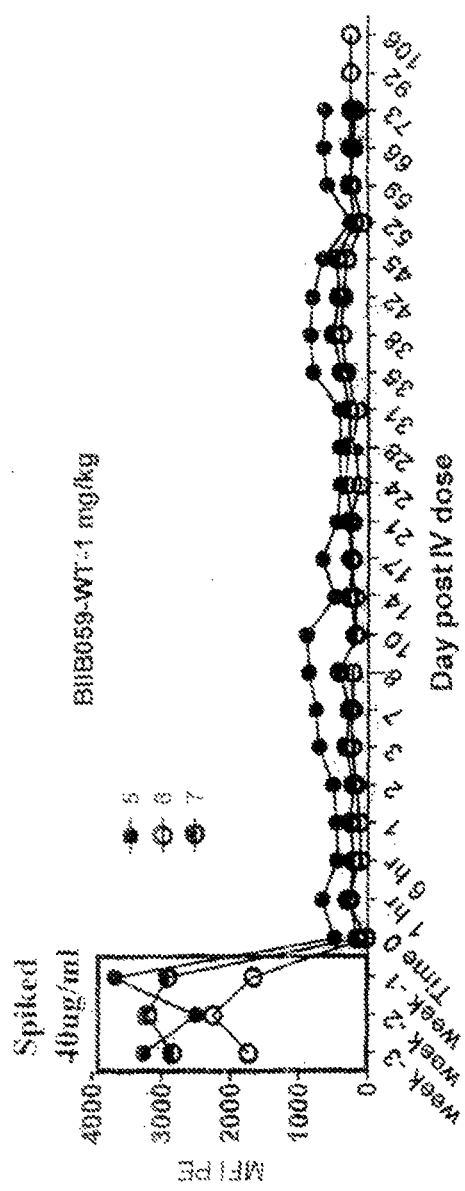
Figure 28C:
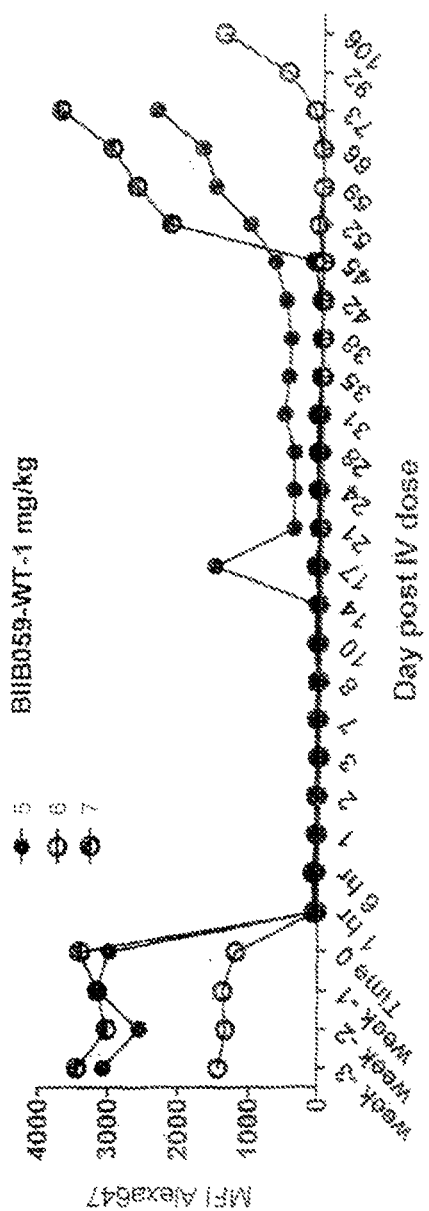

After intravenous (IV) administration of BIIB059 at either 10 mg/kg or 1 mg/kg, no BIIB059 was detected on the surface, even as early as 1 hour post injection of BIIB059 (FIGS. 27 and 28). Also, there was no free BDCA2 as assessed by lack of BIIB059-A647 through 38 days for all treated cynomolgus monkeys, with the exception of cynomolgus monkey 5; the serum concentrations in this cynomolgus monkey dropped rapidly on Day 10, likely due to immunogenicity developed against BIIB059.

After subcutaneous administration of a lower dose of BIIB059 (0.2 mg/kg), BIIB059 was briefly observed on the surface of pDCs (at 1 hour, disappeared by 6 hours). At the same time point (1 hr), some free BDCA2 was observed (13%, 74%, 72% of baseline MFI). Again, no drug was detected throughout rest of the study, and no free BDCA2 receptor was detected until day 14 post BIIB059 injection (FIG. 29).

Figure 31B:
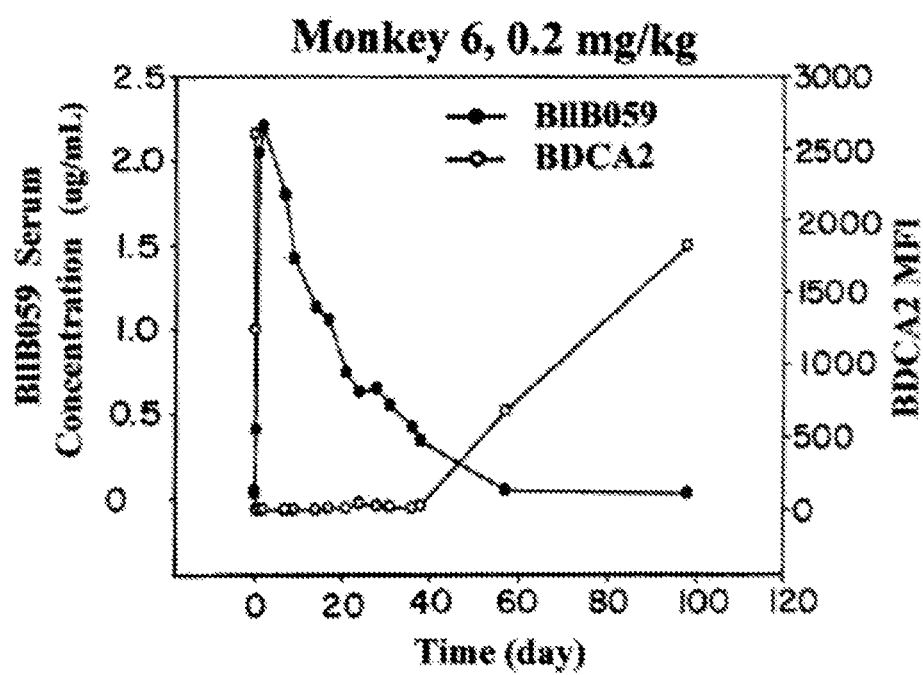

In all cynomolgus monkeys, the reappearance of free BDCA2 coincided with a drop in serum drug levels below 1 µg/ml (FIGS. 30 and 31). Thus, 1 µg/ml appears to be the minimal concentration of BIIB059 needed to mediate internalization of all surface BDCA2.

Table 3 summarizes the $EC_{10}$, $EC_{50}$, and $EC_{90}$ internalization of the BDCA2 receptor on pDCs upon ligation with BIIB059 in cynomolgus monkey whole blood. $EC_{10\text{-}50\text{-}90}$ curves were generated in GraphPad Prism software using a four-parameter fit.

| Cynomolgus monkey | Route | Dose (mg/kg) | EC10 (ug/mL) | EC50 (ug/mL) | EC90 (ug/mL) |
|---|---|---|---|---|---|
| 5 | IV | 1 | 0.003 | 0.087 | 0.370 |
| 6 | IV | 1 | 0.022 | 0.025 | 0.055 |
| 7 | IV | 1 | 0.014 | 0.090 | 0.580 |
| 3 | IV | 10 | 0.100 | 0.150 | 0.220 |
| 8 | IV | 10 | 0.095 | 0.370 | 1.455 |
| 10 | IV | 10 | 0.114 | 0.126 | 0.265 |
| 4 | SC | 0.2 | 0.078 | 0.088 | 0.100 |
| 6 | SC | 0.2 | 0.040 | 0.046 | 0.054 |
| 12 | SC | 0.2 | 0.114 | 0.121 | 0.129 |
| Mean | | | 0.064 | 0.123 | 0.359 |
| Stdev | | | 0.045 | 0.101 | 0.445 |

To summarize, the experiments described in this example show that: in vivo IV administration of high doses (10, and 1 mg/kg) of BIIB059 led to rapid disappearance of both available BDCA2 and bound drug from the cell surface, suggesting receptor internalization. Subcutaneous administration of a low dose (0.2 mg/kg) of BIIB059 resulted in a very transient (at 1 hr) detection of BIIB059 on the pDC surface. By 6 hours, no BIIB059 was detectable on the pDC cell surface. Reappearance of available BDCA2 on cell surface occurred when drug exposure declined below 1 µg/mL.

Figure 16:
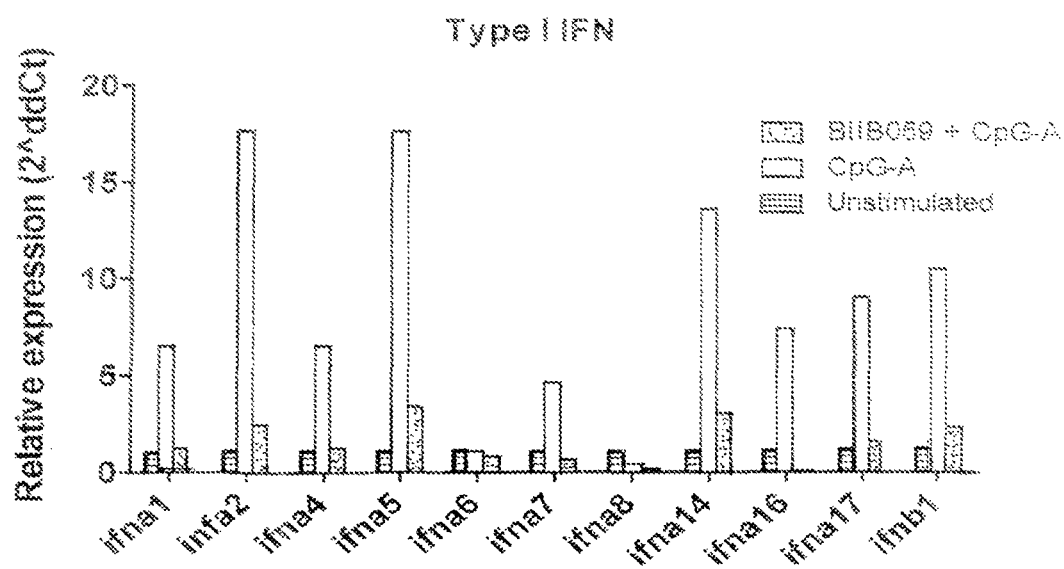
FIG. 16 is a bar graph showing that BIIB059 inhibits expression of type I interferon.
Figure 32:
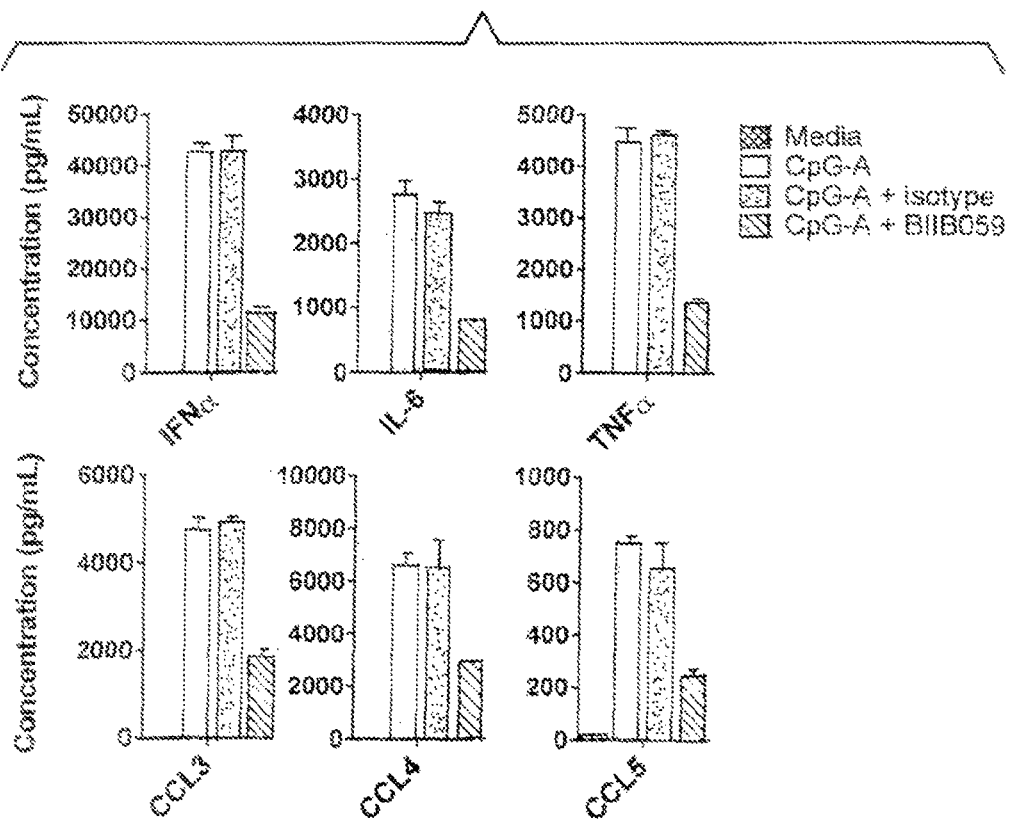
FIG. 32 is series of bar graphs showing the results of ELISA or multiplex assays to measure concentrations of inflammatory cytokines and chemokines produced by pDCs treated with CpG-A, CpG-A in the presence of anti-BDCA2, and CpG-A in the presence of isotype control. Each bar represents the mean and standard deviation (SD) for duplicate wells from a representative healthy human donor out of 5 tested. Vertical lines depict the SD.

Example 33. BIIB059 Inhibits Pro-Inflammatory Mediators in Addition to all Types of Type I IFN BDCA2 ligation suppresses the ability of pDCs to produce type I IFNs in response to TLR ligands (see FIG. 16). To confirm the inhibitory activity of the anti-BDCA2 mAb, BIIB059, purified pDCs from healthy human donors were stimulated with the synthetic TLR9 ligand, CpG-A, in the presence of 10 µg/mL BIIB059 or isotype control mAbs. Specifically, pDCs from human healthy donors were isolated using a two-step magnetic bead separation procedure (MACS kit, Miltenyi Biotec). $5 \times 10^4$ purified human pDCs/well were left untreated (Media) or were stimulated with 1 µM TLR9 ligand (CPG-A) in the presence of either 10 µg/mL of BIIB059 (CpG-A+BIIB059) or isotype control (CpG-A+Iso). The plates containing pDCs were incubated for 18 hours at 37° C. and supernatants collected for use in ELISA or multiplex assays to measure concentrations of inflammatory cytokines and chemokines. These experiments showed that BIIB059 potently inhibited TLR9-induced IFNα and other pDC-derived cytokines such as TNFα and IL-6 as well as TLR-9 induced chemokines such as CCL3, CCL4, CCL5 (FIG. 32).

Figure 33:
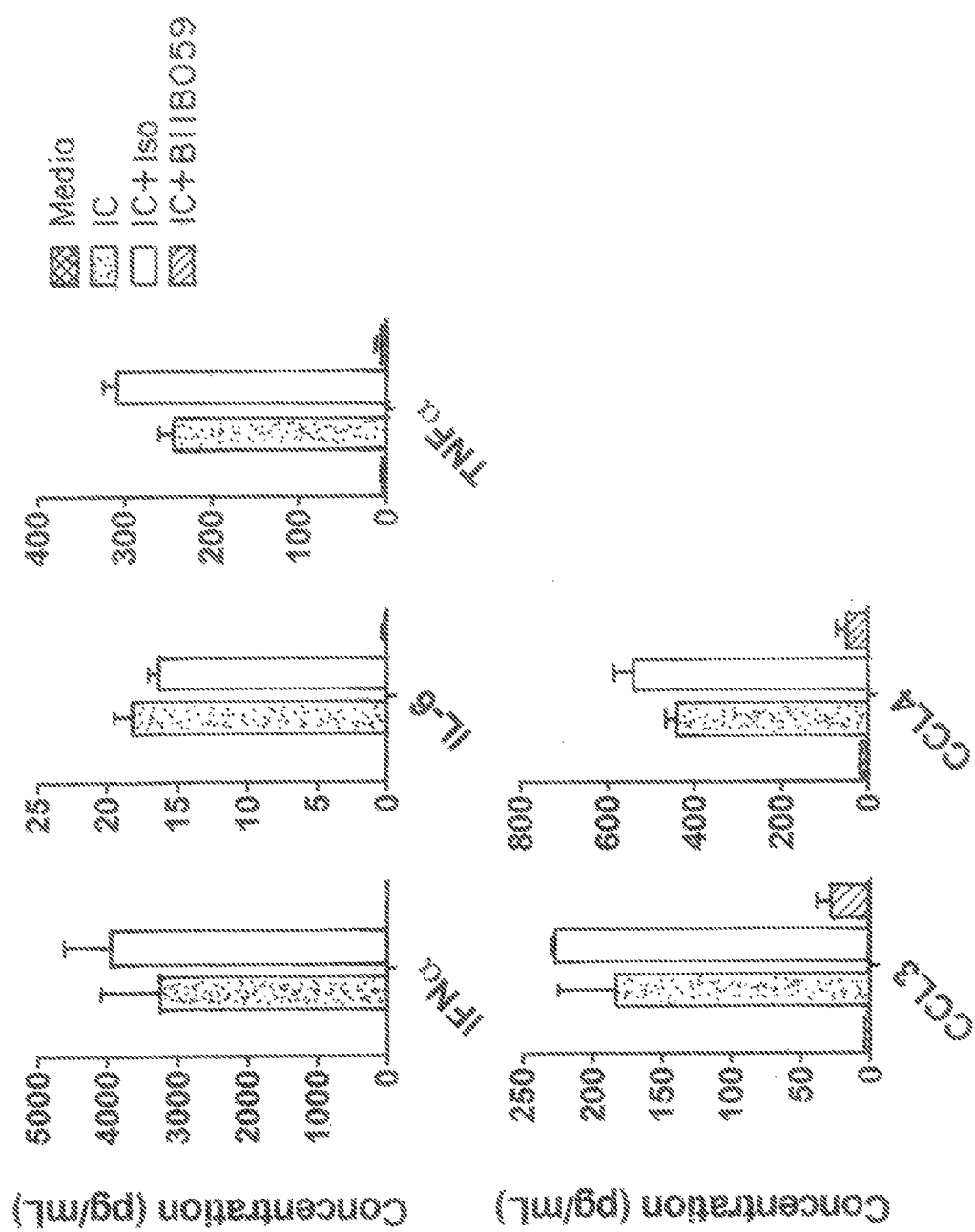
FIG. 33 is series of bar graphs showing the results of ELISA or multiplex assays to measure concentrations of inflammatory cytokines and chemokines produced by pDCs treated with Sm/RNP immune complexes, Sm/RNP immune complexes in the presence of anti-BDCA2, and Sm/RNP immune complexes in the presence of isotype control. Each bar represents the mean and standard deviation (SD) for duplicate wells from a representative healthy human donor out of 5 tested. Vertical lines depict the SD.

The ability of BIIB059 to inhibit the production of IFNα and pro-inflammatory mediators following stimulation with a physiologically relevant ligand, immune complexes, was also investigated. Specifically, Sm/RNP immune complexes (IC) were pre-formed by mixing sm-RNP from calf thymus and anti-RNP antibodies purified form sera of SLE patients for 1 h in serum-free medium. pDCs from human healthy donors were isolated using a two-step magnetic bead separation procedure (MACS kit, Miltenyi Biotec). $5 \times 10^4$ pDCs/well were left untreated (Media) or were stimulated with pre-formed Sm/RNP IC in the presence of either 10 µg/mL of BIIB059 (IC+BIIB059) or isotype control (IC+Iso). The plates containing pDCs were incubated for 18 hours at 37° C. and supernatants collected for use in ELISA or multiplex assays to measure concentrations of inflammatory cytokines and chemokines. These studies showed that BIIB059 potently inhibited Sm/RNP immune complexes-induced IFNα and other pDC-derived cytokines such as TNFα and IL-6. BIIB059 also inhibited chemokines induced by Sm/RNP immune complexes, such as CCL3 and CCL4 (FIG. 33).

Example 34: BIIB059 Inhibits Sm/RNP IC-Induced Transcription of Type I IFN Subtypes by Purified Human pDCs Thirteen IFNα subtypes and a single member of IFNβ exist in humans. The effect of BIIB059 on the transcription of type I IFN subtypes in Sm/RNP IC stimulated pDCs from healthy human donors was evaluated using qualitative polymerase chain reaction (qPCR) assays.

Sm/RNP immune complexes (IC) were pre-formed by mixing sm-RNP from calf thymus and anti-RNP antibodies purified from sera of SLE patients for 30 minutes in serum-free medium. pDCs from human healthy donors were isolated using a two-step magnetic bead separation procedure (MACS kit, Miltenyi Biotec). $7.5 \times 10^5$ purified human pDCs/well were left untreated (Media) or were stimulated with pre-formed Sm/RNP IC in the presence of either 10 µg/mL of BIIB059 (IC+BIIB059) or isotype control (IC+Iso). The plates containing pDC were incubated for 16 hours at 37° C. and 5% CO2. pDC cells were collected and RNA from pDC was isolated for evaluation in qPCR reaction.

Figure 34:
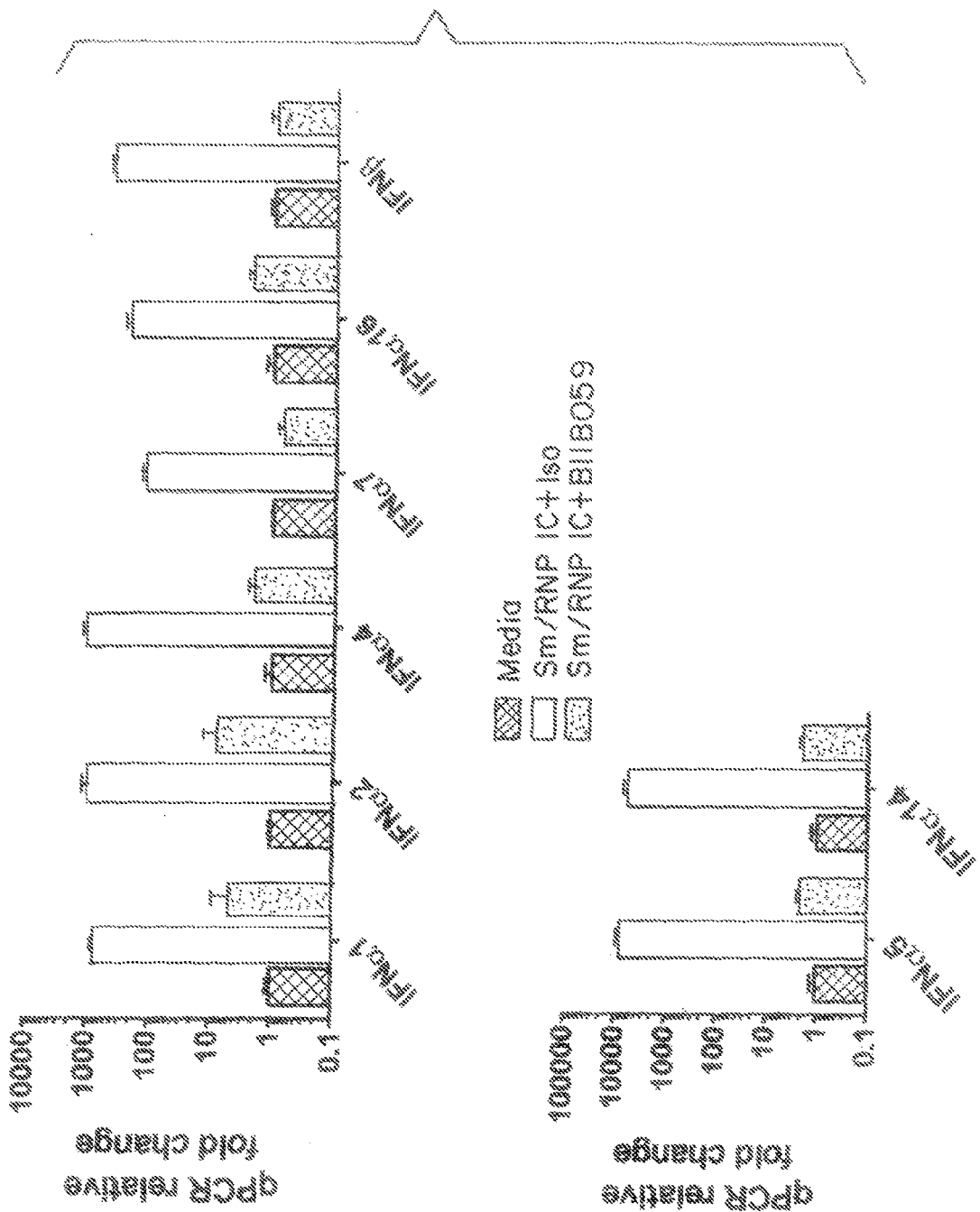
FIG. 34 is a series of bar graphs showing the results of qPCR assays to determine the effect of BIIB059 on the transcription of type I IFN subtypes in Sm/RNP IC stimulated pDCs from healthy human donors. Each bar represent the mean relative fold change for quadruplicate wells from a representative donor out of 3 tested (n=3) and vertical lines depict the standard deviation (SD).

This experiment showed that treatment with BIIB059 inhibited the transcript level of all type I IFN subtypes tested (FIG. 34).

Example 35: BIIB059 Inhibits TLR9-Induced IFNα Production by Human PBMC from Healthy Donors and SLE Patients pDCs are the major producers of IFN in response to TLR7 and TLR9 stimulation. pDCs can produce thousand-fold more IFN than any other cell type. This experiment investigates whether BIIB059 could inhibit TLR9-induced IFNα production in peripheral blood mononuclear cell (PBMC) cultures without the need for pDC isolation. PBMC from healthy human donors or SLE patients were stimulated with 1 or 5 µM of the TLR9 ligand (CpG-A) and treated with concentrations of BIIB059 ranging from 10 µg/mL to 2 ng/mL in a total assay volume of 250 µL/well. The plates were incubated overnight (18 hours) at 37° C. and 5% CO2. Supernatants were collected for evaluation in IFNα ELISA assays.

Figure 35A:
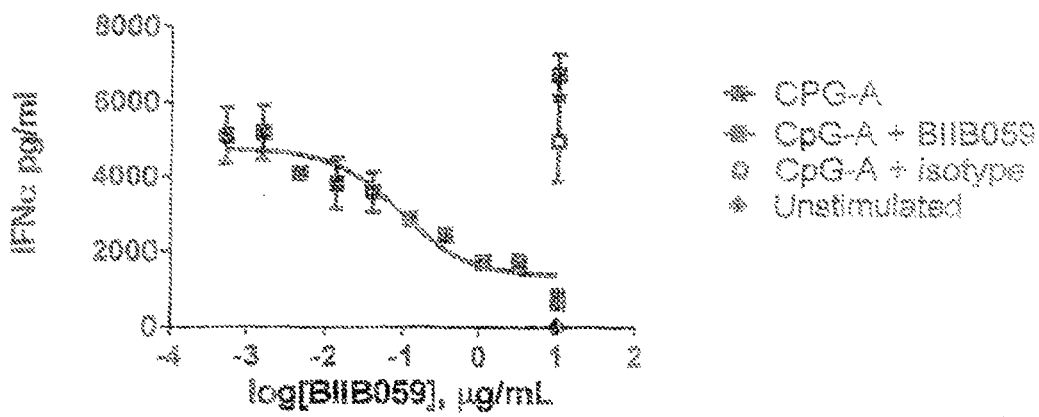
FIG. 35A shows BIIB059-mediated dose dependent inhibition of TLR9-induced IFNα by PBMC from one representative healthy human donor out of 18 tested. Each symbol represents the mean and standard deviation (SD) for duplicate wells.
Figure 35B:
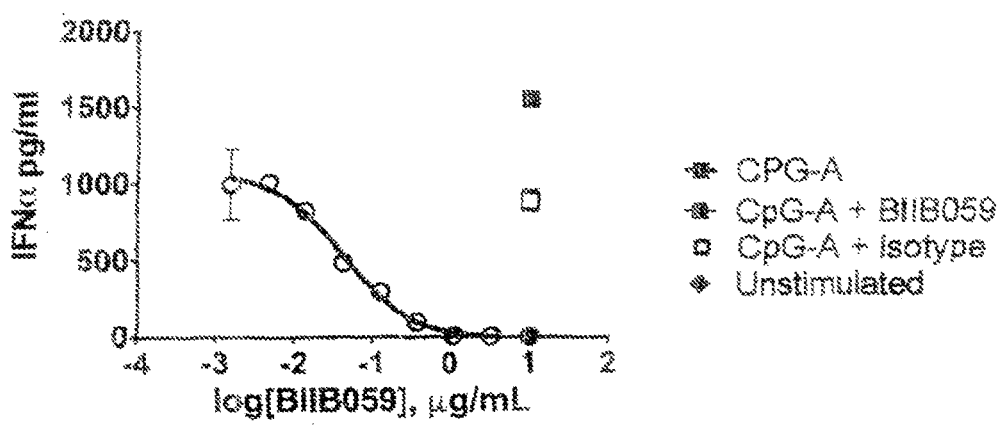
FIG. 35B shows BIIB059-mediated dose dependent inhibition of TLR9-induced IFNα by PBMC from one representative SLE patient out of 11 tested. Each symbol represents the mean and standard deviation (SD) for duplicate wells.
Figure 35C:
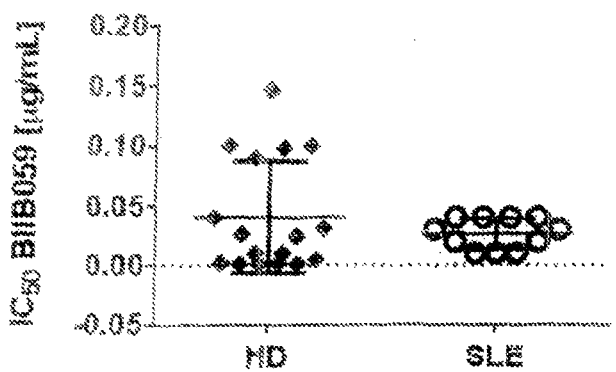
FIG. 35C shows IC50 values for BIIB059 inhibition of TLR9-induced IFNα production by PBMC in healthy human donors (HD) compared to SLE patients (SLE). Each symbol represents an individual donor and vertical lines depict the SD.

This experiment showed that BIIB059 inhibited TLR9-induced IFNα production by PBMC from healthy donors with an average $IC_{50}$ of 0.04+/−0.05 µg/mL (FIGS. 35A and 35C). BIIB059 showed similar potency at inhibiting TLR9-induced IFNα production by PBMC from SLE patients with an average $IC_{50}$ of 0.03+/−0.01 µg/mL (FIGS. 35B and 35C).

Example 36: BIIB059 Inhibits IFNα Production in Whole Blood Stimulated with TLR9 Ligand The activity of BIIB059 was also evaluated in whole blood assays (WBA). Whole blood from healthy human donors was stimulated with TLR9 ligand in the presence of increasing concentrations of BIIB059 and the IC50 of inhibition was calculated for each individual donor. Specifically, whole blood from healthy human donors was incubated with increasing concentrations of BIIB059 ranging from 10 µg/mL to 2 ng/mL or isotype control in a total assay volume of 200 µl/well. CpG-A was added at 75 µg/mL (open square), which was determined to be optimal for stimulation of IFNα production in whole blood. Plates were incubated for 18 hours at 37° C. and supernatants collected for use in IFNα ELISA assays (PBL InterferonSource).

BIIB059 showed a dose dependent inhibition of TLR9-induced IFNα production in whole blood assays and exhibited similar IC50 to that seen with PBMC cultures (FIG. 36).

Example 37: BIIB059 does not Inhibit TLR3-Induced IFNα Production by Human PBMC from Healthy Human Donors This experiment was performed to determine whether other cell types triggered with different TLR ligands are still able to produce type I IFN even in the presence of BIIB059. TLR3 is not expressed in pDCs and therefore TLR3 ligand does not induce IFN production by pDCs. PBMC from human healthy donors were stimulated with poly:IC, which is a TLR3 ligand that can potently induce type I IFN predominantly by monocytes. Specifically, PBMC from healthy human donors were stimulated with 1 µM of the TLR3 ligand (Poly I: C) and treated with concentrations of BIIB059 ranging from 10 µg/mL to 0.5 ng/mL in a total assay volume of 250 µL/well in a 96 well plate. The plates were incubated overnight (18 hours) at 37° C. and 5% CO2. 200 µL of the supernatants were collected for evaluation of IFNα levels by ELISA. As shown in FIG. 37, BIIB059 did not impact TLR3-induced IFNα production by PBMC from healthy human donors.

To summarize, Examples 33-37 show that BIIB059 can potently inhibit TLR 9-stimulated type I interferon by purified pDCs, PBMC, and whole blood cultures. BIIB059 is equally potent at inhibiting TLR9-induced Type I interferon by pDCs from healthy human donors and SLE patients. In addition to inhibiting type I IFN, BIIB059 can inhibit the production of other pDC-derived cytokines and chemokines. BIIB059 specifically inhibits TLR9-induced type I IFN by pDCs and does not impact IFN production by other cell types triggered with a different TLR ligand. Therefore, the in vitro data provided herein support the pharmacological activity and potency of BIIB059 in addition to its specificity for TLR7/9-induced type I IFN by pDCs.

Example 38: BIIB059 Mediates BDCA2 Internalization on Human pDCs

To determine whether BIIB059 induces BDCA2 internalization, human whole blood from 10 healthy human donors was incubated with increasing concentrations of BIIB059 at 37° C. for 16 hours. The remaining cell surface BDCA2 was detected using a FITC-labeled non-cross blocking anti-BDCA2 mAb (clone 2D6).

Specifically, whole blood from 10 healthy human donors was incubated with increasing concentrations of BIIB059 or 10 µg/ml isotype control antibody for 16 hours at 37° C. and 5% CO2 and then incubated for 30 minutes at 4° C. with FITC-labeled non-cross blocking anti-BDCA2 mAb (clone 2D6), anti-HLA-DR, anti-CD123, anti-CD14 and anti-CD20. Whole blood was then incubated for 30 minutes at 4° C. with 50 µL of a staining solution, which included the following mAbs: FITC-labeled non-cross blocking anti-BDCA2 mAb (clone 2D6), anti-HLA-DR, anti-CD123, anti-CD14 and anti-CD20. Red blood cells (RBCs) were lysed using 1× lyse/fix buffer (BD Bioscience).

As shown in FIG. 38, BIIB059 led to a dose dependent decrease in the intensity of FITC-labeled 2D6 staining with an average $EC_{50}$ of 0.017±0.005 µg/mL Example 39: BDCA2 is Rapidly Internalized Upon Ligation with BIIB059

To determine the kinetics of BIIB059-induced BDCA2 internalization, human whole blood was incubated with different concentrations of BIIB059 at 37° C. for various periods. Specifically, whole blood was treated with 10, 1, 0.1 or 0.01 µg/mL of BIIB059 or an isotype control antibody (10 µg/ml) at 37° C. for the periods indicated. The whole blood was then incubated for 30 minutes at 4° C. with 50 µL of a staining solution which included the following mAbs: FITC-labeled non-cross blocking anti-BDCA2 mAb (clone 2D6), anti-HLA-DR, anti-CD123, anti-CD14 and anti-CD20. Red blood cells (RBCs) were lysed and fixed using 1× Lyse/fix buffer (BD Bioscience). As shown in FIG. 39, upon incubation with BIIB059 at 1 µg/ml the intensity of FITC-labeled 2D6 staining rapidly decreased reaching background levels within one hour of incubation. Incubation with a tenfold lower BIIB059 concentration (0.1 µg/ml) delayed internalization of BDCA2 by 2 hours. This data shows that the rate of BDCA2 internalization is dependent on the dose of BIIB059.

Figure 40:
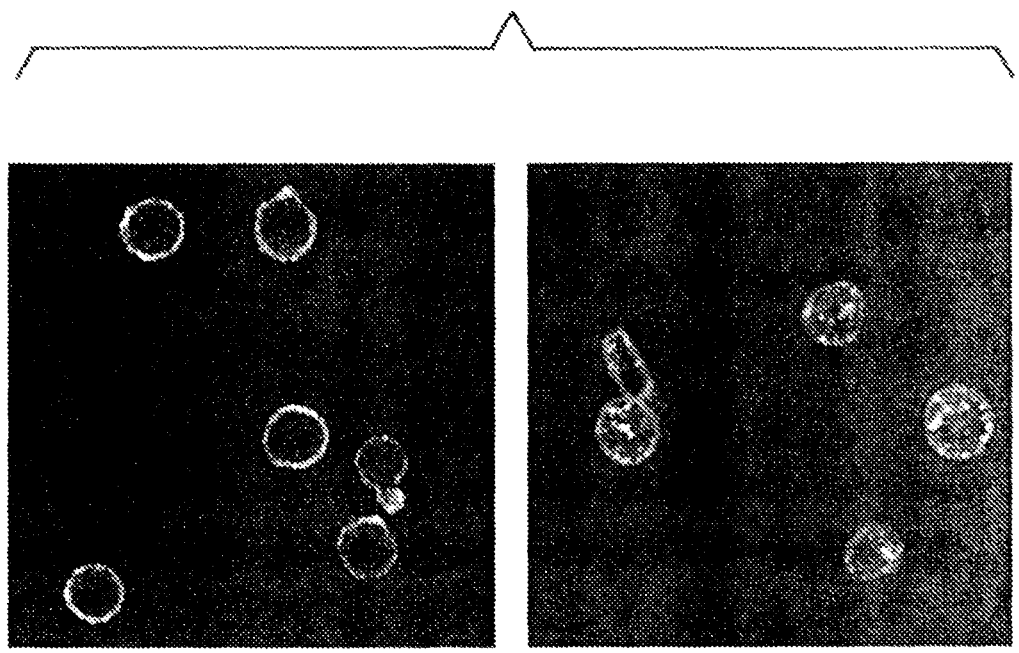
FIG. 40 are confocal images of human pDCs purified from peripheral blood and then incubated with 10 µg/mL of BIIB059-AF647 (white) at 4° C. (left) or at 37° C. in 5% CO2 (right) for 15 min. BIIB059 cell distribution was assessed by confocal microscopy, and a representative picture is shown for each condition.

Example 40: BIIB059 Induce BDCA2 Internalization in Human Plasmacytoid Dendritic Cells To visualize the internalization of BDCA2 after ligation with BIIB059, purified pDCs were incubated with A647-labeled BIIB059 and analyzed by confocal microscopy. As expected, BDCA2 was localized on the cell surface of pDCs at 4° C. After a short incubation at 37° C. BDCA2 was clearly detected inside the cells (FIG. 40).

Figure 41:
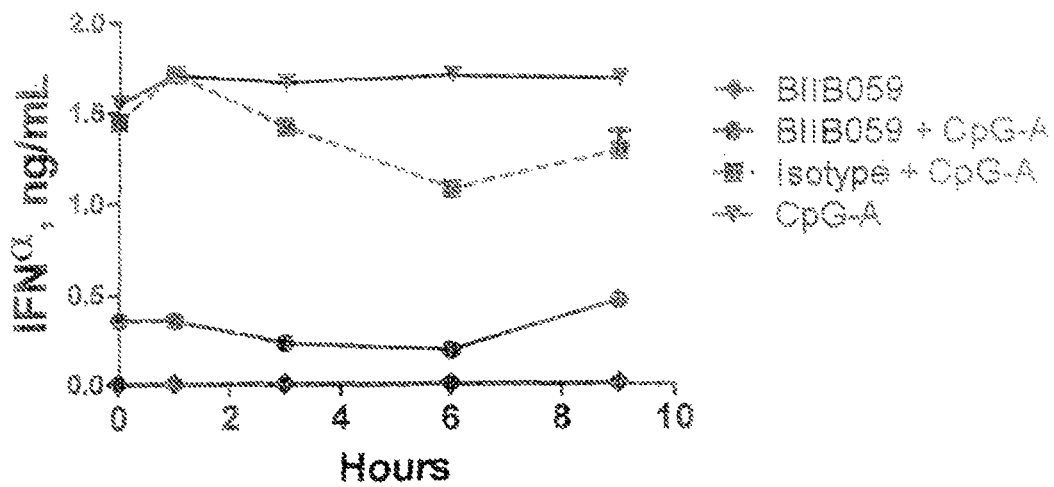
FIG. 41 is a graphical depiction of the effect of internalization of BDCA2 on inhibition of IFNα production. This figure is a representative of 3 independent experiments.

Example 41: Internalization does not Alter BIIB059-Mediated Inhibition of IFN-α Production This experiment investigated whether BDCA2 internalization alters the ability of BIIB059 to inhibit TLR9-induced IFNα production by pDCs. Cells were pre-incubated with BIIB059 at 37° C. for various periods corresponding to maximal BDCA2 internalization and then stimulated with TLR9 ligand for an additional 18 hours. Specifically, whole blood was collected from heparinized venous blood of healthy donors and pre-incubated with BIIB059 or isotope control antibody for the duration indicated. At each time point after pre-incubation, cells were stimulated with 200 μg/mL TLR9 ligand (CpG-A) and incubated for an additional 18 hours at 37° C. Supernatants were collected for use in IFNα ELISA assays (PBL InterferonSource). As shown in FIG. 41, pre-incubation with BIIB059 (up to 9 hours) did not alter the ability of BIIB059 to inhibit TLR9-induced IFNα production in whole blood assays from healthy human donors. These data suggest that BDCA2 internalization might be required for the inhibition of TLR9 signaling.

Example 42: The EC50 of BIIB059-Mediated BDCA2 Internalization on pDCs Correlates with the IC50 of BIIB059-Mediated Inhibition of TLR9-Induced IFNα by pDCs in Whole Blood Assays To further explore the link between the internalization of BDCA2 and the inhibition of TLR9 signaling, the potency of BIIB059-mediated internalization of BDCA2 on pDCs and the inhibition of TLR-mediated IFNα production by pDCs was compared in 10 healthy human donors.

Figure 42:
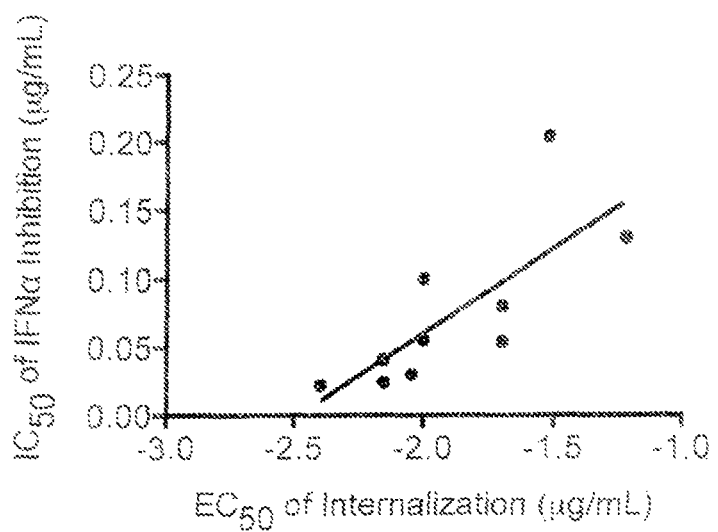
FIG. 42 is a graphical showing that the EC50 values of BIIB059-mediated BDCA2 internalization correlated with IC50 values of BIIB059-mediated inhibition of TLR9-induced IFNα in whole blood assays (n=10). $R^2$ value of 0.57.

To evaluate BIIB059-mediated BDCA2 internalization, whole blood was incubated with BIIB059 for 16 hours. The whole blood was then collected, lysed, and BDCA2 expression was assessed by flow cytometry using the FITC-conjugated non-cross blocking antibody 2D6. To evaluate BIIB059-mediated inhibition of TLR9 induced IFNα by pDCs, whole blood was incubated with increasing concentrations of BIIB059 for 16 hours in the presence of a TLR9 ligand. The supernatants were harvested and evaluated for IFNα by ELISA. The EC50 of BIIB059-mediated BDCA2 internalization was 0.02 μg/mL. The IC50 of BIIB059 mediated inhibition of TLR9 induced IFNα was 0.07 μg/mL. A correlation between the EC50 of BIIB059-mediated internalization of BDCA2 and the IC50 of BIIB059 IFNα inhibition was observed with an R square value of 0.57 (FIG. 42).

Example 43: TLR9 Activation Induces BDCA2 Colocalization with TLR9 and with the Lysosomal Marker LAMP1

To test the hypothesis that BIIB059-mediated TLR9 inhibition requires internalization and localization of BDCA2 into endosomal/lysosomal compartments containing TLR9, confocal microscopy was used to follow the intracellular distribution of BDCA2 after BIIB059 ligation. Purified human pDCs were cultured for 7 days and incubated with A647-labeled BIIB059 for 15 min at 37° C. During the last 10 min of the incubation, cells were treated with 1 μM of the TLR9 ligand CpG-A or left untreated. Cells were stained with fluorescently labeled antibodies to TLR9 and the late endosomal/lysosomal marker, LAMP1, and analyzed by confocal microscopy.

Figure 43A:
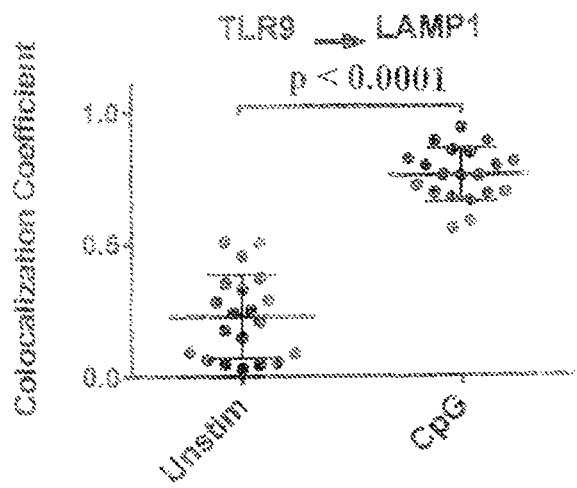
FIG. 43A shows results expressed as the mean and standard deviation (SD) of the Manders colocalization coefficients for TLR9 localization in the LAMP1+ compartment.
Figure 43B:
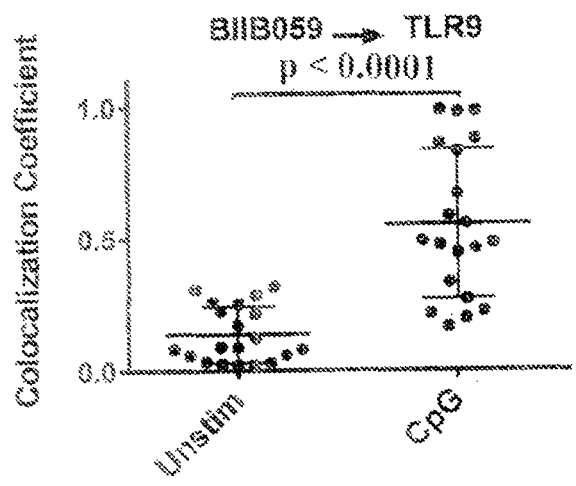
FIG. 43B shows results expressed as the mean and SD of the Manders colocalization coefficients for BIIB059/BDCA2 localization in the TLR9+ compartment.
Figure 43C:
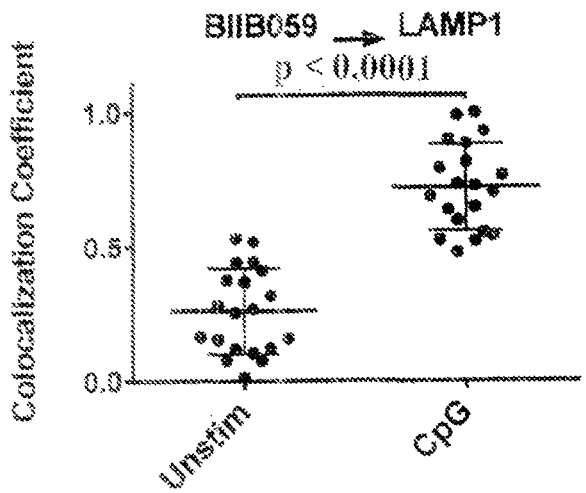
FIG. 43C shows results expressed as the mean and SD of the Manders colocalization coefficients for BIIB059/BDCA2 localization in the LAMP1+ compartment. Each symbol represents an individual cell; horizontal lines represents the mean, vertical lines represents the SD.

TLR9 was recruited to a late endosomal/lysosomal compartment after stimulation with TLR9 ligand, as evidenced by increased colocalization of TLR9 with LAMP1 (FIG. 43). TLR9 stimulation also significantly increased the fraction of BDCA2 colocalizing with TLR9 and LAMP1. These results suggest that BIIB059, when bound to BDCA2, preferentially localizes to intracellular compartments where activated TLR9 is present.

In sum, Examples 38-43 show that BIIB059, a humanized monoclonal antibody against BDCA2, engages BDCA2 and leads to its internalization. Upon stimulation, BDCA2 colocalize with TLR9 in the endosomal/lysosomal compartment where it mediates inhibition of TLR9 signaling. These data suggest that BDCA2 internalization is a necessary step for mediating the inhibition of TLR9-induced pro-inflammatory mediators by pDCs.

Example 44: Effect of BIIB059 on CD62L Levels

Circulating pDCs express high levels of CD62L (L-selectin) and home to high endothelial venules (HEV)-containing lymphoid tissue. PNAd is a ligand for CD62L that is constitutively expressed on HEV and mediates homing of CD62L expressing cells to organized lymphoid tissue. PNAd was found to be expressed by dermal endothelial cells in cutaneous Lupus Erythematosis lesions. By virtue of their CD62L expression pDCs could be recruited to inflamed peripheral tissues expressing PNAd.

To determine whether BIIB059 impacts the expression of CD62L on the surface of human pDCs, whole blood was treated with varying concentrations of BIIB059 for 1 hour at 37° C. without stimulation. Specifically, whole blood from healthy human donors was treated with increasing concentrations of BIIB059 for 1 hour at 37° C. and 5% CO2. The MFI of CD62L was determined by gating on pDCs as defined by CD14−, CD20−, HLA-DR+ and CD123+.

BIIB059 caused a dose-dependent decrease in CD62L expression on the surface of human pDCs as assessed by flow cytometry (FIG. 44). Stimulation of pDCs with TLR ligand did not impact the expression of CD62L (FIG. 44A).

Example 45: Treatment of PBMC with GM6001 Inhibits BIIB059 Mediated CD62L Shedding from the Surface of Human pDCs Metalloproteinase are known to induce CD62L shedding from the surface of immune cells. To investigate whether metalloproteinases are involved in the BIIB059-mediated decrease of surface CD62L, PBMC were prepared from healthy human donors and pre-treated with GM6001 (a metalloproteinase inhibitor) for 30 minutes at 37° C. and 5% CO2, followed by the addition of 10 μg/mL of BIIB059 for 1 hour. The surface expression of CD62L was assayed by flow cytometry. GM6001 inhibited the BIIB059-mediated down-modulation CD62L in a dose dependent manner (FIG. 45). These data suggest that BIIB059 induces CD62L shedding in a metalloproteinase-dependent manner.

In sum, Examples 44 and 45 show that BIIB059 decreases the expression of CD62L on the surface of human pDCs. BIIB059-mediated CD62L downmodulation is inhibited by metalloproteinase inhibitor (GM6001) indicating that BIIB059 induces CD62L shedding from the surface of human pDCs through, at least in part, the activation of metalloproteinases. BIIB059 treatment is therefore expected to reduce or prevent trafficking of pDCs to target organs in SLE.

Example 46: Impact of the Fc Region of BIIB059 on Immune-Complex-Mediated IFN Production by Plasmacytoid Dendritic Cells Fc gamma receptor IIA (CD32a) is a cell surface protein that binds IgG with low affinity. Human plasmacytoid dendritic cells exclusively express Fc gamma receptor IIA, CD32a. Stimulation of pDCs with immune complexes has been shown to be dependent on CD32 Immune complexes are internalized by CD32 and stimulate endosomal TLR7/9 to induce IFN production by pDCs.

Figure 46A:
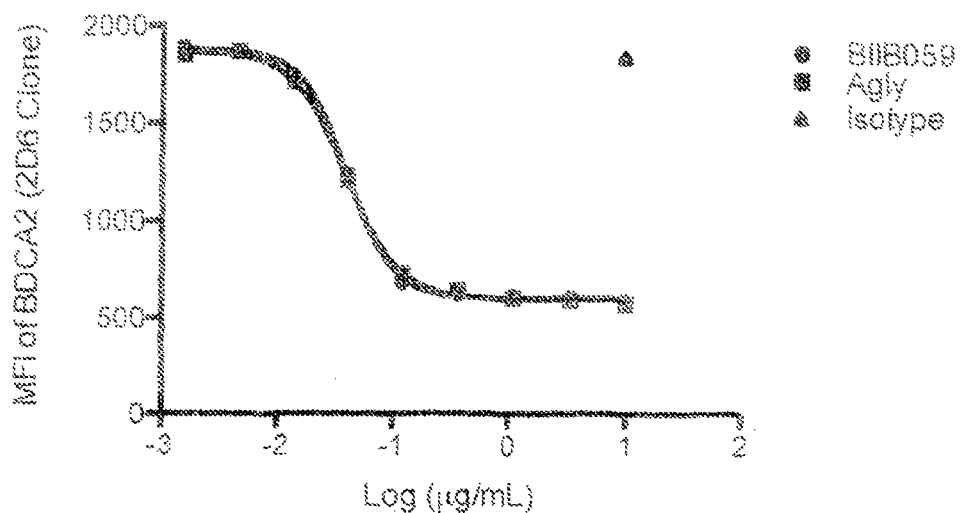
FIG. 46A is a graphical depiction of BIIB059 and 24F4A-Agly mediated dose-dependent internalization of BDCA2 on the surface of pDCs from one representative healthy human donor (n=5). pDCs from human healthy donors were isolated using a two-step magnetic bead separation procedure (MACS kit, Miltenyi Biotec). pDCs were treated with increasing concentrations of BIIB059 (circles) or the a-glycosylated form of the antibody-24F4-Agly-(squares). Cells were also treated with 10 µg/mL of an isotype control (triangle) and incubated for 16 hours at 37° C. pDCs were then stained for surface expression of BDCA2 and CD32.
Figure 46B:
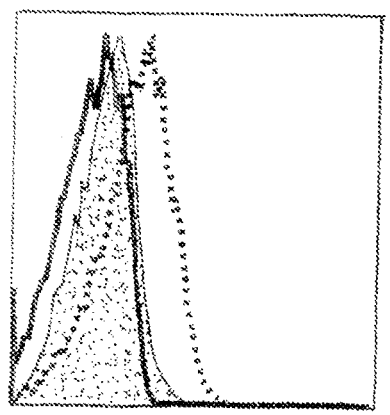
FIG. 46B is a histogram showing levels of CD32 on isolated pDCs treated with 10 µg/mL of BIIB059 (shaded) or the isotype control (dotted) (n=5).
Figure 46C:
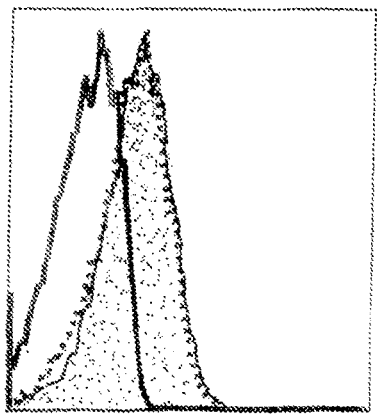
FIG. 46C is a histogram showing CD32 levels on isolated pDCs treated with 10 µg/mL of the a-glycosylated form-24F4-A (shaded) or the isotype control (dotted). Solid line represents the unstained cells (n=5).
Figure 46D:
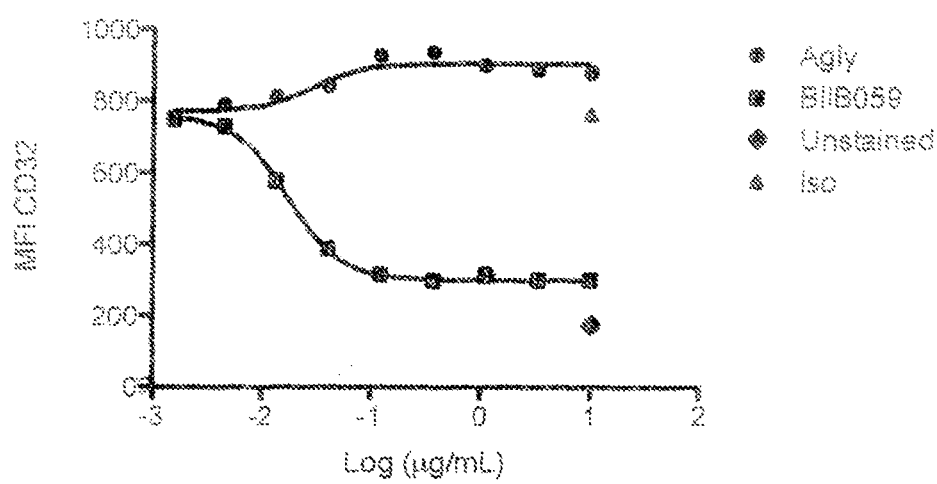
FIG. 46D is a graphical depiction of BIIB059-mediated dose dependent down-modulation of CD32 on the surface of pDCs from one representative healthy human donor (n=5).

To determine the effect of BIIB059 on CD32a surface expression, isolated pDCs were treated with increasing concentrations of BIIB059 or the aglycosylated form of the antibody, 24F4-A, and incubated for 16-hour at 37° C. pDCs were then stained with FITC-labeled BDCA2 and PE-labeled anti-CD32 (clone AT10) and the surface expression of BDCA2 and CD32 was assessed by flow cytometry. BIIB059 and the agly version, 24F4-A, were equally potent in their ability to induce BDCA2 internalization (FIG. 46A). Only BIIB059 was able to induce the down-modulation of CD32 on the cell surface of pDCs as indicated by the dose-dependent decrease in CD32 Mean Fluorescent Intensity (MFI) (FIGS. 46 B-D). Treatment with effector competent istoype control had no effect on CD32 surface levels (FIG. 46). These data indicate that the BIIB059-mediated down-modulation of CD32a levels on the surface of pDCs is specific to the binding of the Fc region of BIIB059.

Figures 46E, 46F:
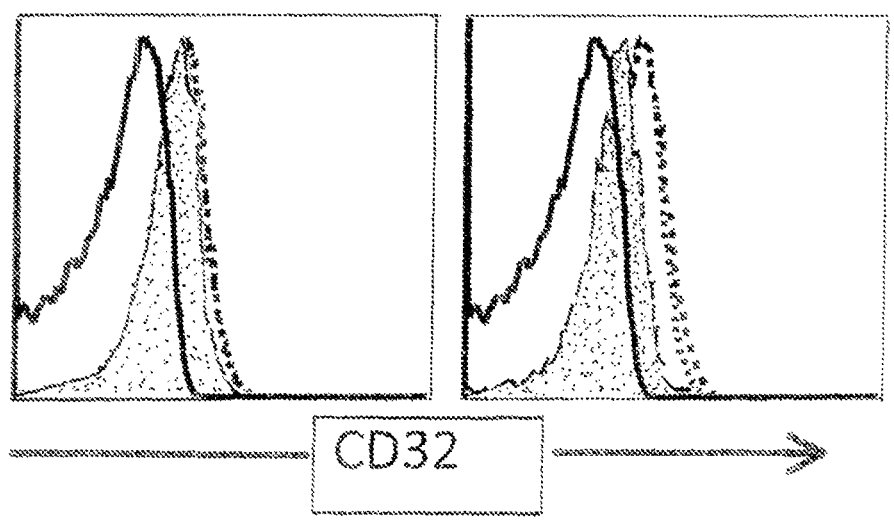
FIG. 46E is a histogram showing levels of CD32 on isolated pDCs treated for 1 hour at 4° C. in the presence of 10 µg/mL of BIIB059 (shaded), the a-glycosylated form (dashed), or an isotype control (dotted). After incubation pDCs were assessed for CD32 surface expression. Solid black line represents unstained cells (n=3).
FIG. 46F is a histogram showing levels of CD32 on isolated pDCs treated for 1 hour at 37° C. in the presence of 10 µg/mL of BIIB059 (shaded), the a-glycosylated form (dashed), or an isotype control (dotted). After incubation pDCs were assessed for CD32 surface expression. Solid black line represents unstained cells (n=3).

To ensure that binding of the Fc region of BIIB059 does not merely mask the epitope of CD32 recognized by the FITC-labeled the anti-CD32 mAb, pDCs were treated with 10 µg/mL of BIIB059 for 1 hour at 4° C. or 37° C. and then stained with labeled anti-CD32. As shown in FIG. 46E, treatment with BIIB059 at 4° C. did not decrease the CD32 MFI indicating that treatment with BIIB059 does not interfere with the binding of labeled anti-CD32 mAb. The fact that CD32a down-modulation occurred only upon incubation with BIIB059 at 37° C. suggests that CD32a could be lost from the cell surface of pDCs.

Figure 47A:
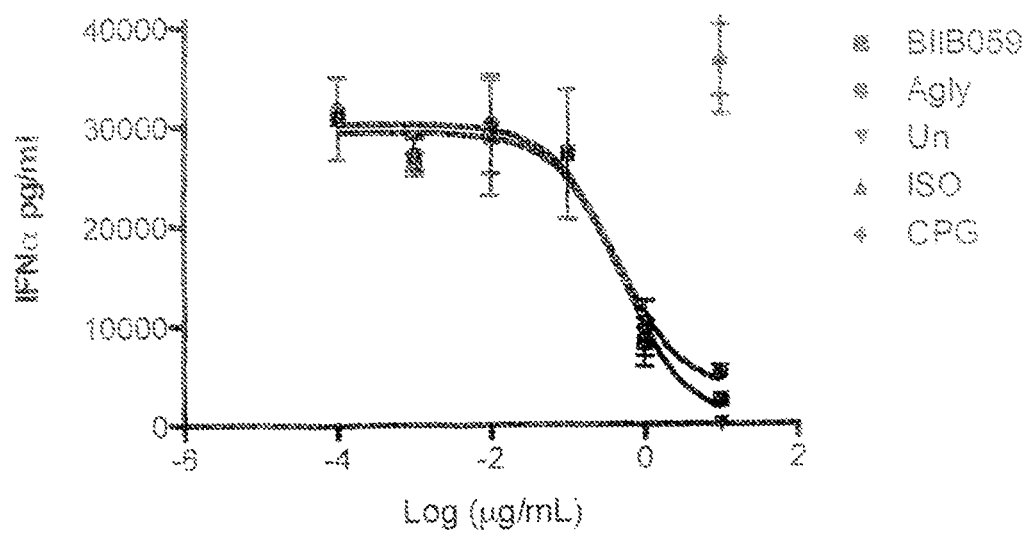
FIG. 47A is a graphical depiction of IFNα levels from isolated pDCs treated with increasing concentrations of BIIB059 (squares), increasing concentrations of the a-glycosylated form of the antibody 24F4-A (circles), or istotype control at 10 µg/mL (triangle). pDCs were stimulated in the presence of CpG-A (75 µg/mL) or left unstimulated (inverted triangle). pDCs were incubated for 16 hours at 37° C. and supernatants were collected and assayed for IFNα by ELISA. Shown is representative experiment out of 2 conducted.
Figure 47B:
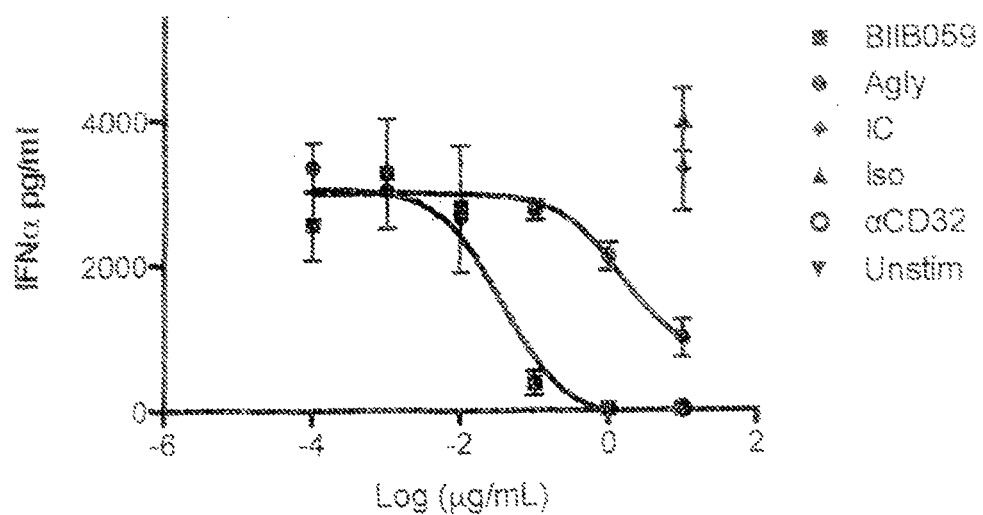
FIG. 47B is a graphical depiction of IFNα levels from isolated pDCs treated with increasing concentrations of BIIB059 (squares), increasing concentrations of the a-glycosylated form of the antibody 24F4-A (circles), istotype control at 10 µg/mL (triangle), or anti-human CD32 mAb at 10 µg/mL. Sm/RNP immune complexes (IC) were preformed by mixing Sm-RNP from calf *thymus* and anti-RNP antibodies purified form sera of SLE patients for 30 minutes in serum-free medium. Isolated cells were stimulated with immune complexes or treated with antigen alone (unstimulated). Cells were incubated for 16 hours at 37° C. and supernatants were collected and assayed for IFNα by ELISA. Shown is a representative figure of 3 conducted. Each symbol represents the mean and standard deviation (SD) for duplicate wells.

To determine whether the down-modulation of CD32a by BIIB059 has a biological impact, pDCs were incubated in the presence of increasing concentrations of BIIB059 or the aglycosylated form, 24F4A-Agly, and stimulated with either immune complexes or the synthetic TLR9 ligand (CPG-A). As expected, BIIB059 and 24F4A-Agly were undistinguishable in their ability to inhibit CPG-A-induced IFNα by pDCs, which is CD32 independent (FIG. 47A). There was a clear separation in potency between BIIB059 and 24F4A-agly when the pDCs were stimulated with immune complexes. BIIB059 inhibited immune complex-induced IFNα with an IC50 of 0.04 compared to an IC50 of 1.4 µg/mL by 24F4A-Agly. (FIG. 47B). These data indicate that BIIB059 down-modulates CD32a by virtue of its functional Fc and therefore inhibits stimulation of pDCs by immune complexes.

Figure 48A:
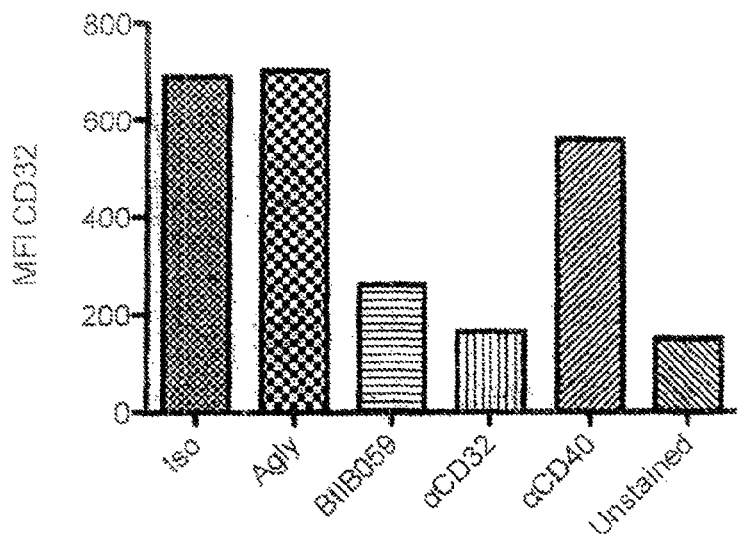
FIG. 48A is a bar graph showing CD32 expression on isolated pDCs treated with immune complexes in the presence of 10 µg/mL of BIIB059, 24F4-A, anti CD32 mAb (AT10 clone), humanized anti CD40 antibody, or isotype control. Cells were incubated for 16 hours at 37° C. pDCs were stained for surface expression of CD32 and CD40.
Figure 48B:
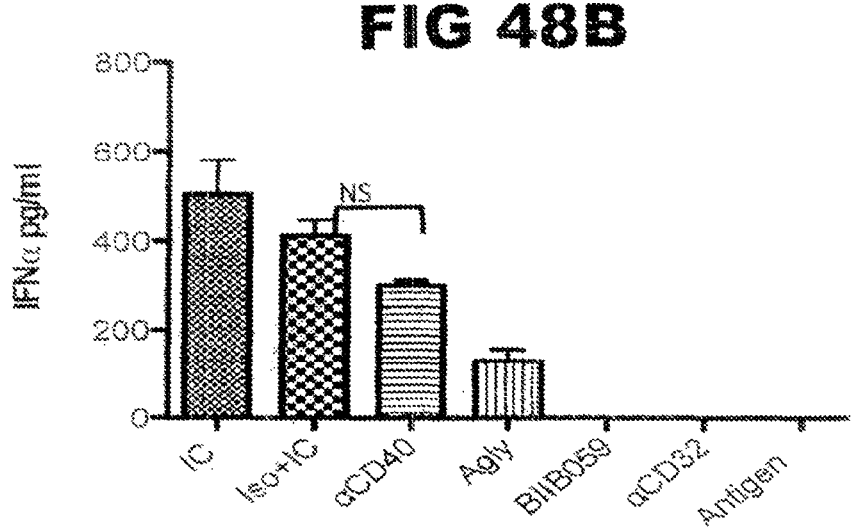
FIG. 48B is a bar graph depicting IFNα levels measured by ELISA in the supernatants collected from A. Shown is a representative figure (n=3).
Figure 48C:
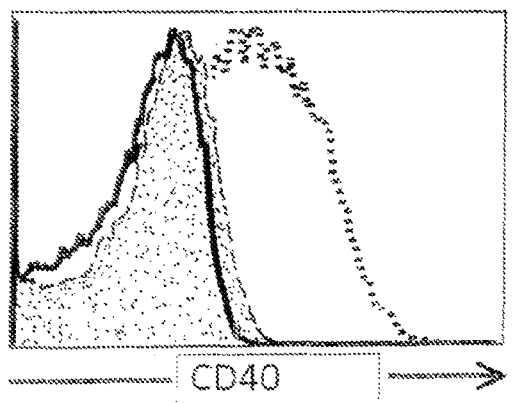
FIG. 48C is a histogram showing CD40 expression on the surface of pDCs. The dotted line represents CD40 expression on the cell surface. The tinted histogram represents levels of CD40 on pDCs after treatment with anti-CD40 antibody. The solid line represents unstained cells.
Figure 49:
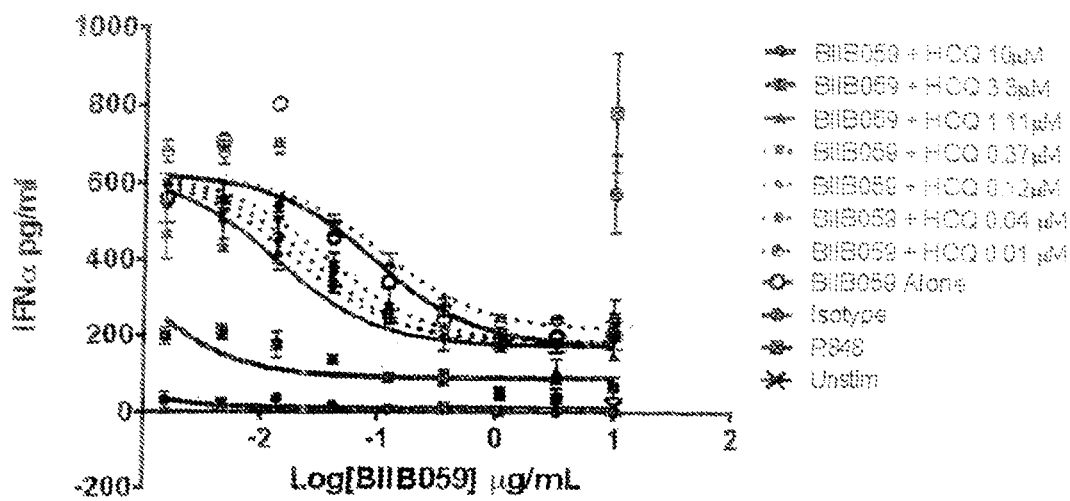
FIG. 49 depicts the impact of HCQ on BIIB059 potency. Each symbol represents IFNα concentrations measured from an individual healthy human donor and vertical lines depict the SD. PBMC from healthy human donors were treated with varying concentrations of BIIB059 alone, HCQ alone or in combination (BIIB059+HCQ) in a total assay volume of 250 µL/well. Concentrations of BIIB059 ranged from 10 µg/mL to 0.1 µg/mL. Concentrations of HCQ ranged from 10 µM to 156 nM. 1×10$^6$ PBMC cells/well were stimulated with 5 µM of the TLR7 ligand (R848). The plates containing PBMC were incubated overnight (18 hours) at 37° C. and 5% CO2. 200 µL of the supernatants were collected for evaluation in IFNα ELISA (PBL Interferon-Source).
Figure 50:
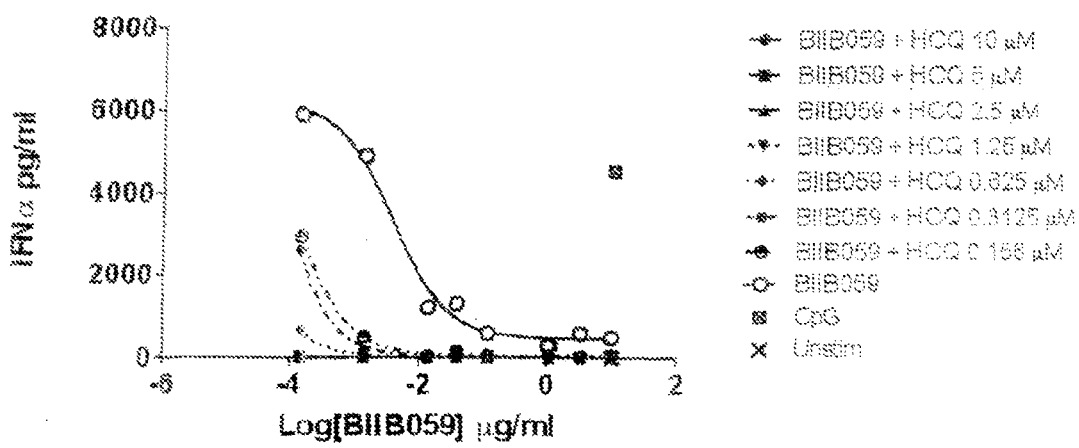
FIG. 50 depicts the impact of HCQ on BIIB059 potency. Each symbol represents IFNα concentrations measured from a representative donor of 2 tested healthy donors and vertical lines depict the standard deviation (SD). PBMC from heparinized venous blood of healthy human donors or SLE patients were isolated by discontinuous gradient centrifugation over Ficoll, washed in PBS and resuspended in complete culture medium (RPMI with 3% FBS). PBMC were treated with varying concentrations of BIIB059 alone, HCQ alone or in combination (BIIB059+HCQ) in a total assay volume of 250 µL/well. Concentrations of BIIB059 ranged from 10 µg/mL to 0.1 µg/mL. Concentrations of HCQ ranged from 10 µM to 156 nM. 1×106 PBMC cells/well were stimulated with 1 µM of the TLR9 ligand (CPG-A). The plates containing PBMC were incubated overnight (18 hours) at 37° C. and 5% CO2. 200 µL of the supernatants were collected for evaluation in IFNα ELISA (PBL InterferonSource).

To confirm that the down-modulation of CD32a was unique to BIIB059, we investigated the effect of a fully humanized anti-CD40 antibody on CD32 levels and immune-complex mediated IFNα production by pDCs. CD40 is a cell surface protein expressed on pDCs. An anti-CD40 antibody with a fully functional Fc has the ability to engage CD40 and bind CD32 on the surface of pDCs. Treatment with anti-CD40 mAb had no effect of CD32 surface expression and no significant effect on IFNα production from immune complex stimulated pDCs (FIGS. 48A and B). Binding of anti CD40 mAb was confirmed by demonstrating maximal CD40 engagement in anti-CD40 treated cells (FIG. 48C).

As shown previously, BDCA2 ligation with BIIB059 or the aglycosylated form 24F4A-Agly leads to receptor internalization and inhibition of TLR9-induced IFNα by pDCs. In this study we show that BIIB059 causes down-modulation of CD32a on pDCs and inhibition of immune complex-stimulated IFNα production by pDCs in an Fc dependent manner. The CD32a down-modulation triggered by BIIB059 does not result from just any antibody with a functional Fc that can bind a cell surface molecule expressed on pDCs. This study highlights the novel therapeutic potential of an effector competent anti-BDCA2 mAb, which can dampen pDC responses through both its Fab'2 and Fc regions leading to enhanced efficacy.

Example 47: Interaction of BIIB059 with Hydroxychloroquine (HCQ)

Antimalarial agents, such as hydroxychloroquine (HCQ), have been used in the treatment of SLE. pDCs from SLE patients treated with HCQ have impaired ability to produce IFNα upon stimulation with TLR7 and TLR9 ligands. Since both BIIB059 and HCQ impact TLR7/9 induced IFNα in pDCs, it was investigated whether the effect of BIIB059 and HCQ could be redundant.

To address this question, human PBMC were prepared from blood from healthy donors and stimulated with either TLR7 or TLR9 ligands in the presence of varying concentrations of BIIB059 alone, HCQ alone, or BIIB059 in combination with HCQ. Supernatants were harvested after 18 hours and assayed for IFNα by ELISA. The addition of HCQ increased the potency of BIIB059 and led to an additive inhibitory effect on TLR7 and TLR9-induced IFNα production by PBMC from healthy human donors. These data demonstrate that the activity of BIIB059 and HCQ are not redundant and highlight the additional therapeutic benefit of BIIB059 when administered with antimalarial compounds such as HCQ.

Example 48: Effect of BIIB059 on BDCA2-Expressing pDCs In Vivo

The objective of this study was to determine if administration of BIIB059 to cynomolgus monkey mediates depletion of pDCs in the peripheral blood.

Four pre-BIIB059 dosing bleeds were collected at weekly intervals from twelve cynomolgus monkeys to establish a baseline pDC frequency for each animal (Table 3).

TABLE 3

Summary of average circulating pDC frequencies in healthy cynomolgus monkey whole blood.
Whole blood was drawn from twelve cynomolgus monkeys once a week for four weeks total. pDCs were identified using flow cytometry as CD20−CD14−CD123+HLA-DR+. pDC as a percent of CD20−CD14− cells was calculated with FlowJo software.

| Cynomolgus monkey donor | percent circulating pDC | | | | | |
|---|---|---|---|---|---|---|
| | 073112 | 080712 | 081312 | 082013 | average | SD |
| 1 | 0.26 | 0.2 | 0.15 | 0.16 | 0.19 | 0.05 |
| 2 | 0.2 | 0.15 | 0.15 | 0.21 | 0.18 | 0.03 |
| 3 | 0.11 | 0.06 | 0.11 | 0.19 | 0.12 | 0.05 |
| 4 | 0.12 | 0.11 | 0.14 | 0.31 | 0.17 | 0.09 |
| 5 | 0.19 | 0.2 | 0.31 | 0.40 | 0.28 | 0.10 |
| 6 | 0.32 | 0.57 | 0.35 | 0.39 | 0.41 | 0.11 |
| 7 | 0.15 | 0.19 | 0.21 | 0.16 | 0.18 | 0.03 |
| 8 | 0.12 | 0.13 | 0.1 | 0.16 | 0.13 | 0.03 |
| 9 | 0.08 | 0.12 | 0.1 | 0.11 | 0.10 | 0.02 |
| 10 | 0.16 | 0.15 | 0.28 | 0.22 | 0.20 | 0.06 |
| 11 | 0.06 | 0.07 | 0.04 | 0.07 | 0.06 | 0.01 |
| 12 | 0.1 | 0.05 | 0.07 | 0.16 | 0.10 | 0.05 |
| average | 0.16 | 0.17 | 0.17 | 0.21 | 0.18 | |
| SD | 0.08 | 0.14 | 0.10 | 0.10 | 0.09 | |

Figure 51:
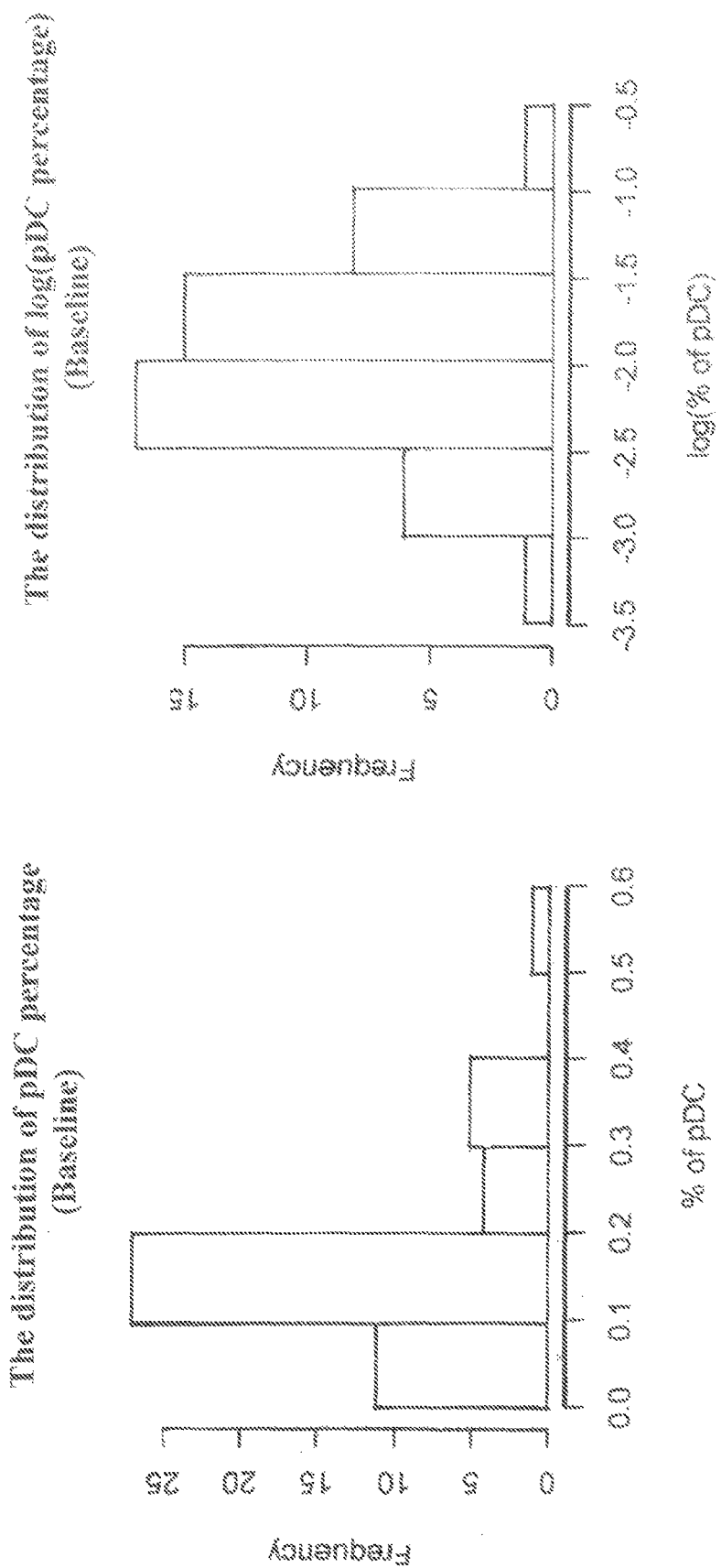
FIG. 51 shows distributions of percent circulating pDC in healthy cynomolgus monkey whole blood on original scale (left panel) and on log scale (right panel). Whole blood was drawn from twelve cynomolgus monkeys once a week for four weeks total. pDCs were identified using flow cytometry as CD20–CD14–CD123+HLA-DR+. pDC as a percent of CD20–CD14– cells was calculated with FlowJo software. Graph was obtained using the R language for statistical computing.
Figure 52:
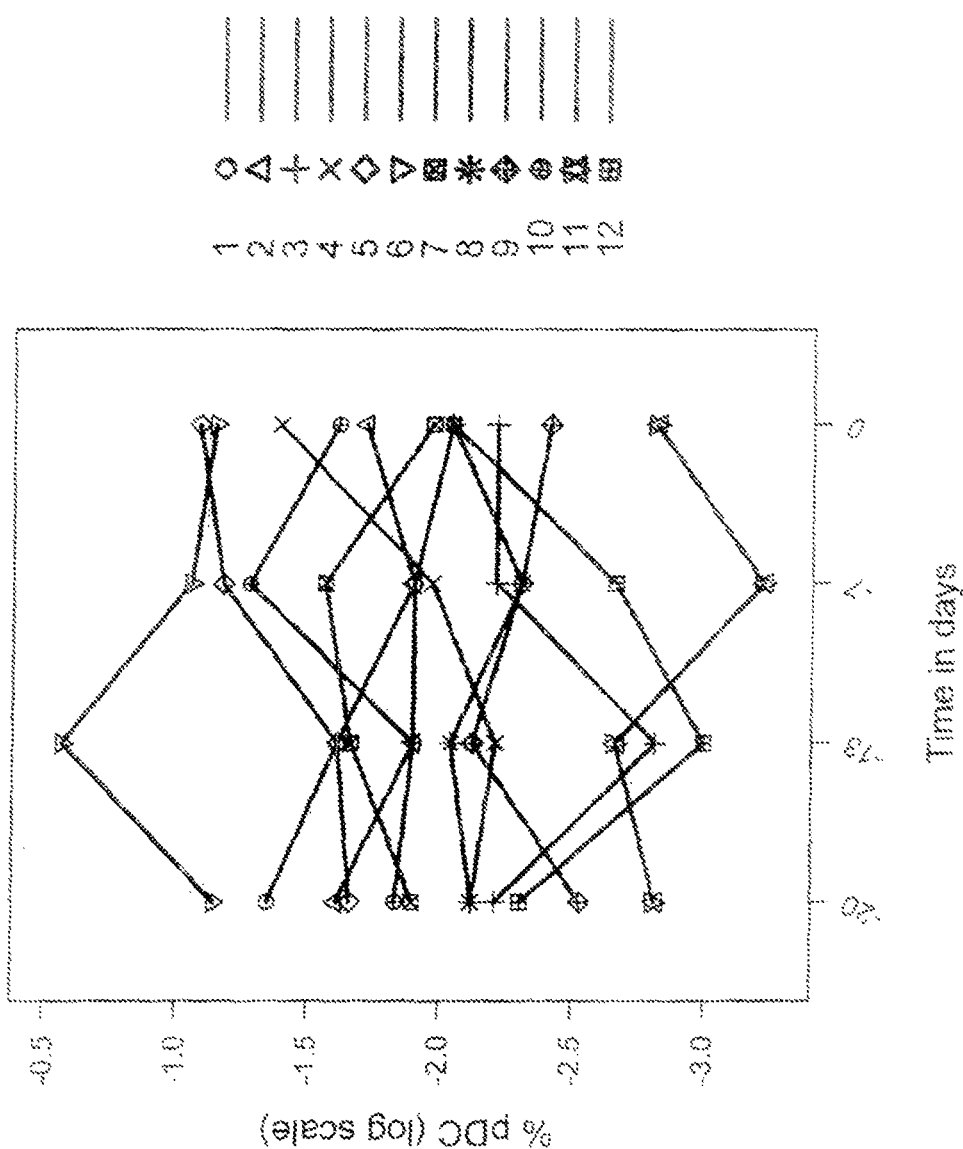
FIG. 52 is a graphical depiction of the percent circulating pDC (on log scale) in healthy cynomolgus monkey whole blood by different time points prior to IV injection of BIIB059. At indicated time points, whole blood was drawn, and pDCs were identified by flow cytometry as CD20–CD14–CD123+HLA-DR+. Percent pDCS was calculated in FlowJo software, and graphed using R software.
Figure 53:
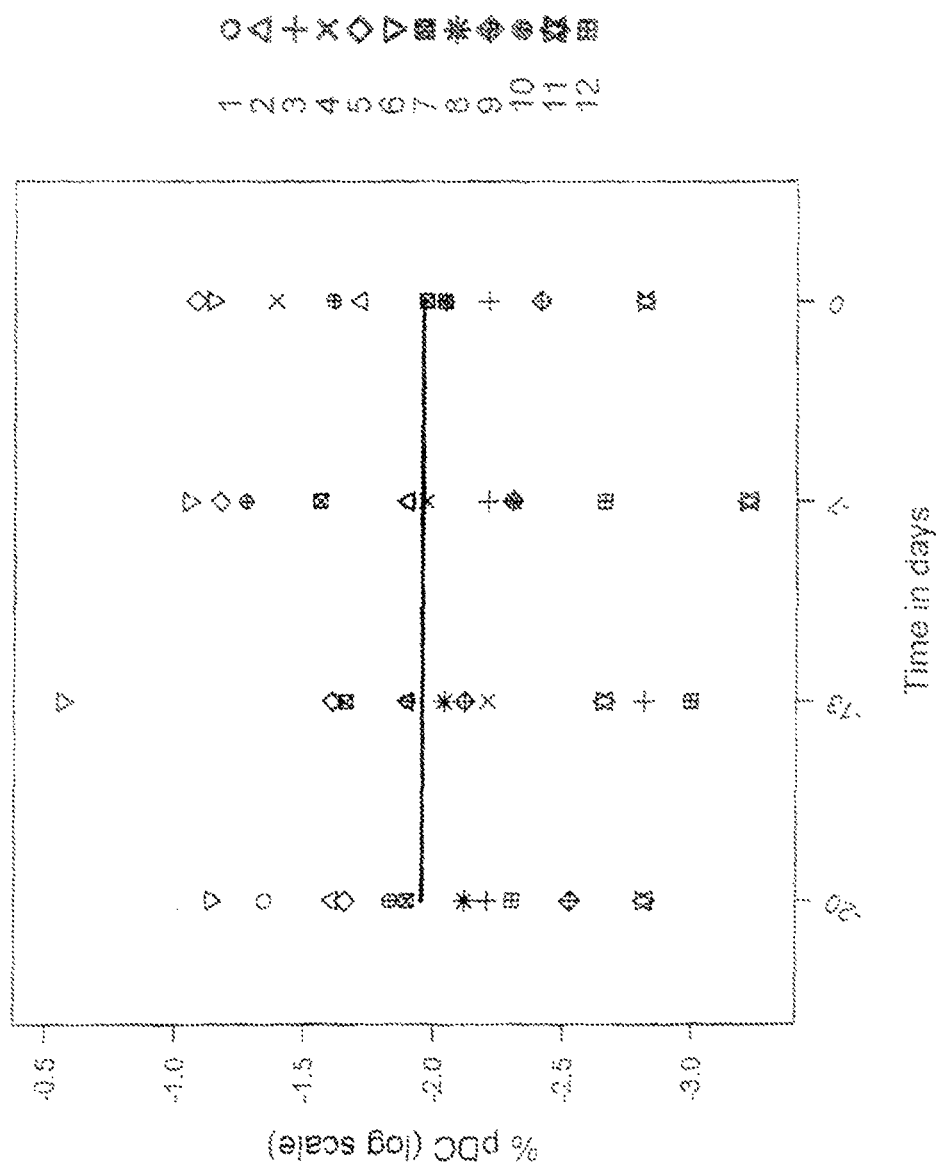
FIG. 53 is a depiction of a final fitted model for percent circulating pDC (on log scale) in healthy cynomolgus monkey whole blood by different time points prior to IV injection of BIIB059. A linear mixed effects model for log (% pDC) values with different time points as the fixed factors and cynos as the random intercepts shows no differences among the ratios of the geometric means % pDC values measured by difference weeks (p-value based on F-test for all time effects equal to zero is 0.67). Graph and statistical analysis were calculated using the R language for statistical computing. The black line shows the final fitted model, which only includes a fixed intercept and the random intercepts for cynomolgus monkeys. lme4 package in R was used to fit the linear mixed effects model.

In all statistical analyses, pDC frequencies were log-transformed to reduce the skewness (FIG. 51). The original distribution of pDC frequencies in the left panel of FIG. 51 was severely right-skewed. However, after a log-transformation, the distribution of the transformed pDC frequencies (FIG. 51, right panel) approximately followed a normal distribution. These log-transformed data were used for all statistical analysis methods. FIG. 52 shows levels of pDC on log scale for each cynomolgus monkey over four time points prior to IV injection. Using a linear mixed effects model with four time points as fixed factors and random intercepts for cynos, we concluded that the geometric means of pDC percentages for all monkeys were equal over the 4 predose time points (FIG. 53, p-value for time based on a F-test: 0.67). This analysis indicated that the geometric mean of percentage of circulating pDCs was relatively stable over time for cynomolgus monkeys.

Figure 54:
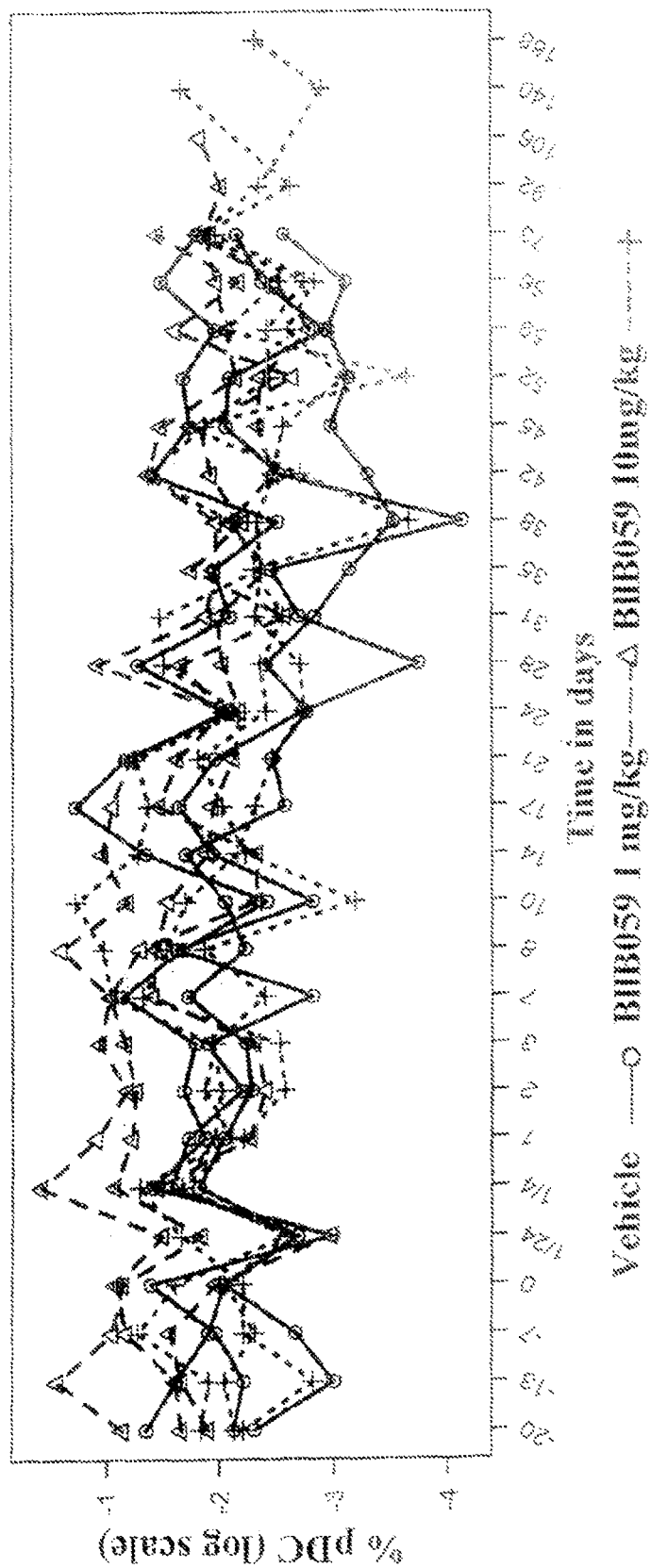
FIG. 54 depicts percent circulating pDC on log scale before and after IV dose of sodium citrate vehicle, BIIB059 1 mg/kg or BIIB059 10 mg/kg in cynomolgus monkey. Three cynomolgus monkeys were administered for each dose group at time 0. At indicated time points, whole blood was drawn, and pDCs were identified by flow cytometry as CD20–CD14–CD123+HLA-DR+. Percent pDCs was calculated in FlowJo software, and graphed using R software.

Nine of these twelve cynomolgus monkeys were divided into 3 groups (3/group), and randomized to include equal representation of BDCA2 density and percent pDC in each group. Cynomolgus monkeys received a single intravenous injection of either vehicle (sodium citrate), 10 mg/kg BIIB059, or 1 mg/kg BIIB059. Flow cytometry was used to identify circulating pDCs in the whole blood as CD20−CD14−CD123+HLA-DR+, and the pDC frequency (on log-scale) at each time point was graphed in R software (FIG. 54). A linear mixed effects model was fitted to log (pDC) frequencies using random intercepts for cynomolgus monkeys and fixed effects for dose group and time period: 1 hour, 6 hours, 1-27 days, and greater than 28 days. To assess whether pDC changed among different dose groups at different time periods, a preliminary model also included the interaction terms for dose group and different time periods. The p-value based on F-test for testing all interaction terms equal to 0 is 0.81, which indicates that there is no difference for the pDC changes among different dose groups. Hence, the final fitted model only included the statistically significant effects for time period and dose group factors (Table 4).

TABLE 4

Fitted model estimates for time points after a single intravenous BIIB059 or vehicle injection.
Estimates for the fixed effects using a linear mixed effects model using random intercepts for cynomolgus monkeys, and fixed factors for dose group and time levels 1 hour, 6 hours, and greater than 28 days, for percent circulating pDC on log scale before and after IV dose of sodium citrate vehicle, BIIB059 1 mg/kg, or BIIB059 at 10 mg/kg in cynomolgus monkeys.

| | effect est. | exp (effect est.) (% pDC ratio) | 95% CI | P |
|---|---|---|---|---|
| time: 1 hr v. others | −0.56 | 0.57 | 0.43 to 0.77 | 0.0003 |
| time: 6 hrs v. others | 0.46 | 1.58 | 1.18 to 2.13 | 0.003 |
| time: >28 days v. others | −0.48 | 0.62 | 0.55 to 0.70 | <0.0001 |
| Group: BIIB059 1 mg/kg v. vehicle | 0.49 | 1.64 | 1.20 to 2.25 | 0.01 |
| Group: BIIB059 10 mg/kg v. vehicle | 0.09 | 1.09 | 0.79 to 1.50 | 0.84 |

Figure 55:
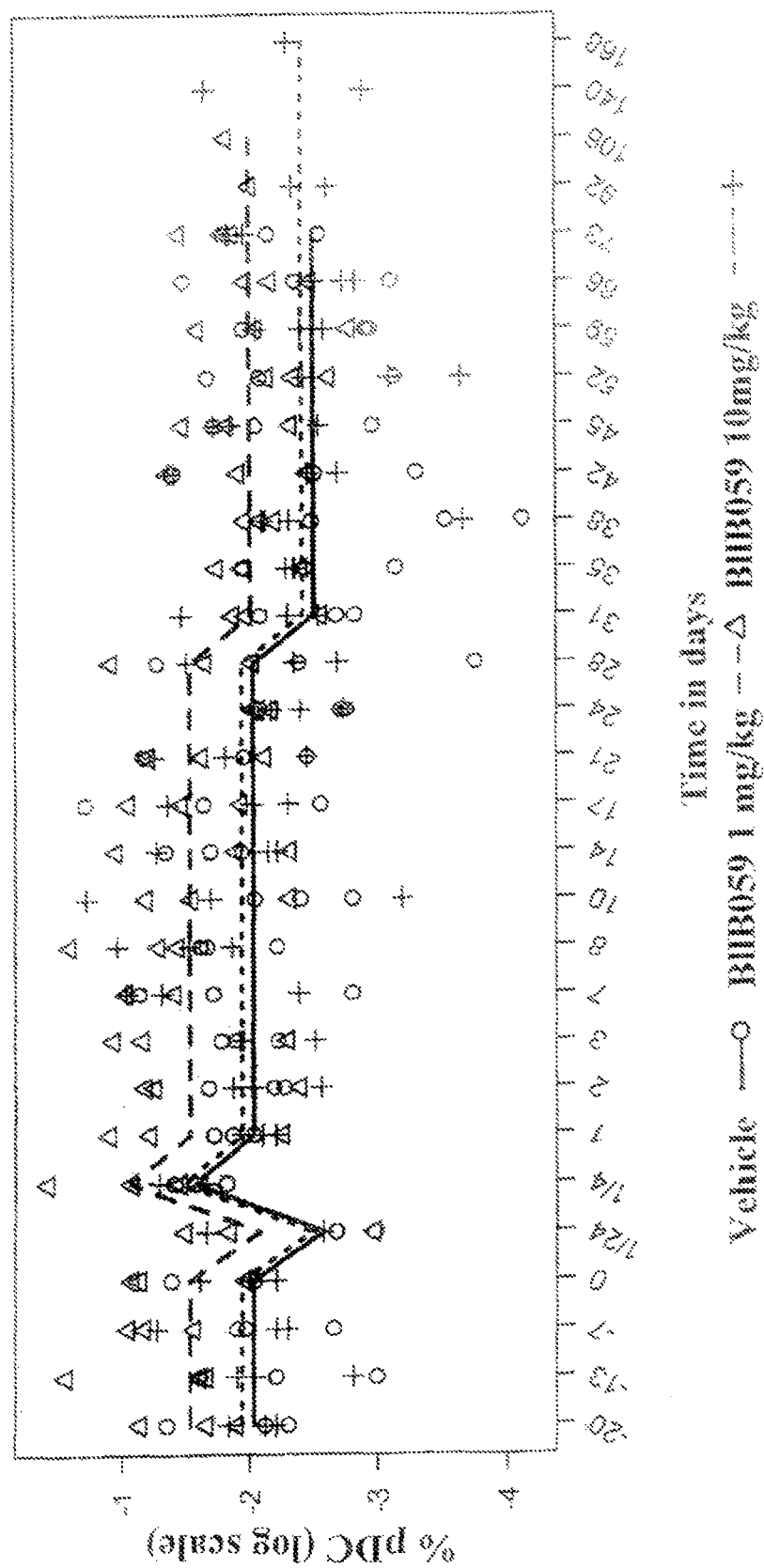
FIG. 55 depicts final fitted model for percent circulating pDC on log scale before and after IV dose of sodium citrate vehicle, BIIB059 1 mg/kg and BIIB059 10 mg/kg in cynomolgus monkeys. A linear mixed effects model for log (% pDC) values with fixed factors for dose group, time levels 1 hour, 6 hours and greater than 28 days, and with random intercept for cynomolgus monkeys. The solid line shows the fitted model. lme4 package in R was used to fit the linear mixed effects model. Graph and statistical analysis were calculated using the R language for statistical computing.

The parameter estimates for the fixed factors were exponentiated in order to interpret them as the ratios of pDC frequencies at these time periods compared to pre-BIIB059 dosing. Overall, the ratio was significantly less than one when comparing the pDC frequencies at 1-hour after IV injection to pre dose pDC frequencies (95% CI: 0.43-0.77, p-value: 0.0003). The ratio was significantly greater than one comparing the pDC frequencies at 6 hours after IV injection to the predose pDC frequencies (95% CI: 1.18-2.12, p-value: 0.003). The ratio was not significantly different from one when comparing the pDC frequencies 1-28 day period after IV injection to the predose pDC frequencies. The ratio was significantly less than one when comparing the pDC frequencies after 28 days after IV injection to the predose pDC frequencies (95% CI: 0.55-0.70, p-value: <0.0001). The final fitted model was plotted in FIG. 55. The results revealed that there was a significant in vivo depletion of circulating pDCs in cynomolgus monkeys at 1 hour, a significant increase of circulating pDCs at 6 hours and a significant depletion of circulating pDCs after 28 days after IV injection, but changes in percent pDC across time were the same for all treatment groups.

Figure 56:
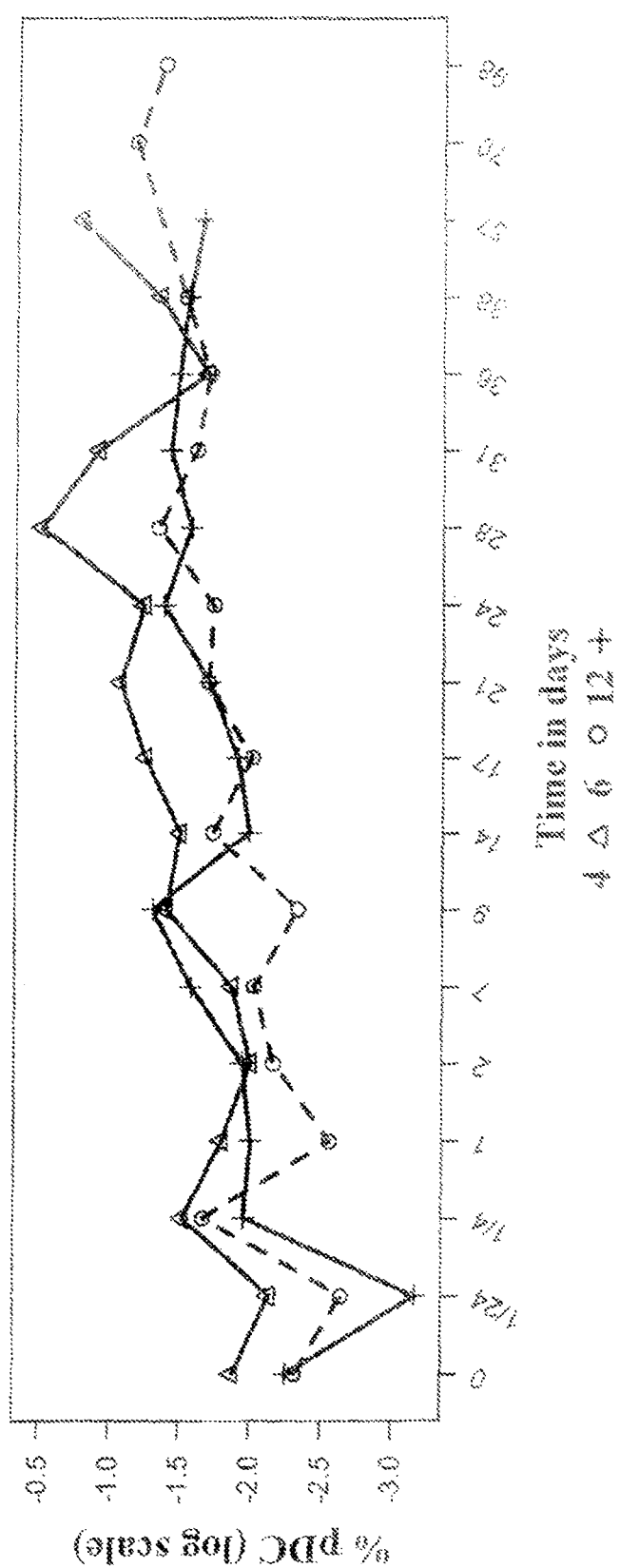
FIG. 56 shows percent circulating pDC after SC dose of BIIB059 0.2 mg/kg in cynomolgus monkey. Cynomolgus monkeys 4, 6 and 12 were administered a single SC injection of BIIB059 0.2 mg/kg at time 0. Out of the three cynomolgus monkeys, cynomolgus monkey 6 was dosed with BIIB059 mg/kg in previous study. Cynomolgus monkeys 4 and 12 were dosed with vehicle in previous study. At indicated time points, whole blood was drawn, and pDCs were identified by flow cytometry as CD20–CD14–CD123+HLA-DR+. Percent pDCs was calculated in FlowJo software, and graphed using R software.

Additionally, after the completion of the IV study time points, three of these cynomolgus monkeys (4, 6, and 12) received a single subcutaneous dose of BIIB059 at 0.2 mg/kg, to evaluate the effect of a lower dose on circulating pDC frequencies. The pDC frequency (on log-scale) at each time point was graphed in R software (FIG. 56). A linear mixed effects model was fitted, using continuous time and time at 1 hour as fixed factors, and cynomolgus monkeys as random intercepts. The results are shown in Table 5.

TABLE 5

Fitted model estimates for time points after a single subcutaneous BIIB059 injection.
Estimates for the fixed effects using a linear mixed effects model using continuous time and time at 1 hour as fixed factors, and cynomolgus monkeys as random intercepts for percent circulating pDC on log scale, before and after a single subcutaneous injection of BIIB059 0.2 mg/kg in cynomolgus monkeys

| | effect est. | exp (effect est.) (% pDC ratio) | 95% CI | P |
|---|---|---|---|---|
| time (continuous) | 0.01 | 1.01 | 1.00 to 1.02 | <0.0001 |
| time: 1 hr v. others | −0.78 | 0.46 | 0.34 to 0.65 | <0.0001 |

Figure 57:
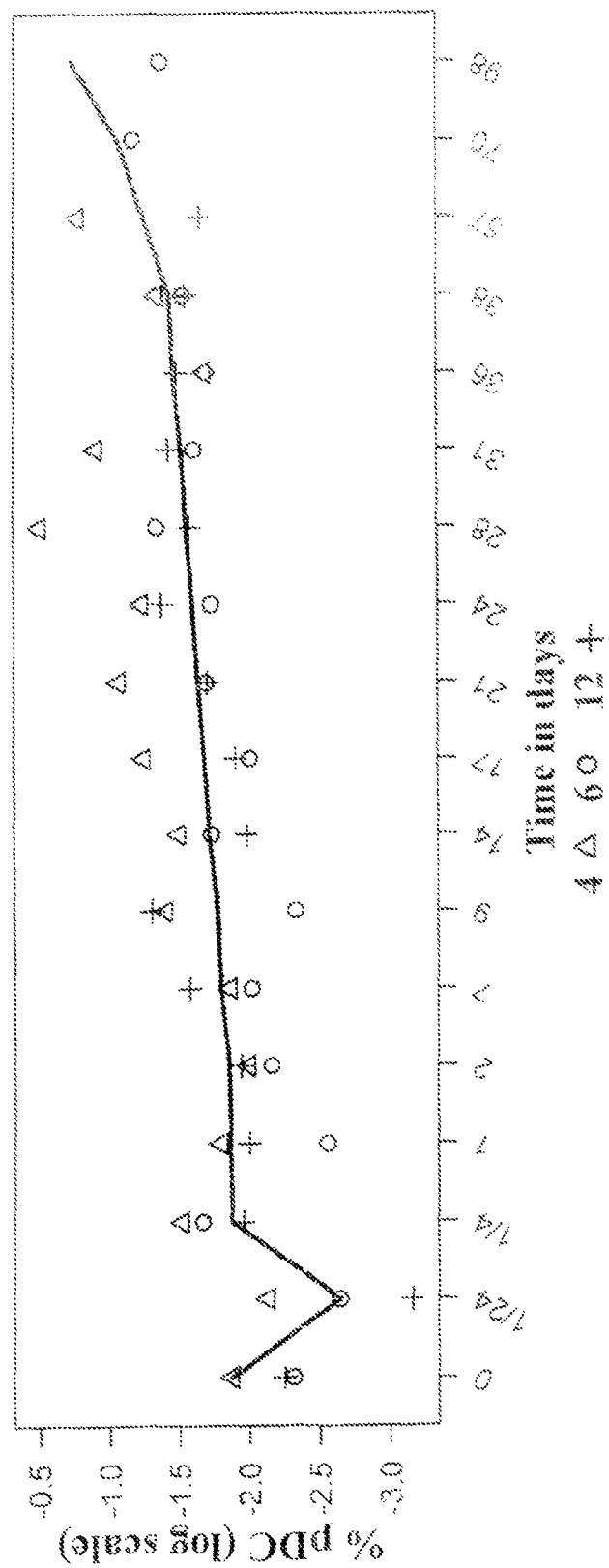
FIG. 57 depicts the final fitted model for percent circulating pDC after SC dose of BIIB059 0.2 mg/kg in cynomolgus monkey. A linear mixed effects model is fitted for log (% pDC) values with fixed effects for continuous time and time at 1 hour, and with cynomolgus monkeys as random intercepts. The solid line shows the fitted model. lme4 package in R was used to fit the linear mixed effects model. Graph and statistical analysis were calculated using the R language for statistical computing.

Similar to the previous results, we observed a significant in vivo depletion of circulating pDCs in cynomolgus monkeys at 1 hour after IV injections (95% CI: 0.34-0.55, p-value<0.0001), but the geometric mean of % pDC for the three cynomolgus monkeys increased steadily as time increased (95% CI: 1.00-1.03 fold change per day, p-value<0.0001). The fitted model was plotted in FIG. 57.

In conclusion, these data show that BIIB059 does not mediate a sustained depletion of pDCs in the blood of cynomolgus monkeys when administered at the tested doses. This is likely due to internalization of BDCA2.

Example 49: Administration of BIIB059 to Cynomolgus Monkeys Results in Inhibition of TLR9-Induced IFNα Production in Ex Vivo Whole Blood Assay The objective of this study was to determine whether BIIB059, when administered to cynomolgus monkeys in vivo, could alter the production of IFNα in response to TLR9 stimulation in an ex vivo whole blood assay (WBA).

Intravenous and subcutaneous dosing routes were evaluated for their ability to impact IFNα induction, which was measured using the MxA bioassay according to the experimental plan outlined in FIG. 58. TLR9 ligand (CpG-A) induced measurable quantities of IFNα in whole blood cultures across all time points and in all cynomolgus monkeys, while no IFNα was detected in the control PBS-treated cultures (data not shown).

Figure 59:
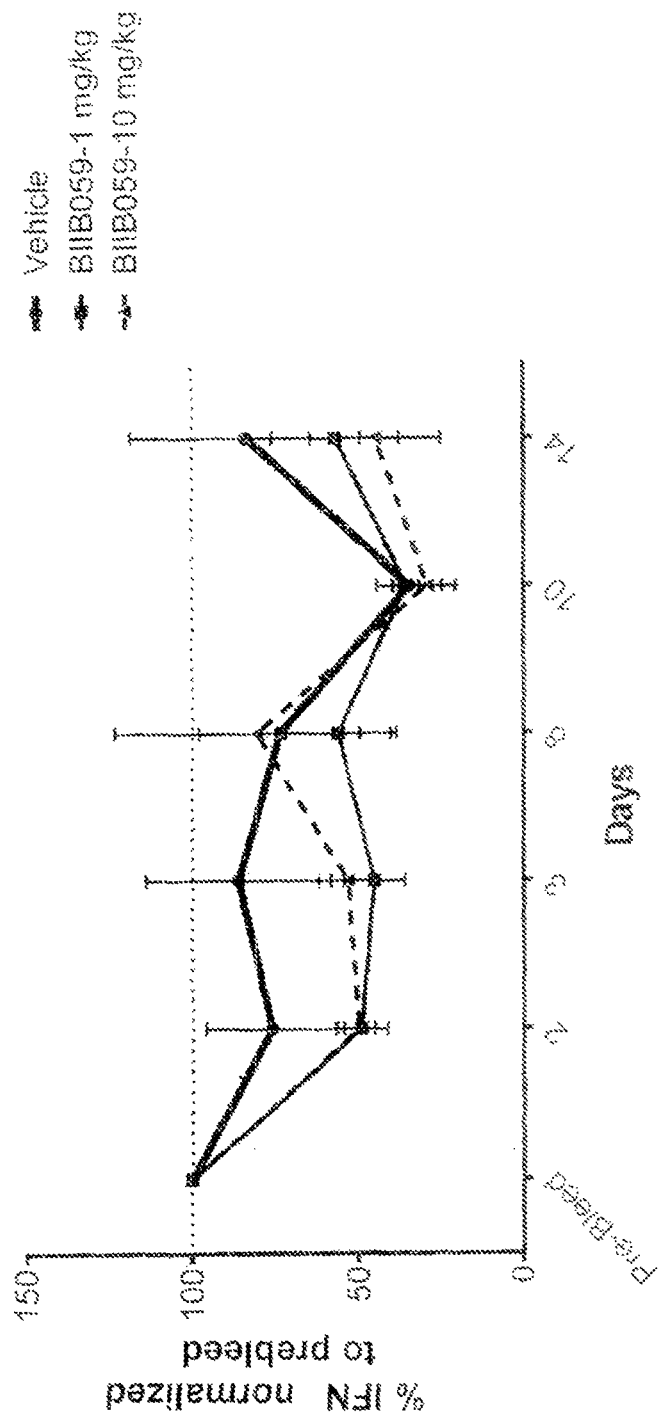
FIG. 59 is a graphical representation of the trend towards reduced TLR9-induced IFNα production in cynomolgus monkeys receiving a single intravenous dose of BIIB059 relative to pre-treatment averages. Whole blood from cynomolgus monkeys treated with a single intravenous dose of vehicle, 1 mg/kg BIIB059, or 10 mg/kg BIIB059 was diluted 1:4 with complete RPMI 1640 and stimulated with CPG-A (2216) to a final concentration of 200 µg/ml in a 96 well round bottom tissue culture plate and incubated at 37° C. 5% CO2 for 18-20 hours. At the end of the culture, the stimulated whole blood was centrifuged to harvest serum. A549 cells were stimulated with the harvested serum for 19-20 hours at 37° C. 5% CO2 to induce MxA protein. After 20 hours, A549 cells were lysed and a sandwich ELISA was performed to detect concentrations of MxA protein. IFNα levels (units/mL) were back calculated from a standard curve generated by treating A549 cells with increasing doses of rIFNα. The mean pre-bleed IFNα concentration was calculated for each monkey by averaging all IFNα measurements from the pre-bleed timepoints (Days −21, −14, −7 and T0). The % IFNα was then calculated for each bleeding timepoint following BIIB059 administration up to day 14 by dividing the concentration of IFNα at that time by the pre-bleed average for that animal and multiplying by 100. These values were then averaged for each treatment group. Graph depicts mean±standard error of the mean. Graph and statistical analysis were calculated using Excel and Graph-Pad 6.0 software (GraphPad, San Diego, Calif.).

For the intravenously-dosed cynomolgus monkeys, IFNα values post-treatment were calculated as percentages of the pre-dose mean for each animal. Data for bleeds after day 14 were excluded from the analysis as the whole blood assay was not performed for the 10 mg/kg BIIB059 group after this time point. A trend towards reduced % IFNα relative to pre-dose mean was observed on several days following drug administration in the 1 mg/kg and 10 mg/kg BIIB059 dosing groups compared to the vehicle group (FIG. 59)

A more comprehensive analysis of the data was performed using two-way mixed effects analysis of variance (ANOVA) to estimate the mean IFNα and the post versus pre differences for each dose group in the IV-study. Data during the first 24 hours following dosing were excluded due to an observed decrease in peripheral blood plasmacytoid dendritic cell percentages. Data for bleeds after day 31 post-dose were excluded from the analysis due to the return of BDCA2 expression observed at this time. For the vehicle dosed group, the geometric mean IFNα was 362 Units/mL (U/mL) pre-dose, and 314 U/mL post-dose; for the 1 mg/kg dosed group, the geometric mean was 399 U/mL pre-dose, and 237 U/mL post-dose; for the 10 mg/kg group, the geometric mean IFNα was 211 U/mL pre-dose, and 102 U/mL post-dose (FIG. 4). The post-pre differences in mean log 10 IFNα were −0.061 (p=0.511) for the Vehicle group, −0.226 (p=0.016) for the 1 mg/kg group, and −0.317 (p=0.004) for the 10 mg/kg group. After anti-log 10 transformation, these results revealed that the Vehicle group had $10^{(-0.061)}$=87% (95% CI: 57%-133%) of the IFNα concentration post-dose compared to pre-dose; the 1 mg/kg group had $10^{(-0.226)}$=59% (95% CI: 39%-91%) of the IFN concentration post-dose compared to pre-dose; and the 10 mg/kg group had $10^{(-0.317)}$=48% (95% CI: 29%-79%) of the IFN concentration post-dose compared to pre-dose (FIG. 60).

For the subcutaneously-dosed cynomolgus monkey cohort, a one-way analysis of variance (ANOVA) with random effects was used to estimate the mean IFNα and the post versus pre differences for the entire group. Data during the first 24 hours following dosing were excluded due to an observed decrease in peripheral blood plasmacytoid dendritic cell percentages. Data for bleeds after day 33 post-dose were excluded from the analysis due to the recovery of BDCA2 expression observed at this time. For the subcutaneously dosed group, the geometric mean IFNα was 1243 U/mL pre-dose and 812 U/mL post-dose, yielding a post/pre ratio of 65%. The post-pre difference in mean log 10 was estimated to be −0.185 (p=0.059) which, after anti-log 10 transformation, corresponds to $10^{(-0.185)}$=65% of the pre-dose geometric mean; the 95% CI of this effect is 41%-102% (FIG. 61).

As only a small number of cynomolgus monkeys were used in the experiment, the IFNα concentration determined for each monkey highly influences the results for that group. The proportion of variation due to animal differences in the intravenous study was 69% of the total variability, with the remainder being primarily due to differences between time points within cynomolgus monkey (26%), and a small amount (<6%) due to assay sources of variation. The variation between cynomolgus monkeys is much larger than the variation between time points within cynomolgus monkeys, suggesting that adding cynomolgus monkeys to this experiment as opposed to more bleeding time points would better power the study. The proportion of variation due to cynomolgus monkey differences in the subcutaneous study was 45% of the total variability, with the remainder being mostly due to differences between time points within cynomolgus monkey, and a negligible amount (<2%) due to assay sources of variation.

The variability observed across cynomolgus monkeys and within cynomolgus monkeys may be due to a number of factors, including fluctuations in physiological conditions of the cynomolgus monkeys, cellular composition of the blood, molecular composition of the cell, and precision of the functional assay.

While there was some fluctuation in plasmacytoid dendritic cell percentages in each animal over time, the % of pDCs in the blood was not affected by treatment with BIIB059 (See Rsch-2013-046) and did not show consistent correlation with IFNα production. Additionally, a rapid and sustained loss of BDCA2 from the cell surface was observed on pDCs following IV and SC BIIB059 administration, suggesting high level of receptor occupancy (See Rsch-2013-043). Taking into account the high level of variability in the responsiveness of pDCs from cynomolgus monkeys to TLR9 stimulation, there was a trend towards dampened IFNα responses following intravenous and subcutaneous administration of BIIB059, with the greatest reduction in the 10 mg/kg IV-dosed group, followed by the 0.2 mg/kg SC-group and then the 1 mg/kg IV-group.

In conclusion, BIIB059 when dosed in vivo to cynomolgus monkeys, showed a trend towards inhibited TLR9-induced IFN production in an ex vivo WBA.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An antibody that specifically binds to human Blood dendritic cell antigen 2 (BDCA2) consisting of the amino acid sequence set forth in SEQ ID NO: 1, wherein the antibody comprises a variable heavy (VH) domain comprising VH complementarity determining region (CDR)1, VH CDR2, and VH CDR3, wherein:
   the VH CDR1 comprises the amino acid sequence GFTF-STYTMS (SEQ ID NO:9);
   the VH CDR2 comprises the amino add sequence TISPGDSFGYYYPDSVQG (SEQ ID NO: 10); and
   the VH CDR3 comprises the amino add sequence DIYYNYGAWFAY (SEQ ID NO: 11); and
   wherein the antibody comprises a variable light (VL) domain comprising VL CDR1, VL CDR2, and VL CDR3, wherein:
   the VL CDR1 comprises the amino add sequence KASQSVDYDGDSYMN (SEQ ID NO:5);
   the VL CDR2 comprises the amino add sequence AASTLES (SEQ ID NO:6); and
   the VL CDR3 comprises the amino add sequence QQANEDPRT (SEQ ID NO:7).

2. The antibody of claim 1, wherein the VH domain comprises the amino add sequence set forth in SEQ ID NO:24.

3. The antibody of claim 1, wherein the antibody comprises a heavy chain and wherein the heavy chain comprises the amino add sequence set forth in SEQ ID NO:4.

4. The antibody of claim 1, wherein the VL domain comprises the amino add sequence set forth in SEQ ID NO:23.

5. The antibody of claim 1, wherein the antibody comprises a light chain and wherein the light chain comprises the amino acid sequence set forth in SEQ ID NO:3.

6. The antibody of claim 1, wherein the VH domain comprises the amino acid sequence set forth in SEQ ID NO:24 and the VL domain comprises the amino acid sequence set forth in SEQ ID NO:23.

7. The antibody of claim 1, wherein the antibody comprises a heavy chain and a light chain, and wherein the heavy chain comprises the amino acid sequence set forth in SEQ ID NO:4 and the light chain comprises the amino acid sequence set forth in SEQ ID NO:3.

8. The antibody of claim 1, wherein the antibody is a humanized antibody.

9. The antibody of claim 1, wherein the antibody is a chimeric antibody.

10. The antibody of claim 1, wherein the antibody comprises an IgG1 heavy chain constant region.

11. An antigen-binding fragment that specifically binds to human Blood dendritic cell antigen 2 (BDCA2) consisting of the amino acid sequence set forth in SEQ ID NO:1, wherein the antigen-binding fragment comprises a variable heavy (VH) domain comprising VH complementarity determining region (CDR)1, VH CDR2, and VH CDR3, wherein:
   the VH CDR1 comprises the amino add sequence GFTF-STYTMS (SEQ ID NO:9);
   the VH CDR2 comprises the amino add sequence TISPGDSFGYYYPDSVQG (SEQ ID NO: 10); and
   the VH CDR3 comprises the amino add sequence DIYYNYGAWFAY (SEQ ID NO: 11); and
   wherein the antigen-binding fragment comprises a variable light (VL) domain comprising VL CDR1, VL CDR2, and VL CDR3, wherein:
   the VL CDR1 comprises the amino add sequence KASQSVDYDGDSYMN (SEQ ID NO:5);
   the VL CDR2 comprises the amino add sequence AASTLES (SEQ ID NO:6); and
   the VL CDR3 comprises the amino add sequence QQANEDPRT (SEQ ID NO:7).

12. The antigen-binding fragment of claim 11, wherein the VH domain comprises the amino add sequence set forth in SEQ ID NO:24.

13. The antigen-binding fragment of claim 11, wherein the VL domain comprises the amino add sequence set forth in SEQ ID NO:23.

14. The antigen-binding fragment of claim 11, wherein the VH domain comprises the amino add sequence set forth in SEQ ID NO:24 and the VL domain comprises the amino add sequence set forth in SEQ ID NO:23.

15. The antigen-binding fragment of claim 11, wherein the antigen-binding fragment is: a single chain antibody, an Fab fragment, an F(ab')2 fragment, an Fab' fragment, an Fsc fragment, an Fv fragment, an scFv, an sc(Fv)2, or a diabody.

16. An isolated cell that produces the antibody of claim 1.

17. An isolated cell that produces the antigen-binding fragment thereof of claim 11.

18. A pharmaceutical composition comprising the antibody of claim 1 and a pharmaceutically acceptable carrier.

19. A pharmaceutical composition comprising the antibody of claim 6 and a pharmaceutically acceptable carrier.

20. A pharmaceutical composition comprising the antibody of claim 7 and a pharmaceutically acceptable carrier.

21. A pharmaceutical composition comprising the antigen-binding fragment of claim 11 and a pharmaceutically acceptable carrier.

22. The pharmaceutical composition of claim 18, wherein the composition comprises 10 to 25 mM citrate, 100 to 200 mM sodium chloride, and a pH of 5.5 to 6.5.

23. The pharmaceutical composition of claim 22, wherein the composition comprises 20 mM sodium citrate, 150 mM sodium chloride, and a pH of 6.0.

24. A method of reducing production of a type I interferon, IL-6, TNF-α, CCL3, CCL4, IP10, and RANTES by a plasmacytoid dendritic cell expressing BDAC2 in a human subject, the method comprising contacting a plasmacytoid dendritic cell that expresses BDCA2 with an effective amount of the antibody of claim 1.

25. A method of treating an inflammatory disorder associated with the presence of plasmacytoid dendritic cells expressing BDCA2 in a human subject having said inflammatory disorder, comprising administering to the human subject an effective amount of the antibody of claim 1.

26. The method of claim 25, wherein the inflammatory disorder is selected from the group consisting of systemic lupus erythematosus, discoid lupus, lupus nephritis, rheumatoid arthritis, inflammatory bowel disease, systemic sclerosis (scleroderma), psoriasis, type I diabetes, dermatomyositis, and polymyositis.

27. The method of claim 25, wherein the inflammatory disorder is systemic lupus erythematosus, discoid lupus, lupus nephritis, or cutaneous lupus.

28. The method of claim 25, wherein the inflammatory disorder is systemic lupus erythematosus.

29. The method of claim 25, wherein the inflammatory disorder is cutaneous lupus erythematosus.

30. The method of claim 25, wherein the inflammatory disorder is moderate to severe lupus with active central nervous system (CNS) and/or renal involvement.

31. The method of claim 25, wherein the inflammatory disorder is moderate to serve lupus without active central nervous system (CNS) and/or renal involvement.

32. A method of treating an autoimmune disease associated with the presence of plasmacytoid dendritic cells expressing BDCA2 in a human subject having said autoimmune disease, comprising administering to the human subject an effective amount of the antibody of claim 1.

33. A method of reducing production of a type 1 interferon, IL-6, TNF-α, CCL3, CCL4, IP10, and RANTES by a plasmacytoid dendritic cell expressing BDCA2 in a human subject, the method comprising contacting a plasmacytoid dendritic cell that expresses BDCA2 with an effective amount of the antibody of claim 6.

34. A method of treating an inflammatory disorder associated with the presence of plasmacytoid dendritic cells expressing BDCA2 in a human subject having said inflammatory disorder, comprising administering to the human subject an effective amount of the antibody of claim 6.

35. The method of claim 34, wherein the inflammatory disorder is selected from the group consisting of systemic lupus erythematosus, discoid lupus, lupus nephritis, rheumatoid arthritis, inflammatory bowel disease, systemic sclerosis (scleroderma), psoriasis, type I diabetes, dermatomyositis, and polymyositis.

36. The method of claim 34, wherein the inflammatory disorder is systemic lupus erythematosus, discoid lupus, lupus nephritis, or cutaneous lupus.

37. The method of claim 34, wherein the inflammatory disorder is moderate to severe lupus with active central nervous system (CNS) and/or renal involvement.

38. The method of claim 34, wherein the inflammatory disorder is moderate to severe lupus without active central nervous system (CNS) and/or renal involvement.

39. The method of claim 34, wherein the inflammatory disorder is systemic lupus erythematosus.

40. The method of claim 34, wherein the inflammatory disorder is cutaneous lupus erythematosus.

41. A method of treating an autoimmune disease associated with the presence of plasmacytoid dendritic cells expressing BDCA2 in a human subject having said autoimmune disease, comprising administering to the human subject an effective amount of the antibody of claim 6.

42. A method of inducing death of a plasmacytoid dendritic cell expressing BDCA2 in a human subject, the method comprising contacting a plasmacytoid dendritic cell expressing BDCA2 of the human subject with the antibody of claim 6, wherein the contacting induces death of the plasmacytoid dendritic cell.

43. A method of reducing production of a type I interferon, IL-6, TNF-α, CCL3, CCL4, IP10, and RANTES by a plasmacytoid dendritic cell expressing BDCA2 in a human subject, the method comprising contacting a plasmacytoid dendritic cell that expresses BDCA2 with an effective amount of the antibody of claim 7.

44. A method of treating an inflammatory disorder associated with the presence of plasmacytoid dendritic cells expressing BDCA2 in a human subject having said inflammatory disorder, comprising administering to the human subject an effective amount of the antibody of claim 7.

45. The method of claim 44, wherein the inflammatory disorder is selected from the group consisting of systemic lupus erythematosus, discoid lupus, lupus nephritis, rheumatoid arthritis, inflammatory bowel disease, systemic sclerosis (scleroderma), psoriasis, type 1 diabetes, dermatomyositis, and polymyositis.

46. The method of claim 44, wherein the inflammatory disorder is systemic lupus erythematosus, discoid lupus, lupus nephritis, or cutaneous lupus.

47. The method of claim 44, wherein the inflammatory disorder is moderate to severe lupus with active central nervous system (CNS) and/or renal involvement.

48. The method of claim 44, wherein the inflammatory disorder is moderate to severe lupus without active central nervous system (CNS) and/or renal involvement.

49. The method of claim 44, wherein the inflammatory disorder is systemic lupus erythematosus.

50. The method of claim 44, wherein the inflammatory disorder is cutaneous lupus erythematosus.

51. A method of treating an autoimmune disease associated with the presence of plasmacytoid dendritic cells expressing BDCA2 in a human subject having said autoimmune disease, comprising administering to the human subject an effective amount of the antibody of claim 7.

52. A method of inducing death of a plasmacytoid dendritic cell expressing BDCA2 in a human subject, the method comprising contacting a plasmacytoid dendritic cell expressing BDCA2 of the human subject with the antibody of claim 7, wherein the contacting induces death of the plasmacytoid dendritic cell.

53. A method of inducing death of a plasmacytoid dendritic cell expressing BDCA2 in a human subject, the method comprising contacting a plasmacytoid dendritic cell expressing BDCA2 of the human subject with the antibody of claim 1, wherein the contacting induces death of the plasmacytoid dendritic cell.

\* \* \* \* \*

UNITED STATES PATENT AND TRADEMARK OFFICE
CERTIFICATE OF CORRECTION

Page 1 of 2

PATENT NO. : 9,902,775 B2
APPLICATION NO. : 14/649297
DATED : February 27, 2018
INVENTOR(S) : Justin A. Caravella et al.

It is certified that error appears in the above-identified patent and that said Letters Patent is hereby corrected as shown below:

In the Claims

Column 229, Claim 1:
Line 23, delete "add" and insert -- acid --.
Line 25, delete "add" and insert -- acid --.
Line 30, delete "add" and insert -- acid --.
Line 32, delete "add" and insert -- acid --.
Line 34, delete "add" and insert -- acid --.

Column 229, Claim 2:
Line 37, delete "add" and insert -- acid --.

Column 229, Claim 3:
Line 42, delete "add" and insert -- acid --.

Column 229, Claim 4:
Line 44, delete "add" and insert -- acid --.

Column 230, Claim 11:
Line 16, delete "add" and insert -- acid --.
Line 18, delete "add" and insert -- acid --.
Line 20, delete "add" and insert -- acid --.
Line 25, delete "add" and insert -- acid --.
Line 27, delete "add" and insert -- acid --.
Line 29, delete "add" and insert -- acid --.

Column 230, Claim 12:
Line 32, delete "add" and insert -- acid --.

Signed and Sealed this
Twenty-fourth Day of April, 2018

Andrei Iancu
*Director of the United States Patent and Trademark Office*

CERTIFICATE OF CORRECTION (continued)
U.S. Pat. No. 9,902,775 B2

Column 230, Claim 13:
Line 35, delete "add" and insert -- acid --.

Column 230, Claim 14:
Line 38, delete "add" and insert -- acid --.
Line 40, delete "add" and insert -- acid --.

Column 230, Claim 24:
Line 66, delete "BDAC2" and insert -- BDCA2 --.

Column 231, Claim 31:
Line 25, delete "serve" and insert -- severe --.

Column 231, Claim 33:
Line 32, delete "type 1" and insert -- type I --.

Column 232, Claim 45:
Line 28, delete "type 1" and insert -- type I --.